(12) United States Patent
Voronina et al.

(10) Patent No.: US 12,342,801 B2
(45) Date of Patent: Jul. 1, 2025

(54) METHODS FOR PRODUCING ANTIGEN-BINDING PROTEINS AGAINST FOREIGN ANTIGENS

(71) Applicant: Regeneron Pharmaceuticals, Inc., Tarrytown, NY (US)

(72) Inventors: Vera Voronina, North Bethesda, MD (US); Lynn Macdonald, Harrison, NY (US); Marine Prissette, Brooklyn, NY (US); Ka-Man Venus Lai, Seattle, WA (US); Ashok Badithe, Basking Ridge, NJ (US); Andrew J. Murphy, Croton-on-Hudson, NY (US); Gustavo Droguett, New City, NY (US); David Frendewey, New York, NY (US); Brian Zambrowicz, Sleepy Hollow, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 710 days.

(21) Appl. No.: 17/553,115

(22) Filed: Dec. 16, 2021

(65) Prior Publication Data

US 2022/0167600 A1 Jun. 2, 2022

Related U.S. Application Data

(63) Continuation of application No. 15/600,466, filed on May 19, 2017, now abandoned.

(60) Provisional application No. 62/368,604, filed on Jul. 29, 2016, provisional application No. 62/339,472, filed on May 20, 2016.

(51) Int. Cl.
| | |
|---|---|
| *A01K 67/0278* | (2024.01) |
| *A01K 67/0271* | (2024.01) |
| *A01K 67/0276* | (2024.01) |
| *C07K 16/00* | (2006.01) |
| *C12N 9/64* | (2006.01) |
| *C12N 15/85* | (2006.01) |
| *C12N 15/90* | (2006.01) |

(52) U.S. Cl.
CPC ...... *A01K 67/0278* (2013.01); *A01K 67/0271* (2013.01); *A01K 67/0276* (2013.01); *C07K 16/00* (2013.01); *C12N 9/6489* (2013.01); *C12N 15/8509* (2013.01); *C12N 15/90* (2013.01); *C12Y 301/00* (2013.01); *C12Y 304/24046* (2013.01); *A01K 2207/05* (2013.01); *A01K 2207/12* (2013.01); *A01K 2207/15* (2013.01); *A01K 2217/00* (2013.01); *A01K 2217/072* (2013.01); *A01K 2217/075* (2013.01); *A01K 2217/15* (2013.01); *A01K 2217/206* (2013.01); *A01K 2227/105* (2013.01); *A01K 2267/01* (2013.01); *A01K 2267/02* (2013.01); *C07K 2317/21* (2013.01); *C07K 2317/24* (2013.01); *C07K 2317/33* (2013.01); *C12N 2015/8518* (2013.01)

(58) Field of Classification Search
CPC ............ A01K 67/0278; A01K 67/0271; A01K 67/0276; A01K 2207/05; A01K 2207/12; A01K 2207/15; A01K 2217/00; A01K 2217/072; A01K 2217/075; C07K 16/00; C12N 9/6489; C12N 15/8509; C12N 15/90; C12Y 301/00; C12Y 304/24046
See application file for complete search history.

(56) References Cited

U.S. PATENT DOCUMENTS

| | | |
|---|---|---|
| 5,747,037 A | 5/1998 | Noelle et al. |
| 5,942,435 A | 8/1999 | Wheeler |
| 6,596,541 B2 | 7/2003 | Murphy et al. |
| 7,105,348 B2 | 9/2006 | Murphy et al. |
| 7,119,248 B1 | 10/2006 | Rajewsky et al. |
| 7,582,298 B2 | 9/2009 | Stevens et al. |
| 8,502,018 B2 | 8/2013 | Murphy et al. |
| 8,642,835 B2 | 2/2014 | Macdonald et al. |
| 8,697,359 B1 | 4/2014 | Zhang |
| 8,697,940 B2 | 4/2014 | Macdonald et al. |
| 8,754,287 B2 | 6/2014 | Macdonald et al. |
| 8,791,323 B2 | 7/2014 | Murphy et al. |
| 9,006,511 B2 | 4/2015 | Macdonald et al. |
| 9,012,717 B2 | 4/2015 | Macdonald et al. |
| 9,029,628 B2 | 5/2015 | Macdonald et al. |
| 9,035,128 B2 | 5/2015 | Macdonald et al. |
| 9,066,502 B2 | 6/2015 | Macdonald et al. |
| 9,150,662 B2 | 10/2015 | Macdonald et al. |
| 9,163,092 B2 | 10/2015 | Macdonald et al. |
| 9,204,624 B2 | 12/2015 | McWhirter et al. |
| 9,206,261 B2 | 12/2015 | Macdonald et al. |
| 9,206,262 B2 | 12/2015 | Macdonald et al. |
| 9,206,263 B2 | 12/2015 | Macdonald et al. |
| 9,226,484 B2 | 1/2016 | Macdonald et al. |

(Continued)

FOREIGN PATENT DOCUMENTS

| | | |
|---|---|---|
| CN | 103429746 A | 12/2013 |
| CN | 105378067 A | 3/2016 |

(Continued)

OTHER PUBLICATIONS

Bassett, A.R., et al., "CRISPR/Cas9 and Genome Editing in *Drosophila*," Journal of Genetics and Genomics (2014), vol. 41, pp. 7-19.

(Continued)

*Primary Examiner* — Titilayo Moloye
(74) *Attorney, Agent, or Firm* — Alston & Bird LLP

(57) ABSTRACT

Methods and compositions are provided for generating antigen-binding proteins against a foreign antigen of interest.

20 Claims, 30 Drawing Sheets
(3 of 30 Drawing Sheet(s) Filed in Color)
Specification includes a Sequence Listing.

(56) References Cited

U.S. PATENT DOCUMENTS

| | | |
|---|---|---|
| 9,301,510 B2 | 4/2016 | McWhirter et al. |
| 9,332,742 B2 | 5/2016 | McWhirter et al. |
| 9,334,334 B2 | 5/2016 | McWhirter et al. |
| 9,822,370 B2 | 11/2017 | Musunuru et al. |
| 11,697,828 B2 | 7/2023 | Frendewey et al. |
| 2002/0106629 A1 | 8/2002 | Murphy et al. |
| 2002/0183275 A1 | 12/2002 | Murphy et al. |
| 2004/0018626 A1 | 1/2004 | Murphy et al. |
| 2007/0061900 A1 | 3/2007 | Murphy et al. |
| 2007/0101446 A1 | 5/2007 | Rajewsky et al. |
| 2007/0280945 A1 | 12/2007 | Stevens et al. |
| 2009/0111126 A1 | 4/2009 | Akamatsu et al. |
| 2011/0145937 A1 | 6/2011 | Macdonald et al. |
| 2011/0195454 A1 | 8/2011 | McWhirter et al. |
| 2011/0258710 A1 | 10/2011 | Murphy et al. |
| 2011/0283376 A1 | 11/2011 | Murphy et al. |
| 2012/0021409 A1 | 1/2012 | McWhirter et al. |
| 2012/0070861 A1 | 3/2012 | Macdonald et al. |
| 2012/0073004 A1 | 3/2012 | Macdonald et al. |
| 2012/0096572 A1 | 4/2012 | Macdonald et al. |
| 2012/0185956 A1 | 7/2012 | Gingras |
| 2012/0192300 A1 | 7/2012 | Babb et al. |
| 2012/0322108 A1 | 12/2012 | Macdonald et al. |
| 2013/0045492 A1 | 2/2013 | Babb et al. |
| 2013/0326647 A1 | 2/2013 | Macdonald et al. |
| 2013/0096287 A1 | 4/2013 | Macdonald et al. |
| 2013/0160153 A1 | 6/2013 | Macdonald et al. |
| 2013/0185821 A1 | 7/2013 | Babb et al. |
| 2013/0198879 A1 | 8/2013 | McWhirter et al. |
| 2013/0198880 A1 | 8/2013 | Babb et al. |
| 2013/0210137 A1 | 8/2013 | Murphy et al. |
| 2013/0247234 A1 | 9/2013 | McWhirter et al. |
| 2013/0247235 A1 | 9/2013 | McWhirter et al. |
| 2013/0247236 A1 | 9/2013 | McWhirter et al. |
| 2013/0254911 A1 | 9/2013 | Macdonald et al. |
| 2013/0302836 A1 | 11/2013 | McWhirter et al. |
| 2013/0323790 A1 | 12/2013 | Macdonald et al. |
| 2013/0323791 A1 | 12/2013 | Macdonald et al. |
| 2013/0333057 A1 | 12/2013 | Macdonald et al. |
| 2014/0013456 A1 | 1/2014 | McWhirter et al. |
| 2014/0013457 A1 | 1/2014 | Murphy et al. |
| 2014/0017228 A1 | 1/2014 | Macdonald et al. |
| 2014/0017229 A1 | 1/2014 | Murphy et al. |
| 2014/0017238 A1 | 1/2014 | Murphy et al. |
| 2014/0017781 A1 | 1/2014 | Murphy et al. |
| 2014/0017782 A1 | 1/2014 | Murphy et al. |
| 2014/0018522 A1 | 1/2014 | Murphy et al. |
| 2014/0020124 A1 | 1/2014 | Murphy et al. |
| 2014/0020125 A1 | 1/2014 | Murphy et al. |
| 2014/0023637 A1 | 1/2014 | Murphy et al. |
| 2014/0033336 A1 | 1/2014 | Murphy et al. |
| 2014/0033337 A1 | 1/2014 | Murphy et al. |
| 2014/0041068 A1 | 2/2014 | Murphy et al. |
| 2014/0065142 A1 | 3/2014 | Roschke et al. |
| 2014/0068797 A1 | 3/2014 | Doudna et al. |
| 2014/0073010 A1 | 3/2014 | Murphy et al. |
| 2014/0082760 A1 | 3/2014 | McWhirter et al. |
| 2014/0130193 A1 | 5/2014 | Macdonald et al. |
| 2014/0130194 A1 | 5/2014 | Macdonald et al. |
| 2014/0137275 A1 | 5/2014 | Macdonald et al. |
| 2014/0154701 A1 | 6/2014 | Macdonald et al. |
| 2014/0179770 A1 | 6/2014 | Zhang et al. |
| 2014/0213773 A1 | 7/2014 | Macdonald et al. |
| 2014/0245468 A1 | 8/2014 | McWhirter et al. |
| 2014/0273233 A1 | 9/2014 | Chen et al. |
| 2014/0289876 A1 | 9/2014 | Macdonald et al. |
| 2014/0309487 A1 | 10/2014 | Lee et al. |
| 2014/0315985 A1 | 10/2014 | May et al. |
| 2014/0329711 A1 | 11/2014 | Murphy et al. |
| 2014/0342458 A1 | 11/2014 | Mali et al. |
| 2015/0020224 A1 | 1/2015 | McWhirter et al. |
| 2015/0024500 A1 | 1/2015 | Yu et al. |
| 2015/0059009 A1 | 2/2015 | McWhirter et al. |
| 2015/0071889 A1 | 3/2015 | Musunuru et al. |
| 2015/0079680 A1 | 3/2015 | Bradley et al. |
| 2015/0082466 A1 | 3/2015 | Clube |
| 2015/0089680 A1 | 3/2015 | Macdonald et al. |
| 2015/0119556 A1 | 4/2015 | McWhirter et al. |
| 2015/0140664 A1 | 5/2015 | Byrne et al. |
| 2015/0152436 A1 | 6/2015 | Musunuru et al. |
| 2015/0173331 A1 | 6/2015 | Macdonald et al. |
| 2015/0173332 A1 | 6/2015 | Macdonald et al. |
| 2015/0176002 A1 | 6/2015 | Macdonald et al. |
| 2015/0176013 A1 | 6/2015 | Musunuru et al. |
| 2015/0196015 A1 | 7/2015 | Macdonald et al. |
| 2015/0197553 A1 | 7/2015 | Macdonald et al. |
| 2015/0197554 A1 | 7/2015 | Macdonald et al. |
| 2015/0197555 A1 | 7/2015 | Macdonald et al. |
| 2015/0197556 A1 | 7/2015 | Macdonald et al. |
| 2015/0197557 A1 | 7/2015 | Macdonald et al. |
| 2015/0201589 A1 | 7/2015 | Macdonald et al. |
| 2015/0210776 A1 | 7/2015 | Macdonald et al. |
| 2015/0232881 A1 | 8/2015 | Glucksmann et al. |
| 2015/0246977 A1 | 9/2015 | Macdonald et al. |
| 2015/0250151 A1 | 9/2015 | McWhirter et al. |
| 2015/0252358 A1 | 9/2015 | Maeder et al. |
| 2015/0289489 A1 | 10/2015 | Macdonald et al. |
| 2015/0291965 A1 | 10/2015 | Zhang et al. |
| 2015/0291966 A1 | 10/2015 | Zhang et al. |
| 2015/0291969 A1 | 10/2015 | Nair et al. |
| 2015/0313193 A1 | 11/2015 | McWhirter et al. |
| 2015/0320023 A1 | 11/2015 | Macdonald et al. |
| 2015/0334998 A1 | 11/2015 | Bradley et al. |
| 2015/0351371 A1 | 12/2015 | Macdonald et al. |
| 2015/0368670 A1 | 12/2015 | Quake et al. |
| 2015/0376583 A1 | 12/2015 | Quake et al. |
| 2015/0376651 A1 | 12/2015 | Frendewey et al. |
| 2016/0017301 A1 | 1/2016 | Khalili et al. |
| 2016/0046960 A1 | 2/2016 | Frendewey et al. |
| 2016/0057979 A1 | 3/2016 | Macdonald et al. |
| 2016/0060359 A1 | 3/2016 | Macdonald et al. |
| 2016/0060655 A1 | 3/2016 | Quake et al. |
| 2016/0060657 A1 | 3/2016 | Frendewey et al. |
| 2016/0100561 A1 | 4/2016 | McWhirter et al. |
| 2016/0122774 A1 | 5/2016 | Duchateau et al. |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153005 A1 | 6/2016 | Zhang et al. |
| 2016/0153006 A1 | 6/2016 | Zhang et al. |
| 2016/0160210 A1 | 6/2016 | Mali et al. |
| 2016/0175462 A1 | 6/2016 | Zhang et al. |
| 2016/0186208 A1 | 6/2016 | Jaenisch et al. |
| 2016/0186213 A1 | 6/2016 | Zhang et al. |
| 2016/0207983 A1 | 7/2016 | Bradley et al. |
| 2016/0208319 A1 | 7/2016 | Berman et al. |
| 2016/0219847 A1 | 8/2016 | McWhirter et al. |
| 2016/0237455 A1 | 8/2016 | Glucksmann et al. |
| 2016/0250300 A1 | 9/2016 | Khalili et al. |
| 2016/0257967 A1 | 9/2016 | Russell et al. |
| 2016/0264995 A1 | 9/2016 | Yamamoto et al. |
| 2016/0281111 A1 | 9/2016 | Cotta-Ramusino et al. |
| 2016/0304855 A1 | 10/2016 | Stark et al. |
| 2016/0340661 A1 | 11/2016 | Cong et al. |
| 2016/0355796 A1 | 12/2016 | Davidson et al. |
| 2017/0002380 A1 | 1/2017 | Buerckstuemmer |
| 2017/0247436 A1 | 8/2017 | Kyratsous et al. |
| 2017/0266320 A1 | 9/2017 | Wagers et al. |
| 2017/0275611 A1 | 9/2017 | Bradley et al. |
| 2017/0332610 A1 | 11/2017 | Voronina et al. |
| 2018/0020646 A1 | 1/2018 | Ueda et al. |
| 2018/0135073 A1 | 5/2018 | Chen et al. |
| 2018/0327761 A1 | 11/2018 | Duchateau et al. |
| 2018/0334665 A1 | 11/2018 | Yu et al. |
| 2018/0355382 A1 | 12/2018 | Bergstrom et al. |
| 2019/0327946 A1 | 10/2019 | Bradley et al. |
| 2019/0338274 A1 | 11/2019 | Bradley et al. |
| 2020/0002722 A1 | 1/2020 | Chen et al. |
| 2020/0002730 A1 | 1/2020 | Frendewey et al. |
| 2020/0002731 A1 | 1/2020 | Frendewey et al. |
| 2020/0029538 A1 | 1/2020 | Mashimo et al. |

(56) References Cited

U.S. PATENT DOCUMENTS

| | | | |
|---|---|---|---|
| 2021/0147879 A1 | 5/2021 | Byrne et al. | |
| 2024/0200054 A1 | 6/2024 | Bradley et al. | |

FOREIGN PATENT DOCUMENTS

| | | | |
|---|---|---|---|
| EP | 0677533 | A2 | 10/1995 |
| EP | 2 738 258 | A2 | 6/2016 |
| EP | 3 239 298 | A1 | 11/2017 |
| EP | 3022304 | B1 | 12/2018 |
| EP | 3071698 | B1 | 9/2019 |
| EP | 3546575 | A1 | 10/2019 |
| EP | 3604543 | A1 | 2/2020 |
| EP | 3418379 | B1 | 12/2020 |
| JP | 2006-187215 | A | 7/2006 |
| JP | 2013-518597 | A | 5/2013 |
| KR | 10-2015-0141987 | A | 12/2015 |
| RU | 2425880 | C2 | 8/2011 |
| WO | WO 2002/036789 | A2 | 5/2002 |
| WO | WO 2011/146121 | A1 | 11/2011 |
| WO | WO 2012/012667 | A2 | 1/2012 |
| WO | WO 2013/041846 | A1 | 3/2013 |
| WO | WO 2013/169802 | A1 | 11/2013 |
| WO | WO 2013/176772 | A1 | 11/2013 |
| WO | WO 2014/093622 | A2 | 6/2014 |
| WO | WO 2014/099744 | A1 | 6/2014 |
| WO | WO 2014/099750 | A2 | 6/2014 |
| WO | WO 2014/130706 | A1 | 8/2014 |
| WO | WO 2014/143381 | A1 | 9/2014 |
| WO | WO 2014/150624 | A1 | 9/2014 |
| WO | WO 2014/165825 | A2 | 10/2014 |
| WO | WO 2014/172470 | A2 | 10/2014 |
| WO | WO 2014/191518 | A1 | 12/2014 |
| WO | WO 2014/204723 | A1 | 12/2014 |
| WO | WO 2014/204724 | A1 | 12/2014 |
| WO | WO 2014/204725 | A1 | 12/2014 |
| WO | WO 2014/204726 | A1 | 12/2014 |
| WO | WO 2014/204728 | A1 | 12/2014 |
| WO | WO 2014/204729 | A1 | 12/2014 |
| WO | WO 2015/006498 | A2 | 1/2015 |
| WO | WO 2015/010114 | A1 | 1/2015 |
| WO | WO 2015/040402 | A1 | 3/2015 |
| WO | WO 2015/048577 | A2 | 4/2015 |
| WO | WO 2015/048690 | A1 | 4/2015 |
| WO | WO 2015/070083 | A1 | 5/2015 |
| WO | WO 2015/077290 | A2 | 5/2015 |
| WO | WO 2015/079057 | A2 | 6/2015 |
| WO | WO 2015/088643 | A1 | 6/2015 |
| WO | WO 2015/089465 | A1 | 6/2015 |
| WO | WO 2015/089473 | A1 | 6/2015 |
| WO | WO 2015/116969 | A2 | 8/2015 |
| WO | WO 2015/117041 | A1 | 8/2015 |
| WO | WO 2015/134812 | A1 | 9/2015 |
| WO | WO 2015/138510 | A1 | 9/2015 |
| WO | WO 2015/138739 | A2 | 9/2015 |
| WO | WO 2015/139008 | A1 | 9/2015 |
| WO | WO 2015/143414 | A2 | 9/2015 |
| WO | WO 2015/148761 | A1 | 10/2015 |
| WO | WO 2015/159086 | A1 | 10/2015 |
| WO | WO 2015/173436 | A1 | 11/2015 |
| WO | WO 2015/184259 | A1 | 12/2015 |
| WO | WO 2015/184262 | A1 | 12/2015 |
| WO | WO 2015/184268 | A1 | 12/2015 |
| WO | WO 2015/188109 | A1 | 12/2015 |
| WO | WO 2015/200805 | A2 | 12/2015 |
| WO | WO 2016/011210 | A1 | 1/2016 |
| WO | WO 2016/011428 | A1 | 1/2016 |
| WO | WO 2016/033246 | A1 | 3/2016 |
| WO | WO 2016/049024 | A2 | 3/2016 |
| WO | WO 2016/049163 | A2 | 3/2016 |
| WO | WO 2016/049258 | A2 | 3/2016 |
| WO | WO 2016/057821 | A2 | 4/2016 |
| WO | WO 2016/061073 | A1 | 4/2016 |
| WO | WO 2016/061481 | A1 | 4/2016 |
| WO | WO 2016/073955 | A2 | 5/2016 |
| WO | WO 2016/073990 | A1 | 5/2016 |
| WO | WO 2016/081923 | A2 | 5/2016 |
| WO | WO 2016/084084 | A1 | 6/2016 |
| WO | WO 2016/089866 | A1 | 6/2016 |
| WO | WO 2016/094872 | A1 | 6/2016 |
| WO | WO 2016/094874 | A1 | 6/2016 |
| WO | WO 2016/112242 | A1 | 7/2016 |
| WO | WO 2016/112351 | A1 | 7/2016 |
| WO | WO 2016/130697 | A1 | 8/2016 |
| WO | WO 2016/135557 | A2 | 9/2016 |
| WO | WO 2016/135558 | A2 | 9/2016 |
| WO | WO 2016/135559 | A2 | 9/2016 |
| WO | WO 2016/142719 | A1 | 9/2016 |
| WO | WO 2016/149678 | A1 | 9/2016 |
| WO | WO 2016/154579 | A2 | 9/2016 |
| WO | WO 2016/160721 | A1 | 10/2016 |
| WO | WO 2016/161380 | A1 | 10/2016 |
| WO | WO 2016/168890 | A1 | 10/2016 |
| WO | WO 2016/174056 | A1 | 11/2016 |
| WO | WO 2016/176690 | A2 | 11/2016 |
| WO | WO 2016/186772 | A2 | 11/2016 |
| WO | WO 2017/062723 | A1 | 4/2017 |
| WO | WO 2017/070032 | A1 | 4/2017 |
| WO | WO 2016/073990 | A2 | 5/2017 |
| WO | WO 2017/079724 | A9 | 5/2017 |
| WO | WO 2017/143062 | A1 | 8/2017 |
| WO | WO 2017/165826 | A1 | 9/2017 |
| WO | WO 2017/173004 | A1 | 10/2017 |
| WO | WO 2017/180859 | A1 | 10/2017 |
| WO | WO 2017/201476 | A1 | 11/2017 |

OTHER PUBLICATIONS

Brevini, et al., "No shortcuts to pig embryonic stem cells," Theriogenology, 74(4):544-550, (2010).

Brevini, et al., "Porcine embryonic stem cells: Facts, challenges and hopes," Theriogenology, 68 Suppl. 1:S206-S213, (2007).

Byrne et al., "Multi-kilobase homozygous targeted gene replacement in human induced pluripotent stem cells," Nucleic Acids Research, Vo. 43(3), p. e21, 2014 (epub Nov. 20, 2014).

Cao, et al., "Isolation and Culture of Primary Bovine Embryonic Stem Cell Colonies by a Novel Method," J. Exp. Zool. A. Ecol. Genet. Physiol., 311(5):368-376, (2009).

Chen et al., "High-frequency genome editing using ssDNA oligonucleotides with zinc-finger nucleases," Nature Methods, vol. 8(9), pp. 753-755, 2011. (Jul. 17, 2011).

Claesson et al., "Antibodies Directed Against Monomorphic and Evolutionary Conserved Self Epitopes may be Generated in 'Knock-Out' Mice. Development of Monoclonal Antibodies Directed Against Monomorphic MHC Class I Determinants," Scand. J. Immunol. 40:257-264, (1994).

Cong et al., "Multiplex Genome Engineering Using CRISPR/Cas Systems," Science, vol. 339(6121), pp. 819-823 plus Supplemental Materials, Jan. 3, 2013.

Dennis, "Welfare Issues of Genetically Modified Animals," ILAR J., 43(2):100-109, (2002).

Frendewey, "VelociGene: Large-scale Modification of Rodent Genomes," Wellcome Trust Advanced Course: Genetic Engineering of Mammalian Stem Cells, Feb. 20, 2015.

Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.

Fujii W., et al., "Efficient generation of large-scale genome-modified mice using gRNA and CAS9 endonuclease," Nucleic Acids Research (2013), vol. 41(20), p. e187.

Gagliardi et al., "Combining CRISPR/Cas9 with large targeting vectors in mouse ES cell electroporations to produce homozygous F0 mice," Program and Abstracts of the 13th Transgenic Technology Meeting (TT2016), Transgenic Res. 25:195-270, (2016).

Gratz et al., "Genome Engineering of *Drosophila* with the CRISPR RNA-Guided Cas9 Nuclease," Genetics, vol. 194, pp. 1029-1035, 2013. (published May 2013).

Gratz et al., "Highly Specific and Efficient CRISPR/Cas9-Catalyzed Homology-Directed Repair in *Drosophila*," Genetics, vol. 196(4), pp. 961-971 plus Supporting Information, Jan. 29, 2014.

(56) References Cited

OTHER PUBLICATIONS

Harrison, M.M., et al., "A CRISPR view of development," Genes & Development (2014), vol. 28(17), pp. 1859-1872.
Houdebine, "Methods to Generate Transgenic Animals," pp. 31-48 in "Genetic Engineering in Livestock: New Applications and Interdisciplinary Perspectives," Ed. Engelhard et al., (2009).
Hsu, P.D., et al., "Development and Applications of CRISPR-Cas9 for Genome Engineering," Cell (2014), vol. 157, pp. 1262-1278.
Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.
Kawamata, et al., "Generation of genetically modified rats from embryonic stem cells," Proc. Natl. Acad. Sci. U.S.A., 7(32):14223-14228, (2010).
Kondo, et al., "Highly Improved Gene Targeting by Germline-Specific Cas9 Expression in *Drosophila*," Genetics, vol. 195, pp. 715-721, Sep. 3, 2013.
Kosicki et al., "Repair of double-strand breaks induced by CRISPR-Cas9 leads to large deletions and complex rearrangements," Nat. Biotechnol., 36(8): 765-771, (Jul. 16, 2018).
Kumar, et al., "Transgenic Mouse Technology: Principles and Methods," Methods Mol. Biol., 590:335-362, (2009).
Latres et al., "Myostatin blockade with a fully human monoclonal antibody induces muscle hypertrophy and reverses muscle atrophy in young and aged mice," Skeletal Muscle 5:34, (2015).
Li et al., "Optimization of Genome Engineering Approaches with the CRISPR/Cas9 System," PLoS One, vol. 9(8), p. e105779, Aug. 28, 2014.
Ma et al., "Heritable multiplex genetic engineering in rats using CRISPR/Cas9," PLoS One, vol. 9(3), p. e89413, Mar. 5, 2014.
MacDonald et al., "Precise and in situ genetic humanization of 6 Mb of mouse immunoglobulin genes," Proc. Natl. Acad. Sci. U.S.A. 111(14):5147-5152, (2014).
Mali et al., "RNA-Guided Human Genome Engineering via Cas9," Science, vol. 339(6121), pp. 823-826 plus Supplemental Materials, Jan. 3, 2013.
Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.
Mashiko et al., "Generation of mutant mice by pronuclear injection of circular plasmid expressing Cas9 and single guided RNA," Sci. Rep., vol. 3, p. 3355, Nov. 27, 2013.
Mullins, et al., "Transgenesis in the rat and larger mammals," J. Clin. Invest. 97(7):1557-1560, (1996).
Murphy et al., "Mice with megabase humanization of their immunoglobulin genes generate antibodies as efficiently as normal mice," Proc. Natl. Acad. Sci. U.S.A. 111(14):5153-5158, (2014).
Murphy, "Making the VelocImmune™ Mouse Using VelociGene® Technology," Regeneron Pharmaceuticals, Inc., Human Antibodies and Hybridomas, Jamaica, May 10-12, 2006.
Nakagawa et al., "Production of knockout mice by DNA microinjection of various CRISPR/Cas9 vectors into freeze-thawed fertilized oocytes," BMC Biotechnology 15:33, (2015).
Parikh et al., "Detailed Phenotypic and Molecular Analyses of Genetically Modified Mice Generated by CRISPR-Cas9-Mediated Editing," PLoS One, vol. 10(1), p. e0116484, Jan. 14, 2015.
Paris, et al., "Equine embryos and embryonic stem cells: defining reliable markers of pluripotency," Theriogenology, 74(4): 516-524, (2010).
Pass et al., "Generation of Antibodies to the Urokinase Receptor (uPAR) by DNA Immunization of uPAR Knockout Mice: Membrane-Bound uPAR is Not Required for an Antibody Response," Scandinavian Journal of Immunology 58:298-305, (2003).
PCT International Search Report and Written Opinion of the International Searching Authority for application PCT/US2017/033648 mailed Aug. 7, 2017.
Peng, Y., et al., "Making designer mutants in model organisms," Development (2014), vol. 141, pp. 4042-4054.
Ran et al., "Double nicking by RNA-guided CRISPR Cas9 for enhanced genome editing specificity," Cell, vol. 154, pp. 1380-1389, 2013.
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Shlomchik, "Sites and stages of autoreactive B cell activation and regulation," Immunity 28(1):18-28, (2008).
Siao et al., "Single-step homozygous humanization induced by dual CRISPR/Cas9 cleavage," Oct. 28, 2015.
Sigmund, "Viewpoint: Are Studies in Genetically Altered Mice Out of Control?," Arterioscler. Thromb. Vasc. Biol., 20(6):1425-1429, (2000).
Singh et al., "Cas9-chromatin binding information enables more accurate CRISPR off-target prediction," Nucleic Acids Res. 43(18):e118, (2015).
Singh et al., "A Mouse Geneticist's Practical Guide to CRISPR Applications," Genetics, vol. 199, pp. 1-15, (2015).
Sokolowski et al., "Cas6 specificity and CRISPR RNA loading in a complex CRISPR-Cas system," Nucleic Acids Res., 42(10):6532-6541, (2014).
Stan, et al., "The diaphragms of fenestrated endothelia: gatekeepers of vascular permeability and blood composition," Dev. Cell, 23(6):1203-1218, (2012).
U.S. Appl. No. 15/600,466 Non-Final Office Action mailed Feb. 19, 2020.
U.S. Appl. No. 15/600,466, Advisory Action and Interview Summary mailed Nov. 18, 2020.
U.S. Appl. No. 15/600,466, Final Office Action mailed Aug. 19, 2020.
U.S. Appl. No. 15/600,466, Non-Final Office Action mailed Mar. 18, 2021.
U.S. Appl. No. 15/600,466, Non-Final Office Action mailed Aug. 23, 2019.
U.S. Appl. No. 15/600,466, Final Office Action mailed Sep. 24, 2021.
Van Der Oost, "New tool for genome surgery," Science, 2013, vol. 339(6121), pp. 768-770.
Wang et al., "Cas9-mediated allelic exchange repairs compound heterozygous recessive mutations in mice," Nat. Biotechnol. 36(9):839-842, (2018).
Wang et al., "One-Step Generation of Mice Carrying Mutations in Multiple Genes by CRISPR/Cas-Mediated Genome Engineering," Cell 153:910-918, (2013).
Wang, et al., Highly efficient generation of bialllelic reporter gene knock-in mice via CRISPR-mediated genome editing of ESCs, Protein Cell, 7(2):152-156 plus supplementary materials, (2016).
Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.
Yang et al., "One-step generation of mice carrying reporter and conditional alleles by CRISPR/Cas-mediated genome engineering," Cell, vol. 154(6), pp. 1370-1379, Aug. 29, 2013.
Yen et al., "Somatic mosaicism and allele complexity induced by CRISPR/Cas9 RNA injections in mouse zygotes," Dev. Biol., vol. 393(1), pp. 3-9, Jun. 28, 2014.
Yoshimi et al., "ssODN-mediated knock-in with CRISPR-Cas for large genomic regions in zygotes," Nat. Commun. 7:10431, (2016).
Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.
Zhou et al., "Dual sgRNAs facilitate CRISPR/Cas9-mediated mouse genome targeting," FEBS J., vol. 281(7), pp. 1717-1725, Feb. 26, 2014.
Zhou, et al., "Developing tTA transgenic rats for inducible and reversible gene expression," Int. J. Biol. Sci., 5(2):171-181, (2009).

(56) References Cited

OTHER PUBLICATIONS

Zhou, H., et al., "Large chromosomal deletions and heritable small genetic changes induced by CRISPR/Cas9 in rice," Nucleic Acids Research (2014), vol. 42(17), pp. 10903-10914.
EP 24161007.0 Extended European Search Report mailed Jun. 12, 2024.
Murphy et al., "Mice with megabase humanization of their immunoglobulin genes generate antibodies as efficiently as normal mice," Proc. Natl. Acad. Sci. U.S.A. 111(14):5153-5158 plus Supporting Information, (2014).
Ingenious, "How a Knockout Mouse is Made," last updated on Jan. 23, 2023, (Apr. 6, 2021) [Retrieved from the Internet Mar. 14, 2023: <URL: https://www.genetargeting.com/knockout/knockout-mouse-made/#:~:text=Knockout%20mice%20are%20designed%20to,protein%20from%20the%20modified%20gene.>].
Lamas-Toranzo, et al., "Strategies to reduce genetic mosaicism following CRISPR-mediated genome edition in bovine embryos," Sci. Rep., 9(1):41900, (Oct. 2019).
Low-Marchelli, "Life After CRISPR—Steps to Take After Creating a New Mutant Mouse," JAX Home, News and Instights, JAX Blog Post, (Mar. 7, 2017) [Retrieved from the Internet Mar. 14, 2023: <URL: https://www.jax.org/news-and-insights/jax-blog/2017/march/life-after-crispr>].
Mehravar, et al., "Mosaicism in CRISPR/Cas9-mediated genome editing," Dev. Biol., 445(2):156-162, (2019).
Zuo, et al., "One-step generation of complete gene knockout mice with monkeys by CRISPR/Cas9-mediated gene editing with multiple sgRNAs," Cell Res., 27(7):933-945, (Jun. 2017).
Kang, et al., "CCR5 Disruption in Induced Pluripotent Stem Cells Using CRISPR/Cas9 Provides Selective Resistance of Immune Cells to CCR5-tropic HIV-1 Virus," Mol. Ther. Nucleic Acids, 4, e268, (2015).
U.S. Appl. No. 62/339,472, filed May 20, 2016, Expired.
U.S. Appl. No. 62/368,604, filed Jul. 29, 2016, Expired.
U.S. Appl. No. 15/600,466, filed May 19, 2017, 2017-0332610, Pending.
PCT/US2017/033648, May 19, 2017, 2017/201476, Expired.

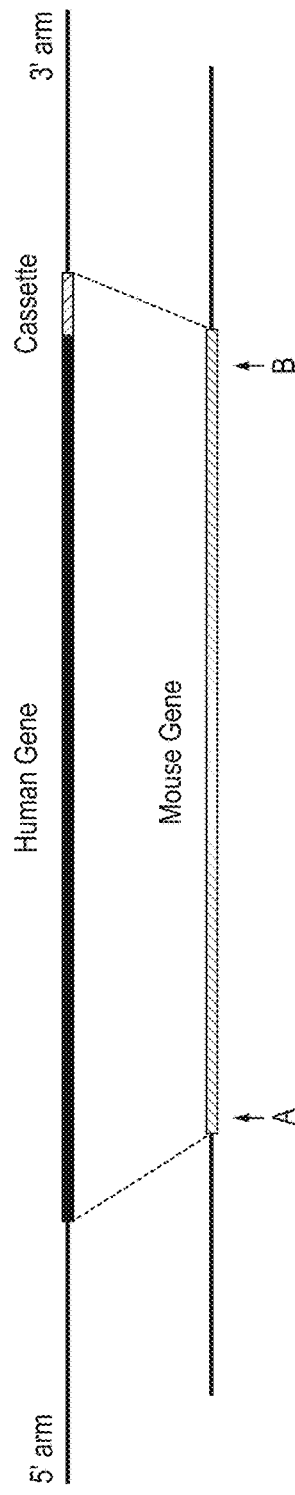
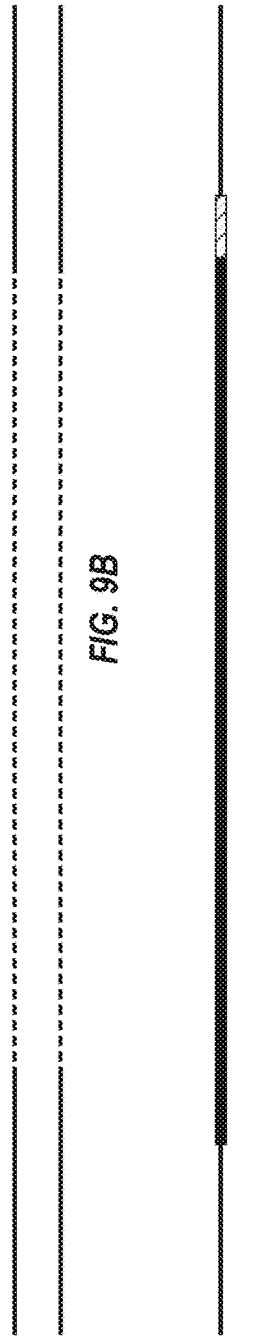
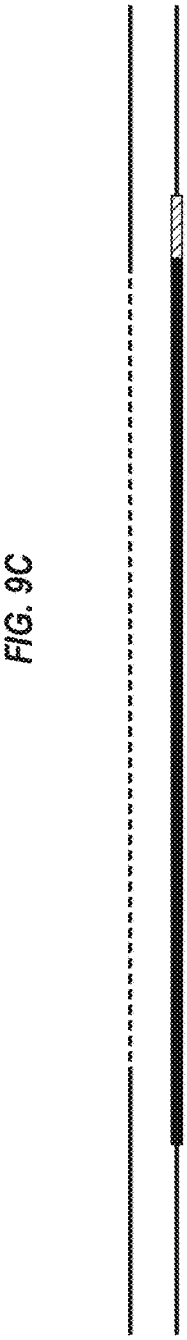
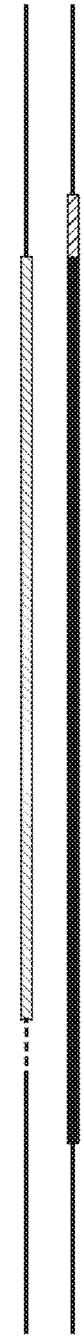
FIG. 9A
FIG. 9B
FIG. 9C
FIG. 9D
FIG. 9E

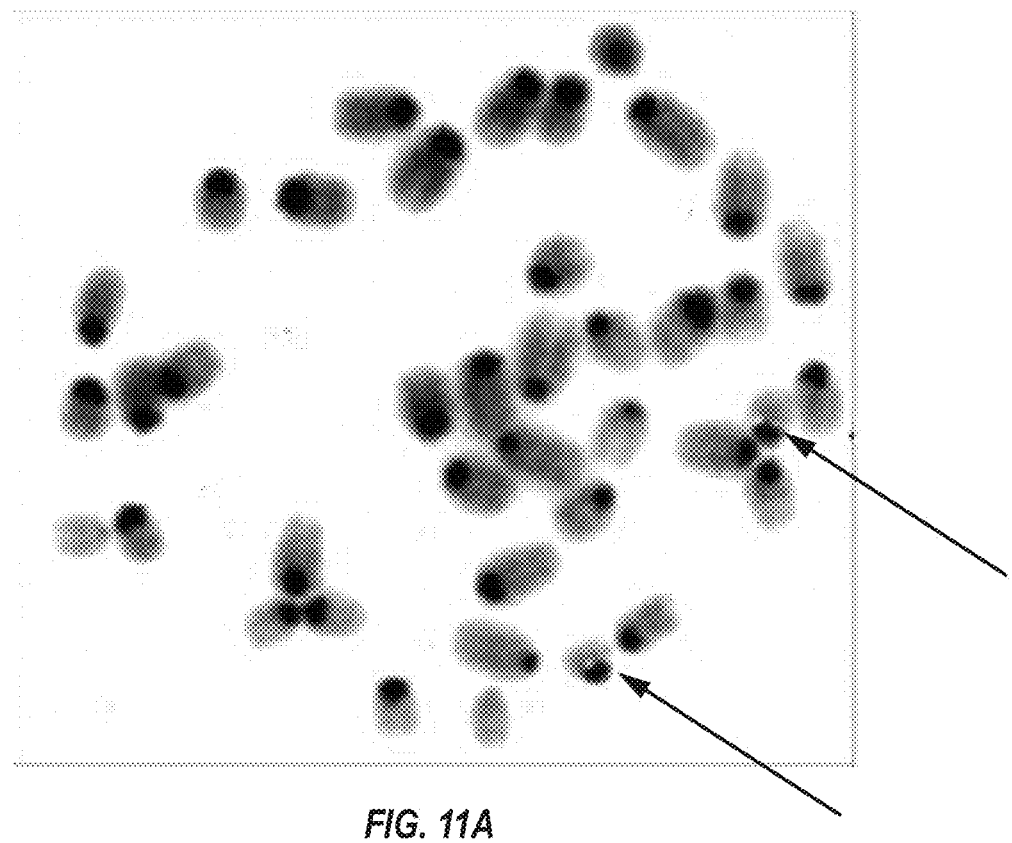
FIG. 11A
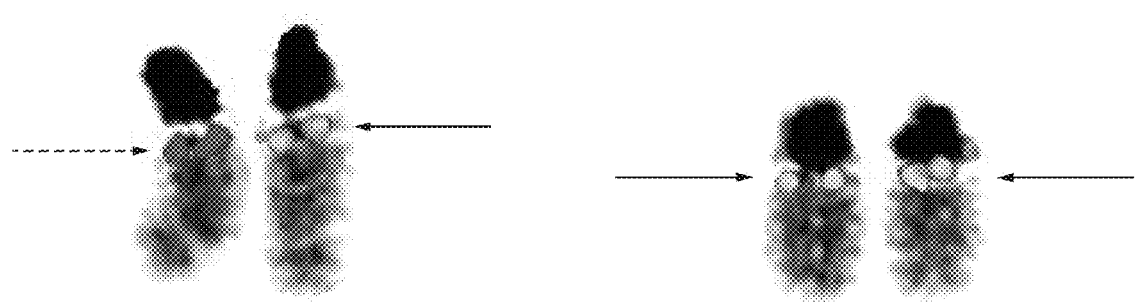
FIG. 11B
FIG. 11C

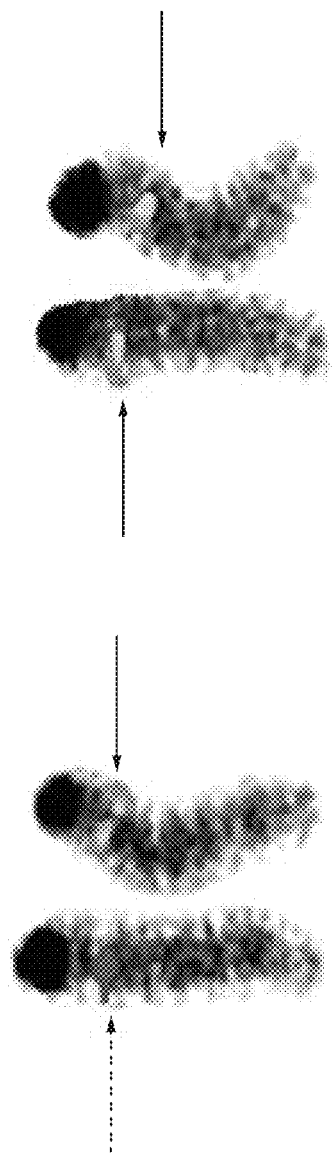
FIG. 13A
FIG. 13B
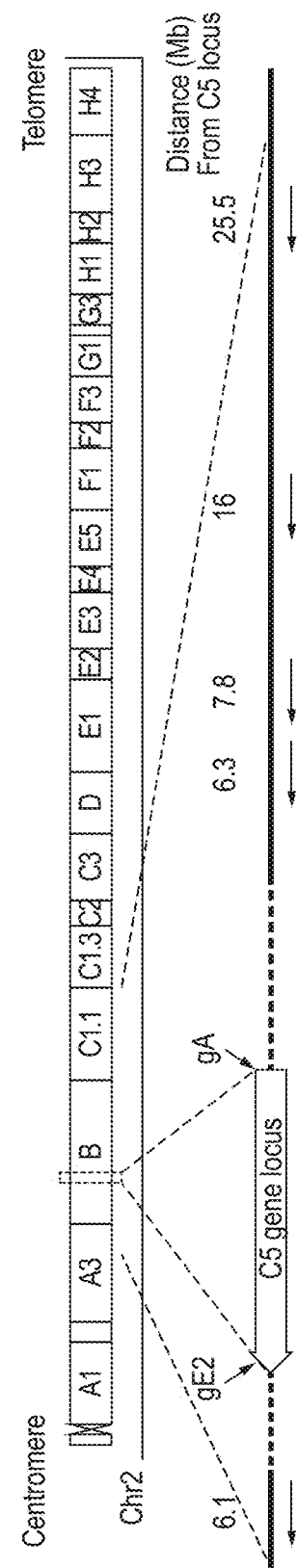
FIG. 14

FIG. 15E

VGF1 control
129 control
B6 control
BR-B4
BP-G7
BO-G11
BO-F10
BO-A8
BC-H9

FIG. 15D

VGF1 control
129 control
B6 control
BR-B4
BP-G7
BO-G11
BO-F10
BO-A8
BC-H9

FIG. 15C

VGF1 control
129 control
B6 control
BR-B4
BP-G7
BO-G11
BO-F10
BO-A8
BC-H9

FIG. 15B

VGF1 control
129 control
B6 control
BR-B4
BP-G7
BO-G11
BO-F10
BO-A8
BC-H9

FIG. 15A

VGF1 control
129 control
B6 control
BR-B4
BP-G7
BO-G11
BO-F10
BO-A8
BC-H9

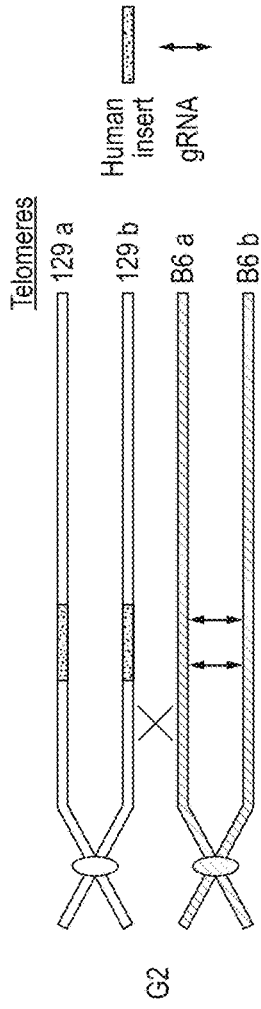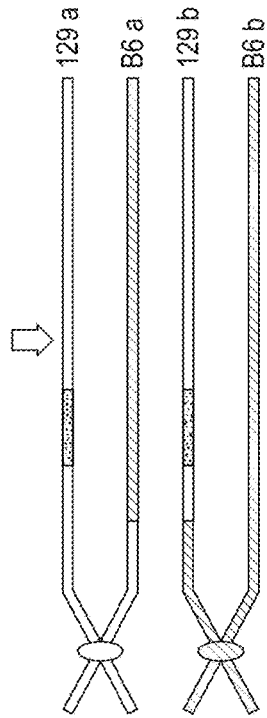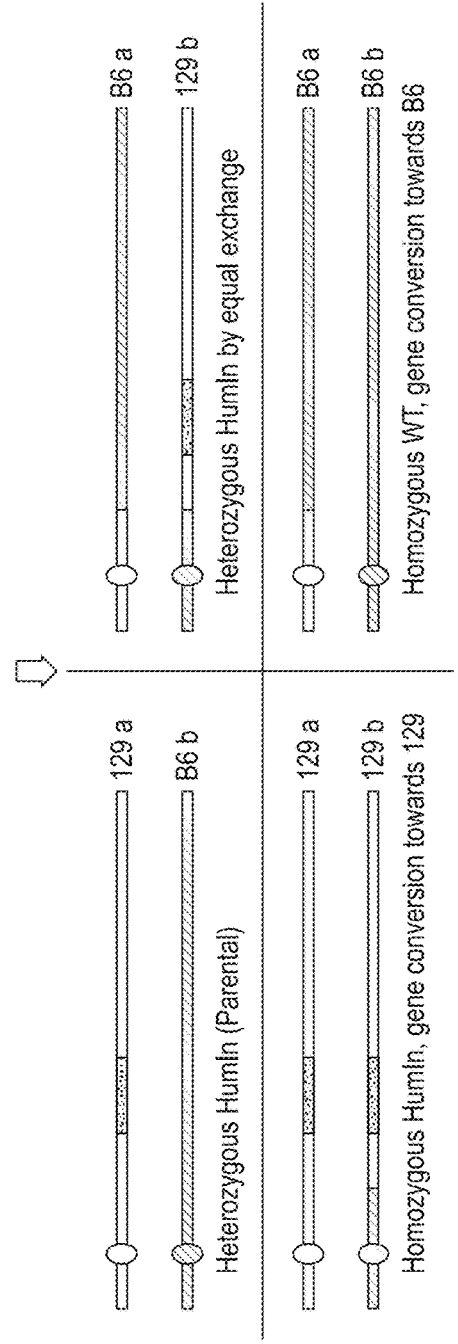
FIG. 17A
FIG. 17B
FIG. 17C

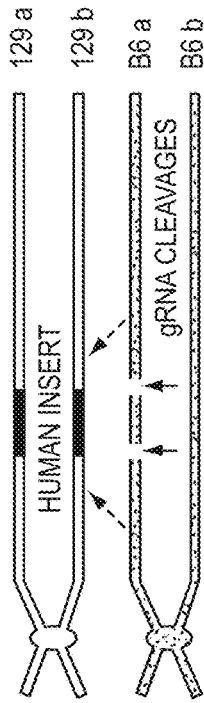
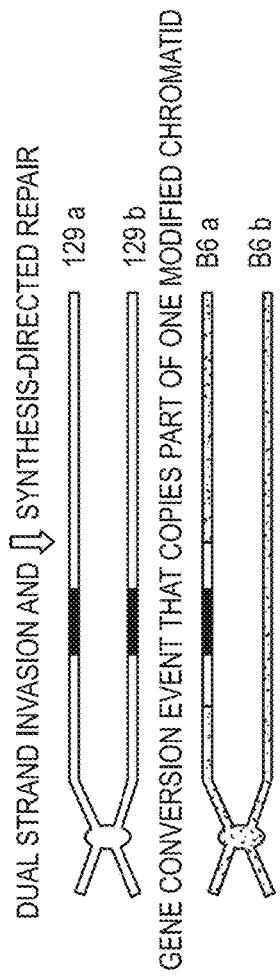
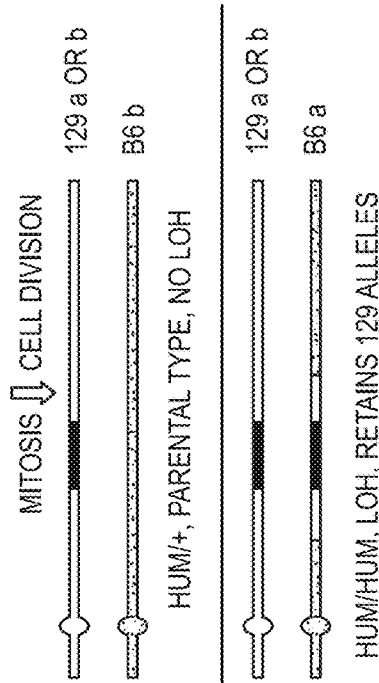

SEQUENCE LISTING

```
<160> NUMBER OF SEQ ID NOS: 152

<210> SEQ ID NO 1
<211> LENGTH: 23
<212> TYPE: DNA
<213> ORGANISM: Artificial Sequence
<220> FEATURE:
<223> OTHER INFORMATION: Guide RNA recognition sequence
<220> FEATURE:
<221> NAME/KEY: misc_feature
<222> LOCATION: (2)...(21)
<223> OTHER INFORMATION: n = A, T, C, or G

<400> SEQUENCE: 1
gnnnnnnnnn nnnnnnnnnn ngg                                          23

<210> SEQ ID NO 2
<211> LENGTH: 23
<212> TYPE: DNA
<213> ORGANISM: Artificial Sequence
<220> FEATURE:
<223> OTHER INFORMATION: Guide RNA recognition sequence
<220> FEATURE:
<221> NAME/KEY: misc_feature
<222> LOCATION: (1)...(21)
<223> OTHER INFORMATION: n = A, T, C, or G

<400> SEQUENCE: 2
```

```
nnnnnnnnnn nnnnnnnnnn ngg                                              23

<210> SEQ ID NO 3
<211> LENGTH: 25
<212> TYPE: DNA
<213> ORGANISM: Artificial Sequence
<220> FEATURE:
<223> OTHER INFORMATION: Guide RNA recognition sequence
<220> FEATURE:
<221> NAME/KEY: misc_feature
<222> LOCATION: (3)...(23)
<223> OTHER INFORMATION: n = A, T, C, or G

<400> SEQUENCE: 3
ggnnnnnnnn nnnnnnnnnn nnngg                                            25

<210> SEQ ID NO 4
<211> LENGTH: 20
<212> TYPE: DNA
<213> ORGANISM: Artificial Sequence
<220> FEATURE:
<223> OTHER INFORMATION: C5 (Hc) gRNA A DNA-targeting segment (100 bp
      from target locus endpoint)

<400> SEQUENCE: 4
atcacaaacc agttaaccgg                                                  20

<210> SEQ ID NO 5
<211> LENGTH: 20
<212> TYPE: DNA
<213> ORGANISM: Artificial Sequence
<220> FEATURE:
<223> OTHER INFORMATION: C5 (Hc) gRNA B DNA-targeting segment (500 bp
      from target locus endpoint)

<400> SEQUENCE: 5
tttcagacga gccgacccgg                                                  20

<210> SEQ ID NO 6
<211> LENGTH: 20
<212> TYPE: DNA
<213> ORGANISM: Artificial Sequence
<220> FEATURE:
<223> OTHER INFORMATION: C5 (Hc) gRNA C DNA-targeting segment (38200 and
      37500 bp from target locus endpoints)

<400> SEQUENCE: 6
tgtgtgtcat agcgatgtcg                                                  20

<210> SEQ ID NO 7
<211> LENGTH: 20
<212> TYPE: DNA
<213> ORGANISM: Artificial Sequence
<220> FEATURE:
<223> OTHER INFORMATION: C5 (Hc) gRNA D DNA-targeting segment (43500 and
      32200 bp from target locus endpoints)

<400> SEQUENCE: 7
aacaggtacc ctatcctcac                                                  20

<210> SEQ ID NO 8
<211> LENGTH: 20
<212> TYPE: DNA
<213> ORGANISM: Artificial Sequence
<220> FEATURE:
<223> OTHER INFORMATION: C5 (Hc) gRNA E DNA-targeting segment (500 bp
      from target locus endpoint)
```

<400> SEQUENCE: 8
ggcccggacc tagtctctct                                               20

<210> SEQ ID NO 9
<211> LENGTH: 20
<212> TYPE: DNA
<213> ORGANISM: Artificial Sequence
<220> FEATURE:
<223> OTHER INFORMATION: C5 (Hc) gRNA E2 DNA-targeting segment (100 bp
      from target locus endpoint)

<400> SEQUENCE: 9
tcgtggttgc atgcgcactg                                               20

<210> SEQ ID NO 10
<211> LENGTH: 20
<212> TYPE: DNA
<213> ORGANISM: Artificial Sequence
<220> FEATURE:
<223> OTHER INFORMATION: Lrp5 gRNA A DNA-targeting segment (50 bp from
      target locus end point)

<400> SEQUENCE: 10
gggaacccac agcatactcc                                               20

<210> SEQ ID NO 11
<211> LENGTH: 20
<212> TYPE: DNA
<213> ORGANISM: Artificial Sequence
<220> FEATURE:
<223> OTHER INFORMATION: Lrp5 gRNA B DNA-targeting segment (500 bp from
      target locus end point)

<400> SEQUENCE: 11
gaatcatgca cggctacccc                                               20

<210> SEQ ID NO 12
<211> LENGTH: 20
<212> TYPE: DNA
<213> ORGANISM: Artificial Sequence
<220> FEATURE:
<223> OTHER INFORMATION: Lrp5 gRNA B2 DNA-targeting segment (1000 bp
      from target locus end point)

<400> SEQUENCE: 12
tgctcctatg gggaggcgcg                                               20

<210> SEQ ID NO 13
<211> LENGTH: 20
<212> TYPE: DNA
<213> ORGANISM: Artificial Sequence
<220> FEATURE:
<223> OTHER INFORMATION: Lrp5 gRNA C DNA-targeting segment (29900 and
      38430 bp from target locus end points)

<400> SEQUENCE: 13
actgagatca atgaccccga                                               20

<210> SEQ ID NO 14
<211> LENGTH: 20
<212> TYPE: DNA
<213> ORGANISM: Artificial Sequence
<220> FEATURE:
<223> OTHER INFORMATION: Lrp5 gRNA D DNA-targeting segment (29950 and
      38380 bp from target locus end points)

-continued

<400> SEQUENCE: 14
gggtcgcccg gaacctctac                                            20

<210> SEQ ID NO 15
<211> LENGTH: 20
<212> TYPE: DNA
<213> ORGANISM: Artificial Sequence
<220> FEATURE:
<223> OTHER INFORMATION: Lrp5 gRNA E2 DNA-targeting segment (1000 bp
      from target locus end point)

<400> SEQUENCE: 15
cttggataac attgataccc                                            20

<210> SEQ ID NO 16
<211> LENGTH: 20
<212> TYPE: DNA
<213> ORGANISM: Artificial Sequence
<220> FEATURE:
<223> OTHER INFORMATION: Lrp5 gRNA E DNA-targeting segment (500 bp from
      target locus end point)

<400> SEQUENCE: 16
ggggcagagc ccttatatca                                            20

<210> SEQ ID NO 17
<211> LENGTH: 20
<212> TYPE: DNA
<213> ORGANISM: Artificial Sequence
<220> FEATURE:
<223> OTHER INFORMATION: Lrp5 gRNA F DNA-targeting segment (50 bp from
      target locus end point)

<400> SEQUENCE: 17
tcgctcacat taatccctag                                            20

<210> SEQ ID NO 18
<211> LENGTH: 20
<212> TYPE: DNA
<213> ORGANISM: Artificial Sequence
<220> FEATURE:
<223> OTHER INFORMATION: Ror1 gRNA A DNA-targeting segment (200 bp from
      target locus end point)

<400> SEQUENCE: 18
tgtgggcctt tgctgatcac                                            20

<210> SEQ ID NO 19
<211> LENGTH: 20
<212> TYPE: DNA
<213> ORGANISM: Artificial Sequence
<220> FEATURE:
<223> OTHER INFORMATION: Ror1 gRNA B DNA-targeting segment (1000 bp from
      target locus end point)

<400> SEQUENCE: 19
aatctatgat cctatggcct                                            20

<210> SEQ ID NO 20
<211> LENGTH: 20
<212> TYPE: DNA
<213> ORGANISM: Artificial Sequence
<220> FEATURE:
<223> OTHER INFORMATION: Ror1 gRNA D DNA-targeting segment (54300 and
      55500 bp from target locus end points)

<400> SEQUENCE: 20
tgccaatagc agtgacttga                                              20

<210> SEQ ID NO 21
<211> LENGTH: 20
<212> TYPE: DNA
<213> ORGANISM: Artificial Sequence
<220> FEATURE:
<223> OTHER INFORMATION: Ror1 gRNA C DNA-targeting segment (54500 and
      55300 bp from target locus end points)

<400> SEQUENCE: 21
gggaagaatg ggctattgtc                                              20

<210> SEQ ID NO 22
<211> LENGTH: 20
<212> TYPE: DNA
<213> ORGANISM: Artificial Sequence
<220> FEATURE:
<223> OTHER INFORMATION: Ror1 gRNA E DNA-targeting segment (1000 bp from
      target locus end point)

<400> SEQUENCE: 22
ggttgtttgt gctgatgacg                                              20

<210> SEQ ID NO 23
<211> LENGTH: 20
<212> TYPE: DNA
<213> ORGANISM: Artificial Sequence
<220> FEATURE:
<223> OTHER INFORMATION: Ror1 gRNA F DNA-targeting segment (200 bp from
      target locus end point)

<400> SEQUENCE: 23
ccgtcctagg ccttctacgt                                              20

<210> SEQ ID NO 24
<211> LENGTH: 20
<212> TYPE: DNA
<213> ORGANISM: Artificial Sequence
<220> FEATURE:
<223> OTHER INFORMATION: Trpa1 gRNA A DNA-targeting segment (100 bp from
      target locus end point)

<400> SEQUENCE: 24
gtactgggga atcggtggtc                                              20

<210> SEQ ID NO 25
<211> LENGTH: 20
<212> TYPE: DNA
<213> ORGANISM: Artificial Sequence
<220> FEATURE:
<223> OTHER INFORMATION: Trpa1 gRNA A2 DNA-targeting segment (500 bp
      from target locus end point)

<400> SEQUENCE: 25
cacgcactcc aaatttatcc                                              20

<210> SEQ ID NO 26
<211> LENGTH: 20
<212> TYPE: DNA
<213> ORGANISM: Artificial Sequence
<220> FEATURE:
<223> OTHER INFORMATION: Trpa1 gRNA B DNA-targeting segment (1000 bp
      from target locus end point)

<400> SEQUENCE: 26
ctaagtgtgt atcagtacat                                           20

<210> SEQ ID NO 27
<211> LENGTH: 20
<212> TYPE: DNA
<213> ORGANISM: Artificial Sequence
<220> FEATURE:
<223> OTHER INFORMATION: Trpa1 gRNA C DNA-targeting segment (25600 and
      19740 bp from target locus end points)

<400> SEQUENCE: 27
tgccctgcac aataagcgca                                           20

<210> SEQ ID NO 28
<211> LENGTH: 20
<212> TYPE: DNA
<213> ORGANISM: Artificial Sequence
<220> FEATURE:
<223> OTHER INFORMATION: Trpa1 gRNA D DNA-targeting segment (26970 and
      18370 bp from target locus end points)

<400> SEQUENCE: 28
actcattgaa acgttatggc                                           20

<210> SEQ ID NO 29
<211> LENGTH: 20
<212> TYPE: DNA
<213> ORGANISM: Artificial Sequence
<220> FEATURE:
<223> OTHER INFORMATION: Trpa1 gRNA E2 DNA-targeting segment (1000 bp
      from target locus end point)

<400> SEQUENCE: 29
agtaagggtg gattaaattc                                           20

<210> SEQ ID NO 30
<211> LENGTH: 20
<212> TYPE: DNA
<213> ORGANISM: Artificial Sequence
<220> FEATURE:
<223> OTHER INFORMATION: Trpa1 gRNA E DNA-targeting segment (500 bp from
      target locus end point)

<400> SEQUENCE: 30
gccatctaga ttcatgtaac                                           20

<210> SEQ ID NO 31
<211> LENGTH: 20
<212> TYPE: DNA
<213> ORGANISM: Artificial Sequence
<220> FEATURE:
<223> OTHER INFORMATION: Trpa1 gRNA F DNA-targeting segment (100 bp from
      target locus end point)

<400> SEQUENCE: 31
gactagaaat gttctgcacc                                           20

<210> SEQ ID NO 32
<211> LENGTH: 21
<212> TYPE: DNA
<213> ORGANISM: Artificial Sequence
<220> FEATURE:
<223> OTHER INFORMATION: 190045 forward primer

<400> SEQUENCE: 32
gagctcatag ccaacagctt g                                         21

<210> SEQ ID NO 33
<211> LENGTH: 20
<212> TYPE: DNA
<213> ORGANISM: Artificial Sequence
<220> FEATURE:
<223> OTHER INFORMATION: 190061 forward primer

<400> SEQUENCE: 33
atgcatcaga tcacgctcag                                               20

<210> SEQ ID NO 34
<211> LENGTH: 20
<212> TYPE: DNA
<213> ORGANISM: Artificial Sequence
<220> FEATURE:
<223> OTHER INFORMATION: 190068 forward primer

<400> SEQUENCE: 34
gtccttgtgg catttccaac                                               20

<210> SEQ ID NO 35
<211> LENGTH: 24
<212> TYPE: DNA
<213> ORGANISM: Artificial Sequence
<220> FEATURE:
<223> OTHER INFORMATION: 190030 forward primer

<400> SEQUENCE: 35
ccagtatggt gtcagttaat agcg                                          24

<210> SEQ ID NO 36
<211> LENGTH: 19
<212> TYPE: DNA
<213> ORGANISM: Artificial Sequence
<220> FEATURE:
<223> OTHER INFORMATION: 190033 forward primer (same as forward primer
      for SV 48.3 in Fig. 6)

<400> SEQUENCE: 36
ctgtgcagaa agcagcctc                                                19

<210> SEQ ID NO 37
<211> LENGTH: 20
<212> TYPE: DNA
<213> ORGANISM: Artificial Sequence
<220> FEATURE:
<223> OTHER INFORMATION: 190013 forward primer

<400> SEQUENCE: 37
cctctccctc taggcacctg                                               20

<210> SEQ ID NO 38
<211> LENGTH: 20
<212> TYPE: DNA
<213> ORGANISM: Artificial Sequence
<220> FEATURE:
<223> OTHER INFORMATION: 190045 reverse primer

<400> SEQUENCE: 38
tctttaaggg ctccgttgtc                                               20

<210> SEQ ID NO 39
<211> LENGTH: 20
<212> TYPE: DNA
<213> ORGANISM: Artificial Sequence
<220> FEATURE:

```
<223> OTHER INFORMATION: 190061 reverse primer

<400> SEQUENCE: 39
aagaccaacc attcacccag                                          20

<210> SEQ ID NO 40
<211> LENGTH: 20
<212> TYPE: DNA
<213> ORGANISM: Artificial Sequence
<220> FEATURE:
<223> OTHER INFORMATION: 190068 reverse primer

<400> SEQUENCE: 40
ttcccagtcc aagtcaaagg                                          20

<210> SEQ ID NO 41
<211> LENGTH: 20
<212> TYPE: DNA
<213> ORGANISM: Artificial Sequence
<220> FEATURE:
<223> OTHER INFORMATION: 190030 reverse primer

<400> SEQUENCE: 41
ctgttatctg caaggcaccc                                          20

<210> SEQ ID NO 42
<211> LENGTH: 20
<212> TYPE: DNA
<213> ORGANISM: Artificial Sequence
<220> FEATURE:
<223> OTHER INFORMATION: 190033 reverse primer (same as reverse primer
      for SV 48.3 in Fig. 6)

<400> SEQUENCE: 42
acaactggat cctgattcgc                                          20

<210> SEQ ID NO 43
<211> LENGTH: 20
<212> TYPE: DNA
<213> ORGANISM: Artificial Sequence
<220> FEATURE:
<223> OTHER INFORMATION: 190013 reverse primer

<400> SEQUENCE: 43
taagagggca tgggtgagac                                          20

<210> SEQ ID NO 44
<211> LENGTH: 20
<212> TYPE: DNA
<213> ORGANISM: Artificial Sequence
<220> FEATURE:
<223> OTHER INFORMATION: C2 probe (B6) - SNV 0.32 in Fig. 6

<400> SEQUENCE: 44
aattcagaag acctatcgta                                          20

<210> SEQ ID NO 45
<211> LENGTH: 21
<212> TYPE: DNA
<213> ORGANISM: Artificial Sequence
<220> FEATURE:
<223> OTHER INFORMATION: T3 probe (B6) - SNV 1.2 in Fig. 6

<400> SEQUENCE: 45
tatgtgtata ggtgtttgga t                                        21
```

```
<210> SEQ ID NO 46
<211> LENGTH: 19
<212> TYPE: DNA
<213> ORGANISM: Artificial Sequence
<220> FEATURE:
<223> OTHER INFORMATION: T6 probe (B6) - SNV 11.1 in Fig. 6

<400> SEQUENCE: 46
tacattgcta aatgaaacc                                                     19

<210> SEQ ID NO 47
<211> LENGTH: 16
<212> TYPE: DNA
<213> ORGANISM: Artificial Sequence
<220> FEATURE:
<223> OTHER INFORMATION: T7 probe (B6) - SNV 13.2 in Fig. 6

<400> SEQUENCE: 47
cgcagtcatg cacata                                                        16

<210> SEQ ID NO 48
<211> LENGTH: 20
<212> TYPE: DNA
<213> ORGANISM: Artificial Sequence
<220> FEATURE:
<223> OTHER INFORMATION: T8 probe (B6) - SNV 17.5 in Fig. 6

<400> SEQUENCE: 48
ttataaagcc cagtatgtac                                                    20

<210> SEQ ID NO 49
<211> LENGTH: 14
<212> TYPE: DNA
<213> ORGANISM: Artificial Sequence
<220> FEATURE:
<223> OTHER INFORMATION: T9 probe (B6) - SNV 25.8 in Fig. 6

<400> SEQUENCE: 49
tgctgcataa tcag                                                          14

<210> SEQ ID NO 50
<211> LENGTH: 18
<212> TYPE: DNA
<213> ORGANISM: Artificial Sequence
<220> FEATURE:
<223> OTHER INFORMATION: T10 probe (B6) - SNV 33.0 in Fig. 6

<400> SEQUENCE: 50
tcaggagtga attggata                                                      18

<210> SEQ ID NO 51
<211> LENGTH: 16
<212> TYPE: DNA
<213> ORGANISM: Artificial Sequence
<220> FEATURE:
<223> OTHER INFORMATION: T11 probe (B6) - SNV 38.3 in Fig. 6

<400> SEQUENCE: 51
ctgctactta cctttg                                                        16

<210> SEQ ID NO 52
<211> LENGTH: 13
<212> TYPE: DNA
<213> ORGANISM: Artificial Sequence
<220> FEATURE:
<223> OTHER INFORMATION: T13 probe (B6) - SNV 49.6 in Fig. 6
```

```
-continued

<400> SEQUENCE: 52
aggaggaaaa cgc                                                      13

<210> SEQ ID NO 53
<211> LENGTH: 17
<212> TYPE: DNA
<213> ORGANISM: Artificial Sequence
<220> FEATURE:
<223> OTHER INFORMATION: T14 probe (B6) - SNV 57.2 in Fig. 6

<400> SEQUENCE: 53
cctttgttcc tcataag                                                  17

<210> SEQ ID NO 54
<211> LENGTH: 20
<212> TYPE: DNA
<213> ORGANISM: Artificial Sequence
<220> FEATURE:
<223> OTHER INFORMATION: C2 probe (129) - SNV 0.32 in Fig. 6

<400> SEQUENCE: 54
aattcagaag acctattgta                                               20

<210> SEQ ID NO 55
<211> LENGTH: 21
<212> TYPE: DNA
<213> ORGANISM: Artificial Sequence
<220> FEATURE:
<223> OTHER INFORMATION: T3 probe (129) - SNV 1.2 in Fig. 6

<400> SEQUENCE: 55
tatgtgtata ggtgtttgca t                                             21

<210> SEQ ID NO 56
<211> LENGTH: 16
<212> TYPE: DNA
<213> ORGANISM: Artificial Sequence
<220> FEATURE:
<223> OTHER INFORMATION: T6 probe (129) - SNV 11.1 in Fig. 6

<400> SEQUENCE: 56
cattgctaca tgaaac                                                   16

<210> SEQ ID NO 57
<211> LENGTH: 16
<212> TYPE: DNA
<213> ORGANISM: Artificial Sequence
<220> FEATURE:
<223> OTHER INFORMATION: T7 probe (129) - SNV 13.2 in Fig. 6

<400> SEQUENCE: 57
cgcagtcatg cacgta                                                   16

<210> SEQ ID NO 58
<211> LENGTH: 23
<212> TYPE: DNA
<213> ORGANISM: Artificial Sequence
<220> FEATURE:
<223> OTHER INFORMATION: T8 probe (129) - SNV 17.5 in Fig. 6

<400> SEQUENCE: 58
tgagaattta taaagcccaa tat                                           23

<210> SEQ ID NO 59
```

-continued

```
<211> LENGTH: 14
<212> TYPE: DNA
<213> ORGANISM: Artificial Sequence
<220> FEATURE:
<223> OTHER INFORMATION: T9 probe (129) - SNV 25.8 in Fig. 6

<400> SEQUENCE: 59
tgctgcatga tcag                                                    14

<210> SEQ ID NO 60
<211> LENGTH: 15
<212> TYPE: DNA
<213> ORGANISM: Artificial Sequence
<220> FEATURE:
<223> OTHER INFORMATION: T10 probe (129) - SNV 33.0 in Fig. 6

<400> SEQUENCE: 60
tcaggagtga atcgg                                                   15

<210> SEQ ID NO 61
<211> LENGTH: 16
<212> TYPE: DNA
<213> ORGANISM: Artificial Sequence
<220> FEATURE:
<223> OTHER INFORMATION: T11 probe (129) - SNV 38.3 in Fig. 6

<400> SEQUENCE: 61
ctgctagtta cctttg                                                  16

<210> SEQ ID NO 62
<211> LENGTH: 15
<212> TYPE: DNA
<213> ORGANISM: Artificial Sequence
<220> FEATURE:
<223> OTHER INFORMATION: T13 probe (129) - SNV 49.6 in Fig. 6

<400> SEQUENCE: 62
aggaggaaga cgcag                                                   15

<210> SEQ ID NO 63
<211> LENGTH: 17
<212> TYPE: DNA
<213> ORGANISM: Artificial Sequence
<220> FEATURE:
<223> OTHER INFORMATION: T14 probe (129) - SNV 57.2 in Fig. 6

<400> SEQUENCE: 63
ctttgttctt cataagc                                                 17

<210> SEQ ID NO 64
<211> LENGTH: 25
<212> TYPE: DNA
<213> ORGANISM: Artificial Sequence
<220> FEATURE:
<223> OTHER INFORMATION: C2 forward primer - SNV 0.32 in Fig. 6

<400> SEQUENCE: 64
atgagggatt tccttaatca gacaa                                        25

<210> SEQ ID NO 65
<211> LENGTH: 29
<212> TYPE: DNA
<213> ORGANISM: Artificial Sequence
<220> FEATURE:
<223> OTHER INFORMATION: T3 forward primer - SNV 1.2 in Fig. 6

<400> SEQUENCE: 65
```
tggtatgttt attcttactc aaggttttg                                29

<210> SEQ ID NO 66
<211> LENGTH: 22
<212> TYPE: DNA
<213> ORGANISM: Artificial Sequence
<220> FEATURE:
<223> OTHER INFORMATION: T6 forward primer - SNV 11.1 in Fig. 6

<400> SEQUENCE: 66
gggcaactga tggaaagaac tc                                       22

<210> SEQ ID NO 67
<211> LENGTH: 23
<212> TYPE: DNA
<213> ORGANISM: Artificial Sequence
<220> FEATURE:
<223> OTHER INFORMATION: T7 forward primer - SNV 13.2 in Fig. 6

<400> SEQUENCE: 67
gactgacgca caaacttgtc ctt                                      23

<210> SEQ ID NO 68
<211> LENGTH: 26
<212> TYPE: DNA
<213> ORGANISM: Artificial Sequence
<220> FEATURE:
<223> OTHER INFORMATION: T8 forward primer - SNV 17.5 in Fig. 6

<400> SEQUENCE: 68
cccaaagcat ataacaagaa caaatg                                   26

<210> SEQ ID NO 69
<211> LENGTH: 18
<212> TYPE: DNA
<213> ORGANISM: Artificial Sequence
<220> FEATURE:
<223> OTHER INFORMATION: T9 forward primer - SNV 25.8 in Fig. 6

<400> SEQUENCE: 69
gcaggacgca ggcgttta                                            18

<210> SEQ ID NO 70
<211> LENGTH: 23
<212> TYPE: DNA
<213> ORGANISM: Artificial Sequence
<220> FEATURE:
<223> OTHER INFORMATION: T10 forward primer - SNV 33.0 in Fig. 6

<400> SEQUENCE: 70
gcatcctcat ggcagtctac atc                                      23

<210> SEQ ID NO 71
<211> LENGTH: 20
<212> TYPE: DNA
<213> ORGANISM: Artificial Sequence
<220> FEATURE:
<223> OTHER INFORMATION: T11 forward primer - SNV 38.3 in Fig. 6

<400> SEQUENCE: 71
cctgcccctt gatgagtgtt                                          20

<210> SEQ ID NO 72
<211> LENGTH: 23
<212> TYPE: DNA

<213> ORGANISM: Artificial Sequence
<220> FEATURE:
<223> OTHER INFORMATION: T13 forward primer - SNV 49.6 in Fig. 6

<400> SEQUENCE: 72
ccctctttga tatgctcgtg tgt                                    23

<210> SEQ ID NO 73
<211> LENGTH: 22
<212> TYPE: DNA
<213> ORGANISM: Artificial Sequence
<220> FEATURE:
<223> OTHER INFORMATION: T14 forward primer - SNV 57.2 in Fig. 6

<400> SEQUENCE: 73
tcccacaggt ccatgtcttt aa                                     22

<210> SEQ ID NO 74
<211> LENGTH: 28
<212> TYPE: DNA
<213> ORGANISM: Artificial Sequence
<220> FEATURE:
<223> OTHER INFORMATION: C2 reverse primer - SNV 0.32 in Fig. 6

<400> SEQUENCE: 74
agactacaat gagctaccat cataaggt                               28

<210> SEQ ID NO 75
<211> LENGTH: 24
<212> TYPE: DNA
<213> ORGANISM: Artificial Sequence
<220> FEATURE:
<223> OTHER INFORMATION: T3 reverse primer - SNV 1.2 in Fig. 6

<400> SEQUENCE: 75
caaccatcta aaactccagt tcca                                   24

<210> SEQ ID NO 76
<211> LENGTH: 28
<212> TYPE: DNA
<213> ORGANISM: Artificial Sequence
<220> FEATURE:
<223> OTHER INFORMATION: T6 reverse primer - SNV 11.1 in Fig. 6

<400> SEQUENCE: 76
tgtgtaacag gacagttgaa tgtagaga                               28

<210> SEQ ID NO 77
<211> LENGTH: 19
<212> TYPE: DNA
<213> ORGANISM: Artificial Sequence
<220> FEATURE:
<223> OTHER INFORMATION: T7 reverse primer - SNV 13.2 in Fig. 6

<400> SEQUENCE: 77
cttaaaaccc gccctgcat                                         19

<210> SEQ ID NO 78
<211> LENGTH: 26
<212> TYPE: DNA
<213> ORGANISM: Artificial Sequence
<220> FEATURE:
<223> OTHER INFORMATION: T8 reverse primer - SNV 17.5 in Fig. 6

<400> SEQUENCE: 78
ctacaggaga tgtggctgtt ctatgt                                 26

<210> SEQ ID NO 79
<211> LENGTH: 22
<212> TYPE: DNA
<213> ORGANISM: Artificial Sequence
<220> FEATURE:
<223> OTHER INFORMATION: T9 reverse primer - SNV 25.8 in Fig. 6

<400> SEQUENCE: 79
tcagcgtgat tcgcttgtag tc                                        22

<210> SEQ ID NO 80
<211> LENGTH: 26
<212> TYPE: DNA
<213> ORGANISM: Artificial Sequence
<220> FEATURE:
<223> OTHER INFORMATION: T10 reverse primer - SNV 33.0 in Fig. 6

<400> SEQUENCE: 80
tgcatagctg tttgaataat gacaag                                    26

<210> SEQ ID NO 81
<211> LENGTH: 21
<212> TYPE: DNA
<213> ORGANISM: Artificial Sequence
<220> FEATURE:
<223> OTHER INFORMATION: T11 reverse primer - SNV 38.3 in Fig. 6

<400> SEQUENCE: 81
tgcagcatct ctgtcaagca a                                         21

<210> SEQ ID NO 82
<211> LENGTH: 24
<212> TYPE: DNA
<213> ORGANISM: Artificial Sequence
<220> FEATURE:
<223> OTHER INFORMATION: T13 reverse primer - SNV 49.6 in Fig. 6

<400> SEQUENCE: 82
gcaacaacat aacccacagc ataa                                      24

<210> SEQ ID NO 83
<211> LENGTH: 23
<212> TYPE: DNA
<213> ORGANISM: Artificial Sequence
<220> FEATURE:
<223> OTHER INFORMATION: T14 reverse primer - SNV 57.2 in Fig. 6

<400> SEQUENCE: 83
gctaagcgtt tggaagaaat tcc                                       23

<210> SEQ ID NO 84
<211> LENGTH: 20
<212> TYPE: DNA
<213> ORGANISM: Artificial Sequence
<220> FEATURE:
<223> OTHER INFORMATION: Forward primer for SV 13.7 in Fig. 6

<400> SEQUENCE: 84
taggctctaa ggatgctggc                                           20

<210> SEQ ID NO 85
<211> LENGTH: 20
<212> TYPE: DNA
<213> ORGANISM: Artificial Sequence
<220> FEATURE:

<223> OTHER INFORMATION: Reverse primer for SV 13.7 in Fig. 6

<400> SEQUENCE: 85
aagcagcttc aaaccctctg　　　　　　　　　　　　　　　　　　　　　　　　20

<210> SEQ ID NO 86
<211> LENGTH: 20
<212> TYPE: DNA
<213> ORGANISM: Artificial Sequence
<220> FEATURE:
<223> OTHER INFORMATION: Forward primer for SV 20.0 in Fig. 6

<400> SEQUENCE: 86
ttacttggcc ttggaactgc　　　　　　　　　　　　　　　　　　　　　　　　20

<210> SEQ ID NO 87
<211> LENGTH: 21
<212> TYPE: DNA
<213> ORGANISM: Artificial Sequence
<220> FEATURE:
<223> OTHER INFORMATION: Reverse primer for SV 20.0 in Fig. 6

<400> SEQUENCE: 87
tgattcgtaa tcgtcactgc c　　　　　　　　　　　　　　　　　　　　　　21

<210> SEQ ID NO 88
<211> LENGTH: 20
<212> TYPE: DNA
<213> ORGANISM: Artificial Sequence
<220> FEATURE:
<223> OTHER INFORMATION: Forward primer for SV 36.9 in Fig. 6

<400> SEQUENCE: 88
tcctgtcccg agaaactgtc　　　　　　　　　　　　　　　　　　　　　　　　20

<210> SEQ ID NO 89
<211> LENGTH: 20
<212> TYPE: DNA
<213> ORGANISM: Artificial Sequence
<220> FEATURE:
<223> OTHER INFORMATION: Reverse primer for SV 36.9 in Fig. 6

<400> SEQUENCE: 89
agctggcttt cagagagctg　　　　　　　　　　　　　　　　　　　　　　　　20

<210> SEQ ID NO 90
<211> LENGTH: 20
<212> TYPE: DNA
<213> ORGANISM: Artificial Sequence
<220> FEATURE:
<223> OTHER INFORMATION: Forward primer for SV 56.7 in Fig. 6

<400> SEQUENCE: 90
ttagaaagtg ccaaccaggc　　　　　　　　　　　　　　　　　　　　　　　　20

<210> SEQ ID NO 91
<211> LENGTH: 20
<212> TYPE: DNA
<213> ORGANISM: Artificial Sequence
<220> FEATURE:
<223> OTHER INFORMATION: Reverse primer for SV 56.7 in Fig. 6

<400> SEQUENCE: 91
ctctggctag gaacaatggc　　　　　　　　　　　　　　　　　　　　　　　　20

```
<210> SEQ ID NO 92
<211> LENGTH: 25
<212> TYPE: DNA
<213> ORGANISM: Artificial Sequence
<220> FEATURE:
<223> OTHER INFORMATION: m-lr-f primer for Lrp5 locus

<400> SEQUENCE: 92
gttaggtgca gggtctactc agctg                                    25

<210> SEQ ID NO 93
<211> LENGTH: 20
<212> TYPE: DNA
<213> ORGANISM: Artificial Sequence
<220> FEATURE:
<223> OTHER INFORMATION: m-5'-f primer for Lrp5 locus

<400> SEQUENCE: 93
ggaggagagg agaagcagcc                                          20

<210> SEQ ID NO 94
<211> LENGTH: 20
<212> TYPE: DNA
<213> ORGANISM: Artificial Sequence
<220> FEATURE:
<223> OTHER INFORMATION: m-A primer for Lrp5 locus

<400> SEQUENCE: 94
ggaggagagg agaagcagcc                                          20

<210> SEQ ID NO 95
<211> LENGTH: 26
<212> TYPE: DNA
<213> ORGANISM: Artificial Sequence
<220> FEATURE:
<223> OTHER INFORMATION: h-lr-r primer for Lrp5 locus

<400> SEQUENCE: 95
gcaaacagcc ttcttcccac attcgg                                   26

<210> SEQ ID NO 96
<211> LENGTH: 24
<212> TYPE: DNA
<213> ORGANISM: Artificial Sequence
<220> FEATURE:
<223> OTHER INFORMATION: m-5'-r primer for Lrp5 locus

<400> SEQUENCE: 96
ttgctttcag tagttcaggt gtgc                                     24

<210> SEQ ID NO 97
<211> LENGTH: 20
<212> TYPE: DNA
<213> ORGANISM: Artificial Sequence
<220> FEATURE:
<223> OTHER INFORMATION: h-5'-r primer for Lrp5 locus

<400> SEQUENCE: 97
ggcgttgtca ggaagttgcc                                          20

<210> SEQ ID NO 98
<211> LENGTH: 22
<212> TYPE: DNA
<213> ORGANISM: Artificial Sequence
<220> FEATURE:
<223> OTHER INFORMATION: m-F primer for Lrp5 locus
```

```
<400> SEQUENCE: 98
tgaagttgag aggcacatga gg                                              22

<210> SEQ ID NO 99
<211> LENGTH: 24
<212> TYPE: DNA
<213> ORGANISM: Artificial Sequence
<220> FEATURE:
<223> OTHER INFORMATION: m-E2 primer for Lrp5 locus

<400> SEQUENCE: 99
tagagtagcc acaggcagca aagc                                            24

<210> SEQ ID NO 100
<211> LENGTH: 22
<212> TYPE: DNA
<213> ORGANISM: Artificial Sequence
<220> FEATURE:
<223> OTHER INFORMATION: 7064retU forward primer

<400> SEQUENCE: 100
cctcctgagc tttcctttgc ag                                              22

<210> SEQ ID NO 101
<211> LENGTH: 25
<212> TYPE: DNA
<213> ORGANISM: Artificial Sequence
<220> FEATURE:
<223> OTHER INFORMATION: 7064retU reverse primer

<400> SEQUENCE: 101
cctagacaac acagacactg tatca                                           25

<210> SEQ ID NO 102
<211> LENGTH: 23
<212> TYPE: DNA
<213> ORGANISM: Artificial Sequence
<220> FEATURE:
<223> OTHER INFORMATION: 7064retU TAQMAN probe

<400> SEQUENCE: 102 ttctgcccctt gaaaaggaga ggc                                            23

<210> SEQ ID NO 103
<211> LENGTH: 18
<212> TYPE: DNA
<213> ORGANISM: Artificial Sequence
<220> FEATURE:
<223> OTHER INFORMATION: 7064retD forward primer

<400> SEQUENCE: 103
cctctgaggc cacctgaa                                                   18

<210> SEQ ID NO 104
<211> LENGTH: 23
<212> TYPE: DNA
<213> ORGANISM: Artificial Sequence
<220> FEATURE:
<223> OTHER INFORMATION: 7064retD reverse primer

<400> SEQUENCE: 104
ccctgacaag ttctgccttc tac                                             23

<210> SEQ ID NO 105
<211> LENGTH: 21
```

```
<212> TYPE: DNA
<213> ORGANISM: Artificial Sequence
<220> FEATURE:
<223> OTHER INFORMATION: 7064retD TAQMAN probe

<400> SEQUENCE: 105
tgcccaagcc tctgcagctt t                                         21

<210> SEQ ID NO 106
<211> LENGTH: 19
<212> TYPE: DNA
<213> ORGANISM: Artificial Sequence
<220> FEATURE:
<223> OTHER INFORMATION: 7140retU forward primer

<400> SEQUENCE: 106
cccagcatct gacgacacc                                            19

<210> SEQ ID NO 107
<211> LENGTH: 21
<212> TYPE: DNA
<213> ORGANISM: Artificial Sequence
<220> FEATURE:
<223> OTHER INFORMATION: 7140retU reverse primer

<400> SEQUENCE: 107
gaccactgtg ggcatctgta g                                         21

<210> SEQ ID NO 108
<211> LENGTH: 27
<212> TYPE: DNA
<213> ORGANISM: Artificial Sequence
<220> FEATURE:
<223> OTHER INFORMATION: 7140retU TAQMAN probe

<400> SEQUENCE: 108
ccgagtctgc tgttactgtt agcatca                                   27

<210> SEQ ID NO 109
<211> LENGTH: 20
<212> TYPE: DNA
<213> ORGANISM: Artificial Sequence
<220> FEATURE:
<223> OTHER INFORMATION: 7140retD forward primer

<400> SEQUENCE: 109
cccgacacct tctgagcatg                                           20

<210> SEQ ID NO 110
<211> LENGTH: 21
<212> TYPE: DNA
<213> ORGANISM: Artificial Sequence
<220> FEATURE:
<223> OTHER INFORMATION: 7140retD reverse primer

<400> SEQUENCE: 110
tgcaggctga gtcaggattt g                                         21

<210> SEQ ID NO 111
<211> LENGTH: 25
<212> TYPE: DNA
<213> ORGANISM: Artificial Sequence
<220> FEATURE:
<223> OTHER INFORMATION: 7140retD TAQMAN probe

<400> SEQUENCE: 111
```

```
tagtcacgtt ttgtgacacc ccaga                                              25

<210> SEQ ID NO 112
<211> LENGTH: 20
<212> TYPE: DNA
<213> ORGANISM: Artificial Sequence
<220> FEATURE:
<223> OTHER INFORMATION: Folh1 gRNA A DNA-targeting segment

<400> SEQUENCE: 112
tgaaccaatt gtgtagcctt                                                    20

<210> SEQ ID NO 113
<211> LENGTH: 20
<212> TYPE: DNA
<213> ORGANISM: Artificial Sequence
<220> FEATURE:
<223> OTHER INFORMATION: Folh1 gRNA A2 DNA-targeting segment

<400> SEQUENCE: 113
aatagtggta aagcaccatg                                                    20

<210> SEQ ID NO 114
<211> LENGTH: 20
<212> TYPE: DNA
<213> ORGANISM: Artificial Sequence
<220> FEATURE:
<223> OTHER INFORMATION: Folh1 gRNA B DNA-targeting segment

<400> SEQUENCE: 114
gtgtgctaag gatcgaagtc                                                    20

<210> SEQ ID NO 115
<211> LENGTH: 20
<212> TYPE: DNA
<213> ORGANISM: Artificial Sequence
<220> FEATURE:
<223> OTHER INFORMATION: Folh1 gRNA C DNA-targeting segment

<400> SEQUENCE: 115
caccgagatg cttgggtatt                                                    20

<210> SEQ ID NO 116
<211> LENGTH: 20
<212> TYPE: DNA
<213> ORGANISM: Artificial Sequence
<220> FEATURE:
<223> OTHER INFORMATION: Folh1 gRNA D DNA-targeting segment

<400> SEQUENCE: 116
tgtaaccgcc ctgaatgacc                                                    20

<210> SEQ ID NO 117
<211> LENGTH: 20
<212> TYPE: DNA
<213> ORGANISM: Artificial Sequence
<220> FEATURE:
<223> OTHER INFORMATION: Folh1 gRNA E DNA-targeting segment

<400> SEQUENCE: 117
aaaagggcat cataaatccc                                                    20

<210> SEQ ID NO 118
<211> LENGTH: 20
<212> TYPE: DNA
<213> ORGANISM: Artificial Sequence
```

```
<220> FEATURE:
<223> OTHER INFORMATION: Folh1 gRNA E2 DNA-targeting segment

<400> SEQUENCE: 118
tcaaaaatag tcatacacct                                              20

<210> SEQ ID NO 119
<211> LENGTH: 20
<212> TYPE: DNA
<213> ORGANISM: Artificial Sequence
<220> FEATURE:
<223> OTHER INFORMATION: Folh1 gRNA F DNA-targeting segment

<400> SEQUENCE: 119
ggtctctagt acattgtaga                                              20

<210> SEQ ID NO 120
<211> LENGTH: 20
<212> TYPE: DNA
<213> ORGANISM: Artificial Sequence
<220> FEATURE:
<223> OTHER INFORMATION: Adamts5 gRNA A DNA-targeting segment

<400> SEQUENCE: 120
ggtggtggtg ctgacggaca                                              20

<210> SEQ ID NO 121
<211> LENGTH: 20
<212> TYPE: DNA
<213> ORGANISM: Artificial Sequence
<220> FEATURE:
<223> OTHER INFORMATION: Adamts5 gRNA A2 DNA-targeting segment

<400> SEQUENCE: 121
tatgagatca acactcgcta                                              20

<210> SEQ ID NO 122
<211> LENGTH: 20
<212> TYPE: DNA
<213> ORGANISM: Artificial Sequence
<220> FEATURE:
<223> OTHER INFORMATION: Adamts5 gRNA B DNA-targeting segment

<400> SEQUENCE: 122
ccaaggactt ccccacgtta                                              20

<210> SEQ ID NO 123
<211> LENGTH: 20
<212> TYPE: DNA
<213> ORGANISM: Artificial Sequence
<220> FEATURE:
<223> OTHER INFORMATION: Adamts5 gRNA C DNA-targeting segment

<400> SEQUENCE: 123
tgcttccctt atgcaagatt                                              20

<210> SEQ ID NO 124
<211> LENGTH: 20
<212> TYPE: DNA
<213> ORGANISM: Artificial Sequence
<220> FEATURE:
<223> OTHER INFORMATION: Adamts5 gRNA D DNA-targeting segment

<400> SEQUENCE: 124
ttaggtaccc tatttgaata                                              20
```

```
<210> SEQ ID NO 125
<211> LENGTH: 20
<212> TYPE: DNA
<213> ORGANISM: Artificial Sequence
<220> FEATURE:
<223> OTHER INFORMATION: Adamts5 gRNA E2 DNA-targeting segment

<400> SEQUENCE: 125
tgcagtgggt gacaggtcca                                              20

<210> SEQ ID NO 126
<211> LENGTH: 20
<212> TYPE: DNA
<213> ORGANISM: Artificial Sequence
<220> FEATURE:
<223> OTHER INFORMATION: Adamts5 gRNA E DNA-targeting segment

<400> SEQUENCE: 126
agggttatac tgacgttgtg                                              20

<210> SEQ ID NO 127
<211> LENGTH: 20
<212> TYPE: DNA
<213> ORGANISM: Artificial Sequence
<220> FEATURE:
<223> OTHER INFORMATION: Adamts5 gRNA F DNA-targeting segment

<400> SEQUENCE: 127
tgtctttcaa ggagggctac                                              20

<210> SEQ ID NO 128
<211> LENGTH: 20
<212> TYPE: DNA
<213> ORGANISM: Artificial Sequence
<220> FEATURE:
<223> OTHER INFORMATION: Dpp4 gRNA A DNA-targeting segment

<400> SEQUENCE: 128
actagtagac ctgaggggtt                                              20

<210> SEQ ID NO 129
<211> LENGTH: 20
<212> TYPE: DNA
<213> ORGANISM: Artificial Sequence
<220> FEATURE:
<223> OTHER INFORMATION: Dpp4 gRNA B DNA-targeting segment

<400> SEQUENCE: 129
gctccagtgt ttaggccttg                                              20

<210> SEQ ID NO 130
<211> LENGTH: 20
<212> TYPE: DNA
<213> ORGANISM: Artificial Sequence
<220> FEATURE:
<223> OTHER INFORMATION: Dpp4 gRNA B2 DNA-targeting segment

<400> SEQUENCE: 130
ggcaagctga aaacgcatgc                                              20

<210> SEQ ID NO 131
<211> LENGTH: 20
<212> TYPE: DNA
<213> ORGANISM: Artificial Sequence
<220> FEATURE:
<223> OTHER INFORMATION: Dpp4 gRNA C DNA-targeting segment
```

```
<400> SEQUENCE: 131
gtagatcgct ttccactacc                                              20

<210> SEQ ID NO 132
<211> LENGTH: 20
<212> TYPE: DNA
<213> ORGANISM: Artificial Sequence
<220> FEATURE:
<223> OTHER INFORMATION: Dpp4 gRNA D DNA-targeting segment

<400> SEQUENCE: 132
gaactccact gctcgtgagc                                              20

<210> SEQ ID NO 133
<211> LENGTH: 20
<212> TYPE: DNA
<213> ORGANISM: Artificial Sequence
<220> FEATURE:
<223> OTHER INFORMATION: Dpp4 gRNA E2 DNA-targeting segment

<400> SEQUENCE: 133
ataggtgggc actattgaag                                              20

<210> SEQ ID NO 134
<211> LENGTH: 20
<212> TYPE: DNA
<213> ORGANISM: Artificial Sequence
<220> FEATURE:
<223> OTHER INFORMATION: Dpp4 gRNA E DNA-targeting segment

<400> SEQUENCE: 134
atgggaaggt ttataccagc                                              20

<210> SEQ ID NO 135
<211> LENGTH: 20
<212> TYPE: DNA
<213> ORGANISM: Artificial Sequence
<220> FEATURE:
<223> OTHER INFORMATION: Dpp4 gRNA F DNA-targeting segment

<400> SEQUENCE: 135
cggtgtaaaa acaacgggaa                                              20

<210> SEQ ID NO 136
<211> LENGTH: 20
<212> TYPE: DNA
<213> ORGANISM: Artificial Sequence
<220> FEATURE:
<223> OTHER INFORMATION: Forward primer for SV 6.1 in Fig. 8

<400> SEQUENCE: 136
ggaatgccaa ggctactgtc                                              20

<210> SEQ ID NO 137
<211> LENGTH: 20
<212> TYPE: DNA
<213> ORGANISM: Artificial Sequence
<220> FEATURE:
<223> OTHER INFORMATION: Reverse primer for SV 6.1 in Fig. 8

<400> SEQUENCE: 137
aaaagtctgc tttgggtggt                                              20

<210> SEQ ID NO 138
```

```
<211> LENGTH: 21
<212> TYPE: DNA
<213> ORGANISM: Artificial Sequence
<220> FEATURE:
<223> OTHER INFORMATION: Forward primer for SV 6.3 in Fig. 8

<400> SEQUENCE: 138
cttcatgaac ctcactcagg a                                              21

<210> SEQ ID NO 139
<211> LENGTH: 21
<212> TYPE: DNA
<213> ORGANISM: Artificial Sequence
<220> FEATURE:
<223> OTHER INFORMATION: Reverse primer for SV 6.3 in Fig. 8

<400> SEQUENCE: 139
tctcggagtc aggatttacc t                                              21

<210> SEQ ID NO 140
<211> LENGTH: 20
<212> TYPE: DNA
<213> ORGANISM: Artificial Sequence
<220> FEATURE:
<223> OTHER INFORMATION: Forward primer for SV 7.8 in Fig. 8

<400> SEQUENCE: 140
tgtctctttg cctgttgctg                                                20

<210> SEQ ID NO 141
<211> LENGTH: 22
<212> TYPE: DNA
<213> ORGANISM: Artificial Sequence
<220> FEATURE:
<223> OTHER INFORMATION: Reverse primer for SV 7.8 in Fig. 8

<400> SEQUENCE: 141
tctgctctac aaggcttacg tg                                             22

<210> SEQ ID NO 142
<211> LENGTH: 20
<212> TYPE: DNA
<213> ORGANISM: Artificial Sequence
<220> FEATURE:
<223> OTHER INFORMATION: Forward primer for SV 16 in Fig. 8

<400> SEQUENCE: 142
caaccaggca gacttacagc                                                20

<210> SEQ ID NO 143
<211> LENGTH: 20
<212> TYPE: DNA
<213> ORGANISM: Artificial Sequence
<220> FEATURE:
<223> OTHER INFORMATION: Reverse primer for SV 16 in Fig. 8

<400> SEQUENCE: 143
ggcctaggaa ccagtcaaaa                                                20

<210> SEQ ID NO 144
<211> LENGTH: 23
<212> TYPE: DNA
<213> ORGANISM: Artificial Sequence
<220> FEATURE:
<223> OTHER INFORMATION: Forward primer for SV 25.5 in Fig. 8

<400> SEQUENCE: 144
```

```
gcttactgga aagctacata ggg                                              23
```

<210> SEQ ID NO 145
<211> LENGTH: 22
<212> TYPE: DNA
<213> ORGANISM: Artificial Sequence
<220> FEATURE:
<223> OTHER INFORMATION: Reverse primer for SV 25.5 in Fig. 8

<400> SEQUENCE: 145

```
caacaacata gaaaccctg tc                                                22
```

<210> SEQ ID NO 146
<211> LENGTH: 6
<212> TYPE: DNA
<213> ORGANISM: Artificial Sequence
<220> FEATURE:
<223> OTHER INFORMATION: S. aureus Cas9 PAM sequence
<220> FEATURE:
<221> NAME/KEY: misc_feature
<222> LOCATION: (1)...(2)
<223> OTHER INFORMATION: n = A, T, C, or G
<220> FEATURE:
<221> NAME/KEY: misc_feature
<222> LOCATION: (4)...(5)
<223> OTHER INFORMATION: r = A or G

<400> SEQUENCE: 146

```
nngrrt                                                                  6
```

<210> SEQ ID NO 147
<211> LENGTH: 5
<212> TYPE: DNA
<213> ORGANISM: Artificial Sequence
<220> FEATURE:
<223> OTHER INFORMATION: S. aureus Cas9 PAM sequence
<220> FEATURE:
<221> NAME/KEY: misc_feature
<222> LOCATION: (1)...(2)
<223> OTHER INFORMATION: n = A, T, C, or G
<220> FEATURE:
<221> NAME/KEY: misc_feature
<222> LOCATION: (4)...(5)
<223> OTHER INFORMATION: r = A or G

<400> SEQUENCE: 147

```
nngrr                                                                   5
```

<210> SEQ ID NO 148
<211> LENGTH: 3155
<212> TYPE: DNA
<213> ORGANISM: Artificial Sequence
<220> FEATURE:
<223> OTHER INFORMATION: Engineered Human Vk1-39Jk5 Locus

<400> SEQUENCE: 148

```
ggcgcgccgt agctttgaat tttaaacatc tatttgacaa gaaatgcata gttccttctc       60
tttaaaataa tgtaatgttt ctttcaagaa taagcttggt ttgatgcctc tctccccaac      120
atgatagaag tgtagcataa atctatgaaa aattccattt ccctgtgcct acaacaacta      180
cctgggattg aaaacttctt cccttgctct agtcctttct tctacaccta cttccacatc      240
atctgtgact caaaacaata cttgtcagga aagatcccgg aaagagcaaa aaagacttcc      300
ttagaggtgt cagagattcc tatgccacta tctgtcatct ctagaagggg ttgtgagtat      360
gaggaagagc agagcttgta aatttctac ttgctttgac ttccactgta tttcctaaca      420
```

```
acaacaacca cagcaacacc cataacatca caggacaaac ttctagtact tccaaggctt    480
tagtctcagt aaatcttctc tacctccatc acagcagcta gaaggtttga tactcataca    540
aatagtactg tagctttctg ttcataattg gaaaaataga caagacccaa tgtaatacag    600
gctttccttc agccagttag cgttcagttt ttggatcacc attgcacaca tatacccagc    660
atatgtctaa tatatatgta gaaatccgtg aagcaagagt tataatagct tgtgttttct    720
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga agaaggaca   1020 gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagttttca cttttaact    1560 caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tgacatccag atgacccagt ctccatcctc cctgtctgca   2400
tctgtaggag acagagtcac catcacttgc cgggcaagtc agagcattag cagctattta   2460
aattggtatc agcagaaacc agggaaagcc cctaagctcc tgatctatgc tgcatccagt   2520
ttgcaaagtg gggtcccatc aaggttcagt ggcagtggat ctgggacaga tttcactctc   2580
accatcagca gtctgcaacc tgaagatttt gcaacttact actgtcaaca gagttacagt   2640 accccctccga tcaccttcgg ccaagggaca cgactggaga ttaaacgtaa gtaattttc   2700 actattgtct tctgaaattt gggtctgatg gccagtattg acttttagag gcttaaatag   2760
gagtttggta aagattggta aatgagggca tttaagattt gccatgggtt gcaaaagtta   2820
```

| aactcagctt caaaaatgga tttggagaaa aaaagattaa attgctctaa actgaatgac | 2880 |
| acaaagtaaa aaaaaaagt gtaactaaaa aggaaccctt gtatttctaa ggagcaaaag | 2940 |
| taaatttatt tttgttcact cttgccaaat attgtattgg ttgttgctga ttatgcatga | 3000 |
| tacagaaaag tggaaaaata catttttag tctttctccc ttttgtttga taaattattt | 3060 |
| tgtcagacaa caataaaaat caatagcacg ccctaagatc tagatgcatg ctcgagtgcc | 3120 |
| atttcattac ctctttctcc gcacccgaca tagat | 3155 |

<210> SEQ ID NO 149
<211> LENGTH: 3166
<212> TYPE: DNA
<213> ORGANISM: Artificial Sequence
<220> FEATURE:
<223> OTHER INFORMATION: Engineered Human Vk3-20Jk1 Locus

<400> SEQUENCE: 149

| ggcgcgccgt agctttgaat ttaaacatc tatttgacaa gaaatgcata gttccttctc | 60 |
| tttaaaataa tgtaatgttt ctttcaagaa taagcttggt ttgatgcctc tctccccaac | 120 |
| atgatagaag tgtagcataa atctatgaaa aattccattt ccctgtgcct acaacaacta | 180 |
| cctgggattg aaaacttctt cccttgctct agtccttct tctacaccta cttccacatc | 240 |
| atctgtgact caaacaata cttgtcagga aagatcccgg aaagagcaaa aaagacttcc | 300 |
| ttagaggtgt cagagattcc tatgccacta tctgtcatct ctagaagggg ttgtgagtat | 360 |
| gaggaagagc agagcttgta aattttctac ttgctttgac ttccactgta tttcctaaca | 420 |
| acaacaacca cagcaacacc cataacatca caggacaaac ttctagtact tccaaggctt | 480 |
| tagtctcagt aaatcttctc tacctccatc acagcagcta aaggtttga tactcataca | 540 |
| aatagtactg tagcttttctg ttcataattg gaaaaataga caagacccaa tgtaatacag | 600 |
| gctttccttc agccagttag cgttcagttt ttggatcacc attgcacaca tatacccagc | 660 |
| atatgtctaa tatatatgta gaaatccgtg aagcaagagt tataatagct tgtgttttct | 720 |
| attgtattgt attttcctct tatatcatct tcttcttcgt tcattaaaaa aaaaccgttc | 780 |
| aagtaggtct aaattaatta ttggatcata agtagataaa atattttatt tcataacaca | 840 |
| ttgacccgat gaatatgttt ctttgccaga catagtcctc atttccaagg taacaagcct | 900 |
| gaaaaaatta tactggagca agtcaacagg taatgatggg agcttttcct tattgtcctg | 960 |
| gggcaagaat aagacaaaag ataacagggt agaataaaga ttgtgtaaga aagaaggaca | 1020 |
| gcaacaggac atgggaacct tttatagagt aacattttga taatggatga tgagaattaa | 1080 |
| tgagttagac agggatgggt gggaatgatt gaaggtgtga gtactttagc acagattaag | 1140 |
| accaaatcat taggatttaa agagttgtgt agagttagtg aaggaaaagc cttagaatta | 1200 |
| aatttggctg cggataaaac attcttggat tagactgaag actcttttct gtgctaagta | 1260 |
| agtatattta tgataatgat gatgactgta gtgctgaata tttaataaat aaaaacaaaa | 1320 |
| ttaattgccg catacataat gtcctgaata ctattgtaaa tgttttatct tatttccttt | 1380 |
| aaactgtcta cagcactata aggtaggtac cagtattgtc acagttacac agatatggaa | 1440 |
| accgagacac agggaagtta agttacttga tcaatttcaa gcaatcggca agccatggag | 1500 |
| catctatgtc agggctgcca ggacatgtga ctgtaaacag aagttttca cttttttaact | 1560 |
| caaagagggt atgtggctgg gttaatgaaa agcttcagga ccctcagaaa acattactaa | 1620 |
| caagcaaatg aaaggtgtat ctggaagatt aagttttaac agactcttca tttccatcga | 1680 |

```
tccaataatg cacttaggga gatgactggg catattgagg ataggaagag agaagtgaaa    1740
acacagcttt ttatattgtt cttaacaggc ttgtgccaaa catcttctgg gtggatttag    1800
gtgattgagg agaagaaaga cacaggagcg aaattctctg agcacaaggg aggagttcta    1860
cactcagact gagccaacag acttttctgg cctgacaacc agggcggcgc aggatgctca    1920
gtgcagagag gaagaagcag gtggtctttg cagctgaaag ctcagctgat ttgcatatgg    1980
agtcattata caacatccca gaattcttta agggcagctg ccaggaagct aagaagcatc    2040
ctctcttcta gctctcagag atggagacag acacactcct gctatgggtg ctgctgctct    2100
gggttccagg tgagggtaca gataagtgtt atgagcaacc tctgtggcca ttatgatgct    2160
ccatgcctct ctgttcttga tcactataat tagggcattt gtcactggtt ttaagtttcc    2220
ccagtcccct gaattttcca ttttctcaga gtgatgtcca aaattattct taaaaattta    2280
aatgaaaagg tcctctgctg tgaaggcttt taaagatata taaaaataat ctttgtgttt    2340
atcattccag gtgccagatg tataccaccg gagaaattgt gttgacgcag tctccaggca    2400
ccctgtcttt gtctccaggg gaaagagcca ccctctcctg cagggccagt cagagtgtta    2460
gcagcagcta cttagcctgg taccagcaga aacctggcca ggctcccagg ctcctcatct    2520
atggtgcatc cagcagggcc actggcatcc cagacaggtt cagtggcagt gggtctggga    2580
cagacttcac tctcaccatc agcagactgg agcctgaaga ttttgcagtg tattactgtc    2640
agcagtatgg tagctcacct tggacgttcg gccaagggac caaggtggaa atcaaacgta    2700
agtaattttt cactattgtc ttctgaaatt tgggtctgat ggccagtatt gacttttaga    2760
ggcttaaata ggagtttggt aaagattggt aaatgagggc atttaagatt tgccatgggt    2820
tgcaaaagtt aaactcagct tcaaaaatgg atttggagaa aaaagatta aattgctcta    2880 aactgaatga cacaaagtaa aaaaaaaaag tgtaactaaa aaggaaccct tgtatttcta    2940
aggagcaaaa gtaaatttat ttttgttcac tcttgccaaa tattgtattg gttgttgctg    3000
attatgcatg atacagaaaa gtggaaaaat acatttttta gtctttctcc cttttgtttg    3060
ataaattatt ttgtcagaca acaataaaaa tcaatagcac gccctaagat ctagatgcat    3120
gctcgagtgc catttcatta cctctttctc cgcacccgac atagat              3166
```

<210> SEQ ID NO 150
<211> LENGTH: 82
<212> TYPE: DNA
<213> ORGANISM: Artificial Sequence
<220> FEATURE:
<223> OTHER INFORMATION: Guide RNA Scaffold v1

<400> SEQUENCE: 150

```
gttggaacca ttcaaaacag catagcaagt taaaataagg ctagtccgtt atcaacttga    60
aaaagtggca ccgagtcggt gc                                              82
```

<210> SEQ ID NO 151
<211> LENGTH: 76
<212> TYPE: DNA
<213> ORGANISM: Artificial Sequence
<220> FEATURE:
<223> OTHER INFORMATION: Guide RNA Scaffold v2

<400> SEQUENCE: 151

```
gttttagagc tagaaatagc aagttaaaat aaggctagtc cgttatcaac ttgaaaaagt    60
ggcaccgagt cggtgc                                                    76
```

```
<210> SEQ ID NO 152
<211> LENGTH: 86
<212> TYPE: DNA
<213> ORGANISM: Artificial Sequence
<220> FEATURE:
<223> OTHER INFORMATION: Guide RNA Scaffold v3

<400> SEQUENCE: 152
gtttaagagc tatgctggaa acagcatagc aagtttaaat aaggctagtc cgttatcaac    60
ttgaaaaagt ggcaccgagt cggtgc                                        86
```

METHODS FOR PRODUCING ANTIGEN-BINDING PROTEINS AGAINST FOREIGN ANTIGENS

CROSS-REFERENCE TO RELATED APPLICATIONS

This application is a continuing application of U.S. application Ser. No. 15/600,466, filed May 19, 2017, which claims the benefit of U.S. Application No. 62/339,472, filed May 20, 2016, and U.S. Application No. 62/368,604, filed Jul. 29, 2016, each of which is herein incorporated by reference in its entirety for all purposes.

REFERENCE TO A SEQUENCE LISTING SUBMITTED AS A TEXT FILE VIA EFS WEB

The Sequence Listing written in file 571554SEQLIST.txt is 38.3 kilobytes, was created on Dec. 16, 2021, and is hereby incorporated by reference.

BACKGROUND

Immunization of non-human animals (e.g., rodents, such as mice or rats) with a "non-self" protein is a commonly used method to obtain specific antigen-binding proteins such as monoclonal antibodies. This approach, however, is dependent on a divergence in sequence between native proteins in the non-human animal and the protein being immunized to enable the non-human animal's immune system to recognize the immunogen as non-self (i.e., foreign). The generation of antibodies against antigens having a high degree of homology with self-antigens can be a difficult task due to immunological tolerance. Because functionally important regions of proteins tend to be conserved across species, immunological tolerance to self-antigens often poses a challenge to the generation of antibodies to these key epitopes.

Although progress has been made in targeting various genomic loci, there still remain many genomic loci that cannot be targeted efficiently or genomic modifications that cannot be achieved efficiently with conventional targeting strategies. The CRISPR/Cas system has provided a new tool for genome editing, but difficulties still remain. For example, difficulties can still arise in some contexts when attempting to create large targeted genomic deletions or other large targeted genetic modifications, particularly in eukaryotic cells and organisms.

In addition, it can be difficult to efficiently produce cells or animals that are homozygous for a targeted genetic modification without subsequent breeding steps, and some loci can be more difficult to target than others to generate homozygous targeted modifications. For example, although F0 generation mice heterozygous for a large targeted genomic deletion can sometimes be obtained via conventional targeting strategies, subsequent breeding of these heterozygous mice is required to produce F1 generation mice that are homozygous for the deletion. These additional breeding steps are costly and time-consuming.

SUMMARY

Methods and compositions are provided for making non-human animals with reduced tolerance of a foreign antigen of interest and for using such animals to generate antigen-binding proteins that bind the foreign antigen of interest. In one aspect, the invention provides a method of making a non-human animal with reduced tolerance of a foreign antigen of interest, comprising: (a) contacting the genome of a non-human animal pluripotent cell that is not a one-cell stage embryo with: (i) a Cas9 protein: (ii) a first guide RNA that hybridizes to a first guide RNA recognition sequence within a first target genomic locus, wherein the first target genomic locus affects expression of a first self-antigen homologous to or sharing an epitope of interest with the foreign antigen of interest; and (iii) a second guide RNA that hybridizes to a second guide RNA recognition sequence within the first target genomic locus; wherein the first target genomic locus is modified in a pair of first and second chromosomes to produce a modified non-human animal pluripotent cell with a biallelic modification, wherein expression of the first self-antigen is decreased; (b) introducing the modified non-human animal pluripotent cell into a host embryo; and (c) implanting the host embryo into a surrogate mother to produce a genetically modified F0 generation non-human animal in which the first target genomic locus is modified in the pair of first and second chromosomes such that expression of the first self-antigen is decreased. Optionally, the pluripotent cell is an embryonic stem (ES) cell. Optionally, the contacting comprises introducing the Cas9 protein, the first guide RNA, and the second guide RNA into the non-human animal pluripotent cell via nucleofection. Optionally, the Cas9 protein is introduced into the non-human animal pluripotent cell in the form of a DNA encoding the Cas9 protein, the first guide RNA is introduced into the non-human animal pluripotent cell in the form of a DNA encoding the first guide RNA, and the second guide RNA is introduced into the non-human animal pluripotent cell in the form of a DNA encoding the second guide RNA.

In some such methods, the contacting step (a) further comprises contacting the genome with: (iv) a third guide RNA that hybridizes to a third guide RNA recognition sequence within the first target genomic locus; and/or (v) a fourth guide RNA that hybridizes to a fourth guide RNA recognition sequence within the first target genomic locus. In some such methods, the contacting step (a) further comprises contacting the genome with: (iv) a third guide RNA that hybridizes to a third guide RNA recognition sequence within a second target genomic locus, wherein the second target genomic locus affects expression of the first self-antigen or a second self-antigen homologous to or sharing an epitope of interest with the foreign antigen of interest; and/or (v) a fourth guide RNA that hybridizes to a fourth guide RNA recognition sequence within the second target genomic locus.

In some such methods, the contacting step (a) further comprises contacting the genome with an exogenous repair template comprising a 5' homology arm that hybridizes to a 5' target sequence at the target genomic locus and a 3' homology arm that hybridizes to a 3' target sequence at the target genomic locus. Optionally, the exogenous repair template further comprises a nucleic acid insert flanked by the 5' homology arm and the 3' homology arm. In some such methods, the nucleic acid insert is homologous or orthologous to the first target genomic locus. In some such methods, the exogenous repair template is between about 50 nucleotides to about 1 kb in length. In some such methods, the exogenous repair template is between about 80 nucleotides to about 200 nucleotides in length. In some such methods, the exogenous repair template is a single-stranded oligodeoxynucleotide. In some such methods, the exogenous repair template is a large targeting vector (LTVEC) that is at least 10 kb in length, and/or the exogenous repair template is an LTVEC, wherein the sum total of the 5' and 3' homology arms of the LTVEC is at least 10 kb in length.

Some such methods further comprise: (d) immunizing the genetically modified F0 generation non-human animal produced in step (c) with the foreign antigen of interest; (e) maintaining the genetically modified F0 generation non-human animal under conditions sufficient to initiate an immune response to the foreign antigen of interest; and (f) obtaining a first nucleic acid sequence encoding a human immunoglobulin heavy chain variable domain and/or a second nucleic acid sequence encoding a human immunoglobulin light chain variable domain from the genetically modified F0 generation non-human animal.

In some such methods, antigen-binding proteins against the foreign antigen of interest obtained following immunization of the genetically modified F0 generation non-human animal with the foreign antigen of interest have a higher titer than antigen-binding proteins obtained following immunization of a control non-human animal that is wild type at the first target genomic locus. In some such methods, a more diverse repertoire of antigen-binding proteins against the foreign antigen of interest is obtained following immunization of the genetically modified F0 generation non-human animal with the foreign antigen of interest compared with antigen-binding proteins obtained following immunization of a control non-human animal that is wild type at the first target genomic locus.

In some such methods, expression of the first self-antigen is eliminated.

In some such methods, the foreign antigen of interest is an ortholog of the first self-antigen. In some such methods, the foreign antigen of interest comprises, consists essentially of, or consists of all or part of a human protein.

In some such methods, the first target genomic locus is modified to comprise an insertion of one or more nucleotides, a deletion of one or more nucleotides, or a replacement of one or more nucleotides. In some such methods, the first target genomic locus is modified to comprise a deletion of one or more nucleotides. In some such methods, contacting step (a) comprises contacting the genome with an exogenous repair template comprising a 5' homology arm that hybridizes to a 5' target sequence at the target genomic locus and a 3' homology arm that hybridizes to a 3' target sequence at the target genomic locus, provided that if the genome is in a one-cell stage embryo the exogenous repair template is no more than 5 kb in length, wherein the exogenous repair template comprises a nucleic acid insert flanked by the 5' homology arm and the 3' homology arm, wherein the nucleic acid insert is homologous or orthologous to the deleted nucleic acid sequence, and wherein the nucleic acid insert replaces the deleted nucleic acid sequence. In some such methods, the deletion is a precise deletion without random insertions and deletions (indels). In some such methods, contacting step (a) comprises contacting the genome with an exogenous repair template comprising a 5' homology arm that hybridizes to a 5' target sequence at the target genomic locus and a 3' homology arm that hybridizes to a 3' target sequence at the target genomic locus, provided that if the genome is in a one-cell stage embryo the exogenous repair template is no more than 5 kb in length, wherein the deleted nucleic acid sequence consists of the nucleic acid sequence between the 5' and 3' target sequences.

In some such methods, the first target genomic locus comprises, consists essentially of, or consists of all or part of a gene encoding the first self-antigen. In some such methods, the modification comprises, consists essentially of, or consists of homozygous deletion of all or part of the gene encoding the first self-antigen. In some such methods, the modification comprises, consists essentially of, or consists of homozygous disruption of the start codon of the gene encoding the first self-antigen.

In some such methods, the first guide RNA recognition sequence comprises the start codon for the gene encoding the first self-antigen or is within about 10, 20, 30, 40, 50, 100, 200, 300, 400, 500, or 1,000 nucleotides of the start codon, and the second guide RNA recognition sequence comprises the stop codon for the gene encoding the first self-antigen or is within about 10, 20, 30, 40, 50, 100, 200, 300, 400, 500, or 1,000 nucleotides of the stop codon. Optionally, the first guide RNA recognition sequence comprises the start codon, and the second guide RNA recognition sequence comprises the stop codon. In some such methods, the first guide RNA recognition sequence comprises a first Cas9 cleavage site and the second guide RNA recognition sequence comprises a second Cas9 cleavage site, wherein the first target genomic locus is modified to comprise a deletion between the first and second Cas9 cleavage sites. Optionally, the deletion is a precise deletion, wherein the deleted nucleic acid sequence consists of the nucleic acid sequence between the first and second Cas9 cleavage sites.

In some such methods, the first and second guide RNA recognition sequences are different, and each of the first and second guide RNA recognition sequences comprises the start codon for the gene encoding the first self-antigen or is within about 10, 20, 30, 40, 50, 100, 200, 300, 400, 500, or 1,000 nucleotides of the start codon. Optionally, each of the first and second guide RNA recognition sequences comprises the start codon.

In some such methods, the first nucleic acid sequence and/or second nucleic acid sequence are obtained from a lymphocyte of the genetically modified non-human animal or from a hybridoma produced from the lymphocyte.

In some such methods, the non-human animal comprises a humanized immunoglobulin locus. In some such methods, the non-human animal is a rodent. In some such methods, the rodent is a mouse. Optionally, the mouse strain comprises a BALB/c strain. Optionally, the mouse strain comprises BALB/c, C57BL/6, and 129 strains. Optionally, the mouse strain is 50% BALB/c, 25% C57BL/6, and 25% 129. Optionally, the MHC haplotype of the mouse is MHC$^{b/d}$.

In some such methods, the mouse comprises in its germline human unrearranged variable region gene segments inserted at an endogenous mouse immunoglobulin locus. Optionally, the human unrearranged variable region gene segments are heavy chain gene segments, and the mouse immunoglobulin locus is a heavy chain locus. Optionally, the human unrearranged variable region gene segments are light chain segments, and the mouse immunoglobulin locus is a light chain locus. Optionally, the light chain gene segments are human kappa or lambda light chain gene segments. In some such methods, the mouse comprises in its germline human unrearranged variable region gene segments operably linked to a mouse constant region gene, wherein the mouse lacks a human constant region gene, and wherein the mouse constant region gene is at an endogenous mouse immunoglobulin locus. In some such methods, the mouse comprises: (a) a hybrid heavy chain locus comprising an insertion of the human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (b) a hybrid light chain locus comprising an insertion of human immunoglobulin light chain V and J gene segments, wherein the human V and J gene segments are operably linked to a mouse immunoglobulin light chain constant region gene sequence; wherein (a) rearranges to form a hybrid heavy chain sequence comprising a human variable region operably linked to a mouse constant region, and (b) rearranges to form a hybrid light chain sequence comprising a human variable region operably linked to a mouse constant region, and wherein the mouse is incapable of forming an antibody that comprises a human variable region and a human constant region. In some such methods, the mouse comprises a modification of an immunoglobulin heavy chain locus, wherein the modification reduces or eliminates endogenous ADAM6 function, and wherein the mouse comprises an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse. Optionally, the ectopic nucleic acid sequence encoding the mouse ADAM6 protein, ortholog thereof, homolog thereof, or fragment thereof is present at the human heavy chain variable region locus. Optionally, the ectopic nucleic acid sequence encoding the mouse ADAM6 protein, ortholog thereof, homology thereof, or fragment thereof is present at a location other than the human heavy chain variable region locus.

In some such methods, the mouse comprises in its germline a humanized immunoglobulin light chain variable locus comprising no more than one or no more than two rearranged human light chain V/J sequences operably linked to a light chain constant region. Optionally, the light chain constant region gene is a mouse gene. In some such methods, the mouse further comprises a humanized immunoglobulin heavy chain variable locus comprising at least one unrearranged human V, at least one unrearranged human D, and at least one unrearranged human J segment operably linked to a heavy chain constant region gene. Optionally, the heavy chain constant region gene is a mouse gene. In some such methods, the mouse comprises a humanized heavy chain immunoglobulin variable locus and a humanized light chain immunoglobulin variable locus, wherein the mouse expresses a single light chain. In some such methods, the mouse comprises: (a) a single rearranged human immunoglobulin light chain variable region ($V_L/J_L$) that encodes a human $V_L$ domain of an immunoglobulin light chain, wherein the single rearranged human $V_L/J_L$ region is selected from a human Vκ1-39/J gene segment or a human Vκ3-20/J gene segment; and (b) a replacement of endogenous heavy chain variable ($V_H$) gene segments with one or more human VH gene segments, wherein the human $V_H$ gene segments are operably linked to an endogenous heavy chain constant ($C_H$) region gene, and the human $V_H$ gene segments are capable of rearranging and forming a human/mouse chimeric heavy chain gene. In some such methods, the mouse expresses a population of antibodies, and the mouse's germline includes only a single immunoglobulin kappa light chain variable region gene that is a rearranged human germline kappa light chain variable region gene, wherein the mouse is either heterozygous for the single immunoglobulin kappa light chain variable region gene in that it contains only one copy, or is homozygous for the single immunoglobulin kappa light chain variable region gene in that it contains two copies, the mouse being characterized by active affinity maturation so that: (i) each immunoglobulin kappa light chain of the population comprises a light chain variable domain that is encoded by the rearranged human germline kappa light chain variable region gene, or by a somatically mutated variant thereof; (ii) the population includes antibodies comprising the immunoglobulin kappa light chains whose light chain variable domain is encoded by the rearranged human germline kappa light chain variable region gene and antibodies comprising the immunoglobulin kappa light chains whose light chain variable domain is encoded by the somatically mutated variants thereof; and (iii) the mouse generates a diverse collection of somatically mutated high affinity heavy chains that successfully pair with the immunoglobulin kappa light chains to form the antibodies of the population. Optionally, the mouse is heterozygous or homozygous in its germline for: (a) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (b) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene. In some such methods, the mouse comprises a modification of an immunoglobulin heavy chain locus, wherein the modification reduces or eliminates endogenous ADAM6 function, and wherein the mouse comprises an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse. Optionally, the ectopic nucleic acid sequence encoding the mouse ADAM6 protein, ortholog thereof, homolog thereof, or fragment thereof is present at the human heavy chain variable region locus. Optionally, the ectopic nucleic acid sequence encoding the mouse ADAM6 protein, ortholog thereof, homology thereof, or fragment thereof is present at a location other than the human heavy chain variable region locus.

In some such methods, the mouse has a genome comprising a modification of an immunoglobulin heavy chain locus, wherein the modification reduces or eliminates endogenous ADAM6 function, and the mouse further comprises a nucleic acid sequence encoding a non-human animal ADAM6 protein or an ortholog or homolog thereof or a functional fragment of the corresponding ADAM6 protein. Optionally, the mouse's genome comprises: (a) ectopic placement of an ADAM6 gene; and (b) a human immunoglobulin heavy chain variable region locus comprising an insertion of one or more human $V_H$ gene segments, one or more human $D_H$ gene segments, and one or more human $J_H$ gene segments into the endogenous non-human animal heavy chain locus, wherein the human $V_H$, $D_H$ and $J_H$ gene segments are operably linked to a heavy chain constant region gene; so that the mouse is characterized in that: (i) it is fertile; and (ii) when it is immunized with an antigen, it generates antibodies comprising heavy chain variable domains encoded by the one or more human $V_H$, one or more human $D_H$, and one or more human $J_H$ gene segments, operably linked to heavy chain constant domains encoded by the heavy chain constant region gene, wherein the antibodies show specific binding to the antigen.

In some such methods, the non-human animal is a mouse that is at least partially derived from a BALB/c strain, wherein the mouse comprises a humanized immunoglobulin locus, wherein the foreign antigen of interest is all or part of a human protein that is orthologous to the first self-antigen, and the first target genomic locus comprises all or part of a gene encoding the first self-antigen, wherein the first guide RNA recognition site comprises the start codon for the gene encoding the first self-antigen and the second guide RNA recognition site comprises the stop codon for the gene encoding the first self-antigen, and wherein the modification comprises a homozygous deletion of all or part of the gene encoding the first self-antigen, whereby expression of the first-self-antigen is eliminated. Optionally, the mouse comprises: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) a hybrid heavy chain locus comprising an insertion of the human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (c) a hybrid light chain locus comprising an insertion of human immunoglobulin light chain V and J gene segments, wherein the human V and J gene segments are operably linked to a mouse immunoglobulin light chain constant region gene sequence; wherein (b) rearranges to form a hybrid heavy chain sequence comprising a human variable region operably linked to a mouse constant region, and (c) rearranges to form a hybrid light chain sequence comprising a human variable region operably linked to a mouse constant region, and wherein the mouse is incapable of forming an antibody that comprises a human variable region and a human constant region. Optionally, the mouse is heterozygous or homozygous in its germline for: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (c) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

In some such methods, wherein the non-human animal is a mouse that is at least partially derived from a BALB/c strain, wherein the mouse comprises a humanized immunoglobulin locus, wherein the foreign antigen of interest is all or part of a human protein that is orthologous to the first self-antigen, and the first target genomic locus comprises all or part of a gene encoding the first self-antigen, wherein the first guide RNA recognition site comprises the start codon for the gene encoding the first self-antigen and the second guide RNA recognition site comprises the stop codon for the gene encoding the first self-antigen, and wherein the modification comprises homozygous disruption of the start codon for the gene encoding the first self-antigen, whereby expression of the first self-antigen is eliminated. Optionally, the mouse comprises: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) a hybrid heavy chain locus comprising an insertion of the human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (c) a hybrid light chain locus comprising an insertion of human immunoglobulin light chain V and J gene segments, wherein the human V and J gene segments are operably linked to a mouse immunoglobulin light chain constant region gene sequence; wherein (b) rearranges to form a hybrid heavy chain sequence comprising a human variable region operably linked to a mouse constant region, and (c) rearranges to form a hybrid light chain sequence comprising a human variable region operably linked to a mouse constant region, and wherein the mouse is incapable of forming an antibody that comprises a human variable region and a human constant region. Optionally, the mouse is heterozygous or homozygous in its germline for: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (c) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

In some methods, the non-human animal pluripotent cell is a hybrid cell, and the method further comprises: (a') comparing the sequence of corresponding first and second chromosomes in a homologous chromosome pair within the first target genomic locus, and selecting a target region within the first target genomic locus prior to the contacting step (a) based on the target region having a higher percentage of sequence identity between the corresponding first and second chromosomes in the homologous chromosome pair relative to all or part of the remainder of the first target genomic locus. Optionally, the target region has a higher percentage of sequence identity between the corresponding first and second chromosomes in the homologous chromosome pair relative to the remainder of the first target genomic locus. Optionally, the target region has at least 99.9% sequence identity between the corresponding first and second chromosomes, and the remainder of the first target genomic locus has no more than 99.8% sequence identity between the corresponding first and second chromosomes. Optionally, the target region is identical in the corresponding first and second chromosomes in the homologous chromosome pair. Optionally, the target region is within the longest possible stretch of contiguous allelic sequence identity within the first target genomic locus.

In some such methods, the target region comprises, consists essentially of, or consists of the first guide RNA recognition sequence and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the first guide RNA recognition sequence, and the second guide RNA recognition sequence and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the second guide RNA recognition sequence. Optionally, step (a') comprises comparing two or more segments of the first target genomic locus, wherein each segment comprises, consists essentially of, or consists of a different guide RNA recognition sequence not present elsewhere in the genome and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the different guide RNA recognition sequence, and selecting as the target region the two segments having the highest percentage of sequence identity relative to the other segments. Optionally, the one or more segments comprise, consist essentially of, or consist of segments corresponding with each different guide RNA recognition sequence in the first target genomic locus but not present elsewhere in the genome.

In some such methods, the target region comprises, consists essentially of, or consists of the region between the first and second guide RNA recognition sequences. Optionally, step (a') comprises comparing two or more segments of the first target genomic locus, wherein each segment comprises, consists essentially of, or consists of the region between a different pair of guide RNA recognition sequences, wherein the guide RNA recognition sequences are not present elsewhere in the genome, and selecting as the target region the segment having the highest percentage of sequence identity relative to the other segments. Optionally, the one or more segments comprise, consist essentially of, or consist of segments corresponding with each different pair of guide RNA recognition sequences in the first target genomic locus, wherein the guide RNA recognition sequences are not present elsewhere in the genome.

In some such methods, the target region comprises, consists essentially of, or consists of the region between the first and second guide RNA recognition sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the first and second guide RNA recognition sequences. Optionally, step (a') comprises comparing two or more segments of the first target genomic locus, wherein each segment comprises, consists essentially of, or consists of the region between a different pair of guide RNA recognition sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the different pair of guide RNA recognition sequences, wherein the guide RNA recognition sequences are not present elsewhere in the genome, and selecting as the target region the segment having the highest percentage of sequence identity relative to the other segments. Optionally, the one or more segments comprise, consist essentially of, or consist of segments corresponding with each different pair of guide RNA recognition sequences in the first target genomic locus, wherein the guide RNA recognition sequences are not present elsewhere in the genome.

In some such methods, wherein the target region comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the first and second guide RNA recognition sequences. Optionally, step (a') comprises comparing two or more non-contiguous segments of the first target genomic locus, wherein each non-contiguous segment comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between a different pair of guide RNA recognition sequences, wherein the guide RNA recognition sequences are not present elsewhere in the genome, and selecting as the target region the non-contiguous segment having the highest percentage of sequence identity relative to the other non-contiguous segments. Optionally, the one or more non-contiguous segments comprise, consist essentially of, or consist of non-contiguous segments corresponding with each different pair of guide RNA recognition sequences in the first target genomic locus, wherein the guide RNA recognition sequences are not present elsewhere in the genome.

In some such methods, the target region comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the genomic region between the first and second guide RNA recognition sequences. Optionally, step (a') comprises comparing two or more non-contiguous segments of the first target genomic locus, wherein each non-contiguous segment comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the genomic region between a different pair of guide RNA recognition sequences, wherein the guide RNA recognition sequences are not present elsewhere in the genome, and selecting as the target region the non-contiguous segment having the highest percentage of sequence identity relative to the other non-contiguous segments. Optionally, the one or more non-contiguous segments comprise, consist essentially of, or consist of non-contiguous segments corresponding with each different pair of guide RNA recognition sequences in the first target genomic locus, wherein the guide RNA recognition sequences are not present elsewhere in the genome.

In some such methods, the target region in step (a') comprises, consists essentially of, or consists of the region flanked by the 5' and 3' target sequences. In some such methods, the target region in step (a') comprises, consists essentially of, or consists of the region flanked by and including the 5' and 3' target sequences. In some such methods, the target region in step (a') comprises, consists essentially of, or consists of the 5' target sequence and/or the 3' target sequence. Optionally, the target genomic locus in step (a') comprises, consists essentially of, or consists of the 5' target sequence and the 3' target sequence. In some such methods, the target region in step (a') comprises, consists essentially of, or consists of the region between the 5' and 3' target sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the region between the 5' and 3' target sequences. In some such methods, the target region in step (a') comprises, consists essentially of, or consists of the region between the 5' and 3' target sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the region between the 5' and 3' target sequences. In some such methods, the target region in step (a') comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the region between the 5' and 3' target sequences. In some such methods, the target region in step (a') comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the region between the 5' and 3' target sequences.

In another aspect, the invention provides a method of making a non-human animal with reduced tolerance of a foreign antigen of interest, comprising: (a) contacting the genome of a non-human animal one-cell stage embryo with: (i) a Cas9 protein; (ii) a first guide RNA that hybridizes to a first guide RNA recognition sequence within a first target genomic locus, wherein the first target genomic locus affects expression of a first self-antigen homologous to or sharing an epitope of interest with the foreign antigen of interest; and (iii) a second guide RNA that hybridizes to a second guide RNA recognition sequence within the first target genomic locus; wherein the first target genomic locus is modified in a pair of first and second chromosomes to produce a biallelic modification, wherein the modified non-human animal one-cell stage embryo in which expression of the first self-antigen is decreased; and (b) implanting the modified non-human animal one-cell stage embryo into a surrogate mother to produce a genetically modified F0 generation non-human animal in which the first target genomic locus is modified in the pair of first and second chromosomes such that expression of the first self-antigen is decreased. Optionally, the contacting comprises introducing the Cas9 protein, the first guide RNA, and the second guide RNA into the non-human animal one-cell stage embryo via nucleofection. Optionally, the Cas9 protein is introduced into the non-human animal one-cell stage embryo in the form of a DNA encoding the Cas9 protein, the first guide RNA is introduced into the non-human animal one-cell stage embryo in the form of a DNA encoding the first guide RNA, and the second guide RNA is introduced into the non-human animal one-cell stage embryo in the form of a DNA encoding the second guide RNA.

In some such methods, contacting step (a) further comprises contacting the genome with: (iv) a third guide RNA that hybridizes to a third guide RNA recognition sequence within the first target genomic locus; and/or (v) a fourth guide RNA that hybridizes to a fourth guide RNA recognition sequence within the first target genomic locus. In some such methods, contacting step (a) further comprises contacting the genome with: (iv) a third guide RNA that hybridizes to a third guide RNA recognition sequence within a second target genomic locus, wherein the second target genomic locus affects expression of the first self-antigen or a second self-antigen homologous to or sharing an epitope of interest with the foreign antigen of interest; and/or (v) a fourth guide RNA that hybridizes to a fourth guide RNA recognition sequence within the second target genomic locus.

In some such methods, the contacting step (a) further comprises contacting the genome with an exogenous repair template comprising a 5' homology arm that hybridizes to a 5' target sequence at the target genomic locus and a 3' homology arm that hybridizes to a 3' target sequence at the target genomic locus, wherein the exogenous repair template is between about 50 nucleotides to about 5 kb in length. Optionally, the exogenous repair template further comprises a nucleic acid insert flanked by the 5' homology arm and the 3' homology arm. In some such methods, the nucleic acid insert is homologous or orthologous to the first target genomic locus. In some such methods, the exogenous repair template is between about 50 nucleotides to about 1 kb in length. In some such methods, the exogenous repair template is between about 80 nucleotides to about 200 nucleotides in length. In some such methods, the exogenous repair template is a single-stranded oligodeoxynucleotide.

Some such methods further comprise: (c) immunizing the genetically modified F0 generation non-human animal produced in step (b) with the foreign antigen of interest; (d) maintaining the genetically modified F0 generation non-human animal under conditions sufficient to initiate an immune response to the foreign antigen of interest; and (e) obtaining a first nucleic acid sequence encoding a human immunoglobulin heavy chain variable domain and/or a second nucleic acid sequence encoding a human immunoglobulin light chain variable domain from the genetically modified F0 generation non-human animal.

In some such methods, antigen-binding proteins against the foreign antigen of interest obtained following immunization of the genetically modified F0 generation non-human animal with the foreign antigen of interest have a higher titer than antigen-binding proteins obtained following immunization of a control non-human animal that is wild type at the first target genomic locus. In some such methods, a more diverse repertoire of antigen-binding proteins against the foreign antigen of interest is obtained following immunization of the genetically modified F0 generation non-human animal with the foreign antigen of interest compared with antigen-binding proteins obtained following immunization of a control non-human animal that is wild type at the first target genomic locus.

In some such methods, expression of the first self-antigen is eliminated.

In some such methods, the foreign antigen of interest is an ortholog of the first self-antigen. In some such methods, the foreign antigen of interest comprises, consists essentially of, or consists of all or part of a human protein.

In some such methods, the first target genomic locus is modified to comprise an insertion of one or more nucleotides, a deletion of one or more nucleotides, or a replacement of one or more nucleotides. In some such methods, the first target genomic locus is modified to comprise a deletion of one or more nucleotides. In some such methods, contacting step (a) comprises contacting the genome with an exogenous repair template comprising a 5' homology arm that hybridizes to a 5' target sequence at the target genomic locus and a 3' homology arm that hybridizes to a 3' target sequence at the target genomic locus, provided that if the genome is in a one-cell stage embryo the exogenous repair template is no more than 5 kb in length, wherein the exogenous repair template comprises a nucleic acid insert flanked by the 5' homology arm and the 3' homology arm, wherein the nucleic acid insert is homologous or orthologous to the deleted nucleic acid sequence, and wherein the nucleic acid insert replaces the deleted nucleic acid sequence. In some such methods, the deletion is a precise deletion without random insertions and deletions (indels). In some such methods, contacting step (a) comprises contacting the genome with an exogenous repair template comprising a 5' homology arm that hybridizes to a 5' target sequence at the target genomic locus and a 3' homology arm that hybridizes to a 3' target sequence at the target genomic locus, provided that if the genome is in a one-cell stage embryo the exogenous repair template is no more than 5 kb in length, wherein the deleted nucleic acid sequence consists of the nucleic acid sequence between the 5' and 3' target sequences.

In some such methods, the first target genomic locus comprises, consists essentially of, or consists of all or part of a gene encoding the first self-antigen. In some such methods, the modification comprises, consists essentially of, or consists of homozygous deletion of all or part of the gene encoding the first self-antigen. In some such methods, the modification comprises, consists essentially of, or consists of homozygous disruption of the start codon of the gene encoding the first self-antigen.

In some such methods, the first guide RNA recognition sequence comprises the start codon for the gene encoding the first self-antigen or is within about 10, 20, 30, 40, 50, 100, 200, 300, 400, 500, or 1,000 nucleotides of the start codon, and the second guide RNA recognition sequence comprises the stop codon for the gene encoding the first self-antigen or is within about 10, 20, 30, 40, 50, 100, 200, 300, 400, 500, or 1,000 nucleotides of the stop codon. Optionally, the first guide RNA recognition sequence comprises the start codon, and the second guide RNA recognition sequence comprises the stop codon. In some such methods, the first guide RNA recognition sequence comprises a first Cas9 cleavage site and the second guide RNA recognition sequence comprises a second Cas9 cleavage site, wherein the first target genomic locus is modified to comprise a deletion between the first and second Cas9 cleavage sites. Optionally, the deletion is a precise deletion, wherein the deleted nucleic acid sequence consists of the nucleic acid sequence between the first and second Cas9 cleavage sites.

In some such methods, the first and second guide RNA recognition sequences are different, and each of the first and second guide RNA recognition sequences comprises the start codon for the gene encoding the first self-antigen or is within about 10, 20, 30, 40, 50, 100, 200, 300, 400, 500, or 1,000 nucleotides of the start codon. Optionally, each of the first and second guide RNA recognition sequences comprises the start codon.

In some such methods, the first nucleic acid sequence and/or second nucleic acid sequence are obtained from a lymphocyte of the genetically modified non-human animal or from a hybridoma produced from the lymphocyte.

In some such methods, the non-human animal comprises a humanized immunoglobulin locus. In some such methods, the non-human animal is a rodent. In some such methods, the rodent is a mouse. Optionally, the mouse strain comprises a BALB/c strain. Optionally, the mouse strain comprises BALB/c, C57BL/6, and 129 strains. Optionally, the mouse strain is 50% BALB/c, 25% C57BL/6, and 25% 129. Optionally, the MHC haplotype of the mouse is $MHC^{b/d}$.

In some such methods, the mouse comprises in its germline human unrearranged variable region gene segments inserted at an endogenous mouse immunoglobulin locus. Optionally, the human unrearranged variable region gene segments are heavy chain gene segments, and the mouse immunoglobulin locus is a heavy chain locus. Optionally, the human unrearranged variable region gene segments are light chain segments, and the mouse immunoglobulin locus is a light chain locus. Optionally, the light chain gene segments are human kappa or lambda light chain gene segments. In some such methods, the mouse comprises in its germline human unrearranged variable region gene segments operably linked to a mouse constant region gene, wherein the mouse lacks a human constant region gene, and wherein the mouse constant region gene is at an endogenous mouse immunoglobulin locus. In some such methods, the mouse comprises: (a) a hybrid heavy chain locus comprising an insertion of the human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (b) a hybrid light chain locus comprising an insertion of human immunoglobulin light chain V and J gene segments, wherein the human V and J gene segments are operably linked to a mouse immunoglobulin light chain constant region gene sequence; wherein (a) rearranges to form a hybrid heavy chain sequence comprising a human variable region operably linked to a mouse constant region, and (b) rearranges to form a hybrid light chain sequence comprising a human variable region operably linked to a mouse constant region, and wherein the mouse is incapable of forming an antibody that comprises a human variable region and a human constant region. In some such methods, the mouse comprises a modification of an immunoglobulin heavy chain locus, wherein the modification reduces or eliminates endogenous ADAM6 function, and wherein the mouse comprises an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse. Optionally, the ectopic nucleic acid sequence encoding the mouse ADAM6 protein, ortholog thereof, homolog thereof, or fragment thereof is present at the human heavy chain variable region locus. Optionally, the ectopic nucleic acid sequence encoding the mouse ADAM6 protein, ortholog thereof, homology thereof, or fragment thereof is present at a location other than the human heavy chain variable region locus.

In some such methods, the mouse comprises in its germline a humanized immunoglobulin light chain variable locus comprising no more than one or no more than two rearranged human light chain V/J sequences operably linked to a light chain constant region. Optionally, the light chain constant region gene is a mouse gene. In some such methods, the mouse further comprises a humanized immunoglobulin heavy chain variable locus comprising at least one unrearranged human V, at least one unrearranged human D, and at least one unrearranged human J segment operably linked to a heavy chain constant region gene. Optionally, the heavy chain constant region gene is a mouse gene. In some such methods, the mouse comprises a humanized heavy chain immunoglobulin variable locus and a humanized light chain immunoglobulin variable locus, wherein the mouse expresses a single light chain. In some such methods, the mouse comprises: (a) a single rearranged human immunoglobulin light chain variable region ($V_L/J_L$) that encodes a human $V_L$ domain of an immunoglobulin light chain, wherein the single rearranged human $V_L/J_L$ region is selected from a human Vκ1-39/J gene segment or a human Vκ3-20/J gene segment; and (b) a replacement of endogenous heavy chain variable ($V_H$) gene segments with one or more human $V_H$ gene segments, wherein the human $V_H$ gene segments are operably linked to an endogenous heavy chain constant ($C_H$) region gene, and the human $V_H$ gene segments are capable of rearranging and forming a human/mouse chimeric heavy chain gene. In some such methods, the mouse expresses a population of antibodies, and the mouse's germline includes only a single immunoglobulin kappa light chain variable region gene that is a rearranged human germline kappa light chain variable region gene, wherein the mouse is either heterozygous for the single immunoglobulin kappa light chain variable region gene in that it contains only one copy, or is homozygous for the single immunoglobulin kappa light chain variable region gene in that it contains two copies, the mouse being characterized by active affinity maturation so that: (i) each immunoglobulin kappa light chain of the population comprises a light chain variable domain that is encoded by the rearranged human germline kappa light chain variable region gene, or by a somatically mutated variant thereof; (ii) the population includes antibodies comprising the immunoglobulin kappa light chains whose light chain variable domain is encoded by the rearranged human germline kappa light chain variable region gene and antibodies comprising the immunoglobulin kappa light chains whose light chain variable domain is encoded by the somatically mutated variants thereof; and (iii) the mouse generates a diverse collection of somatically mutated high affinity heavy chains that successfully pair with the immunoglobulin kappa light chains to form the antibodies of the population. Optionally, the mouse is heterozygous or homozygous in its germline for: (a) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (b) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene. In some such methods, the mouse comprises a modification of an immunoglobulin heavy chain locus, wherein the modification reduces or eliminates endogenous ADAM6 function, and wherein the mouse comprises an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse. Optionally, the ectopic nucleic acid sequence encoding the mouse ADAM6 protein, ortholog thereof, homolog thereof, or fragment thereof is present at the human heavy chain variable region locus. Optionally, the ectopic nucleic acid sequence encoding the mouse ADAM6 protein, ortholog thereof, homology thereof, or fragment thereof is present at a location other than the human heavy chain variable region locus.

In some such methods, the mouse has a genome comprising a modification of an immunoglobulin heavy chain locus, wherein the modification reduces or eliminates endogenous ADAM6 function, and the mouse further comprises a nucleic acid sequence encoding a non-human animal ADAM6 protein or an ortholog or homolog thereof or a functional fragment of the corresponding ADAM6 protein. Optionally, the mouse's genome comprises: (a) ectopic placement of an ADAM6 gene; and (b) a human immunoglobulin heavy chain variable region locus comprising an insertion of one or more human $V_H$ gene segments, one or more human $D_H$ gene segments, and one or more human $J_H$ gene segments into the endogenous non-human animal heavy chain locus, wherein the human $V_H$, $D_H$ and $J_H$ gene segments are operably linked to a heavy chain constant region gene; so that the mouse is characterized in that: (i) it is fertile; and (ii) when it is immunized with an antigen, it generates antibodies comprising heavy chain variable domains encoded by the one or more human $V_H$, one or more human $D_H$, and one or more human $J_H$ gene segments, operably linked to heavy chain constant domains encoded by the heavy chain constant region gene, wherein the antibodies show specific binding to the antigen.

In some such methods, the non-human animal is a mouse that is at least partially derived from a BALB/c strain, wherein the mouse comprises a humanized immunoglobulin locus, wherein the foreign antigen of interest is all or part of a human protein that is orthologous to the first self-antigen, and the first target genomic locus comprises all or part of a gene encoding the first self-antigen, wherein the first guide RNA recognition site comprises the start codon for the gene encoding the first self-antigen and the second guide RNA recognition site comprises the stop codon for the gene encoding the first self-antigen, and wherein the modification comprises a homozygous deletion of all or part of the gene encoding the first self-antigen, whereby expression of the first-self-antigen is eliminated. Optionally, the mouse comprises: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) a hybrid heavy chain locus comprising an insertion of the human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (c) a hybrid light chain locus comprising an insertion of human immunoglobulin light chain V and J gene segments, wherein the human V and J gene segments are operably linked to a mouse immunoglobulin light chain constant region gene sequence; wherein (b) rearranges to form a hybrid heavy chain sequence comprising a human variable region operably linked to a mouse constant region, and (c) rearranges to form a hybrid light chain sequence comprising a human variable region operably linked to a mouse constant region, and wherein the mouse is incapable of forming an antibody that comprises a human variable region and a human constant region. Optionally, the mouse is heterozygous or homozygous in its germline for: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (c) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

In some such methods, wherein the non-human animal is a mouse that is at least partially derived from a BALB/c strain, wherein the mouse comprises a humanized immunoglobulin locus, wherein the foreign antigen of interest is all or part of a human protein that is orthologous to the first self-antigen, and the first target genomic locus comprises all or part of a gene encoding the first self-antigen, wherein the first guide RNA recognition site comprises the start codon for the gene encoding the first self-antigen and the second guide RNA recognition site comprises the stop codon for the gene encoding the first self-antigen, and wherein the modification comprises homozygous disruption of the start codon for the gene encoding the first self-antigen, whereby expression of the first self-antigen is eliminated. Optionally, the mouse comprises: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) a hybrid heavy chain locus comprising an insertion of the human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (c) a hybrid light chain locus comprising an insertion of human immunoglobulin light chain V and J gene segments, wherein the human V and J gene segments are operably linked to a mouse immunoglobulin light chain constant region gene sequence; wherein (b) rearranges to form a hybrid heavy chain sequence comprising a human variable region operably linked to a mouse constant region, and (c) rearranges to form a hybrid light chain sequence comprising a human variable region operably linked to a mouse constant region, and wherein the mouse is incapable of forming an antibody that comprises a human variable region and a human constant region. Optionally, the mouse is heterozygous or homozygous in its germline for: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (c) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

In some methods, the non-human animal one-cell stage embryo is a hybrid one-cell stage embryo, and the method further comprises: (a') comparing the sequence of corresponding first and second chromosomes in a homologous chromosome pair within the first target genomic locus, and selecting a target region within the first target genomic locus prior to the contacting step (a) based on the target region having a higher percentage of sequence identity between the corresponding first and second chromosomes in the homologous chromosome pair relative to all or part of the remainder of the first target genomic locus. Optionally, the target region has a higher percentage of sequence identity between the corresponding first and second chromosomes in the homologous chromosome pair relative to the remainder of the first target genomic locus. Optionally, the target region has at least 99.9% sequence identity between the corresponding first and second chromosomes, and the remainder of the first target genomic locus has no more than 99.8% sequence identity between the corresponding first and second chromosomes. Optionally, the target region is identical in the corresponding first and second chromosomes in the homologous chromosome pair. Optionally, the target region is within the longest possible stretch of contiguous allelic sequence identity within the first target genomic locus.

In some such methods, the target region comprises, consists essentially of, or consists of the first guide RNA recognition sequence and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the first guide RNA recognition sequence, and the second guide RNA recognition sequence and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the second guide RNA recognition sequence. Optionally, step (a') comprises comparing two or more segments of the first target genomic locus, wherein each segment comprises, consists essentially of, or consists of a different guide RNA recognition sequence not present elsewhere in the genome and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the different guide RNA recognition sequence, and selecting as the target region the two segments having the highest percentage of sequence identity relative to the other segments. Optionally, the one or more segments comprise, consist essentially of, or consist of segments corresponding with each different guide RNA recognition sequence in the first target genomic locus but not present elsewhere in the genome.

In some such methods, the target region comprises, consists essentially of, or consists of the region between the first and second guide RNA recognition sequences. Optionally, step (a') comprises comparing two or more segments of the first target genomic locus, wherein each segment comprises, consists essentially of, or consists of the region between a different pair of guide RNA recognition sequences, wherein the guide RNA recognition sequences are not present elsewhere in the genome, and selecting as the target region the segment having the highest percentage of sequence identity relative to the other segments. Optionally, the one or more segments comprise, consist essentially of, or consist of segments corresponding with each different pair of guide RNA recognition sequences in the first target genomic locus, wherein the guide RNA recognition sequences are not present elsewhere in the genome.

In some such methods, the target region comprises, consists essentially of, or consists of the region between the first and second guide RNA recognition sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the first and second guide RNA recognition sequences. Optionally, step (a') comprises comparing two or more segments of the first target genomic locus, wherein each segment comprises, consists essentially of, or consists of the region between a different pair of guide RNA recognition sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the different pair of guide RNA recognition sequences, wherein the guide RNA recognition sequences are not present elsewhere in the genome, and selecting as the target region the segment having the highest percentage of sequence identity relative to the other segments. Optionally, the one or more segments comprise, consist essentially of, or consist of segments corresponding with each different pair of guide RNA recognition sequences in the first target genomic locus, wherein the guide RNA recognition sequences are not present elsewhere in the genome.

In some such methods, wherein the target region comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the first and second guide RNA recognition sequences. Optionally, step (a') comprises comparing two or more non-contiguous segments of the first target genomic locus, wherein each non-contiguous segment comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between a different pair of guide RNA recognition sequences, wherein the guide RNA recognition sequences are not present elsewhere in the genome, and selecting as the target region the non-contiguous segment having the highest percentage of sequence identity relative to the other non-contiguous segments. Optionally, the one or more non-contiguous segments comprise, consist essentially of, or consist of non-contiguous segments corresponding with each different pair of guide RNA recognition sequences in the first target genomic locus, wherein the guide RNA recognition sequences are not present elsewhere in the genome.

In some such methods, the target region comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the genomic region between the first and second guide RNA recognition sequences. Optionally, step (a') comprises comparing two or more non-contiguous segments of the first target genomic locus, wherein each non-contiguous segment comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the genomic region between a different pair of guide RNA recognition sequences, wherein the guide RNA recognition sequences are not present elsewhere in the genome, and selecting as the target region the non-contiguous segment having the highest percentage of sequence identity relative to the other non-contiguous segments. Optionally, the one or more non-contiguous segments comprise, consist essentially of, or consist of non-contiguous segments corresponding with each different pair of guide RNA recognition sequences in the first target genomic locus, wherein the guide RNA recognition sequences are not present elsewhere in the genome.

In some such methods, the target region in step (a') comprises, consists essentially of, or consists of the region flanked by the 5' and 3' target sequences. In some such methods, the target region in step (a') comprises, consists essentially of, or consists of the region flanked by and including the 5' and 3' target sequences. In some such methods, the target region in step (a') comprises, consists essentially of, or consists of the 5' target sequence and/or the 3' target sequence. Optionally, the target genomic locus in step (a') comprises, consists essentially of, or consists of the 5' target sequence and the 3' target sequence. In some such methods, the target region in step (a') comprises, consists essentially of, or consists of the region between the 5' and 3' target sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the region between the 5' and 3' target sequences. In some such methods, the target region in step (a') comprises, consists essentially of, or consists of the region between the 5' and 3' target sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the region between the 5' and 3' target sequences. In some such methods, the target region in step (a') comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the region between the 5' and 3' target sequences. In some such methods, the target region in step (a') comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on each side of the region between the 5' and 3' target sequences.

In another aspect, provided is a method of generating antigen-binding proteins against a foreign antigen of interest, comprising: (a) making a genetically modified non-human animal with reduced tolerance of a foreign antigen of interest, comprising: (i) introducing into a non-human animal one-cell stage embryo or a non-human animal pluripotent cell that is not a one-cell stage embryo: (I) a Cas9 protein; (II) a first guide RNA that hybridizes to a first guide RNA recognition sequence within a target genomic locus, wherein the target genomic locus comprises all or part of a gene encoding a self-antigen homologous to or sharing an epitope of interest with the foreign antigen of interest; and (III) a second guide RNA that hybridizes to a second guide RNA recognition sequence within the target genomic locus; wherein the target genomic locus is modified in a pair of corresponding first and second chromosomes to produce a modified non-human animal one-cell stage embryo or a modified non-human animal pluripotent cell with a biallelic modification, wherein expression of the self-antigen is eliminated; and (ii) producing a genetically modified F0 generation non-human animal from the modified non-human animal one-cell stage embryo or the modified non-human animal pluripotent cell, wherein the target genomic locus is modified in the pair of corresponding first and second chromosomes in the genetically modified F0 generation non-human animal such that expression of the self-antigen is eliminated; (b) immunizing the genetically modified F0 generation non-human animal produced in step (a) with the foreign antigen of interest; and (c) maintaining the genetically modified F0 generation non-human animal under conditions sufficient to initiate an immune response to the foreign antigen of interest, wherein the genetically modified F0 generation non-human animal produces antigen-binding proteins against the foreign antigen of interest.

In some methods, the cell in step (a)(i) is the non-human animal pluripotent stem cell, and the producing the genetically modified F0 generation non-human animal in step (a)(ii) comprises: (I) introducing the modified non-human animal pluripotent cell into a host embryo; and (II) implanting the host embryo into a surrogate mother to produce the genetically modified F0 generation non-human animal in which the target genomic locus is modified in the pair of corresponding first and second chromosomes such that expression of the self-antigen is eliminated. Optionally, the pluripotent cell is an embryonic stem (ES) cell. In some methods, the cell in step (a)(i) is the non-human animal one-cell stage embryo, and the producing the genetically modified F0 generation non-human animal in step (a)(ii) comprises implanting the modified non-human animal one-cell stage embryo into a surrogate mother to produce the genetically modified F0 generation non-human animal in which the target genomic locus is modified in the pair of corresponding first and second chromosomes such that expression of the self-antigen is eliminated.

Some such methods further comprise making a hybridoma from B cells isolated from the immunized, genetically modified F0 generation non-human animal. Some such methods further comprise obtaining from the immunized, genetically modified F0 generation non-human animal a first nucleic acid sequence encoding an immunoglobulin heavy chain variable domain of one of the antigen-binding proteins against the foreign antigen of interest and/or a second nucleic acid sequence encoding an immunoglobulin light chain variable domain of one of the antigen-binding proteins against the foreign antigen of interest. Optionally, the first nucleic acid sequence and/or the second nucleic acid sequence are obtained from a lymphocyte (e.g., B cell) of the genetically modified F0 generation non-human animal or from a hybridoma produced from the lymphocyte. Optionally, the genetically modified F0 generation non-human animal comprises a humanized immunoglobulin locus, and wherein the first nucleic acid sequence encodes a human immunoglobulin heavy chain variable domain, and the second nucleic acid sequence encodes a human immunoglobulin light chain variable domain.

In some such methods, the antigen-binding proteins produced by the genetically modified F0 generation non-human animal against the foreign antigen of interest have a higher titer than antigen-binding proteins produced by a control non-human animal that is wild type at the target genomic locus following immunization of the control non-human animal with the foreign antigen of interest. In some such methods, a more diverse repertoire of antigen-binding proteins against the foreign antigen of interest is produced by the genetically modified F0 generation non-human animal following immunization of the genetically modified F0 generation non-human animal with the foreign antigen of interest compared with antigen-binding proteins produced by a control non-human animal that is wild type at the target genomic locus following immunization of the control non-human animal with the foreign antigen of interest. In some such methods, the antigen-binding proteins produced by the genetically modified F0 generation non-human animal against the foreign antigen of interest use a greater diversity of heavy chain V gene segments and/or light chain V gene segments compared with antigen-binding proteins produced by a control non-human animal that is wild type at the target genomic locus following immunization of the control non-human animal with the foreign antigen of interest. In some such methods, some of the antigen-binding proteins produced by the genetically modified F0 generation non-human animal against the foreign antigen of interest cross-react with the self-antigen.

In some such methods, the first guide RNA recognition sequence is 5' of the second guide RNA recognition sequence in the target genomic locus, and step (a)(i) further comprises performing a retention assay to determine the copy number is two for a region 5' and within about 1 kb of the first guide RNA recognition sequence and/or for a region 3' and within about 1 kb of the second guide RNA recognition sequence.

In some such methods, the foreign antigen of interest is an ortholog of the self-antigen. In some such methods, the foreign antigen of interest comprises of all or part of a human protein.

In some such methods, the target genomic locus is modified to comprise an insertion of one or more nucleotides, a deletion of one or more nucleotides, or a replacement of one or more nucleotides. Optionally, the deletion is a precise deletion without random insertions and deletions (indels).

In some such methods, the first guide RNA recognition sequence comprises the start codon for the gene encoding the self-antigen or is within about 10, 20, 30, 40, 50, 100, 200, 300, 400, 500, or 1,000 nucleotides of the start codon, and the second guide RNA recognition sequence comprises the stop codon for the gene encoding the self-antigen or is within about 10, 20, 30, 40, 50, 100, 200, 300, 400, 500, or 1,000 nucleotides of the stop codon. In some such methods, the first and second guide RNA recognition sequences are different, and each of the first and second guide RNA recognition sequences comprises the start codon for the gene encoding the self-antigen or is within about 10, 20, 30, 40, 50, 100, 200, 300, 400, 500, or 1,000 nucleotides of the start codon.

In some such methods, the target genomic locus is modified to comprise a biallelic deletion of between about 0.1 kb to about 200 kb. In some such methods, the modification comprises a biallelic deletion of all or part of the gene encoding the self-antigen. In some such methods, the modification comprises a biallelic disruption of the start codon of the gene encoding the self-antigen.

In some such methods, the introducing step (a)(i) further comprises introducing into the non-human animal pluripotent cell or the non-human animal one-cell stage embryo:

(iv) a third guide RNA that hybridizes to a third guide RNA recognition sequence within the target genomic locus; and/or (v) a fourth guide RNA that hybridizes to a fourth guide RNA recognition sequence within the target genomic locus.

In some such methods, the cell in step (a)(i) is the non-human animal pluripotent stem cell, and the Cas9 protein, the first guide RNA, and the second guide RNA are each introduced into the non-human animal pluripotent stem cell in the form of DNA. In some such methods, the cell in step (a)(i) is the non-human animal pluripotent stem cell, and the Cas9 protein, the first guide RNA, and the second guide RNA are each introduced into the non-human animal pluripotent stem cell by electroporation or nucleofection. In some such methods, the cell in step (a)(i) is the non-human animal one-cell stage embryo, and the Cas9 protein, the first guide RNA, and the second guide RNA are each introduced into the non-human animal one-cell stage embryo in the form of RNA. In some such methods, the cell in step (a)(i) is the non-human animal one-cell stage embryo, and the Cas9 protein, the first guide RNA, and the second guide RNA are introduced into the non-human animal one-cell stage embryo by pronuclear injection or cytoplasmic injection.

In some such methods, an exogenous repair template is not introduced in step (a)(i). In some such methods, the introducing step (a)(i) further comprises introducing into the non-human animal pluripotent cell or the non-human animal one-cell stage embryo an exogenous repair template comprising a 5' homology arm that hybridizes to a 5' target sequence at the target genomic locus and a 3' homology arm that hybridizes to a 3' target sequence at the target genomic locus, provided that if the cell in step (a)(i) is the non-human animal one-cell stage embryo, the exogenous repair template is no more than about 5 kb in length. Optionally, the exogenous repair template further comprises a nucleic acid insert flanked by the 5' homology arm and the 3' homology arm. Optionally, the nucleic acid insert is homologous or orthologous to the target genomic locus. Optionally, the exogenous repair template is between about 50 nucleotides to about 1 kb in length. Optionally, the exogenous repair template is between about 80 nucleotides to about 200 nucleotides in length. Optionally, the exogenous repair template is a single-stranded oligodeoxynucleotide. Optionally, the cell in step (a)(i) is the non-human animal pluripotent cell, and (a) the exogenous repair template is a large targeting vector (LTVEC) that is at least 10 kb in length; or (b) the exogenous repair template is an LTVEC, wherein the sum total of the 5' and 3' homology arms of the LTVEC is at least 10 kb in length. Optionally, the target genomic locus is modified to comprise a deletion of one or more nucleotides, and the deleted nucleic acid sequence consists of the nucleic acid sequence between the 5' and 3' target sequences. Optionally, the exogenous repair template comprises a nucleic acid insert flanked by the 5' homology arm and the 3' homology arm, the nucleic acid insert is homologous or orthologous to the deleted nucleic acid sequence, the target genomic locus is modified to comprise a deletion of one or more nucleotides, and the nucleic acid insert replaces the deleted nucleic acid sequence.

In some such methods, the non-human animal comprises a humanized immunoglobulin locus. In some such methods, the non-human animal is a rodent. Optionally, the rodent is a mouse. Optionally, the mouse strain comprises a BALB/c strain. Optionally, the mouse strain comprises BALB/c, C57BL/6, and 129 strains. Optionally, the mouse strain is 50% BALB/c, 25% C57BL/6, and 25% 129. Optionally, the WIC haplotype of the mouse is $MHC^{b/d}$.

In some such methods, the mouse comprises in its germline human unrearranged variable region gene segments inserted at an endogenous mouse immunoglobulin locus. Optionally, the human unrearranged variable region gene segments are heavy chain gene segments, and the mouse immunoglobulin locus is a heavy chain locus, and/or wherein the human unrearranged variable region gene segments are kappa or lambda light chain segments, and the mouse immunoglobulin locus is a light chain locus. Optionally, the mouse comprises in its germline human unrearranged variable region gene segments operably linked to a mouse constant region gene, wherein the mouse lacks a human constant region gene, and wherein the mouse constant region gene is at an endogenous mouse immunoglobulin locus. Optionally, the mouse comprises: (a) a hybrid heavy chain locus comprising an insertion of human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (b) a hybrid light chain locus comprising an insertion of human immunoglobulin light chain V and J gene segments, wherein the human V and J gene segments are operably linked to a mouse immunoglobulin light chain constant region gene sequence; wherein (a) rearranges to form a hybrid heavy chain sequence comprising a human variable region operably linked to a mouse constant region, and (b) rearranges to form a hybrid light chain sequence comprising a human variable region operably linked to a mouse constant region, and wherein the mouse is incapable of forming an antibody that comprises a human variable region and a human constant region.

In some such methods, the mouse comprises in its germline a humanized immunoglobulin light chain variable locus comprising no more than one or no more than two rearranged human light chain V/J sequences operably linked to a mouse light chain constant region, and wherein the mouse further comprises a humanized immunoglobulin heavy chain variable locus comprising at least one unrearranged human V, at least one unrearranged human D, and at least one unrearranged human J segment operably linked to a mouse heavy chain constant region gene. Optionally, the mouse comprises a humanized heavy chain immunoglobulin variable locus and a humanized light chain immunoglobulin variable locus, wherein the mouse expresses a single light chain. Optionally, the mouse comprises: (a) a single rearranged human immunoglobulin light chain variable region ($V_L/J_L$) that encodes a human $V_L$ domain of an immunoglobulin light chain, wherein the single rearranged human $V_L/J_L$ region is selected from a human Vκ1-39/Jκ5 gene segment or a human Vκ3-20/Jκ1 gene segment; and (b) a replacement of endogenous heavy chain variable ($V_H$) gene segments with one or more human $V_H$ gene segments, wherein the human $V_H$ gene segments are operably linked to an endogenous heavy chain constant ($C_H$) region gene, and the human $V_H$ gene segments are capable of rearranging and forming a human/mouse chimeric heavy chain gene. Optionally, the mouse expresses a population of antibodies, and the mouse's germline includes only a single immunoglobulin kappa light chain variable region gene that is a rearranged human germline kappa light chain variable region gene, wherein the mouse is either heterozygous for the single immunoglobulin kappa light chain variable region gene in that it contains only one copy, or is homozygous for the single immunoglobulin kappa light chain variable region gene in that it contains two copies, the mouse being characterized by active affinity maturation so that: (i) each immunoglobulin kappa light chain of the population comprises a light chain variable domain that is encoded by the rearranged human germline kappa light chain variable region gene, or by a somatically mutated variant thereof; (ii) the population includes antibodies comprising the immunoglobulin kappa light chains whose light chain variable domain is encoded by the rearranged human germline kappa light chain variable region gene and antibodies comprising the immunoglobulin kappa light chains whose light chain variable domain is encoded by the somatically mutated variants thereof; and (iii) the mouse generates a diverse collection of somatically mutated high affinity heavy chains that successfully pair with the immunoglobulin kappa light chains to form the antibodies of the population. Optionally, the mouse is heterozygous or homozygous in its germline for: (a) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (b) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

In some such methods, the mouse comprises a modification of an immunoglobulin heavy chain locus, wherein the modification reduces or eliminates endogenous ADAM6 function, wherein the mouse comprises an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse, and wherein the ectopic nucleic acid sequence encoding the mouse ADAM6 protein, ortholog thereof, homolog thereof, or fragment thereof is present at the human heavy chain variable region locus.

In some such methods, the non-human animal is a mouse that is at least partially derived from a BALB/c strain, and the mouse comprises a humanized immunoglobulin locus, wherein the foreign antigen of interest is all or part of a human protein that is orthologous to the self-antigen, wherein the first guide RNA recognition sequence comprises the start codon for the gene encoding the self-antigen or is within about 10, 20, 30, 40, 50, 100, 200, 300, 400, 500, or 1,000 nucleotides of the start codon and the second guide RNA recognition sequence comprises the stop codon for the gene encoding the self-antigen or is within about 10, 20, 30, 40, 50, 100, 200, 300, 400, 500, or 1,000 nucleotides of the stop codon, and wherein the modification comprises a biallelic deletion of all or part of the gene encoding the self-antigen, whereby expression of the self-antigen is eliminated. In some such methods, the non-human animal is a mouse that is at least partially derived from a BALB/c strain, and the mouse comprises a humanized immunoglobulin locus, wherein the foreign antigen of interest is all or part of a human protein that is orthologous to the self-antigen, wherein the first guide RNA recognition sequence comprises the start codon for the gene encoding the self-antigen and the second guide RNA recognition sequence comprises the stop codon for the gene encoding the self-antigen or is within about 10, 20, 30, 40, 50, 100, 200, 300, 400, 500, or 1,000 nucleotides of the start codon, and wherein the modification comprises biallelic disruption of the start codon for the gene encoding the self-antigen, whereby expression of the self-antigen is eliminated. Optionally, the mouse comprises: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) a hybrid heavy chain locus comprising an insertion of human immunoglobulin heavy chain V, D, and J gene segments, wherein the human heavy chain immunoglobulin V, D, and J gene segments are operably linked to a mouse immunoglobulin heavy chain gene, wherein the mouse immunoglobulin heavy chain gene is at an endogenous mouse immunoglobulin locus; and (c) a hybrid light chain locus comprising an insertion of human immunoglobulin light chain V and J gene segments, wherein the human V and J gene segments are operably linked to a mouse immunoglobulin light chain constant region gene sequence; wherein (b) rearranges to form a hybrid heavy chain sequence comprising a human variable region operably linked to a mouse constant region, and (c) rearranges to form a hybrid light chain sequence comprising a human variable region operably linked to a mouse constant region, and wherein the mouse is incapable of forming an antibody that comprises a human variable region and a human constant region. Optionally, the mouse is heterozygous or homozygous in its germline for: (a) an ectopic nucleic acid sequence encoding a mouse ADAM6 protein, an ortholog thereof, a homolog thereof, or a fragment thereof, wherein the ADAM6 protein, ortholog thereof, homolog thereof, or fragment thereof is functional in a male mouse; (b) an insertion at an endogenous mouse κ immunoglobulin light chain variable region locus of a rearranged Vκ/Jκ sequence comprising: (i) a single human germline Vκ sequence, which single human germline Vκ sequence is present in SEQ ID NO: 148 or SEQ ID NO: 149; and (ii) a single human germline Jκ sequence, wherein the rearranged Vκ/Jκ sequence is operably linked to the endogenous mouse κ constant region; and (c) an insertion at an endogenous mouse immunoglobulin heavy chain variable region locus of a plurality of human immunoglobulin heavy chain variable region gene segments, wherein the human immunoglobulin heavy chain variable region gene segments are operably linked to an endogenous mouse immunoglobulin heavy chain constant region, and the human immunoglobulin heavy chain variable region gene segments are capable of rearranging and forming a rearranged human/mouse chimeric immunoglobulin heavy chain gene.

In some such methods, the non-human animal pluripotent cell is a hybrid cell or the non-human mammalian one-cell stage embryo is a hybrid one-cell stage embryo, and wherein the method further comprises: (a') comparing the sequence of the pair of corresponding first and second chromosomes within the target genomic locus, and selecting a target region within the target genomic locus prior to the contacting step (a) based on the target region having a higher percentage of sequence identity between the pair of corresponding first and second chromosomes relative to all or part of the remainder of the target genomic locus, wherein the target region comprises: the first guide RNA recognition sequence and at least 10 bp, 20 bp, 30 bp, 40 bp, 50 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6, kb, 7 kb, 8 kb, 9 kb, or 10 kb of flanking sequence on the 5' side, the 3' side, or each side of the first guide RNA recognition sequence, and/or the second guide RNA recognition sequence and at least 10 bp, 20 bp, 30 bp, 40 bp, 50 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6, kb, 7 kb, 8 kb, 9 kb, or 10 kb of flanking sequence on the 5' side, the 3' side, or each side of the second guide RNA recognition sequence. Optionally, the target region has a higher percentage of sequence identity between the pair of corresponding first and second relative to the remainder of the target genomic locus. Optionally, the target region has at least 99.9% sequence identity between the pair of corresponding first and second chromosomes, and the remainder of the target genomic locus has no more than 99.8% sequence identity between the pair of corresponding first and second chromosomes.

In another aspect, provided are methods of making a genetically modified non-human animal with reduced tolerance of a foreign antigen of interest, comprising: (a) introducing into a non-human animal one-cell stage embryo or a non-human animal pluripotent cell that is not a one-cell stage embryo: (i) a Cas9 protein; (ii) a first guide RNA that hybridizes to a first guide RNA recognition sequence within a target genomic locus, wherein the target genomic locus comprises all or part of a gene encoding a self-antigen homologous to or sharing an epitope of interest with the foreign antigen of interest; and (iii) a second guide RNA that hybridizes to a second guide RNA recognition sequence within the target genomic locus; wherein the target genomic locus is modified in a pair of corresponding first and second chromosomes to produce a modified non-human animal one-cell stage embryo or a modified non-human animal pluripotent cell with a biallelic modification, wherein expression of the self-antigen is eliminated; and (b) producing a genetically modified F0 generation non-human animal from the modified non-human animal one-cell stage embryo or the modified non-human animal pluripotent cell, wherein the target genomic locus is modified in the pair of corresponding first and second chromosomes in the genetically modified F0 generation non-human animal such that expression of the self-antigen is eliminated.

Such methods can comprise, for example, any of the variations disclosed above for the methods of generating antigen-binding proteins against a foreign antigen of interest. For example, in some such methods, the cell in step (a) is the non-human animal pluripotent stem cell, and the producing the genetically modified F0 generation non-human animal in step (b) comprises: (I) introducing the modified non-human animal pluripotent cell into a host embryo; and (II) implanting the host embryo into a surrogate mother to produce the genetically modified F0 generation non-human animal in which the target genomic locus is modified in the pair of corresponding first and second chromosomes such that expression of the self-antigen is eliminated. Optionally, the pluripotent cell is an embryonic stem (ES) cell. In some such methods, the cell in step (a) is the non-human animal one-cell stage embryo, and the producing the genetically modified F0 generation non-human animal in step (b) comprises implanting the modified non-human animal one-cell stage embryo into a surrogate mother to produce the genetically modified F0 generation non-human animal in which the target genomic locus is modified in the pair of corresponding first and second chromosomes such that expression of the self-antigen is eliminated. In some such methods, the foreign antigen of interest is an ortholog of the self-antigen. In some such methods, the first guide RNA recognition sequence comprises the start codon for the gene encoding the self-antigen or is within about 10, 20, 30, 40, 50, 100, 200, 300, 400, 500, or 1,000 nucleotides of the start codon, and the second guide RNA recognition sequence comprises the stop codon for the gene encoding the self-antigen or is within about 10, 20, 30, 40, 50, 100, 200, 300, 400, 500, or 1,000 nucleotides of the stop codon. In some such methods, the first and second guide RNA recognition sequences are different, and each of the first and second guide RNA recognition sequences comprises the start codon for the gene encoding the self-antigen or is within about 10, 20, 30, 40, 50, 100, 200, 300, 400, 500, or 1,000 nucleotides of the start codon. In some such methods, the first guide RNA recognition sequence is 5' of the second guide RNA recognition sequence in the target genomic locus, and step (a)(i) further comprises performing a retention assay to determine the copy number is two for a region 5' and within about 1 kb of the first guide RNA recognition sequence and/or for a region 3' and within about 1 kb of the second guide RNA recognition sequence. In some such methods, the modification comprises a biallelic deletion of all or part of the gene encoding the self-antigen. In some such methods, the modification comprises a biallelic disruption of the start codon of the gene encoding the self-antigen. In some such methods, the non-human animal is a mouse.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 9A shows a general schematic for simultaneous deletion of a mouse gene and replacement with a corresponding human version using an LTVEC and two guide RNAs (guide RNAs A and B). The LTVEC is shown in the top portion of FIG. 9A, and the mouse gene locus is shown in the bottom portion of FIG. 9A. The positions of the Cas9 cleavage sites guided by the two guide RNAs are indicated by the arrows below the mouse gene sequence.

FIGS. 9B-9E show the unique biallelic modifications (allele types) that occur at a greater frequency when two guide RNAs are used. The thick lines with diagonal hatching indicate the mouse gene, the dotted lines indicate deletions in the mouse gene, and the thick black lines indicate insertion of the human gene. FIG. 9B shows homozygous collapsed alleles (large CRISPR-induced deletion). FIG. 9C shows homozygous targeted alleles. FIG. 9D shows hemizygous targeted alleles. FIG. 9E shows compound heterozygous alleles.

FIG. 10A shows results from long-range PCR assays for selected ES cell clones using primers m-1r-f and m-5'-r, which establish linkage between the human insert and sequences outside of those homologous to the 5' homology arm, thereby proving correct targeting. FIG. 10B shows results from 5' Del J, 5' Ins J, Del A+F, and Del A+E2 PCR assays. 5' Del J depicts the PCR products using m-5'-f and m-5-r, which amplifies the wild-type sequence surrounding the gRNA A cleavage site to establish retention or loss of this sequence. 5' Ins J depicts the PCR products using m-5'-f and h-5'-r primers, which establish a linkage between the human insert and the mouse genome. The assay will give a positive result in both targeted and random integrated clones. Del A+F depicts the expected amplicon size (359 bp) and actual bands for large deletion mediated by dual gRNA A and F cleavage in clones BO-F10 and AW-A8. Del A+E2 depicts the same idea for clone BA-A7. NT indicates no template, +/+ indicates parental VGF1 hybrid ES cell wild-type control, H/+ indicates heterozygous humanized genotype, H/Δ indicates hemizygous humanized genotype, H/H indicates homozygous humanized genotype, and Δ/Δ indicates homozygous deleted genotype.

FIGS. 11A-11C show fluorescence in situ hybridization (FISH) analysis of mouse ES cell clones AW-D9 (FIG. 11A) and BA-D5 (FIG. 11C), which were targeted with the Lrp5 humanization LTVEC combined with Cas9 and two gRNAs, and clone BS-C4 (FIG. 11B), which was targeted with the LTVEC alone. Arrows indicate the positions of hybridization signals on band B of chromosome 19. A red signal indicates hybridization with only the mouse probe (dashed arrow, FIG. 11B). A yellow mixed color signal indicates hybridization with both the red mouse probe and the green human probe. One chromosome 19 band B having a red signal (dashed arrow) and the other chromosome 19 band B having a yellow signal (solid arrow) confirmed targeting to the correct locus and the heterozygous genotype for the BS-C4 clone (FIG. 11B). The B bands of both chromosomes 19 having a yellow signal (solid arrows, FIGS. 11A and 11C) confirmed targeting to the correct locus and the homozygous genotypes for the AW-D9 and BS-C4 clones.

FIGS. 13A and 13B show fluorescence in situ hybridization (FISH) analysis of mouse ES cell clones Q-E9 (FIG. 13A) and O-E3 (FIG. 13B), which were targeted with the Hc humanization LTVEC combined with Cas9 and two gRNAs. Arrows indicate the positions of hybridization signals on band B of chromosome 2. A red signal indicates hybridization with only the mouse probe (dashed arrow, FIG. 13A). A yellow mixed color signal indicates hybridization with both the red mouse probe and the green human probe (solid arrow). One chromosome 2 band B having a red signal (dashed arrow) and the other chromosome 2 band B having a yellow signal (solid arrow) confirmed targeting to the correct locus and the heterozygous genotype for the Q-E9 clone (FIG. 13A). The B bands of both chromosomes 2 having a yellow signal (solid arrows, FIG. 13B) confirmed targeting to the correct locus and the homozygous genotype for the O-E3 clone.

FIG. 14 shows a schematic of the chromosome containing the mouse C5 gene with assays designed to examine gene conversion or mitotic recombination events mediated by two guide RNAs by analyzing loss of heterozygosity (LOH) in VGF1 hybrid ES cells. The approximate positions of the structural variant (SV) polymorphism PCR probes are shown by horizontal arrows with their distances (in Mb) from the C5 locus given above. The positions of the gRNA recognition sequences for E2 and A are shown by diagonal arrows above the representation of the C5 gene locus.

FIGS. 15A-15E show the results of structural variation (SV) assays of clones BR-B4, BP-G7, BO-G11, BO-F10, B0-A8, and BC-H9, with VGF1 (F1H4), 129, and B6 DNA used as controls. The assays were done at the following distances telomeric to the Lrp5 locus: 13.7 Mb (FIG. 15A), 20.0 Mb (FIG. 15B), 36.9 Mb (FIG. 15C), 48.3 Mb (FIG. 15D), and 56.7 Mb (FIG. 15E). The positions of the PCR products for B6 and 129 alleles are shown by the arrows.

FIGS. 17A-17C are a schematic showing a possible mechanism for mitotic recombination during G2 phase of the cell cycle that can produce homozygous events and wide-spread gene conversion detected by loss of heterozygosity. FIG. 17A shows replicated homologous chromosomes showing the two chromatids in a hybrid 129/B6 ES cell heterozygous for a targeted humanization on the 129 homolog. Double-headed arrows indicate potential double strand breaks generated by dual gRNA-directed Cas9 cleavage that promotes reciprocal exchange by homologous recombination between chromatids on homologous chromosomes, shown as a cross-over on the centromeric side of the targeted allele, resulting in the hybrid chromatids shown in FIG. 17B. FIG. 17C shows that after mitosis and cell division, four types of chromosomes segregation into daughter cells are possible. Two with retention of heterozygosity, a parental type heterozygote (Hum/+, upper left) and a heterozygote by equal exchange (Hum/+, upper right), cannot be distinguished by LOH assays. Two others show loss of heterozygosity, a humanized homozygote (Hum/Hum, e.g. clone BO-A8, lower left) with loss of telomeric B6 alleles and a wild type homozygote (+/+, lower right) with loss of telomeric 129 alleles. This latter type will be lost because it does not retain the drug resistance cassette of the humanized allele.

FIG. 18A shows reciprocal chromatid exchange by mitotic crossover where a heterozygous modification occurs on the 129 chromosome before genome replication or after genome replication followed by gene conversion between sister chromatids.

FIG. 18B shows reciprocal chromatid exchange by mitotic crossover where a single 129 chromatid is modified after genome replication. FIG. 18C shows reciprocal chromatid exchange by mitotic crossover where no LTVEC targeting has occurred, but Cas9 cleavage has occurred on either the 129 or B6 chromosome (B6 cleavage shown). FIG. 18D shows chromatid copying by break-induced replication where a heterozygous modification occurs on the 129 chromosome before genome replication or after genome replication followed by gene conversion between sister chromatids. FIG. 18E shows chromatid copying by break-induced replication where a single 129 chromatid is modified after genome replication. FIG. 18F shows chromatid copying by break-induced replication where no LTVEC targeting has occurred, but Cas9 cleavage has occurred on either the 129 or B6 chromosome (B6 cleavage shown).

6N strain (represented in the three rows in the bottom portion of the figure). The MP and RGC variants are different mice from the same strain. The vertical lines in each of the three rows represent the single nucleotide variations compared to the reference sequence.

FIGS. 27A-27C are a schematic showing a possible mechanism for mitotic recombination during G2 phase of the cell cycle that can produce homozygous events and gene conversion detected by local loss of heterozygosity. FIG. 27A shows replicated homologous chromosomes showing the two chromatids in a hybrid 129/B6 ES cell heterozygous for a targeted humanization on the 129 homolog. The heterozygous modification on the 129 homolog occurs before genome replication, or a single 129 chromatid is modified after genome replication followed by inter-chromatid gene conversion. Double-headed arrows indicate potential double strand breaks generated by dual gRNA-directed Cas9 cleavage that promotes dual strand invasion and synthesis-directed repair, shown by the diagonal dashed arrows, resulting in hybrid chromatids produced by a gene conversion event that copies a small part of one modified chromatid, as shown in FIG. 27B. FIG. 27C shows that after mitosis and cell division, two types of chromosomes segregation into daughter cells are possible: one with retention of heterozygosity (a parental type heterozygote (Hum/+, upper) with no loss of heterozygosity, and one with local loss of heterozygosity surrounding the targeted modification (Hum/Hum, bottom, retains 129 alleles).

Figure 28:
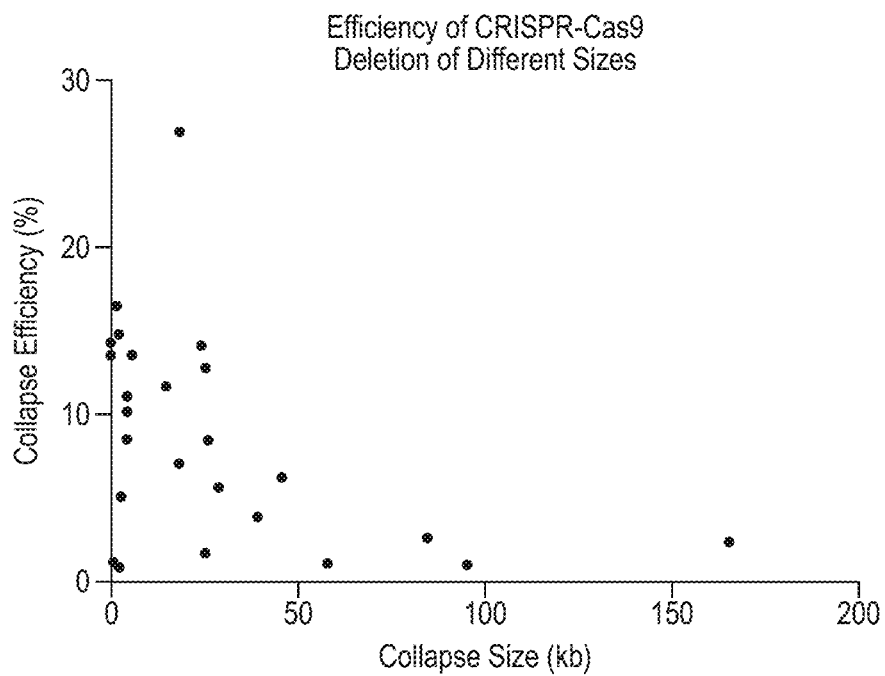

FIG. 28 shows the efficiency of CRISPR/Cas9-mediated deletion in VI-3 and ULC 1-39 embryonic stem (ES) cells for different self-antigen targets of different sizes using paired guide RNAs targeting the start and stop codon regions of the genes encoding the self-antigens, alone or in combination with a large targeting vector.

Figure 29:
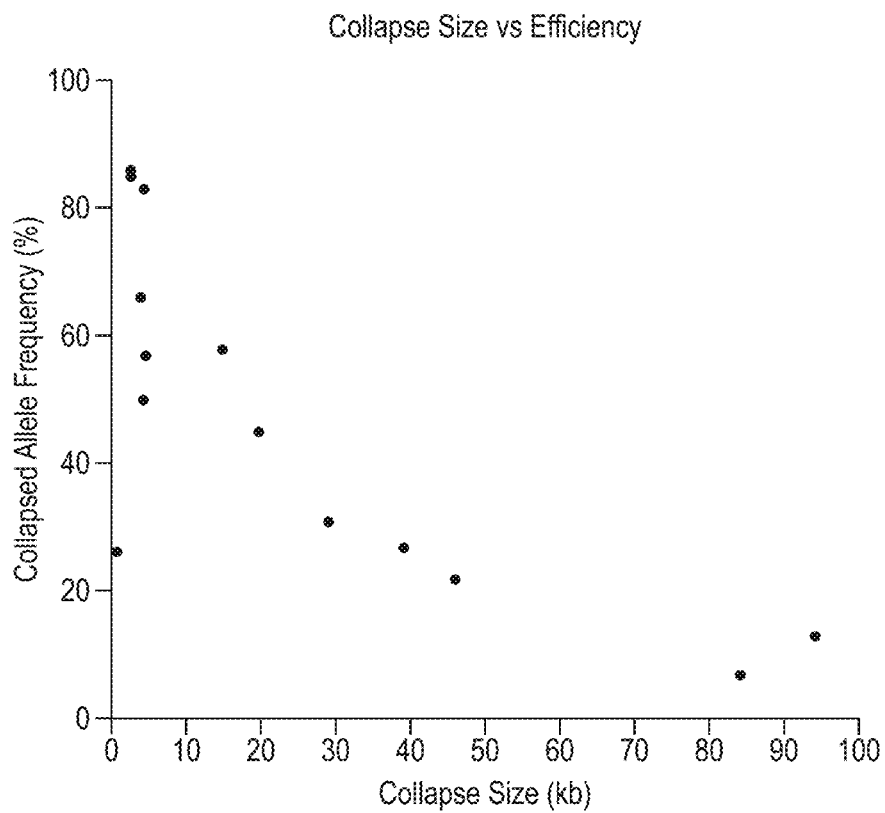

FIG. 29 shows the percentage of mouse pups produced with collapsed alleles following targeting of VI-3 and ULC 1-39 one-cell stage embryos with CRISPR/Cas9 to target different self-antigen targets of different sizes for deletion using paired guide RNAs targeting the start and stop codon regions of the genes encoding the self-antigens.

Figure 30B:
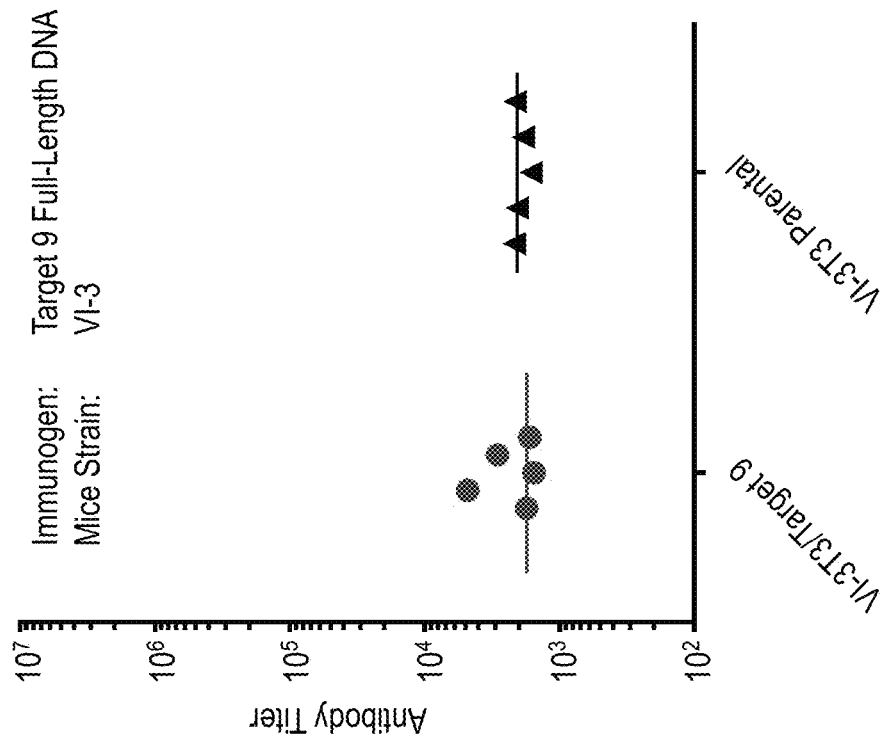
Figure 30A:
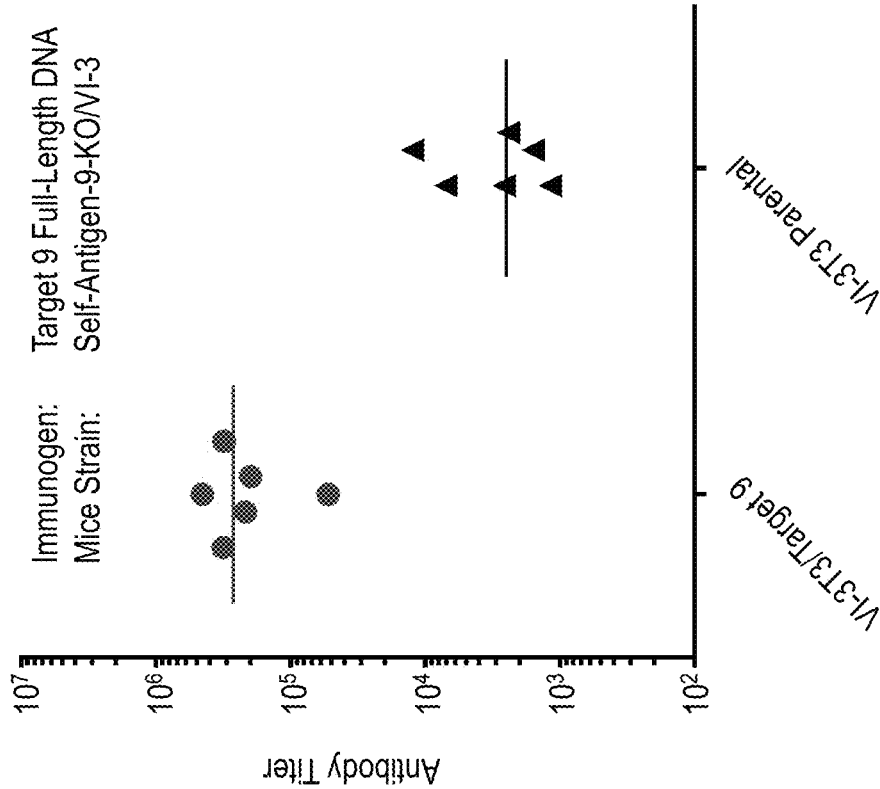

FIGS. 30A and 30B show antibody titer data for a human target antigen (Target 9) in wild type VI-3-Adam6 mice (FIG. 30B) and in VI3-Adam6 mice that are homozygous null for an endogenous gene encoding a self-antigen orthologous to Target 9 (Self-Antigen 9) (FIG. 30A) following immunization with Target 9 full-length DNA on parental VI-3T3 cells and VI-3T3 cells engineered to express Target 9.

Figure 31B:
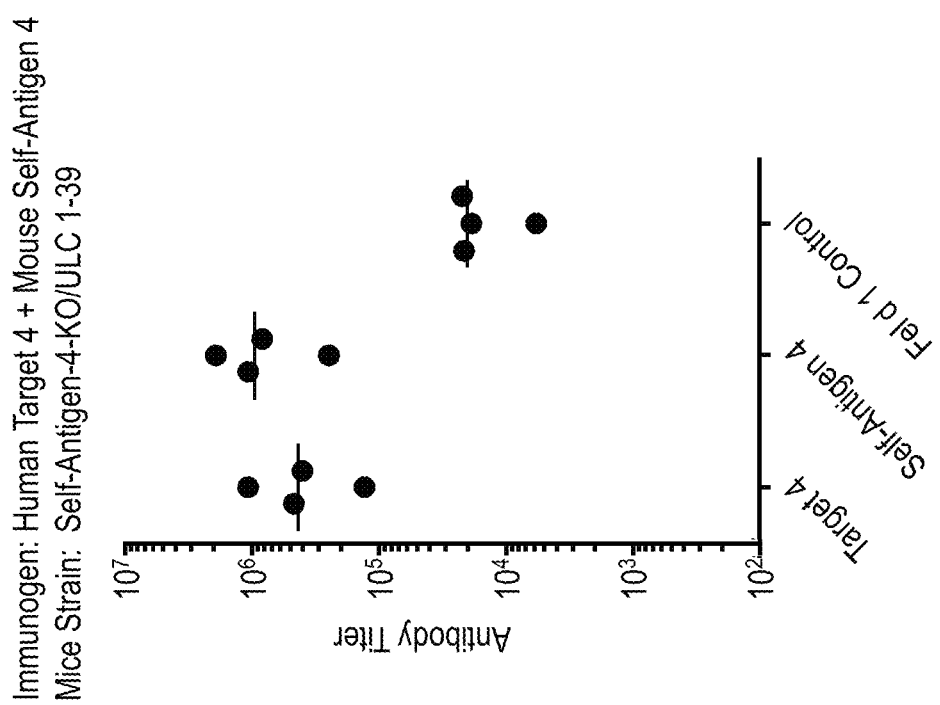
Figure 31A:
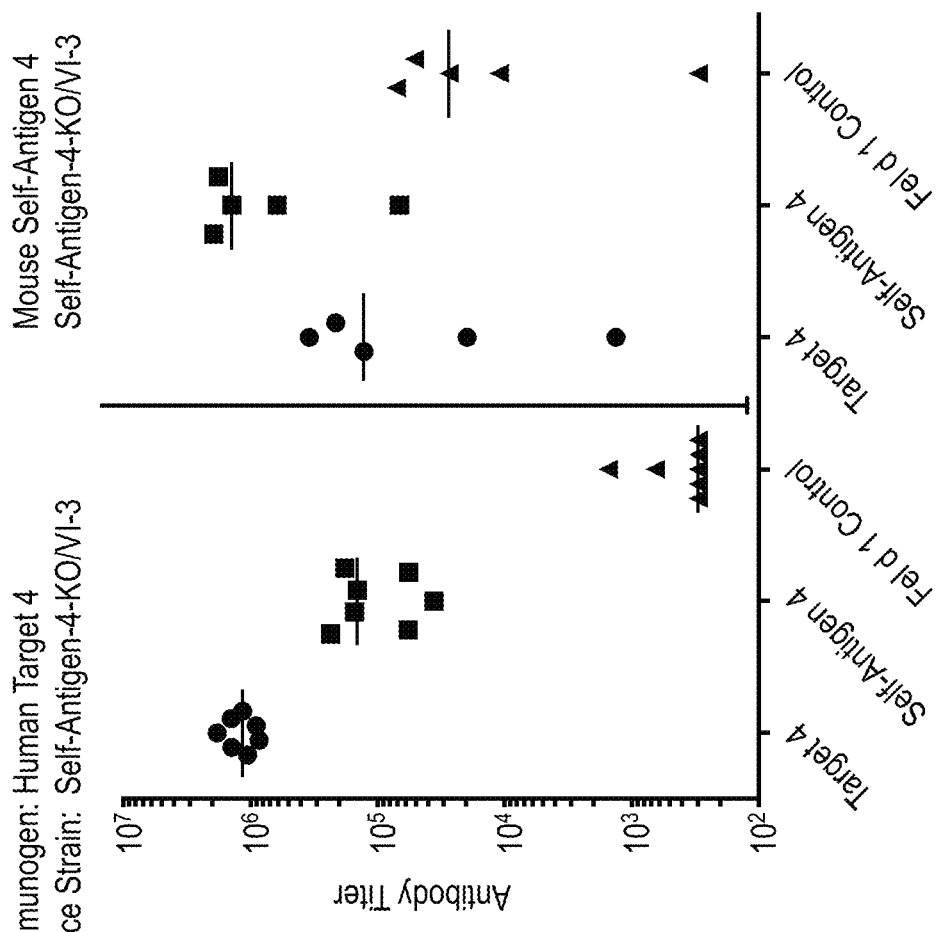

FIGS. 31A and 31B show antibody titer data for a human target antigen (Target 4) and for the corresponding orthologous mouse self-antigen (Self-Antigen 4). FIG. 31A shows antibody titer data for human Target 4 and mouse Self-Antigen 4 in VI3-Adam6 mice that are homozygous null for the endogenous gene encoding Self-Antigen 4. FIG. 31B shows antibody titer data for a combination of human Target 4 and mouse Self-Antigen 4 in ULC 1-39 mice that are homozygous null for the endogenous gene encoding Self-Antigen 4.

Figure 32:
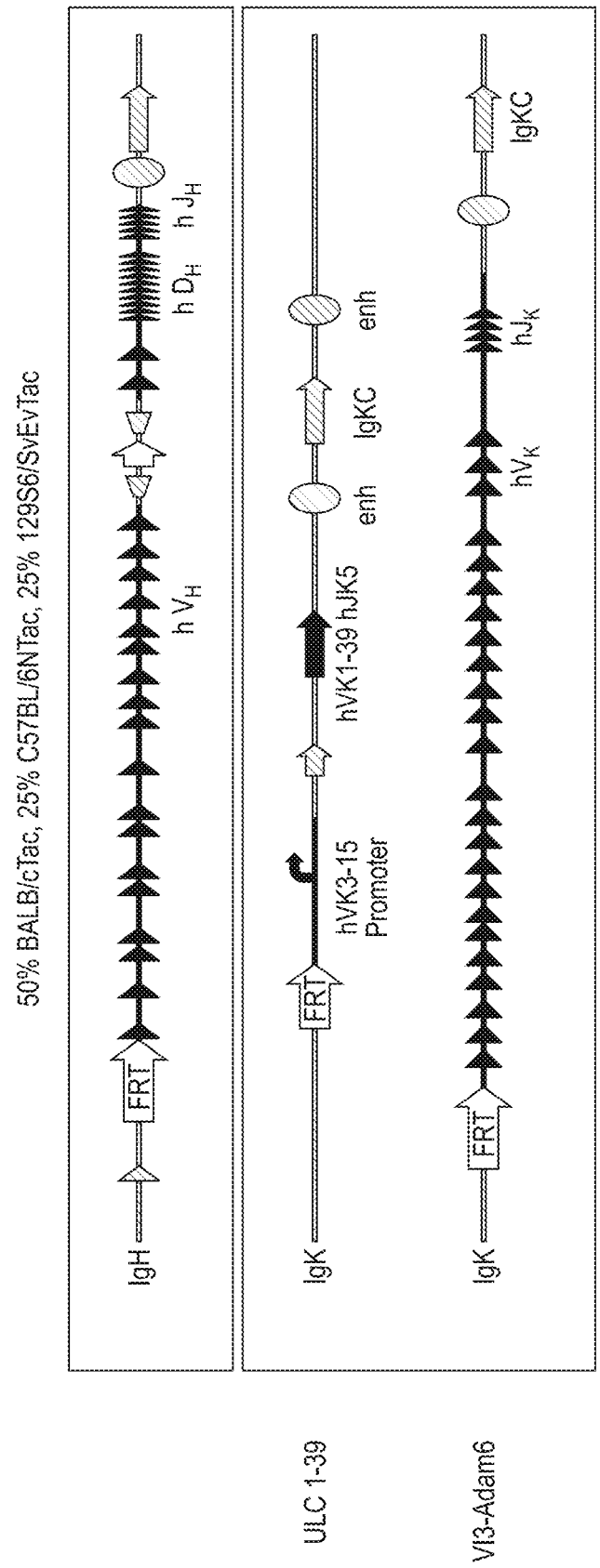

FIG. 32 shows a schematic for the immunoglobulin heavy chain locus (top) and the immunoglobulin light chain loci (bottom) in VI3-Adam6 and ULC 1-39 mice, which each have a genetic background of 50% BALB/cTac, 25% C57BL/6NTac, and 25% 12956/SvEvTac. In the VI3-Adam6 mice, the endogenous mouse immunoglobulin heavy and light chain variable region are replaced with the corresponding human DNA along with reinserted mouse Adam6 genes (Adam6b and Adam6a, represented by trapezoids). In the Universal Light Chain (ULC 1-39) mice, the endogenous mouse immunoglobulin heavy chain variable region is replaced with the corresponding human DNA along with a reinserted mouse Adam6 gene, and the immunoglobulin light chain variable region comprises a single rearranged human immunoglobulin light chain nucleotide sequence (Vκ1-39/Jκ5) operably linked to the hVκ3-15 promoter. Human segments are depicted in black, and mouse segments are indicated by diagonal lines

DEFINITIONS

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "wild type" includes entities having a structure and/or activity as found in a normal (as contrasted with mutant, diseased, altered, or so forth) state or context. Wild type gene and polypeptides often exist in multiple different forms (e.g., alleles).

The term "isolated" with respect to proteins and nucleic acid includes proteins and nucleic acids that are relatively purified with respect to other bacterial, viral or cellular components that may normally be present in situ, up to and including a substantially pure preparation of the protein and the polynucleotide. The term "isolated" also includes proteins and nucleic acids that have no naturally occurring counterpart, have been chemically synthesized and are thus substantially uncontaminated by other proteins or nucleic acids, or has been separated or purified from most other cellular components with which they are naturally accompanied (e.g., other cellular proteins, polynucleotides, or cellular components).

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "Lrp5 locus" may refer to the specific location of an Lrp5 gene, Lrp5 DNA sequence, LRP5-encoding sequence, or Lrp5 position on a chromosome of the genome of an organism that has been identified as to where such a sequence resides. An "Lrp5 locus" may comprise a regulatory element of an Lrp5 gene, including, for example, an enhancer, a promoter, 5' and/or 3' UTR, or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence). As another example, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target within the target nucleic acid sequence to which they are targeted. For example, a gRNA in which 18 of 20 nucleotides are complementary to a target, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, Cas9 proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "substantial identity" as used herein to refer to shared epitopes includes sequences that contain identical residues in corresponding positions. For example, two sequences can be considered to be substantially identical if at least 70%, 75%, 80%, 85%, 90%, 91%, 92%, 93%, 94%, 95%, 96%, 97%, 98%, 99% or more of their corresponding residues are identical over a relevant stretch of residues. The relevant stretch can be, for example, a complete sequence or can be at least 5, 10, 15, or more residues.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

The term "germline" in reference to an immunoglobulin nucleic acid sequence includes a nucleic acid sequence that can be passed to progeny.

The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

The term "antigen" refers to a substance, whether an entire molecule or a domain within a molecule, which is capable of eliciting production of antibodies with binding specificity to that substance. The term antigen also includes substances, which in wild type host organisms would not elicit antibody production by virtue of self-recognition, but can elicit such a response in a host animal with appropriate genetic engineering to break immunological tolerance.

The term "epitope" refers to a site on an antigen to which an antigen-binding protein (e.g., antibody) binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

The term "self" when used in conjunction with antigens or epitopes describes antigens or epitopes which would not be recognized or be only poorly recognized by the B-cell receptors of a wild type member of the host species by virtue of being included among the substances which are normally biosynthesized by the host species, or to which the host species is normally exposed. Such substances induce tolerance of the host immune system. The term "foreign" when used in conjunction with antigens or epitopes describes antigens or epitopes that are not self-antigens or self-epitopes. A foreign antigen is any antigen which is not normally produced by the host species.

The term "antibody" includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains: $C_H1$, $C_H2$ and $C_H3$. Each light chain comprises a light chain variable domain and a light chain constant region ($C_L$). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$M or lower (e.g., about $1 \times 10^{-9}$M, $1 \times 10^{-10}$ M, $1 \times 10^{-11}$ M, or about $1 \times 10^{-12}$M). In one embodiment, $K_D$ is measured by surface plasmon resonance, e.g., BIACORE™; in another embodiment, $K_D$ is measured by ELISA.

The term "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the world wide web (www) at the URL "imgt.org."

The term "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the internet on the world wide web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The term "complementary determining region" or "CDR," as used herein, includes an amino acid sequence encoded by a nucleic acid sequence of an organism's immunoglobulin genes that normally (i.e., in a wild type animal) appears between two framework regions in a variable region of a light or a heavy chain of an immunoglobulin molecule (e.g., an antibody or a T cell receptor). A CDR can be encoded by, for example, a germline sequence or a rearranged sequence, and, for example, by a naïve or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as a result of splicing or connecting the sequences (e.g., V-D-J recombination to form a heavy chain CDR3."

The term "unrearranged" includes the state of an immunoglobulin locus wherein V gene segments and J gene segments (for heavy chains, D gene segments as well) are maintained separately but are capable of being joined to form a rearranged V(D)J gene that comprises a single V, (D), J of the V(D)J repertoire.

The term heavy chain variable region locus includes a location on a chromosome, e.g., a mouse chromosome, where wild type heavy chain variable ($V_H$), heavy chain diversity ($D_H$), and heavy chain joining ($J_H$) region DNA sequences are found.

The term kappa light chain variable region locus includes a location on a chromosome, e.g., a mouse chromosome, where wild type λ variable (Vκ) and λ joining (Jλ) region DNA sequences are found.

The term lambda light chain variable region locus includes a location on a chromosome, e.g., a mouse chromosome, where wild type λ variable (Vλ) and λ joining (Jλ) region DNA sequences are found.

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "hybrid" include cells or strains that have one or more sequence variations (e.g., have allelic variation) at one or more target genomic loci between first and second chromosomes in a homologous chromosome pair. For example, hybrid cells can be derived from progeny of mating between two genetically dissimilar parents (i.e., a cross between parents that differ in one or more genes). As an example, a hybrid can be generated by crossing two distinct inbred lines (i.e., lines bred for genetic homogeneity). All humans are considered hybrid.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas9 protein" or "at least one Cas9 protein" can include a plurality of Cas9 proteins, including mixtures thereof.

Statistically significant means p≤0.05.

DETAILED DESCRIPTION

I. Overview

Provided herein are compositions and improved methods for producing antigen-binding proteins (e.g., antibodies) that bind an epitope on a foreign target antigen of interest (e.g., a human target antigen of interest) that shares the epitope with a self-antigen or is homologous to the self-antigen. Such methods comprise reducing tolerance of the foreign antigen in non-human animals such as rodents (e.g., mice or rats) (optionally comprising in their germline humanized immunoglobulin heavy and/or light chain loci) by employing two or more guide RNAs (gRNAs) to create paired double-strand breaks at different sites within a single target genomic locus. Optionally, the cell comprising the target genomic locus is a hybrid cell, and the methods further comprise selecting a target region within a target genomic locus to undergo a targeted genetic modification such that the target region has a higher degree of sequence identity between corresponding first and second chromosomes in a homologous chromosome pair relative to all or part of the remainder of the target genomic locus. Such paired double-strand breaks affect the expression of the self-antigen to decrease or eliminate expression of the self-antigen or to decrease or eliminate expression of the epitope from the self-antigen that is shared with the foreign antigen. Such genetically modified non-human animals comprising humanized immunoglobulin heavy and light chain loci and also harboring such a mutation in the target genomic locus can then be immunized with the foreign antigen, the non-human animal can be maintained under conditions sufficient for the non-human animal produces an immune response to the foreign antigen, and an antigen-binding protein that binds the foreign antigen can be obtained from the non-human animal or a cell from the non-human animal.

Mice used for producing antibodies against human antigens, such as mice comprising in their germline humanized immunoglobulin heavy and/or light chain loci, typically are derived from a combination of strains that includes BALB/c due to the increased capacity of BALB/c strains for producing a diverse repertoire of antibodies compared to other mouse strains. However, compared to embryonic stem (ES) cells typically used to generate targeted genetic modifications in mice (e.g., the F1H4 (VGF1) cells described herein), ES cells derived from such strains of antibody-producing mice typically have a reduced capacity for being targeted in culture and/or producing F0 generation mice having the targeted genetic modification and transmitting the targeted modification through the germline. Consequently, conventional methods to generate target knockout mice to overcome tolerance involve multiple rounds of breeding and/or serial targeting, with the entire process for delivering mice homozygous for a null allele at the target of interest and ready for immunization taking about 15-16 months.

The methods described herein advantageously reduce this time to approximately 4 to 5 months (and mouse pups homozygous for a null allele at the target of interest can be delivered in ~3 months). In addition to the shorter time frame, the methods described herein decrease the number of rounds of electroporation required to generate homozygous modifications, reduce the number of passages and time in culture needed, reduce the number of cells needed, and streamline the process due to targeting vectors not being required and screening accordingly being simplified. The methods described herein advantageously result in an increased diversity of antibodies following immunization with the foreign antigen of interest due to an increased usage of heavy chain and light chain V gene segments compared to mice in which expression of the self-antigen is not abolished. In addition, the methods described herein result in antibodies produced against a greater diversity of epitopes following immunization with the foreign antigen of interest due to production of antibodies that cross-react with the corresponding self-antigen (i.e., antibodies that bind epitopes that overlap between the self-antigen and the foreign antigen of interest), thereby enabling the production of a larger pool of antibodies against the foreign antigen of interest.

II. Methods of Modifying a Target Genomic Locus to Break Tolerance

Immunization of non-human animals (e.g., rodents, such as mice or rats) comprising in their germline humanized immunoglobulin heavy and/or light chain loci with a "non-self" protein is a commonly used method to obtain specific antigen-binding proteins such as monoclonal antibodies. The immunization approach is attractive because it has the potential to provide high-affinity antigen-binding proteins that have been matured in vivo and can be both cost-effective and time-effective. This approach, however, is dependent on a divergence in sequence between native proteins in the non-human animal and the protein being immunized to enable the non-human animal's immune system to recognize the immunogen as non-self (i.e., foreign).

B cell receptors are assembled through a series of recombination events from ordered arrangement of gene segments (e.g., V, D, and J), and this assembly of gene segments is known to be imprecise and generates receptors having affinity for various antigens, including self-antigens. Despite this capacity to generate B cell receptors that bind self-molecules, the immune system is equipped with several self-tolerance mechanisms to avoid development and expansion of such auto-reactive B cell receptors and discriminate self from non-self thereby preventing autoimmunity. See, e.g., Shlomchik (2008) *Immunity* 28:18-28 and Kumar and Mohan (2008) 40(3):208-23, each of which is herein incorporated by reference in its entirety for all purposes. Thus, the generation of human antibodies in non-human animals having humanized immunoglobulin loci against human antigens having a high degree of homology (e.g., structural homology or sequence homology) with self-antigens of a non-human animal can be a difficult task due to immunological tolerance. Because functionally important regions of proteins tend to be conserved across species, immunological tolerance to self-antigens often poses a challenge to the generation of antibodies to these key epitopes. Immunization of non-human animals (e.g., rodents, such as mice or rats) with foreign (e.g., human) antigens that are highly similar or "homologous" yields weak or non-existent antibody responses and, therefore, makes it problematic to obtain antigen-binding proteins (e.g., antibodies) with binding directed to such human antigens. As an example, the amount of sequence identity shared by the endogenous protein (self-antigen) and the foreign target antigen could be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the immune system does not recognize the target antigen as foreign. For example, shared epitopes between a foreign antigen and a self-antigen in a non-human animal can make mounting an effective immune response against the foreign antigen in the non-human animal problematic because immunological tolerance depletes and/or deletes B cells that express neutralizing antibodies against the foreign antigen. To overcome this tolerance and obtain monoclonal antibodies that bind self-antigens or homologs thereof (e.g., human homologs) in non-human animals, specific genetically modified or knockout non-human animals can be generated to remove genes (or shared epitopes of interest) encoding the non-human animal protein that shares significant homology and/or is highly conserved with its human counterpart genes encoding the antigen being used for immunization. See, e.g., U.S. Pat. No. 7,119,248, herein incorporated by reference in its entirety for all purposes. Generating such non-human animals, however, can be both costly and time-consuming.

Figure 1:
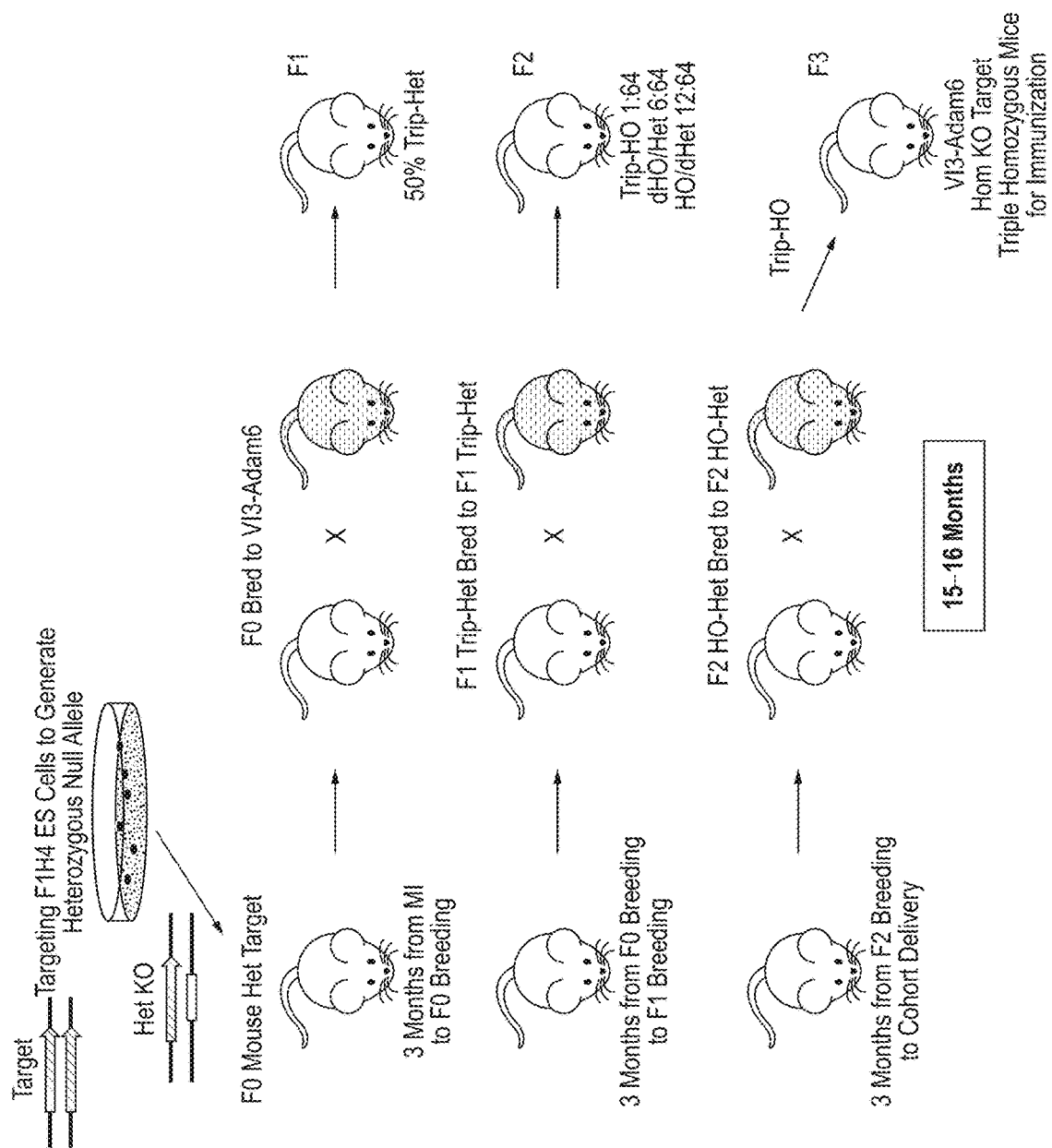
FIG. 1 shows the traditional approach to breaking immunological tolerance in VELOCIMMUNE® mice (VI-3; homozygous humanized at both IgH and Igκ). In the traditional approach, heterozygous knockout (null) alleles of a gene encoding a self-antigen homologous to a foreign target antigen of interest are created in F1H4 embryonic stem (ES) cells. The time from design of the targeting vectors to the generation of the F0 mice heterozygous for the knockout is approximately 5 months. VI-3 mice are then bred to the F0 mice carrying the heterozygous knockout mutation at the endogenous gene encoding the self-antigen homologous to the foreign target antigen of interest. In order to generate triple homozygous mice (homozygous null for the target of interest and homozygous humanized at both IgH and Igκ) suitable for immunization, two further generations of breeding are required. The entire process from design of the targeting vectors to generation of the triple homozygous mice takes approximately 15 to 16 months.
Figure 2:
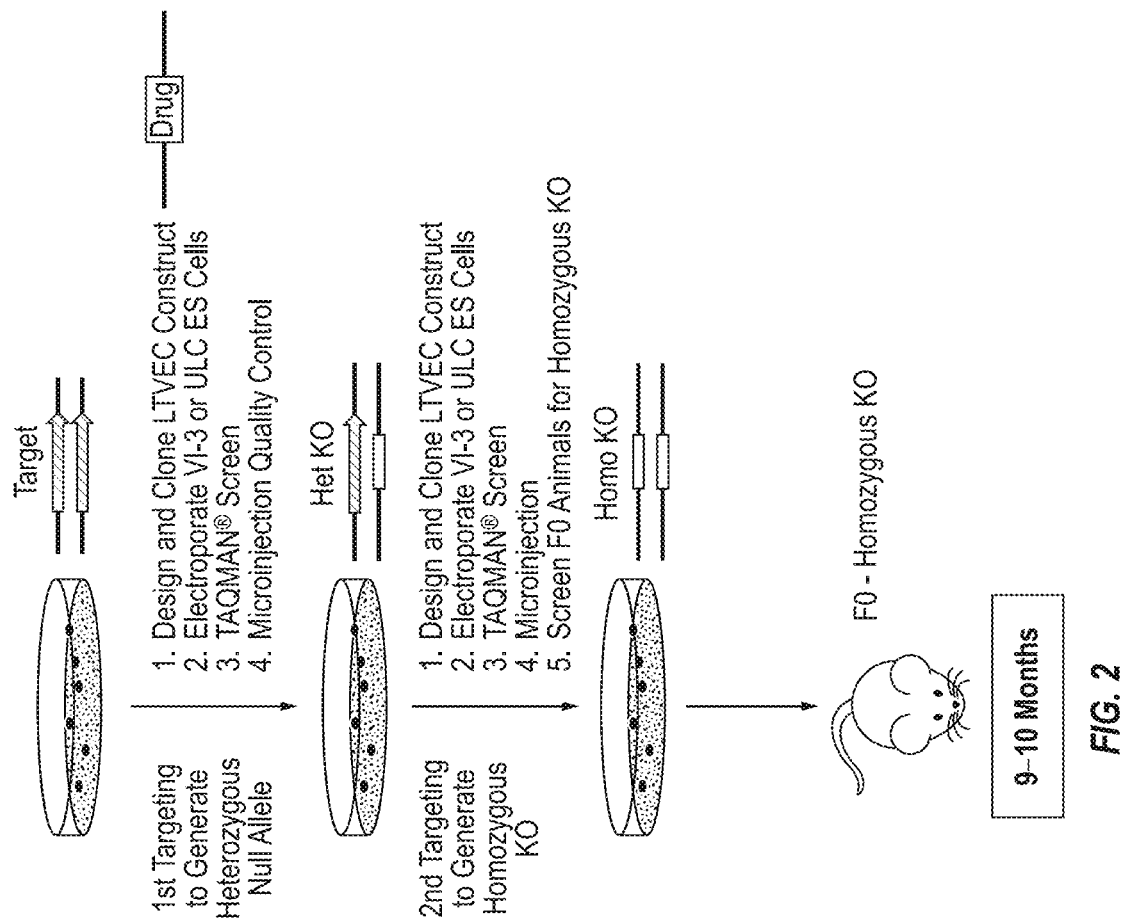
FIG. 2 shows an accelerated process for breaking immunological tolerance in VELOCIMMUNE® (VI-3) mice or in Universal Light Chain (0 or Common Light Chain) mice. In this process, ES cells derived from VI-3 or ULC mice are targeted to create heterozygous null alleles of an endogenous gene encoding a self-antigen homologous to a foreign target antigen of interest. Sequential targeting steps are required to obtain homozygous null VI-3 or ULC ES cell clones.

Conventional methods to generate target knockout mice to overcome tolerance involve multiple rounds of breeding and/or serial targeting. Mice used for producing antibodies against human antigens, such as mice comprising in their germline humanized immunoglobulin heavy and/or light chain loci (e.g., VELOCIMMUNE® mice, which are homozygous humanized at both IgH and Igκ loci), typically are derived from a combination of strains that includes BALB/c due to the increased capacity of BALB/c strains for producing a diverse repertoire of antibodies compared to other mouse strains. However, compared to embryonic stem (ES) cells typically used to generate targeted genetic modifications in mice (e.g., the F1H4 (VGF1) cells described herein that are comprised of 50% 129SvS6 strain and 50% C57BL/6N strain), ES cells derived from such strains of antibody-producing mice typically have a reduced capacity for being targeted in culture and/or producing F0 generation mice having the targeted genetic modification and transmitting the targeted modification through the germline. Thus, the traditional approach to breaking immunological tolerance in antibody-producing mice such as VELOCIMMUNE® mice involves first targeting the gene encoding the self-antigen in an ES cell line (e.g., F1H4) that is more receptive to targeting and transmitting the targeted modification through the germline. In such an approach, large targeting vectors (LTVECs) are designed, knockout (null) alleles are created in F1H4 ES cells, and F0 mice carrying a heterozygous knockout mutation at the target of interest are generated (typical timeframe of 5 months). The VELOCIMMUNE® mice are then bred to the F0 mice carrying a heterozygous knockout mutation at the target of interest. In order to generate triple homozygous mice (homozygous null for the target of interest and homozygous humanized at both IgH and Igκ) suitable for immunization, two more generations of breeding are required. The entire process takes approximately 15 to 16 months (see, e.g., FIG. 1) and is more effective than the serial targeting approach described below (see, e.g., FIG. 2).

Alternatively, a large targeting vector (LTVEC) can be designed and constructed and then electroporated into embryonic stem (ES) cells derived from the antibody-producing mice (e.g., VELOCIMMUNE® mice or VELOCIMMUNE® mice comprising a functional ectopic mouse Adam6 gene ("VI-3 mice")) to generate a heterozygous modification in the endogenous gene encoding the self-antigen that is homologous to or sharing an epitope of interest with the target antigen. A second round of targeting is then undertaken to generate a homozygous modification. Although less time-consuming than the breeding approach described above, this process can still be time-consuming, taking approximately 9 to 10 months to create an F0 mouse ready for immunization with the target antigen (see, e.g., FIG. 2). In addition, such methods require multiple rounds of electroporation and longer culturing times with more passages, all of which result in reduced pluripotency and a decreased ability to generate F0 mice for generating antigen-binding proteins. See, e.g., Buehr et al. (2008) *Cell* 135: 1287-1298; Li et al. (2008) *Cell* 135(7): 1299-1310; and Liu et al. (1997) *Dev. Dyn.* 209:85-91, each of which is herein incorporated by reference in its entirety for all purposes.

Figure 3:
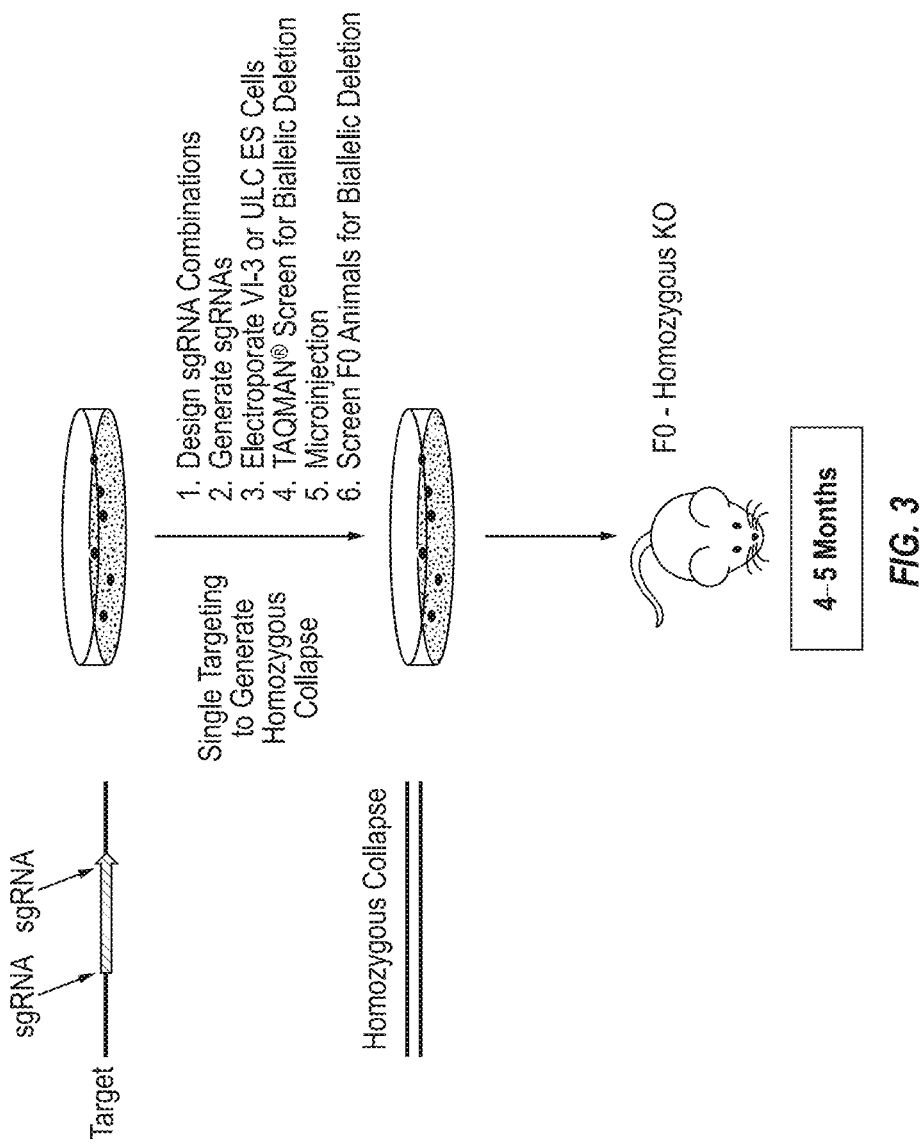
FIG. 3 shows a further accelerated process for breaking tolerance in VELOCIMMUNE® (VI-3) mice or in Universal Light Chain (or Common Light Chain) (ULC) mice. In this process, VI-3 or ULC ES cells are targeted with CRISPR/Cas9 and paired guide RNAs to generate homozygous collapse of an endogenous gene encoding a self-antigen homologous to a foreign target antigen of interest in a single step. TAQMAN® screening can include, for example, both loss-of-allele and retention assays.

The methods described herein advantageously reduce this time to approximately 4 to 5 months (see, e.g., FIG. 3; mouse pups homozygous for a null allele at the target of interest can be delivered in ~3 months but are then aged for 4-5 weeks prior to immunization). In addition to the shorter time frame, the methods described herein decrease the number of rounds of electroporation required to generate homozygous modifications, reduce the number of passages and time in culture needed, and reduce the number of cells needed. The screening is more simple and streamlined because, for example, no gain-of-allele probes are needed, and no copy number calibration is needed. The methods described herein also result in an increased diversity of antibodies following immunization with the foreign antigen of interest due to an increased usage of heavy chain and light chain V gene segments compared to mice in which expression of the self-antigen is not abolished. In addition, the methods described herein can result in antibodies produced against a greater diversity of epitopes following immunization with the foreign antigen of interest due to production of antibodies that cross-react with the corresponding self-antigen (i.e., antibodies that bind epitopes that overlap between the self-antigen and the foreign antigen of interest), thereby enabling the production of a larger pool of antibodies against the foreign antigen of interest.

Provided herein are various methods for modifying a target genomic locus to break tolerance. The methods can occur ex vivo or in vivo, and they can utilize two or more guide RNAs (e.g., two gRNAs, three guide RNAs, or four guide RNAs) that target different regions within a single target genomic locus that affects expression of a self-antigen homologous to or sharing an epitope of interest with a foreign antigen of interest and form two or more complexes with a Cas protein and cleave the target nucleic acid. The two or more guide RNAs can be used either alone or in combination with an exogenous repair template, provided that if the cell is a one-cell stage embryo, for example, the exogenous repair template can be less than 5 kb in length.

Such methods promote the creation of biallelic genetic modifications at a target locus and can comprise genome collapsing or other targeted modifications such as simultaneous deletion of a nucleic acid sequence within the genome and replacement with an exogenous nucleic acid sequence. In comparison to targeting with one gRNA, which produces biallelic modifications at a low frequency, targeting with two or more gRNAs results in the creation of biallelic modifications (e.g., homozygously targeted cells, homozygously deleted cells, and compound heterozygously targeted cells including hemizygously targeted cells) at a significantly increased rate.

Repair in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, herein incorporated by reference in its entirety for all purposes. NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break.

Repair of the target nucleic acid mediated by an exogenous repair template can include any process of exchange of genetic information between the two polynucleotides. For example, NHEJ can also result in the targeted integration of an exogenous repair template through direct ligation of the break ends with the ends of the exogenous repair template (i.e., NHEJ-based capture). Such NHEJ-mediated targeted integration can be preferred for insertion of an exogenous repair template when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous repair template and the cleaved genomic sequence, or via ligation of sticky ends (i.e., having 5' or 3' overhangs) using an exogenous repair template that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Repair can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

To make non-human animals with reduced tolerance of a foreign target antigen of interest, one or more target genomic loci affecting expression of a self-antigen homologous to or sharing an epitope with the foreign antigen of interest can be targeted to decrease expression of the self-antigen. Preferably, expression of the self-antigen is eliminated. Expression of the self-antigen is considered to be eliminated if the self-antigen is no longer expressed (e.g., if the self-antigen is a protein, the protein is no longer expressed, or if the self-antigen is a particular epitope on a protein, proteins comprising that epitope are no longer expressed).

In one example, the genome of a non-human animal pluripotent cell that is not a one-cell stage embryo (e.g., an embryonic stem (ES) cell) can be contacted with a Cas protein, a first guide RNA that hybridizes to a first guide RNA recognition sequence within the target genomic locus, and a second guide RNA that hybridizes to a second guide RNA recognition sequence within the target genomic locus. In another example, the genome of a non-human animal one-cell stage embryo can be contacted with a Cas protein, a first guide RNA that hybridizes to a first guide RNA recognition sequence within the target genomic locus, and a second guide RNA that hybridizes to a second guide RNA recognition sequence within the target genomic locus.

In some methods provided herein, the cell being targeted is a hybrid cell as defined elsewhere herein. Such methods can also comprise selecting a target region within a target genomic locus as described elsewhere herein. The target region can be selected so that it has a high percentage of sequence identity between corresponding first and second chromosomes in a homologous chromosome pair relative to other segments of the target genomic locus or the remainder of the target genomic locus. As an example, selecting a target region can comprise comparing the sequence of corresponding first and second chromosomes in a homologous chromosome pair within a target genomic locus, and selecting a target region having a higher percentage of sequence identity between the corresponding first and second chromosomes in the homologous chromosome pair relative to all or part of the remainder of the target genomic locus. Methods of selecting a target region as described in more detail elsewhere herein.

Optionally, the genome can be further contacted with additional guide RNAs that hybridize to guide RNA recognition sequences within the target genomic locus (or within a second target genomic locus that affects expression of the self-antigen or that affects expression of a second self-antigen that is homologous to or sharing an epitope of interest with the foreign antigen of interest), such as a third guide RNA that hybridizes to a third guide RNA recognition sequence within the target genomic locus or the third guide RNA and a fourth guide RNA that hybridizes to a fourth guide RNA recognition sequence within the target genomic locus. The contacting can comprise introducing the Cas protein and guide RNAs into the cell in any form and by any means as described in further detail elsewhere herein. The guide RNAs form complexes with the Cas protein and direct it to the guide RNA recognition sequences at the target genomic locus, where the Cas protein cleaves the target genomic locus at Cas protein cleavage sites within the guide RNA recognition sequences. Cleavage by the Cas protein can create a double-strand break or a single-strand break (e.g., if the Cas protein is a nickase). Examples and variations of Cas proteins and guide RNAs that can be used in the methods are described elsewhere herein. Cleavage by the Cas protein at the target genomic locus can modify the target genomic locus in a pair of first and second chromosomes to produce a biallelic modification that decreases expression of the self-antigen.

The foreign antigen of interest can be any foreign antigen for which antigen-binding proteins are desired. For example, the foreign antigen of interest can comprise, consist essentially of, or consist of all or part of a viral protein, a bacterial protein, a mammalian protein, a simian protein, a canine protein, a feline protein, an equine protein, a bovine protein, a rodent protein (e.g., rat or mouse), or a human protein. For example, the foreign antigen of interest can comprise, consist essentially of, or consist of a human protein with one or more mutations or variations. The foreign antigen of interest and the self-antigen can be homologous. For example, the foreign antigen of interest and the self-antigen can be orthologous or paralogous. Alternatively or in addition, the foreign antigen of interest and the self-antigen can comprise, consist essentially of, or consist of a shared epitope. Shared epitopes can exist between homologous proteins, or can exist between dissimilar proteins that are not homologous. Either the linear amino acid sequence and/or the conformational fit (e.g., similar antigenic surfaces even in the absence of primary sequence homology) of the epitope may be shared. For example, shared epitopes include epitopes that are substantially identical. If an epitope is shared between two antigens, an antibody against the epitope on the first antigen will typically also bind the epitope on the second antigen.

The contacting can occur in the absence of an exogenous repair template or in the presence of an exogenous repair template that recombines with the target genomic locus to generate a targeted genetic modification. For example, the cell can be a one-cell stage embryo, and the exogenous repair template can be less than 5 kb in length. Examples of exogenous repair templates are described elsewhere herein.

In some such methods, the repair of the target nucleic acid by the exogenous repair template occurs via homology-directed repair (HDR). Homology-directed repair can occur when the Cas protein cleaves both strands of DNA at the target genomic locus to create a double-strand break, when the Cas protein is a nickase that cleaves one strand of DNA at the target genomic locus to create a single-strand break, or when paired Cas nickases are used to create a double-strand break formed by two offset nicks. In such methods, the exogenous repair template comprises 5' and 3' homology arms corresponding to 5' and 3' target sequences at the target genomic locus. The guide RNA recognition sequences or cleavage sites can be adjacent to the 5' target sequence, adjacent to the 3' target sequence, adjacent to both the 5' target sequence and the 3' target sequence, or adjacent to neither the 5' target sequence nor the 3' target sequence. Sequences that are adjacent to each other include sequences within about 10, 20, 30, 40, 50, 100, 200, 300, 400, 500, or 1,000 nucleotides of each other. Optionally, the exogenous repair template can further comprise a nucleic acid insert flanked by the 5' and 3' homology arms, and the nucleic acid insert is inserted between the 5' and 3' target sequences. If no nucleic acid insert is present, the exogenous repair template can function to delete the genomic sequence between the 5' and 3' target sequences.

Alternatively, the repair of the target nucleic acid by the exogenous repair template can occur via non-homologous end joining (NHEJ)-mediated ligation. In such methods, at least one end of the exogenous repair template comprises a short single-stranded region that is complementary to at least one overhang created by Cas-mediated cleavage at the target genomic locus. The complementary end in the exogenous repair template can flank a nucleic acid insert. For example, each end of the exogenous repair template can comprise a short single-stranded region that is complementary to an overhang created by Cas-mediated cleavage at the target genomic locus, and these complementary regions in the exogenous repair template can flank a nucleic acid insert. Overhangs (i.e., staggered ends) can be created by resection of the blunt ends of a double-strand break created by Cas-mediated cleavage. Such resection can generate the regions of microhomology needed for fragment joining, but this can create unwanted or uncontrollable alterations in the target nucleic acid. Alternatively, such overhangs can be created by using paired Cas nickases. For example, if the Cas protein is a nickase, the target genomic locus can be contacted with first and second guide RNAs that target opposite strands of DNA, whereby the genome is modified through double nicking. This can be accomplished by contacting the target genomic locus with two guide RNAs that hybridize to different guide RNA recognition sequence within the target genomic locus. The two guide RNAs form two complexes with the Cas nickase, and the Cas nickase nicks a first strand of the target genomic locus within one of the guide RNA recognition sequences and nicks a second strand of the target genomic locus within the other guide RNA recognition sequence. The exogenous repair template then recombines with the target genomic locus to generate the targeted genetic modification.

In some methods, the nucleic acid insert comprises a sequence that is homologous or orthologous to all or part of a gene encoding the self-antigen. This can be useful, for example, when knocking out the self-antigen may result in embryonic lethality. The nucleic acid insert can be in an exogenous repair template in any form described herein (e.g., targeting vector, LTVEC, ssODN, and so forth), and the nucleic acid insert can further comprise a selection cassette (e.g., a self-deleting selection cassette) or can lack a selection cassette. In such methods, for example, all or part of the gene encoding the self-antigen can be deleted and replaced with a corresponding homologous or orthologous sequence. For example, all of the gene encoding the self-antigen can be deleted and replaced with a corresponding homologous or orthologous sequence, or a portion of the gene encoding a particular motif or region of the self-antigen can be deleted and replaced with a corresponding homologous or orthologous sequence. Optionally, the corresponding homologous or orthologous sequence can be from another species. For example, if the self-antigen is a mouse antigen, the corresponding homologous or orthologous sequence can be, for example, a homologous or orthologous rat, hamster, cat, dog, turtle, lemur, or human sequence. Alternatively or additionally, the homologous or orthologous sequence can comprise one or more point mutations (e.g., 1, 2, 3, 4, 5, or more) compared with the sequence being replaced. Such point mutations can serve, for example, to eliminate expression of one or more epitopes in the self-antigen. Such epitopes may be epitopes that are shared with the foreign antigen of interest. Optionally, such point mutations can result in a conservative amino acid substitution (e.g., substitution of aspartic acid [Asp, D] with glutamic acid [Glu, E]) in the encoded polypeptide. Such amino acid substitutions can result in expression of a self-antigen that retains the function of the wild-type self-antigen but lacks an epitope that is present on the foreign antigen of interest and is shared with the wild-type self-antigen. Likewise, deletion of all or part of the gene encoding the self-antigen and replacement with a corresponding homologous or orthologous sequence that lacks an epitope that is shared between the foreign antigen of interest and the self-antigen can result in expression of a homologue or orthologue of the self-antigen that retains the function of the wild-type self-antigen but lacks the epitope that is present on the foreign antigen of interest and is shared with the wild-type self-antigen. Antigen-binding proteins against those epitopes can then be generated.

The modified non-human animal pluripotent cell can then be used to generate a genetically modified non-human animal using the methods described elsewhere herein. For example, the modified non-human animal pluripotent cell can be introduced into a host embryo, and the host embryo can be implanted into a surrogate mother to produce a genetically modified F0 generation non-human animal in which the target genomic locus is modified in a pair of first and second chromosomes to have a biallelic modification such that expression of the self-antigen is reduced or eliminated. In the case of a one-cell stage embryo, a genetically modified embryo can be selected and then implanted into a surrogate mother to produce a genetically modified F0 generation non-human animal in which the target genomic locus is modified in a pair of first and second chromosomes to have a biallelic modification such that expression of the self-antigen is reduced or eliminated. The F0 generation non-human animals can then be used to generate antigen-binding proteins against the foreign antigen of interest using the methods described elsewhere herein.

A. Selecting a Target Region

Targeted gene modification by homologous recombination between an exogenous repair template (e.g., targeting vector) and a target genomic locus can be very inefficient, especially in cell types other than rodent embryonic stem cells. Induction of one or more double strand DNA breaks by CRISPR/Cas9-directed cleavage can promote homozygous gene targeting by homologous recombination (HR) between an exogenous repair template (e.g., a targeting vector) and a target genomic locus. CRISPR/Cas9 can also promote homozygous insertion or deletion mutations (i.e., biallelic alterations that are identical) by non-homologous end-joining (NHEJ) repair mechanisms. For gene modifications that involve very large humanizations, combining a targeting vector with a CRISPR/Cas9 nuclease system guided by two guide RNAs that target a single target genomic locus can further enhance targeting efficiency beyond that achieved with one guide RNA. In comparison to targeting with one guide RNA, which produces biallelic modifications at a low frequency or not at all, targeting with two guide RNAs results in the creation of homozygously targeted cells, homozygously deleted cells, and compound heterozygously targeted cells (including hemizygously targeted cells) at a significantly increased rate. At some genomic loci, however, obtaining homozygously targeted cells or homozygously deleted cells can still be difficult.

Unlike in inbred mouse and rat strains typically used in lab settings, which are homozygous at virtually all of their genomic loci, the sequence of two alleles at a target genomic locus in hybrid cells (e.g., in all humans) will typically not be 100% identical. However, as demonstrated in the Examples provided herein, the frequency of homozygous genomic alteration, whether the initial CRISPR/Cas9-induced modification was produced by HR or NHEJ, depends on the extent of sequence similarity between the two alleles of the target genomic locus. This observation implies that CRISPR/Cas9-induced homozygous gene modification is a homology-dependent phenomenon. In support of this, CRISPR/Cas9-induced homozygous modifications are often accompanied by loss of heterozygosity (LOH) of allelic sequence and structural variants (single nucleotide variants, SNVs, or structural variants, SVs) linked to the target genomic locus on the same chromosome, as demonstrated in the Examples herein. The LOH can either involve a local gene conversion mechanism for variants on either side of the target genomic locus or a long-range gene conversion (polar gene conversion) involving all variants on the telomeric side of the target genomic locus. Such gene conversion events must be the result of homology-driven mitotic recombination mechanisms.

This knowledge provides guidance for designing CRISPR/Cas9-assisted homozygous targeting experiments. Choosing target regions in which the two alleles share a high degree of sequence identity gives the highest chance of success. CRISPR/Cas9-assisted homozygous targeting at target regions with a high degree of sequence variance between the two alleles are less likely to be successful. Even at loci with a high density of SNVs and SVs, success rates could be improved by the use of guide RNAs or nuclease agents that recognize sequences within the longest possible stretch of contiguous allelic sequence identity within the target genomic locus or within stretches of the target genomic locus in which allelic sequence identity is maximized.

The methods described herein can involve selecting a target region such that sequence identity can be maximized for all or part of the target region between corresponding first and second chromosomes in a homologous chromosome pair. In hybrid cells, the sequence on one copy of a homologous chromosome pair will typically have some differences when compared to the other copy of a chromosome pair (e.g., single nucleotide variations). Thus, such methods can comprise comparing the sequence of corresponding first and second chromosomes in a homologous chromosome pair (for example, a human cell has 23 homologous chromosome pairs) in a target genomic locus and then selecting a target region within the target genomic locus such that sequence identity is maximized for all or part of the target region between the corresponding first and second chromosomes in a homologous chromosome pair. If no sequences are available, such methods can further comprise sequencing the target genomic locus on each single chromosome within a homologous chromosome pair prior to comparing the sequence.

The target region can comprise, consist essentially of, or consist of, for example, any segment or region targeted by one of the two or more guide RNAs or one or more exogenous repair templates in the methods disclosed herein, or any segment or region flanking a segment or region targeted by one of the two or more guide RNAs or one or more exogenous repair templates in the methods disclosed herein. The target region can be a contiguous genomic sequence or a non-contiguous genomic sequence. For example, a target region can comprise, consist essentially of, or consist of a genomic segment or region targeted for deletion, a genomic segment or region targeted for replacement, or a genomic segment or region targeted for insertion by the methods disclosed herein, and/or can comprise, consist essentially of, or consist of the 5' and/or 3' sequence flanking the genomic segment or genomic region targeted for deletion, replacement, or insertion by the methods disclosed herein. Preferably, the target region comprises, consists essentially of, or consists of the sequence immediately upstream and/or the sequence immediately downstream of a region targeted for deletion, replacement, or insertion by the methods disclosed herein (e.g., the sequence upstream and/or downstream of the region between two guide RNA recognition sequences or cleavage sites, or the sequence upstream and/or downstream the region between 5' and 3' target sequences of an exogenous repair template). As an example, if two guide RNAs are used, the target region can comprise, consist essentially of, or consist of the 5' (i.e., upstream) and 3' (i.e., downstream) sequence flanking the region between the guide RNA recognition sequences or the Cas cleavage sites. Examples of lengths of flanking sequences are disclosed elsewhere herein.

In some methods, for example, an exogenous repair template can first be designed, and guide RNAs can then be designed within the region flanked by the 5' and 3' target sequences of the exogenous repair template to maximize sequence identity in the regions within and/or flanking (5' side, 3' side, or each side) the guide RNA recognition sequences (e.g., flanking the region between the two guide RNA recognition sequences furthest apart, if two or more guide RNAs are used). Alternatively, in some methods, for example, two or more guide RNAs can first be designed, and an exogenous repair template can then be designed so that the 5' and 3' target sequences are flanking the two or more guide RNA recognition sequences and so that sequence identity is maximized in the regions within and/or flanking (5' side, 3' side, or each side) the 5' and 3' target sequences (e.g., flanking the region between the 5' and 3' target sequences).

As an example, the target region can comprise, consist essentially of, or consist of a guide RNA recognition sequence for one of the two or more guide RNAs. Alternatively or in addition, the target region can comprise, consist essentially of, or consist of the 5' and/or 3' sequence flanking the guide RNA recognition sequence. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

As another example, the target region can comprise, consist essentially of, or consist of two or more guide RNA recognition sequences. Alternatively or in addition, the target region can comprise, consist essentially of, or consist of the 5' and/or 3' sequence flanking the guide RNA recognition sequences. In methods in which two guide RNAs are used, for example, the target region can comprise, consist essentially of, or consist of a genomic region flanked by the two guide RNA recognition sequences or cleavage sites or a genomic region flanked by and including the two guide RNA recognition sequences or cleavage sites. Alternatively or in addition, the target region can comprise, consist essentially of, or consist of the 5' and/or 3' sequence flanking the region between the two guide RNA recognition sequences or cleavage sites or flanking the region between and including the two guide RNA recognition sequences or cleavage sites. Similar target regions can be selected in methods in which more than two guide RNAs are used, except that in place of the genomic region flanked by the two guide RNA recognition sequences or cleavage sites as above would be the genomic region flanked by the guide RNA recognition sequences of cleavage sites furthest apart. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

In methods in which an exogenous repair template is used, for example, the target region can comprise, consist essentially of, or consist of the region flanked by the 5' and 3' target sequences or the region flanked by and including the 5' and 3' target sequences. Alternatively or additionally, the target region can comprise, consist essentially of, or consist of 5' and/or 3' sequence flanking the genomic region between the 5' and 3' target sequences or the 5' and/or 3' sequence flanking the genomic region between the 5' and 3' target sequences. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

Allelic sequence identity can be maximized for all of the target region or a part of the target region. As an example, allelic sequence identity can be maximized for the genomic region corresponding with at least one or each guide RNA recognition sequence or for regions comprising at least one or each guide RNA recognition sequence. For example, allelic sequence identity can be maximized for at least one or each guide RNA recognition sequence. Alternatively, allelic sequence identity can be maximized for at least one or each guide RNA recognition sequence and the 5' and/or 3' sequence flanking the at least one or each guide RNA recognition sequence. Alternatively, allelic sequence identity can be maximized for the 5' and/or 3' sequence flanking the at least one or each guide RNA recognition sequence. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

Alternatively or additionally, allelic sequence identity can be maximized for the genomic regions corresponding with the 5' and/or 3' target sequences for an exogenous repair template or for regions comprising at least one or each of the 5' and 3' target sequence. For example, allelic sequence identity can be maximized for at least one or each of the 5' and 3' target sequences. Alternatively, allelic sequence identity can be maximized for at least one or each of the 5' and 3' target sequences and the 5' and/or 3' sequence flanking the at least one or each of the 5' and 3' target sequences.

Alternatively, allelic sequence identity can be maximized for the 5' and/or 3' sequence flanking the at least one or each of the 5' and 3' target sequences. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

Alternatively or additionally, allelic sequence identity can be maximized for the sequence flanking a region targeted for deletion, replacement, or insertion. For example, in methods using two guide RNAs, allelic sequence identity can be maximized for the 5' and/or 3' sequence flanking the region between the two cleavage sites or the two guide RNA recognition sequences. In methods using three or more guide RNAs, allelic sequence identity can be maximized for the 5' and/or 3' sequence flanking the region between the two cleavage sites or the two guide RNA recognition sequences that are furthest apart. As another example, in methods using exogenous repair templates, allelic sequence identity can be maximized for the 5' and/or 3' sequence flanking the region between the 5' and 3' target sequences for the exogenous repair template (i.e., the genomic region targeted for deletion by the exogenous repair template). The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50 kb, 60 kb, 70 kb, 80 kb, 90 kb, 100 kb, 110 kb, 120 kb, 130 kb, 140 kb, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50 kb, 60 kb, 70 kb, 80 kb, 90 kb, 100 kb, 110 kb, 120 kb, 130 kb, 140 kb, or 150 kb of flanking sequence.

Selecting a target region such that sequence identity is maximized for all or part of the target region between corresponding first and second chromosomes in a homologous chromosome pair does not necessarily mean looking at a target genomic locus on first and second chromosomes in a homologous chromosome pair and picking the region with the highest allelic sequence identity relative to the remainder of the target genomic locus but instead can take into account other factors. For example, if the target region comprises, consists essentially of, or consists of one or more guide RNA recognition sequences and/or sequence flanking the one or more guide RNA recognition sequences, other factors that can be taken into account include, for example, what putative guide RNA recognition sequences are located in the region, whether the putative guide RNA recognition sequences are unique, where within the region a putative guide RNA recognition sequence is located, how successful or specific the putative guide RNA recognition sequences in a region are predicted to be, the proximity of the putative guide RNA recognition sequences within the region to suitable 5' and 3' target sequences for an exogenous repair template, the proximity of putative guide RNA recognition sequences within the region to other putative guide RNA recognition sequences, the proximity of putative guide RNA recognition sequences within the region to a mutation targeted for correction, and so forth. For example, preferably a guide RNA recognition sequence is a unique target site not present elsewhere in the genome. See, e.g., US 2014/0186843, herein incorporated by reference in its entirety for all purposes. Likewise, guide RNA specificity can relate to and can be optimized by varying GC content and targeting sequence length, and algorithms are available for designing or evaluating a guide RNA targeting sequence that minimizes off-target binding or interaction of the guide RNA. See, e.g., WO 2016/094872, herein incorporated by reference in its entirety for all purposes. In some methods, Cas9 proteins from different species can be considered or used (e.g., *S. pyogenes* Cas9 and *S. aureus* Cas9) to increase the number of potential guide RNA recognition sequences due to the increased number of available PAM sequences.

In one example, the target region can be selected such that all or part of the target region has a high percentage of sequence identity between corresponding first and second chromosomes in a homologous chromosome pair. For example, the target region can be selected such that all or part of the target region has a minimum percentage of sequence identity between corresponding first and second chromosomes in a homologous chromosome pair, such as at least 95%, 95.5%, 96%, 96.5%, 97%, 97.5%, 98%, 98.5%, 99%, 99.1%, 99.2%, 99.3%, 99.4%, 99.5%, 99.55%, 99.6%, 99.65%, 99.7%, 99.75%, 99.8%, 99.85%, 99.9%, 99.95%, or 100% sequence identity.

In another example, the target region can be selected such that all or part of the target region has a low number or low density of single nucleotide variations between corresponding first and second chromosomes in a homologous chromosome pair. For example, the target region can be selected such that all or part of the target region has a maximum density of single nucleotide variations between corresponding first and second chromosomes in a homologous chromosome pair, such as no more than 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1 or zero single nucleotide variations per kb of sequence.

Optionally, the target region can be identical in the corresponding first and second chromosomes in the homologous chromosome pair. Optionally, the target region can be within the longest possible stretch of contiguous sequence identity within the target genomic locus.

Alternatively or additionally, the target region within a target genomic locus can be selected such that all or part of the target region has a high percentage of sequence identity or low number or low density of single nucleotide variations between corresponding first and second chromosomes in a homologous chromosome pair relative to other regions within the target genomic locus.

For example, the target region can have a higher percentage of sequence identity or a lower density of single nucleotide variations relative to all or part of the remainder of the target genomic locus. For example, the target region can have at least 99.9% sequence identity between the corresponding first and second homologous chromosomes, and the remainder of the target genomic locus has no more than 99.8% sequence identity between the corresponding first and second chromosomes.

For example, the target region can comprise, consist essentially of, or consist of one or more target genomic regions corresponding with one or more guide RNA recognition sequences, and the target region can have a high percentage of sequence identity or a low density of single nucleotide variations relative to other segments of the target genomic locus, such as genomic regions corresponding with one or more other potential guide RNA recognition sequences within the target genomic locus. As one example, the target region can comprise, consist essentially of, or consist of at least one or each of the one or more guide RNA recognition sequences, and the target region can have a high percentage of sequence identity or a low density of single nucleotide variations relative to other segments of the target genomic locus, such as one or more other potential guide RNA recognition sequences within the target genomic locus. As another example, the target region can comprise, consist essentially of, or consist of at least one or each of the one or more guide RNA recognition sequence and 5' and/or 3' sequence flanking the at least one or each of the one or more guide RNA recognition sequences, and the target region can have a high percentage of sequence identity or a low density of single nucleotide variations relative to other segments of the target genomic locus, such as one or more other potential guide RNA recognition sequences and their 5' and/or 3' flanking sequence within the target genomic locus. As yet another example, the target region can comprise, consist essentially of, or consist of the 5' and/or 3' sequence flanking at least one or each of the one or more guide RNA recognition sequences, and the target region can have a high percentage of sequence identity or a low density of single nucleotide variations relative to other segments of the target genomic locus, such as the 5' and/or 3' flanking sequence of one or more other potential guide RNA recognition sequences within the target genomic locus. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

In methods in which two guide RNAs are used, the target region can comprise, consist essentially of, or consist of a first target genomic region corresponding with the first guide RNA recognition sequence and/or within a second target genomic region corresponding with the second guide RNA recognition sequence, and the target region can have a high percentage of sequence identity or a low density of single nucleotide variations relative to other segments of the target genomic locus, such as genomic regions corresponding with one or more other potential guide RNA recognition sequences within the target genomic locus. For example, the target region can comprise, consist essentially of, or consist of the first guide RNA recognition sequence and/or the second guide RNA recognition sequence, and the target region can have a high percentage of sequence identity or a low density of single nucleotide variations relative to other segments of the target genomic locus, such as one or more other potential guide RNA recognition sequences within the target genomic locus. As another example, the target region can comprise, consist essentially of, or consist of a high percentage of the first guide RNA recognition sequence and 5' and/or 3' sequence flanking the first guide RNA recognition sequence and/or a the second guide RNA recognition sequence and 5' and/or 3' sequence flanking the second guide RNA recognition sequence, and the target region can have a high percentage of sequence identity or a low density of single nucleotide variations relative to other segments of the target genomic locus, such as genomic regions corresponding with one or more other potential guide RNA recognition sequences and their 5' and/or 3' flanking sequence within the target genomic locus. As yet another example, the target region can comprise, consist essentially of, or consist of the 5' and/or 3' sequence flanking the first guide RNA recognition sequence and/or the 5' and/or 3' sequence flanking the second guide RNA recognition sequence, and the target region can have a high percentage of sequence identity or a low density of single nucleotide variations relative to other segments of the target genomic locus, such as the 5' and/or 3' sequence flanking one or more other potential guide RNA recognition sequences within the target genomic locus. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

Thus, in methods in which one guide RNA is considered in selecting the target region, for example, selecting the target region can comprise comparing two or more segments of the target genomic locus, wherein each segment comprises, consists essentially of, or consists of a different guide RNA recognition sequence not present elsewhere in the genome and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the different guide RNA recognition sequence, and selecting as the target region the segment having the highest percentage of sequence identity relative to the other segments. If two or more guide RNAs are used, the method can comprise selecting as the target region the two or more segments having the highest percentage of sequence identity relative to other segments. Optionally, the one or more segments can comprise, consist essentially of, or consist of segments corresponding with each guide RNA recognition sequence in the target genomic locus but not present elsewhere in the genome.

Alternatively or additionally, in methods in which two guide RNAs are used, the target region can comprise, consist essentially of, or consist of the region between the first and second guide RNA recognition sequences or the first and second cleavage sites, and the target region can have a high percentage of sequence identity or a low density of single nucleotide variations relative to other segments of the target genomic locus, such as the region between one or more other pairs of potential guide RNA recognition sequences or cleavage sites within the target genomic locus. If three or more guide RNAs are used, the relevant region would be the region between the two guide RNA recognition sequences or the two cleavage sites that are furthest apart.

Thus, in methods in which two guide RNAs are used, for example, selecting the target region can comprise comparing two or more segments of the target genomic locus, wherein each segment comprises, consists essentially of, or consists of the region between a different pair of guide RNA recognition sequences, wherein the guide RNA recognition sequences are not present elsewhere in the genome, and selecting as the target region the segment having the highest percentage of sequence identity relative to the other segments. Optionally, the one or more segments comprise, consist essentially of, or consist of segments corresponding with each different pair of guide RNA recognition sequences in the target genomic locus, wherein the guide RNA recognition sequences are not present elsewhere in the genome.

Alternatively or additionally, in methods in which two guide RNAs are used, the target region can comprise, consist essentially of, or consist of region between the first and second guide RNA recognition sequences or the first and second cleavage sites and the 5' and/or 3' sequence flanking the genomic region between the first and second guide RNA recognition sequences or the first and second cleavage sites, and the target region can have a high percentage of sequence identity or a low density of single nucleotide variations relative to other segments of the target genomic locus, such as the region between one or more other pairs of potential guide RNA recognition sequences or cleavage sites within the target genomic locus and the 5' and/or 3' sequence flanking genomic regions between one or more other pairs of potential guide RNA recognition sequences or cleavage sites. Preferably, the target region can comprise, consist essentially of, or consist of the genomic region between the first and second guide RNA recognition sequences or the first and second cleavage sites and the 5' and 3' sequence flanking the genomic region between the first and second guide RNA recognition sequences or the first and second cleavage sites, and the target region can have a high percentage of sequence identity or a low density of single nucleotide variations relative to other segments of the target genomic locus, such as the region between one or more other pairs of potential guide RNA recognition sequences or cleavage sites within the target genomic locus and the 5' and 3' sequence flanking genomic regions between one or more other pairs of potential guide RNA recognition sequences or cleavage sites. If three or more guide RNAs are used, the relevant region would be the 5' and/or 3' sequence flanking the genomic region between the two guide RNA recognition sequences or the two cleavage sites that are furthest apart. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

Thus, in methods in which two guide RNAs are used, for example, selecting the target region can comprise comparing two or more segments of the target genomic locus, wherein each segment comprises, consists essentially of, or consists of the region between a different pair of guide RNA recognition sequences and at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between the different pair of guide RNA recognition sequences, wherein the guide RNA recognition sequences are not present elsewhere in the genome, and selecting as the target region the segment having the highest percentage of sequence identity relative to the other segments. Optionally, the one or more segments comprise, consist essentially of, or consist of segments corresponding with each different pair of guide RNA recognition sequences in the target genomic locus, wherein the guide RNA recognition sequences are not present elsewhere in the genome.

Alternatively or additionally, in methods in which two guide RNAs are used, the target region can comprise, consist essentially of, or consist of the 5' and/or 3' sequence flanking the genomic region between the first and second guide RNA recognition sequences or the first and second cleavage sites, and the target region can have a high percentage of sequence identity or a low density of single nucleotide variations relative to other segments of the target genomic locus, such as the 5' and/or 3' sequence flanking genomic regions between one or more other pairs of potential guide RNA recognition sequences or cleavage sites within the target genomic locus. Preferably, the target region can comprise, consist essentially of, or consist of the 5' and 3' sequence flanking the genomic region between the first and second guide RNA recognition sequences or the first and second cleavage sites, and the target region can have a high percentage of sequence identity or a low density of single nucleotide variations relative to other segments of the target genomic locus, such as the 5' and 3' sequence flanking genomic regions between one or more other pairs of potential guide RNA recognition sequences or cleavage sites within the target genomic locus. If three or more guide RNAs are used, the relevant region would be the 5' and/or 3' sequence flanking the genomic region between the two guide RNA recognition sequences or the two cleavage sites that are furthest apart. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

Thus, in methods in which two guide RNAs are used, for example, selecting the target region can comprise comparing two or more non-contiguous segments of the target genomic locus, wherein each non-contiguous segment comprises, consists essentially of, or consists of at least 10 bp, 20 bp, 30 bp, 40 bp, 50 bp, 100 bp, 200 bp, 300 bp, 400 bp, 500 bp, 600 bp, 700 bp, 800 bp, 900 bp, 1,000 bp, 1 kb, 2 kb, 3 kb, 4 kb, 5 kb, 6, kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, or 150 kb of flanking sequence on the 5' side, the 3' side, or each side of the genomic region between a different pair of guide RNA recognition sequences, wherein the guide RNA recognition sequences are not present elsewhere in the genome, and selecting as the target region the non-contiguous segment having the highest percentage of sequence identity relative to the other non-contiguous segments. Optionally, the one or more non-contiguous segments comprise, consist essentially of, or consist of non-contiguous segments corresponding with each different pair of guide RNA recognition sequences in the target genomic locus, wherein the guide RNA recognition sequences are not present elsewhere in the genome.

In methods in which an exogenous repair templates are used, the target region can comprise, consist essentially of, or consist of the region between the 5' and 3' target sequences, and the target region can have a high percentage of sequence identity or a low density of single nucleotide variations relative to other segments of the target genomic locus. Alternatively or additionally, the target region can comprise, consist essentially of, or consist of the 5' and/or 3' target sequences, and the target region can have a high percentage of sequence identity or a low density of single nucleotide variations relative to other segments of the target genomic locus. Preferably, the target region can comprise, consist essentially of, or consist of the 5' and 3' target sequences, and the target region can have a high percentage of sequence identity or a low density of single nucleotide variations relative to other segments of the target genomic locus. For example, the target region can comprise, consist essentially of, or consist of the region flanked by and including the 5' and 3' target sequences, and the target region can have a high percentage of sequence identity or a low density of single nucleotide variations relative to other segments of the target genomic locus.

Likewise, in methods in which an exogenous repair template is used, the target region can comprise, consist essentially of, or consist of the 5' and/or 3' sequence flanking the genomic region between the 5' and 3' target sequences of the exogenous repair template or the 5' and/or 3' sequence flanking the genomic region between and including the 5' and 3' target sequences of the exogenous repair template, and the target region can have a high percentage of sequence identity or a low density of single nucleotide variations relative to other segments of the target genomic locus. Preferably, the target region can comprise, consist essentially of, or consist of the 5' and 3' sequence flanking the genomic region between the 5' and 3' target sequences of the exogenous repair template or within the 5' and 3' sequence flanking the genomic region between and including the 5' and 3' target sequences of the exogenous repair template, and the target region can have a high percentage of sequence identity or a low density of single nucleotide variations relative to other segments of the target genomic locus. Alternatively, the target region can comprise, consist essentially of, or consist of the region between the 5' and 3' target sequences of the exogenous repair template and 5' and/or 3' sequence flanking the genomic region between the 5' and 3' target sequences, and the target region can have a high percentage of sequence identity or a low density of single nucleotide variations relative to other segments of the target genomic locus. Preferably, the target region can comprise, consist essentially of, or consist of the region between the 5' and 3' target sequences of the exogenous repair template and 5' and 3' sequence flanking the genomic region between the 5' and 3' target sequences, and the target region can have a high percentage of sequence identity or a low density of single nucleotide variations relative to other segments of the target genomic locus. The 5' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence. Likewise, the 3' flanking sequence can be, for example, at least 10, 20, 30, 40, 50, 100, 200, 300, 400, 500, 600, 700, 800, 900, or 1,000 bp of flanking sequence or at least 1, 2, 3, 4, 5, 6, 7, 8, 9, 10, 20, 30, 40, 50, 60, 70, 80, 90, 100, 110, 120, 130, 140, or 150 kb of flanking sequence.

A target region modified by the methods disclosed herein can include any segment or region (contiguous or non-contiguous) of DNA within a cell. The target region can be native to the cell, can be a heterologous or exogenous segment of DNA that was integrated into the genome of the cell, or can be a combination thereof. Such heterologous or exogenous segments of DNA can include transgenes, expression cassettes, polynucleotide encoding selection makers, or heterologous or exogenous regions of genomic DNA.

B. CRISPR/Cas Systems

The methods disclosed herein utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. Alternatively a CRISPR/Cas system can be, for example, a type V system (e.g., subtype V-A or subtype V-B). The methods and compositions disclosed herein employ CRISPR/Cas systems by utilizing CRISPR complexes (comprising a guide RNA (gRNA) complexed with a Cas protein) for site-directed cleavage of nucleic acids.

The CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together. Other CRISPR/Cas systems employ a Cas protein that does not occur naturally, and other CRISPR/Cas systems employ a gRNA that does not occur naturally.

(1) Cas Proteins

Cas proteins generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break in the target nucleic acid (e.g., a double-strand break with blunt ends), or it can be a nickase that creates a single-strand break in the target nucleic acid.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein from a type II CRISPR/Cas system. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus w atsoni, P seudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp *Microcoleus chthonoplastes, Oscillatoria* sp., *Petrotoga mobilis, Thermosipho africanus, Acaryochloris marina, Neisseria meningitidis,* or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (Sa Cas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3):759-771, herein incorporated by reference in its entirety for all purposes. Exemplary Cpf1 proteins are from *Francisella tularensis* 1, *Francisella tularensis* subsp. *novicida, Prevotella albensis*, Lachnospiraceae bacterium MC2017 1, *Butyrivibrio proteoclasticus*, Peregrinibacteria bacterium GW2011 GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a guide RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null Cas protein). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), Lachnospiraceae bacterium ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

An example of a Cas fusion protein is a Cas protein fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Other suitable NLSs include alpha-importin NLS. Such subcellular localization signals can be located at the N-terminus, the C-terminus, or anywhere within the Cas protein. An NLS can comprise a stretch of basic amino acids, and can be a monopartite sequence or a bipartite sequence. Optionally, the Cas protein comprises two or more NLSs, including an NLS (e.g., an alpha-importin NLS) at the N-terminus and/or an NLS (e.g., an SV40 NLS) at the C-terminus.

Cas proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290, herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas9 proteins can also be tethered to exogenous repair templates or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous repair template or labeled nucleic acid can be tethered to the C-terminus, the N-terminus, or to an internal region within the Cas9 protein. Preferably, the exogenous repair template or labeled nucleic acid is tethered to the C-terminus or the N-terminus of the Cas9 protein. Likewise, the Cas9 protein can be tethered to the 5' end, the 3' end, or to an internal region within the exogenous repair template or labeled nucleic acid. That is, the exogenous repair template or labeled nucleic acid can be tethered in any orientation and polarity. Preferably, the Cas9 protein is tethered to the 5' end or the 3' end of the exogenous repair template or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

(2) Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence or cleavage. The terms "guide RNA" and "gRNA" include both double-molecule gRNAs (i.e., modular gRNAs) and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to a guide RNA recognition sequence. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence (i.e., the guide RNA recognition sequence) in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from S. pyogenes, a typical DNA-targeting segment is between 16 and 20 nucleotides in length or between 17 and 20 nucleotides in length. For Cas9 from S. aureus, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from S. pyogenes include 171-nucleotide, 89-nucleotide, 75-nucleotide, and 65-nucleotide versions. See, e.g., Deltcheva et al. (2011) Nature 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting sequence and the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the guide RNA recognition sequence within the target DNA can be at least 60% over about 20 contiguous nucleotides. As an example, the percent complementarity between the DNA-targeting sequence and the guide RNA recognition sequence within the target DNA is 100% over the 14 contiguous nucleotides at the 5' end of the guide RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the guide RNA recognition sequence within the target DNA is 100% over the seven contiguous nucleotides at the 5' end of the guide RNA recognition sequence within the complementary strand of the target DNA and as low as 0% over the remainder. In such a case, the DNA-targeting sequence can be considered to be 7 nucleotides in length. In some guide RNAs, at least 17 nucleotides within the DNA-target sequence are complementary to the target DNA. For example, the DNA-targeting sequence can be 20 nucleotides in length and can comprise 1, 2, or 3 mismatches with the target DNA (the guide RNA recognition sequence). Preferably, the mismatches are not adjacent to a protospacer adjacent motif (PAM) sequence (e.g., the mismatches are in the 5' end of the DNA-targeting sequence, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs have the DNA-targeting segment and a scaffold sequence (i.e., the protein-binding or Cas-binding sequence of the guide RNA). Exemplary scaffold sequences include:

```
                                     (SEQ ID NO: 150)
GTTGGAACCATTCAAAACAGCATAGCAAGTTAAAATAAGGCTAGTCCGT

TATCAACTTGAAAAAGTGGCACCGAGTCGGTGC;

(SEQ ID NO: 151)
GTTTTAGAGCTAGAAATAGCAAGTTAAAATAAGGCTAGTCCGTTATCAA

CTTGAAAAAGTGGCACCGAGTCGGTGC;
and (SEQ ID NO: 152)
GTTTAAGAGCTATGCTGGAAACAGCATAGCAAGTTTAAATAAGGCTAGT

CCGTTATCAACTTGAAAAAGTGGCACCGAGTCGGTGC.
```

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be prepared by chemical synthesis.

The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising an exogenous repair template and/or a vector comprising a nucleic acid encoding a Cas protein. Alternatively, it can be in a vector or a plasmid that is separate from the vector comprising an exogenous repair template and/or the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

(3) Guide RNA Recognition Sequences

The term "guide RNA recognition sequence" includes nucleic acid sequences present in a target DNA to which a DNA-targeting segment of a gRNA will bind, provided sufficient conditions for binding exist. For example, guide RNA recognition sequences include sequences to which a guide RNA is designed to have complementarity, where hybridization between a guide RNA recognition sequence and a DNA targeting sequence promotes the formation of a CRISPR complex. Full complementarity is not necessarily required, provided that there is sufficient complementarity to cause hybridization and promote formation of a CRISPR complex. Guide RNA recognition sequences also include cleavage sites for Cas proteins, described in more detail below. A guide RNA recognition sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence of the nickase on the first strand is separated from the guide RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific binding and cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA recognition sequence. Optionally, the guide RNA recognition sequence can be flanked on the 3' end by the PAM. Alternatively, the guide RNA recognition sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-$CCN_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT (SEQ ID NO: 146) or NNGRR (SEQ ID NO: 147), where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

Examples of guide RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas9 protein, such as GN19NGG (SEQ ID NO: 1) or $N_{20}$NGG (SEQ ID NO: 2) (see, e.g., WO 2014/165825, herein incorporated by reference in its entirety for all purposes). The guanine at the 5' end can facilitate transcription by RNA polymerase in cells. Other examples of guide RNA recognition sequences can include two guanine nucleotides at the 5' end (e.g., GG$N_{20}$NGG; SEQ ID NO: 3) to facilitate efficient transcription by T7 polymerase in vitro. See, e.g., WO 2014/065596, herein incorporated by reference in its entirety for all purposes. Other guide RNA recognition sequences can have between 4-22 nucleotides in length of SEQ ID NOS: 1-3, including the 5' G or GG and the 3' GG or NGG. Yet other guide RNA recognition sequences can have between 14 and 20 nucleotides in length of SEQ ID NOS: 1-3.

The guide RNA recognition sequence can be any nucleic acid sequence endogenous or exogenous to a cell. The guide RNA recognition sequence can be a sequence coding a gene product (e.g., a protein) or a non-coding sequence (e.g., a regulatory sequence) or can include both.

C. Exogenous Repair Templates

The methods and compositions disclosed herein can utilize exogenous repair templates to modify a target genomic locus following cleavage of the target genomic locus with a Cas protein. For example, the cell can be a one-cell stage embryo, and the exogenous repair template can be less 5 kb in length. In cell types other than one-cell stage embryos, the exogenous repair template (e.g., targeting vector) can be longer. For example, in cell types other than one-cell stage embryos, the exogenous repair template can be a large targeting vector (LTVEC) as described elsewhere herein (e.g., a targeting vector having a length of at least 10 kb or having 5' and 3' homology arms having a sum total of at least 10 kb). Using exogenous repair templates in combination with Cas proteins may result in more precise modifications at the target genomic locus by promoting homology-directed repair.

In such methods, the Cas protein cleaves the target genomic locus to create a single-strand break (nick) or double-strand break, and the exogenous repair template recombines the target nucleic acid via non-homologous end joining (NHEJ)-mediated ligation or through a homology-directed repair event. Optionally, repair with the exogenous repair template removes or disrupts the guide RNA recognition sequence or the Cas cleavage site so that alleles that have been targeted cannot be re-targeted by the Cas protein.

Exogenous repair templates can comprise deoxyribonucleic acid (DNA) or ribonucleic acid (RNA), they can be single-stranded or double-stranded, and they can be in linear or circular form. For example, an exogenous repair template can be a single-stranded oligodeoxynucleotide (ssODN). See, e.g., Yoshimi et al. (2016) *Nat. Commun.* 7:10431, herein incorporated by reference in its entirety for all purposes. An exemplary exogenous repair template is between about 50 nucleotides to about 5 kb in length, is between about 50 nucleotides to about 3 kb in length, or is between about 50 to about 1,000 nucleotides in length. Other exemplary exogenous repair templates are between about 40 to about 200 nucleotides in length. For example, an exogenous repair template can be between about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Alternatively, an exogenous repair template can be between about 50 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Alternatively, an exogenous repair template can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. Alternatively, an exogenous repair template can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. In cell types other than one-cell stage embryos, the exogenous repair template (e.g., targeting vector) can be longer. For example, in cell types other than one-cell stage embryos, the exogenous repair template can be a large targeting vector (LTVEC) as described elsewhere herein.

In one example, an exogenous repair template is an ssODN that is between about 80 nucleotides and about 200 nucleotides in length. In another example, an exogenous repair templates is an ssODN that is between about 80 nucleotides and about 3 kb in length. Such an ssODN can have homology arms, for example, that are each between about 40 nucleotides and about 60 nucleotides in length.

Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous repair templates can include modifications or sequences that provide for additional desirable features (e.g., modified or regulated stability; tracking or detecting with a fluorescent label; a binding site for a protein or protein complex; and so forth). Exogenous repair templates can comprise one or more fluorescent labels, purification tags, epitope tags, or a combination thereof. For example, an exogenous repair template can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and -6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous repair template that has been directly integrated into a cleaved target nucleic acid having protruding ends compatible with the ends of the exogenous repair template. The label or tag can be at the 5' end, the 3' end, or internally within the exogenous repair template. For example, an exogenous repair template can be conjugated at 5' end with the IR700 fluorophore from Integrated DNA Technologies (5'IRDYE® 700).

Exogenous repair templates can also comprise nucleic acid inserts including segments of DNA to be integrated at target genomic loci. Integration of a nucleic acid insert at a target genomic locus can result in addition of a nucleic acid sequence of interest to the target genomic locus, deletion of a nucleic acid sequence of interest at the target genomic locus, or replacement of a nucleic acid sequence of interest at the target genomic locus (i.e., deletion and insertion). Some exogenous repair templates are designed for insertion of a nucleic acid insert at a target genomic locus without any corresponding deletion at the target genomic locus. Other exogenous repair templates are designed to delete a nucleic acid sequence of interest at a target genomic locus without any corresponding insertion of a nucleic acid insert. Yet other exogenous repair templates are designed to delete a nucleic acid sequence of interest at a target genomic locus and replace it with a nucleic acid insert.

The nucleic acid insert or the corresponding nucleic acid at the target genomic locus being deleted and/or replaced can be various lengths. An exemplary nucleic acid insert or corresponding nucleic acid at the target genomic locus being deleted and/or replaced is between about 1 nucleotide to about 5 kb in length or is between about 1 nucleotide to about 1,000 nucleotides in length. For example, a nucleic acid insert or a corresponding nucleic acid at the target genomic locus being deleted and/or replaced can be between about 1 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Likewise, a nucleic acid insert or a corresponding nucleic acid at the target genomic locus being deleted and/or replaced can be between about 1 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Likewise, a nucleic acid insert or a corresponding nucleic acid at the target genomic locus being deleted and/or replaced can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. A nucleic acid being deleted from a target genomic locus can also be between about 1 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, about 90 kb to about 100 kb, about 100 kb to about 200 kb, about 200 kb to about 300 kb, about 300 kb to about 400 kb, about 400 kb to about 500 kb, about 500 kb to about 600 kb, about 600 kb to about 700 kb, about 700 kb to about 800 kb, about 800 kb to about 900 kb, about 900 kb to about 1 Mb or longer. Alternatively, a nucleic acid being deleted from a target genomic locus can be between about 1 Mb to about 1.5 Mb, about 1.5 Mb to about 2 Mb, about 2 Mb to about 2.5 Mb, about 2.5 Mb to about 3 Mb, about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

The nucleic acid insert can comprise genomic DNA or any other type of DNA. For example, the nucleic acid insert can be from a prokaryote, a eukaryote, a yeast, a bird (e.g., chicken), a non-human mammal, a rodent, a human, a rat, a mouse, a hamster, a rabbit, a pig, a bovine, a deer, a sheep, a goat, a cat, a dog, a ferret, a primate (e.g., marmoset, rhesus monkey), a domesticated mammal, an agricultural mammal, a turtle, or any other organism of interest.

The nucleic acid insert can comprise a sequence that is homologous or orthologous to all or part of a gene encoding the self-antigen (e.g., a portion of the gene encoding a particular motif or region of the self-antigen). The homologous sequence can be from a different species or the same species. For example, the nucleic acid insert can comprise a sequence that comprises one or more point mutations (e.g., 1, 2, 3, 4, 5, or more) compared with a sequence targeted for replacement at the target genomic locus. Optionally, such point mutations can result in a conservative amino acid substitution (e.g., substitution of aspartic acid [Asp, D] with glutamic acid [Glu, E]) in the encoded polypeptide.

The nucleic acid insert or the corresponding nucleic acid at the target genomic locus being deleted and/or replaced can be a coding region such as an exon; a non-coding region such as an intron, an untranslated region, or a regulatory region (e.g., a promoter, an enhancer, or a transcriptional repressor-binding element); or any combination thereof.

The nucleic acid insert can also comprise a conditional allele. The conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

Nucleic acid inserts can also comprise a polynucleotide encoding a selection marker. Alternatively, the nucleic acid inserts can lack a polynucleotide encoding a selection marker. The selection marker can be contained in a selection cassette. Optionally, the selection cassette can be a self-deleting cassette. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. Exemplary selection markers include neomycin phosphotransferase (neo$^r$), hygromycin B phosphotransferase (hyg$^r$), puromycin-N-acetyltransferase (puro$^r$), blasticidin S deaminase (bs$^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A given cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein.

The nucleic acid insert can comprise a nucleic acid flanked with site-specific recombination target sequences. Alternatively, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In one example, the site-specific recombination sites flank a polynucleotide encoding a selection marker and/or a reporter gene contained within the nucleic acid insert. Following integration of the nucleic acid insert at a targeted locus, the sequences between the site-specific recombination sites can be removed. Optionally, two exogenous repair templates can be used, each with a nucleic acid insert comprising a site-specific recombination site. The exogenous repair templates can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res*. 31:418-420; Roberts et al., (2003) *Nucleic Acids Res*. 31:1805-1812; and Belfort et al. (2002) in Mobile DNA II, pp. 761-783, Eds. Craigie et al., (ASM Press, Washington, DC)).

(1) Repair Templates for Non-Homologous-End-Joining-Mediated Insertion

Some exogenous repair templates have short single-stranded regions at the 5' end and/or the 3' end that are complementary to one or more overhangs created by Cas-protein-mediated cleavage at the target genomic locus. These overhangs can also be referred to as 5' and 3' homology arms. For example, some exogenous repair templates have short single-stranded regions at the 5' end and/or the 3' end that are complementary to one or more overhangs created by Cas-protein-mediated cleavage at 5' and/or 3' target sequences at the target genomic locus. Some such exogenous repair templates have a complementary region only at the 5' end or only at the 3' end. For example, some such exogenous repair templates have a complementary region only at the 5' end complementary to an overhang created at a 5' target sequence at the target genomic locus or only at the 3' end complementary to an overhang created at a 3' target sequence at the target genomic locus. Other such exogenous repair templates have complementary regions at both the 5' and 3' ends. For example, other such exogenous repair templates have complementary regions at both the 5' and 3' ends e.g., complementary to first and second overhangs, respectively, generated by Cas-mediated cleavage at the target genomic locus. For example, if the exogenous repair template is double-stranded, the single-stranded complementary regions can extend from the 5' end of the top strand of the repair template and the 5' end of the bottom strand of the repair template, creating 5' overhangs on each end. Alternatively, the single-stranded complementary region can extend from the 3' end of the top strand of the repair template and from the 3' end of the bottom strand of the template, creating 3' overhangs.

The complementary regions can be of any length sufficient to promote ligation between the exogenous repair template and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA recognition sequences corresponding with first, second, third, and fourth guide RNAs. The first and second guide RNA recognition sequences can be positioned to create a first cleavage site such that the nicks created by the first and second nickases on the first and second strands of DNA create a double-strand break (i.e., the first cleavage site comprises the nicks within the first and second guide RNA recognition sequences). Likewise, the third and fourth guide RNA recognition sequences can be positioned to create a second cleavage site such that the nicks created by the third and fourth nickases on the first and second strands of DNA create a double-strand break (i.e., the second cleavage site comprises the nicks within the third and fourth guide RNA recognition sequences). Preferably, the nicks within the first and second guide RNA recognition sequences and/or the third and fourth guide RNA recognition sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous repair template can be designed with single-stranded complementary regions that are complementary to the overhangs created by the nicks within the first and second guide RNA recognition sequences and by the nicks within the third and fourth guide RNA recognition sequences. Such an exogenous repair template can then be inserted by non-homologous-end-joining-mediated ligation.

(2) Repair Templates for Insertion by Homology-Directed Repair

Some exogenous repair templates comprise homology arms. If the exogenous repair template also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous repair template. The 5' and 3' homology arms correspond to regions within the target genomic locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25 to about 30, about 30 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternatively, for example, they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library, or can be derived from synthetic DNA.

When a CRISPR/Cas system is used in combination with an exogenous repair template, the 5' and 3' target sequences are preferably located in sufficient proximity to the Cas cleavage site (e.g., within sufficient proximity to a guide RNA recognition sequence) so as to promote the occurrence of a homologous recombination event between the target sequences and the homology arms upon a single-strand break (nick) or double-strand break at the Cas cleavage site. The term "Cas cleavage site" includes a DNA sequence at which a nick or double-strand break is created by a Cas enzyme (e.g., a Cas9 protein complexed with a guide RNA). The target sequences within the targeted locus that correspond to the 5' and 3' homology arms of the exogenous repair template are "located in sufficient proximity" to a Cas cleavage site if the distance is such as to promote the occurrence of a homologous recombination event between the 5' and 3' target sequences and the homology arms upon a single-strand break or double-strand break at the Cas cleavage site. Thus, the target sequences corresponding to the 5' and/or 3' homology arms of the exogenous repair template can be, for example, within at least 1 nucleotide of a given Cas cleavage site or within at least 10 nucleotides to about 1,000 nucleotides of a given Cas cleavage site. As an example, the Cas cleavage site can be immediately adjacent to at least one or both of the target sequences.

Alternatively, a given cleavage site can be varying lengths from the 5' target sequence, the 3' target sequence, or both target sequences. For example, if two guide RNAs are used, the first and/or second guide RNA recognition sequences or the first and/or second cleavage sites can be located between the 5' and 3' target sequences or can be adjacent to or in proximity to the 5' target sequence and/or the 3' target sequence, such as within 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 250 kb, 300 kb, 350 kb, 400 kb, 450 kb, or 500 kb of the 5' and/or 3' target sequences. Alternatively, the first and/or second guide RNA recognition sequences or the first and/or second cleavage sites can be located at least 50 bp, at least 100 bp, at least 200 bp, at least 300 bp, at least 400 bp, at least 500 bp, at least 600 bp, at least 700 bp, at least 800 bp, at least 900 bp, at least 1 kb, at least 2 kb, at least 3 kb, at least 4 kb, at least 5 kb, at least 6 kb, at least 7 kb, at least 8 kb, at least 9 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb from the 5' and/or 3' target sequences. For example, the first and/or second guide RNA recognition sequence or the first and/or second cleavage sites can be located between about 50 bp to about 100 bp, about 200 bp to about 300 bp, about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 100 kb, about 100 kb to about 150 kb, about 150 kb to about 200 kb, about 200 kb to about 300 kb, about 300 kb to about 400 kb, or about 400 kb to about 500 kb from the 5' and/or 3' target sequences. Alternatively, the first and/or second guide RNA recognition sequences or the first and/or second cleavage sites can be located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from the 5' and/or 3' target sequences. For example, the first guide RNA recognition sequence or the first cleavage site can be located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from the 5' target sequence or from both the 5' and 3' target sequences. Likewise, the second guide RNA recognition sequence or the second cleavage site can be located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from the 3' target sequence or from both the 5' and 3' target sequences.

The spatial relationship of the target sequences that correspond to the homology arms of the exogenous repair template and the Cas cleavage site can vary. For example, target sequences can be located 5' to the Cas cleavage site, target sequences can be located 3' to the Cas cleavage site, or the target sequences can flank the Cas cleavage site.

In cells other than one-cell stage embryos, the exogenous repair template can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; and 7,105,348; and in WO 2002/036789, each of which is herein incorporated by reference in its entirety for all purposes. LTVECs can be in linear form or in circular form.

LTVECs can be of any length and are typically at least 10 kb in length. For example, an LTVEC can be from about 50 kb to about 300 kb, from about 50 kb to about 75 kb, from about 75 kb to about 100 kb, from about 100 kb to 125 kb, from about 125 kb to about 150 kb, from about 150 kb to about 175 kb, from about 175 kb to about 200 kb, from about 200 kb to about 225 kb, from about 225 kb to about 250 kb, from about 250 kb to about 275 kb or from about 275 kb to about 300 kb. An LTVEC can also be from about 50 kb to about 500 kb, from about 100 kb to about 125 kb, from about 300 kb to about 325 kb, from about 325 kb to about 350 kb, from about 350 kb to about 375 kb, from about 375 kb to about 400 kb, from about 400 kb to about 425 kb, from about 425 kb to about 450 kb, from about 450 kb to about 475 kb, or from about 475 kb to about 500 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR The sum total of the 5' homology arm and the 3' homology arm in an LTVEC is typically at least 10 kb. As an example, the 5' homology arm can range from about 5 kb to about 100 kb and/or the 3' homology arm can range from about 5 kb to about 100 kb. As another example, the 5' homology arm can range from about 5 kb to about 150 kb and/or the 3' homology arm can range from about 5 kb to about 150 kb. Each homology arm can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. The sum total of the 5' and 3' homology arms can be, for example, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. The sum total of the 5' and 3' homology arms can also be, for example, from about 200 kb to about 250 kb, from about 250 kb to about 300 kb, from about 300 kb to about 350 kb, or from about 350 kb to about 400 kb. Alternatively, each homology arm can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Each homology arm can also be at least 250 kb, at least 300 kb, at least 350 kb, or at least 400 kb.

LTVECs can comprise nucleic acid inserts having nucleic acid sequences larger than those typically used by other approaches intended to perform homologous recombination in cells. For example, an LTVEC can comprise a nucleic acid insert ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, or greater. The LTVEC can also comprise a nucleic acid insert ranging, for example, from about 1 kb to about 5 kb, from about 400 kb to about 450 kb, from about 450 kb to about 500 kb, or greater. Alternatively, the nucleic acid insert can be at least 1 kb, at least 5 kb, at least 10 kb, at least 20 kb, at least 30 kb, at least 40 kb, at least 60 kb, at least 80 kb, at least 100 kb, at least 150 kb, at least 200 kb, at least 250 kb, at least 300 kb, at least 350 kb, at least 400 kb, at least 450 kb, or at least 500 kb.

D. Contacting the Genome of a Cell and Introducing Nucleic Acids or Proteins into Cells Contacting the genome of a cell can comprise introducing one or more Cas proteins or nucleic acids encoding Cas proteins, one or more guide RNAs or nucleic acids encoding guide RNAs (i.e., one or more CRISPR RNAs and one or more tracrRNAs), and one or more exogenous repair templates into the cell, provided that if the cell is a one-cell stage embryo, for example, the exogenous repair template can be less than 5 kb in length. Contacting the genome of cell (e.g., contacting a cell) can comprise introducing only one of the above components, one or more of the components, or all of the components into the cell. "Introducing" includes presenting to the cell the nucleic acid or protein in such a manner that the sequence gains access to the interior of the cell. The introducing can be accomplished by any means, and one or more of the components (e.g., two of the components, or all of the components) can be introduced into the cell simultaneously or sequentially in any combination. For example, an exogenous repair template can be introduced prior to the introduction of a Cas protein and a guide RNA, or it can be introduced following introduction of the Cas protein and the guide RNA (e.g., the exogenous repair template can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes.

A Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. When introduced in the form of a DNA, the DNA encoding a guide RNA can be operably linked to a promoter active in the cell. Such DNAs can be in one or more expression constructs.

A guide RNA can be introduced into the cell in the form of an RNA or in the form of a DNA encoding the guide RNA. When introduced in the form of a DNA, the DNA encoding a guide RNA can be operably linked to a promoter active in the cell. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of separate nucleic acid molecules).

In some methods, DNA encoding a nuclease agent (e.g., a Cas protein and a guide RNA) and/or DNA encoding an exogenous repair template can be introduced into a cell via DNA minicircles. See, e.g., WO 2014/182700, herein incorporated by reference in its entirety for all purposes. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods provided herein do not depend on a particular method for introducing a nucleic acid or protein into the cell, only that the nucleic acid or protein gains access to the interior of a least one cell. Methods for introducing nucleic acids and proteins into various cell types are known in the art and include, for example, stable transfection methods, transient transfection methods, and virus-mediated methods.

Transfection protocols as well as protocols for introducing nucleic acids or proteins into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by lentivirus, by retrovirus, by transfection, by lipid-mediated transfection, or by nucleofection. Introduction of nucleic acids or proteins into a cell can also be mediated by adeno-associated virus. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell (e.g., a one-cell stage embryo) can also be accomplished by microinjection. In one-cell stage embryos, microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a nucleic acid encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); Meyer et al. (2010) *Proc. Natl. Acad. Sci. USA* 107:15022-15026 and Meyer et al. (2012) *Proc. Natl. Acad. Sci. USA* 109:9354-9359. Introduction into one-cell stage embryos can also be accomplished by electroporation.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In some cases, the cells employed in the methods and compositions have a DNA construct stably incorporated into their genome. In such cases, the contacting can comprise providing a cell with the construct already stably incorporated into its genome. For example, a cell employed in the methods disclosed herein may have a preexisting Cas-encoding gene stably incorporated into its genome (i.e., a Cas-ready cell). "Stably incorporated" or "stably introduced" or "stably integrated" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

E. Target Genomic Loci and Locations of Guide RNA Recognition Sequences

The target genomic locus can be any genomic locus that affects expression of a self-antigen homologous to or sharing an epitope of interest with the foreign target antigen of interest. Preferably, the target genomic locus comprises, consists essentially of, or consists of all or part of the gene encoding the self-antigen. As an example, the target genomic locus can comprise, consist essentially of, or consist of a region comprising the start codon of a gene encoding the self-antigen, or can comprise, consist essentially of, or consist of the entire coding region of the gene. Alternatively, the target genomic locus can comprise, consist essentially of, or consist of another genomic locus that affects expression of the gene encoding the self-antigen. An example of such a genomic locus is all or part of a gene encoding a transcriptional regulator required for expression of the gene encoding the self-antigen. In some methods, multiple target genomic loci can be targeted. As an example, if there are multiple genes encoding multiple self-antigens homologous to or sharing an epitope of interest with the foreign antigen of interest, each of the multiple genes can be targeted, either sequentially or simultaneously.

The first and second guide RNA recognition sequences can be anywhere within the target genomic locus. For example, the first and second guide RNA recognition sequences can flank all or part of a gene encoding a self-antigen that is homologous to or sharing an epitope of interest with a foreign target antigen of interest. In one example, the first guide RNA recognition sequence comprises the start codon for the gene encoding the self-antigen or is within about 10, 20, 30, 40, 50, 100, 200, 300, 400, 500, or 1,000 nucleotides of the start codon, and the second guide RNA recognition sequence comprises the stop codon for the gene encoding the self-antigen or is within about 10, 20, 30, 40, 50, 100, 200, 300, 400, 500, or 1,000 nucleotides of the stop codon. For example, the first guide RNA recognition sequence can comprise the start codon, and the second guide RNA recognition can comprise the stop codon. If third and fourth guide RNAs are also used, the third and fourth guide RNA recognition sequences can also be anywhere within the target genomic locus. For example, two of the guide RNA recognition sequences (e.g., the first and third, wherein the first and third guide RNA recognition sequences are different and optionally overlapping) can comprise the start codon for the gene encoding the self-antigen or can be within about 10, 20, 30, 40, 50, 100, 200, 300, 400, 500, or 1,000 nucleotides of the start codon, and the other two guide RNA recognition sequences (e.g. the second and fourth, wherein the second and fourth guide RNA recognition sequences are different and optionally overlapping) can comprise the stop codon for the gene encoding the self-antigen or can be within about 10, 20, 30, 40, 50, 100, 200, 300, 400, 500, or 1,000 nucleotides of the stop codon. Targeting both the start and stop codons can result in deletion of the coding sequence for the gene encoding the self-antigen and thereby eliminate expression of the self-antigen.

In another example, the first and second guide RNA recognition sequences are different and each comprises the start codon for the gene encoding the self-antigen or is within about 10, 20, 30, 40, 50, 100, 200, 300, 400, 500, or 1,000 nucleotides of the start codon. For example, the first and second guide RNA recognition sequences can be overlapping and can each comprise the start codon. If third and/or fourth guide RNAs are also used, the third and fourth guide RNA recognition sequences can be anywhere within the target genomic locus. For example, the third and fourth guide RNA recognition sequences can be different from each other and different from the first and second guide RNA recognition sequences, and each of the third and fourth guide RNA recognition sequences can also comprise the start codon for the gene encoding the self-antigen or can be within about 10, 20, 30, 40, 50, 100, 200, 300, 400, 500, or 1,000 nucleotides of the start codon. Targeting the start codon can disrupt the start codon and thereby eliminate expression of the gene encoding the self-antigen.

If third and fourth guide RNAs (or additional guide RNAs) are used, additional target genomic loci affecting expression of the first self-antigen or affecting expression of other self-antigens (e.g., a second self-antigen) homologous to or sharing an epitope of interest with the foreign antigen of interest can also be targeted to decrease expression of the first self-antigen and/or the other self-antigens. As an example, in some methods a gene encoding a first self-antigen homologous to or sharing an epitope of interest with the foreign antigen of interest can be targeted, and a second gene encoding a second self-antigen homologous to or sharing an epitope of interest with the foreign antigen of interest can be targeted.

F. Mechanisms of Recombination and Methods for Altering Prevalence of Non-Homologous End Joining, Gene Conversion, or Homologous Recombination Recombination includes any process of exchange of genetic information between two polynucleotides and can occur by any mechanism. Recombination in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, herein incorporated by reference in its entirety for all purposes. Likewise, repair of a target nucleic acid mediated by an exogenous repair template can include any process of exchange of genetic information between the two polynucleotides.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous repair template through direct ligation of the break ends with the ends of the exogenous repair template (i.e., NHEJ-based capture). Such NHEJ-mediated targeted integration can be preferred for insertion of an exogenous repair template when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous repair template and the cleaved genomic sequence, or via ligation of sticky ends (i.e., having 5' or 3' overhangs) using an exogenous repair template that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Recombination can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Recombination can be between first and second chromosomes in a homologous chromosome pair. Such means can include, for example, loss of heterozygosity (LOH), gene conversion, or crossover events occurring by any known recombination mechanism. Without wishing to be bound by theory, LOH can occur, for example, via mitotic recombination, with or without gene conversion, or via chromosome loss and duplication. See, e.g., Lefebvre et al. (2001) *Nat. Genet.* 27:257-258, herein incorporated by reference in its entirety for all purposes. Gene conversion in this context can include unidirectional transfer of genetic material from a donor sequence to a highly homologous acceptor (i.e., the non-reciprocal exchange of genetic information from one molecule to its homologue). Gene conversion includes any means for copying of an allele by any known recombination mechanism. For example, gene conversion can involve the non-reciprocal transfer of genetic information from an intact sequence to a homologous region containing a double-strand break, and it can occur between sister chromatids, homologous chromosomes, or homologous sequences on either the same chromatid or on different chromosomes. See, e.g., Chen et al. (2007) *Nat. Rev. Genet.* 8:762-775, herein incorporated by reference in its entirety for all purposes. In specific cases, gene conversion results directly from homologous recombination as a result of copying genetic information from a homologous chromosome. This can lead to localized loss of heterozygosity (LOH) when the homologous sequences are non-identical.

As an example, LOH could occur through reciprocal chromatid exchange by mitotic cross over, or by chromatid copying by break-induced replication. In either case, a heterozygous modification could occur in which one chromosome is targeted before genome replication. Alternatively, a single chromatid could be targeted after genome replication, followed by inter-chromatid gene conversion.

In any of the methods disclosed herein, the cell can be a cell that has been modified to increase or decrease NHEJ activity. Likewise, the cell can be a cell that has been modified to increase gene conversion or HDR activity. Such modifications can comprise modifications in the expression or activity of genes involved in regulating NHEJ, gene conversion, and/or HDR. For example, decreasing the activity of NHEJ and/or increasing the activity of HDR can promote biallelic collapsing of genomic regions between nuclease recognition sequences (e.g., guide RNA recognition sequences) corresponding to two nuclease agents (e.g., Cas protein and two guide RNAs). Without wishing to be bound by any particular theory, one mechanism by which a biallelic genomic collapse can occur is by NHEJ-mediated repair or HDR-mediated repair within a first allele and creation of an identical second allele via HDR mechanisms, such as gene conversion (see Example 1). Thus, promoting HDR-mediated pathways (e.g., by decreasing NHEJ activity or by increasing HDR activity can also promote biallelic collapsing of genomic regions. Similarly, without wishing to be bound by any particular theory, conversion of a heterozygous cell to a homozygous cell by using paired nuclease agents (e.g., Cas protein and paired guide RNAs) that target a single locus can be promoted if NHEJ activity is decreased and HDR activity (e.g., gene conversion activity) is correspondingly increased.

Inhibitors can be used to increase or decrease NHEJ activity or to increase or decrease HDR activity. Such inhibitors can be, for example, small molecules or inhibitory nucleic acids such as short interfering nucleic acids (e.g., short interfering RNA (siRNA), double-stranded RNA (dsRNA), micro-RNA (miRNA), and short hairpin RNA (shRNA)) or antisense oligonucleotides specific for a gene transcript. Inhibitors can be directed at enzymes involved in NHEJ or HDR or their upstream regulation by post-translational modification via, for example, phosphorylation, ubiquitylation, and sumoylation.

In mammalian cells, NHEJ is the predominant DSB repair mechanism and is active throughout the cell cycle. In vertebrates, the "canonical" or "classical" NHEJ pathway (C-NHEJ) requires several core factors, including DNA-PK, Ku70-80, Artemis, ligase IV (Lig4), XRCC4, CLF, and Pol μ to repair a DSB. See Kasparek & Humphrey (2011) *Seminars in Cell & Dev. Biol.* 22:886-897, herein incorporated by reference in its entirety for all purposes. During NHEJ, DNA ends are bound by the highly abundant end-protecting Ku protein, which functions as a docking station for loading of the other NHEJ components.

Thus, in some of the methods disclosed herein, the cell has been modified to reduce or eliminate or to increase the expression or activity of factors involved in C-NHEJ. For example, in some methods, the cell has been modified to reduce or eliminate DNA-PK, Ku70-80, Artemis, ligase IV (Lig4), XRCC4, CLF, and/or Pol μ expression or activity. In specific methods, the cell has been modified to reduce or eliminate DNA-PK expression or activity or to increase DNA-PK expression or activity (e.g., expression or activity of DNA-PKcs; exemplary UniProt sequence designated P97313). Examples of DNA-PKcs inhibitors include, for example, NU7026, and NU7441. See, e.g., U.S. Pat. No. 6,974,867, herein incorporated by reference in its entirety for all purposes. In specific methods, the cell has been modified to reduce or eliminate ligase IV expression or activity or to increase ligase IV expression or activity. An example of a ligase IV inhibitor is SCR7.

Inhibitors targeting cell cycle checkpoint proteins like ATM (e.g., KU55933), CHK1/CHK2 (e.g., KLD1162 or CHIR-124) and ATR (e.g., VE 821) can also be used to either synergistically enhance the effects of specific DNA repair inhibitors or to prevent unintended side-effects like cell cycle arrest and/or apoptosis (see Ciccia et al. (2010) *Mol Cell* 40:179, herein incorporated by reference in its entirety for all purposes).

Disruption of C-NHEJ can increase levels of abnormal joining mediated by "alternative" NHEJ (A-NHEJ) pathways and can also increase HR repair. A-NHEJ pathways display a bias towards microhomology-mediated joins and follow slower kinetics than C-NHEJ. Several factors, including the MRN complex (MRE11, RAD50, NBS1), CtIP, XRCC1, PARP, Lig1, and Lig3 have been proposed to participate. See Kasparek & Humphrey (2011) *Seminars in Cell & Dev. Biol.* 22:886-897 and Claybon et al. (2010) *Nucleic Acids Res.* 38(21):7538-7545, each of which is herein incorporated by reference in its entirety for all purposes.

Thus, in some of the methods disclosed herein, the cell has been modified to reduce or eliminate or to increase the expression or activity of factors involved in A-NHEJ. For example, in some methods, the cell has been modified to reduce or eliminate MRE11, RAD50, NBS1, CtIP, XRCC1, PARP (e.g., PARP1), Lig1, and/or Lig3 expression or activity. In other methods, the cell has been modified to increase MRE11, RAD50, NBS1, CtIP, XRCC1, PARP (e.g., PARP1), Lig1, and/or Lig3 expression or activity. In specific methods, the cell has been modified to reduce or eliminate PARP1 expression or activity or to increase PARP1 expression or activity (exemplary UniProt sequence designated P11103). Examples of PARP inhibitors (e.g., NU1025, Iniparib, Olaparib) include nicotinamides; isoquinolinones and dihydroisoquinolinones; benzimidazoles and indoles; phthalazin-1(2H)-ones and quinazolinones; isoindolinones and analogues and derivatives thereof; phenanthridines and phenanthridinones; benzopyrones and analogues and derivatives thereof; unsaturated hydroximic acid derivatives and analogues and derivatives thereof; pyridazines, including fused pyridazines and analogues and derivatives thereof and/or other compounds such as caffeine, theophylline, and thymidine, and analogues and derivatives thereof. See, e.g., U.S. Pat. No. 8,071,579, herein incorporated by reference in its entirety for all purposes.

C-NHEJ also exhibits a competitive relationship with HR such that disrupting C-NHEJ can also lead to increased HR repair. Such competition between NHEJ and HR can be exploited as disrupting NHEJ can lead to enhanced gene targeting through reduced random integration and possibly increased target integration by homologous recombination.

There are several forms of homologous recombination repair, including single-strand annealing, gene conversion, crossovers, and break-induced replication. Single-strand annealing is a minor form of HR repair in which homologous single-stranded sequences on either side of a resected DSB anneal, resulting in chromosome reconstitution. Single-strand annealing generates deletions of varying size, depending on the distance separating the two regions of sequence homology. Gene conversion includes the non-reciprocal exchange of genetic information from one molecule to its homologue, resulting directly from HR as a result of copying genetic information from a homologous chromosome. This can lead to localized LOH when the homologous sequences are non-identical. Normally, the extent of gene conversion is limited to a few hundred base pairs. However, long tract gene conversion has been reported in some genetic backgrounds, including RAD51C deficiency. See Nagaraju et al. (2006) *Mol. Cell. Biol.* 26:8075-8086, herein incorporated by reference in its entirety for all purposes. Crossovers can occur, for example, between homologous chromosomes, and have the potential to lead to reciprocal translocations if occurring in G1 or non-reciprocal translocations and LOH extending from the break site to the distal telomere if occurring in G2. Break-induced replication is a variant of HR in which following strand invasion, DNA replication continues through to the end of the chromosome. Thus, there are many mechanisms by which HR can promote LOH.

Thus, in some of the methods disclosed herein, the cell has been modified to reduce or eliminate or to increase the expression or activity of factors involved in HR. For example, in some methods, the cell has been modified to increase RAD51, RAD52, RAD54, RAD55, RAD51C, BRCA1, and/or BRCA2 expression or activity. In other methods, the cell has been modified to reduce or eliminate RAD51, RAD52, RAD54, RAD55, RAD51C, BRCA1, and/or BRCA2 expression or activity.

In some methods, the expression or activity of yet other proteins involved in regulating NHEJ and/or HR can be altered. For example, in some methods, the cell has been modified to reduce or eliminate Chk2 expression or activity, to reduce or eliminate Clspn expression or activity, to reduce or eliminate Setd2 expression or activity, to increase Kat2a expression or activity, and/or to increase Rad51 expression or activity. In other methods, the cell has been modified to increase Chk2 expression or activity, to increase Clspn expression or activity, to increase Setd2 expression or activity, to reduce or eliminate Kat2a expression or activity, and/or to reduce or eliminate Rad51 expression or activity.

Chk2 (also known as Chek2 and Rad53; *S. pombe* homolog is Cds1) is a serine/threonine protein kinase required for checkpoint-mediated cell cycle arrest, activation of DNA repair, and apoptosis in response to the presence of DNA double-strand breaks. See Blaikley et al. (2014) *Nucleic Acids Research* 42:5644-5656, herein incorporated by reference in its entirety for all purposes. Clspn (also known as Claspin; *S. pombe* homolog is Mrc1) is a protein required for checkpoint mediated cell cycle arrest in response to DNA damage. Deletion of homologs of Chk2 or Clspn in *S. pombe* has been reported to result in a hyper-recombinant phenotype exhibiting significantly elevated levels of break-induced gene conversion compared to wild type. Specifically, levels of gene conversion were reported to be significantly increased, whereas levels of non-homologous end joining (NHEJ), sister chromatid conversion (SCC), and loss of heterozygosity (LOH) were reported to be decreased. See Blaikley et al. (2014) *Nucleic Acids Research* 42:5644-5656.

Kat2a (also known as Gcn5 and Gcn512) is a ubiquitous histone acetyltransferase that promotes transcriptional activation and has been reported to be associated with double-strand break repair. Kat2a-dependent hi stone H3 lysine 36 (H3K36) acetylation increases chromatin accessibility, increases resection, and promotes homologous recombination while suppressing non-homologous end joining. See Pai et al. (2014) *Nat. Commun.* 5:4091, herein incorporated by reference in its entirety for all purposes. Setd2 (also known as Kiaa1732, Kmt3a, and Set2) is a histone methyltransferase that specifically trimethylates lysine 36 of histone H3 (H3K36me3) using demethylated lysine 36 (H3K36me2) as a substrate. Setd2-dependent H3K36 methylation reduces chromatin accessibility, reduces resection, and promotes NHEJ. See Pai et al. (2014) *Nat. Commun.* 5:4091.

Rad 51 (also known as Reca, Rad51A, and DNA repair protein Rad51 homolog 1) is a protein that functions with Rad52 and other proteins to effect strand exchange during homologous recombination, forming heteroduplex DNA that is resolved by mismatch repair to yield a gene conversion tract. In mammalian cells, Rad51 and Rad52 overexpression have been reported to increase the frequency of homologous recombination and gene conversion. See Yanez & Porter (1999) *Gene Ther.* 6:1282-1290 and Lambert & Lopez (2000) *EMBO J.* 19:3090-3099, herein incorporated by reference in its entirety for all purposes.

Modifications in the expression or activity of genes involved in regulating NHEJ, gene conversion, and/or homology-directed repair can be spatially or temporally specific and can also be inducible or temporary and reversible. For example, various forms of cassettes can be constructed to allow for deletion in specific cell or tissue types, at specific developmental stages, or upon induction. Such cassettes can employ a recombinase system in which the cassette is flanked on both sides by recombinase recognition sites and can be removed using a recombinase expressed in the desired cell type, expressed at the desired developmental stage, or expressed or activated upon induction. Such cassettes can further be constructed to include an array of pairs of different recombinase recognition sites that are placed such that null, conditional, or combination conditional/null alleles can be generated, as described in US 2011/0104799, herein incorporated by reference in its entirety for all purposes. Regulation of recombinase genes can be controlled in various ways, such as by operably linking a recombinase gene to a cell-specific, tissue-specific, or developmentally regulated promoter (or other regulatory element), or by operably linking a recombinase gene to a 3'-UTR that comprises a recognition site for an miRNA that is active only in particular cell types, tissue types, or developmental stages. A recombinase can also be regulated, for example, by employing a fusion protein placing the recombinase under the control of an effector or metabolite (e.g., CreER$^{T2}$, whose activity is positively controlled by tamoxifen), or by placing the recombinase gene under the control of an inducible promoter (e.g., one whose activity is controlled by doxycycline and TetR or TetR variants). Examples of various forms of cassettes and means of regulating recombinase genes are provided, for example, in U.S. Pat. Nos. 8,518,392; 8,354,389; and 8,697,851, each of which is incorporated by reference in its entirety.

In other methods disclosed herein, the cell has been modified to increase or decrease NHEJ activity or to increase gene conversion or HDR activity by blocking the cell at a phase of the cell cycle, such as the M-phase or the S-phase of the cell cycle. See, e.g., WO 2016/036754, herein incorporated by references in its entirety for all purposes. This can be achieved with a cell cycle blocking composition. Examples of such compositions include nocodazole, hydroxyurea; colchicine; demecolcine (colcemid); lovastatin; mimosine; thymidine; aphidicolin; latrunculin A; and latrunculin B. Such modifications can comprise modifications in the expression or activity of genes involved in regulating NHEJ, gene conversion, and/or HDR.

G. Types of Targeted Genetic Modifications

Various types of targeted genetic modifications can be introduced using the methods described herein. Such targeted genetic modifications can include any modification that reduces or eliminates expression of a self-antigen that is homologous to or shares an epitope of interest with the foreign target antigen of interest. Preferably, such modifications disrupt the target genomic locus. Examples of disruption include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation). Disruption can result in inactivation (i.e., loss of function) or loss of an allele. Such targeted genetic modifications can include, for example, insertion of one or more nucleotides, deletion of one or more nucleotides, or substitution (replacement) of one or more nucleotides. Such insertions, deletions, or replacements can result, for example, in a point mutation, a knockout of a nucleic acid sequence of interest or a portion thereof, a knock-in of a nucleic acid sequence of interest or a portion thereof, a replacement of an endogenous nucleic acid sequence with a heterologous or exogenous nucleic acid sequence, alteration of a regulatory element (e.g., promoter or enhancer), a missense mutation, a nonsense mutation, a frame-shift mutation, a truncation mutation, a null mutation, or a combination thereof. For example, at least 1, 2, 3, 4, 5, 7, 8, 9, 10 or more nucleotides can be changed (e.g., deleted, inserted, or substituted) to form the targeted genetic modification. The deletions, insertions, or replacements can be of any size, as disclosed elsewhere herein. See, e.g., Wang et al. (2013) Cell 153:910-918; Mandalos et al. (2012) PLOS One 7:e45768; and Wang et al. (2013) Nat Biotechnol. 31:530-532, each of which is herein incorporated by reference in its. Such mutations can result in a reduction of expression or elimination of expression (e.g., mRNA and/or protein expression) of the self-antigen (e.g., deletion of an allele).

The targeted genetic modification (e.g., insertion, deletion, or substitution) can occur at one or more locations in the target genomic locus. For example, the targeted genetic modification can comprise two separate modifications at two locations within the target genomic locus if two exogenous repair templates are used.

In methods in which an exogenous repair template is used, for example, a deletion can be between the 5' and 3' target sequences. In methods in which two or more guide RNAs are used, the deletion can be between the first and second guide RNA recognition sequences or the first and second Cas cleavage sites. Such deletions can be any length. The deleted nucleic acid can be, for example, from about 1 bp to about 5 bp, from about 5 bp to about 10 bp, from about 10 bp to about 50 bp, from about 50 bp to about 100 bp, from about 100 bp to about 200 bp, from about 200 bp to about 300 bp, from about 300 bp to about 400 bp, from about 400 bp to about 500 bp, from about 500 bp to about 1 kb, from about 1 kb to about 5 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

Alternatively, the deleted nucleic acid can be, for example, at least 1 bp, at least 5 bp, at least 10 bp, at least 50 bp, at least 100 bp, at least 200 bp, at least 300 bp, at least 400 bp, at least 500 bp, at least 1 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb or greater. In some cases, the deleted nucleic acid can be at least 550 kb, at least 600 kb, at least 650 kb, at least 700 kb, at least 750 kb, at least 800 kb, at least 850 kb, at least 900 kb, at least 950 kb, at least 1 Mb, at least 1.5 Mb, at least 2 Mb, at least 2.5 Mb, at least 3 Mb, at least 4 Mb, at least 5 Mb, at least 10 Mb, at least 20 Mb, at least 30 Mb, at least 40 Mb, at least 50 Mb, at least 60 Mb, at least 70 Mb, at least 80 Mb, at least 90 Mb, or at least 100 Mb (e.g., most of a chromosome).

In a specific example, the deletion size can be between about 0.1 kb and about 1 Mb, between about 0.1 kb and about 900 kb, between about 0.1 kb and about 400 kb, between about 0.1 kb and about 200 kb, between about 0.1 kb and about 100 kb, or up to about 1 Mb, up to about 900 kb, up to about 400 kb, up to about 200 kb, or up to about 100 kb. In a specific example, the deletion size can be between about 0.1-200, 0.1-190, 0.1-180, 0.1-170, 0.1-160, 0.1-150, 0.1-140, 0.1-130, 0.1-120, 0.1-110, 0.1-100, 0.1-90, 0.1-80, 0.1-70, 0.1-60, 0.1-50, 0.1-40, 0.1-30, 0.1-20 0.1-10, 0.1-9, 0.1-8, 0.1-7, 0.1-6, 0.1-5, 0.1-4, 0.1-3, 0.1-2, or 0.1-1 kb. The biallelic deletion (collapse) efficiency in targeted cell clones such as targeted embryonic stem cell clones (i.e., percentage of screened clones with biallelic deletion) can be between about 1-100%, 1-90%, 1-80%, 1-70%, 1-60%, 1-50%, 1-40%, 1-30%, or 1-27%, or can be at least about 1%, 2%, 3%, 4%, 5%, 6%, 7%, 8%, 9%, 10%, 11%, 12%, 13%, 14%, 15%, 16%, 17%, 18%, 19%, 20%, or 25%. For example, in one embodiment the deletion size is about 50 kb or less and the biallelic deletion efficiency is between about 1-30% or 1-27%, or the deletion size is about 50 kb or higher (e.g., between about 50 kb to about 200 kb) and the biallelic deletion efficiency is about 1-5% or 1-3%. In experiments in which one-cell stage embryos are targeted, the biallelic deletion (collapse) efficiency in live pups born following CRISPR/Cas injection in one-cell stage embryos (i.e., percentage of live pups with biallelic deletions) can be between about 1-100%, 1-90%, or 1-85%, or at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, or 85%. For example, in one embodiment the deletion size is about 50 kb or less and the biallelic deletion efficiency is between about 1-85% or 20-85%, or the deletion size is about 50 kb or higher (e.g., between about 50 kb to about 100 kb) and the biallelic deletion efficiency is about 1-20% or 1-15%.

In methods in which an exogenous repair template is used, for example, an insertion can be between the 5' and 3' target sequences. Such insertions can be of any length. For example, the inserted nucleic acid can be, for example, from about 1 bp to about 5 bp, from about 5 bp to about 10 bp, from about 10 bp to about 50 bp, from about 50 bp to about 100 bp, from about 100 bp to about 200 bp, from about 200 bp to about 300 bp, from about 300 bp to about 400 bp, from about 400 bp to about 500 bp, from about 500 bp to about 1 kb, from about 1 kb to about 5 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 450 kb, from about 450 kb to about 500 kb, or greater. Alternatively, the insertion can be at least 1 bp, at least 5 bp, at least 10 bp, at least 50 bp, at least 100 bp, at least 200 bp, at least 300 bp, at least 400 bp, at least 500 bp, at least 1 kb, at least 5 kb, at least 10 kb, at least 20 kb, at least 30 kb, at least 40 kb, at least 60 kb, at least 80 kb, at least 100 kb, at least 150 kb, at least 200 kb, at least 250 kb, at least 300 kb, at least 350 kb, at least 400 kb, at least 450 kb, or at least 500 kb.

The targeted genetic modification can be a precise modification or an imprecise modification. For example, in methods using an exogenous repair template, the deletion can be a precise deletion wherein the deleted nucleic acid consists of only the nucleic acid sequence between the 5' and 3' homology arms such that there are no additional insertions or deletions (indels) at the modified target genomic locus. Similarly, if paired gRNAs are used that flank the entire coding region of a gene encoding the self-antigen, the deletion between the first and second Cas protein cleavage sites can be a precise deletion wherein the deleted nucleic acid consists of only the nucleic acid sequence between the first and second Cas protein cleavage sites such that there are no additional insertions or deletions (indels) at the modified target genomic locus. In methods in which both an exogenous repair template and paired gRNAs flanking a region of interest are used, the deletion can be either of the precise deletions mentioned above. Alternatively, the deletion between the first and second Cas protein cleavage sites can be an imprecise deletion extending beyond the first and second Cas protein cleavage sites, consistent with imprecise repair by non-homologous end joining (NHEJ), resulting in additional deletions and/or insertions at the modified genomic locus. For example, the deletion can extend about 1, 2, 3, 4, 5, 10, 20, 30, 40, 50, 100, 200, 300, 400, or 500 bp or more beyond the first and second Cas protein cleavage sites. Likewise, the modified genomic locus can comprise additional insertions consistent with imprecise repair by NHEJ, such as insertions of about 1, 2, 3, 4, 5, 10, 20, 30, 40, 50, 100, 200, 300, 400, or 500 bp or more. Use of exogenous repair templates (e.g., single-stranded oligodeoxynucleotides (ssODNs) together with the CRISPR/Cas9 can increase the chances for precise modifications by promoting homology-directed repair rather than NHEJ.

The targeted modification can comprise replacement of a sequence at the target genomic locus (e.g., all or part of the gene encoding the self-antigen, such as a portion of the gene encoding a particular region or motif of the self-antigen) with a corresponding homologous or orthologous sequence. Deletion of all or part of the gene encoding the self-antigen and replacement with a corresponding homologous or orthologous sequence that lacks an epitope that is shared between the foreign antigen of interest and the self-antigen can result in expression of a homologue or orthologue of the self-antigen that retains the function of the wild-type self-antigen but lacks the epitope that is present on the foreign antigen of interest and is shared with the wild-type self-antigen. Alternatively or additionally, the targeted modification can comprise one or more point mutations (e.g., 1, 2, 3, 4, 5, or more) at the target genomic locus (e.g., all or part of the gene encoding the self-antigen). Such point mutations can serve, for example, to eliminate expression of one or more epitopes in the self-antigen that are shared with the foreign antigen of interest. Optionally, such point mutations can result in a conservative amino acid substitution (e.g., substitution of aspartic acid [Asp, D] with glutamic acid [Glu, E]) in the encoded polypeptide. Such amino acid substitutions can result in expression of a self-antigen that retains the function of the wild-type self-antigen but lacks an epitope that is present on the foreign antigen of interest and is shared with the wild-type self-antigen.

The methods described herein promote and increase the frequency of biallelic and particularly homozygous modifications. In particular, by contacting the cell with first and second first and second guide RNAs that target first and second guide RNA recognition sequences within the target genomic locus, the efficiency of producing biallelic modifications can be increased compared to contacting the cell with either guide RNA alone. The efficiency of producing biallelic modifications can also be increased by contacting the cell with the first, second, and third guide RNAs that target guide RNA recognition sequences within the target genomic locus, or the first, second, third, and fourth guide RNAs that target guide RNA recognition sequences within the target genomic locus. In addition or alternatively, the efficiency of producing biallelic modifications and particularly homozygous modifications can be increased by selecting a target genomic locus so that the sequence identity is maximized between corresponding first and second chromosomes in a homologous chromosome pair in all or part of the target genomic locus. Methods for selecting such target genomic loci are described in further detail elsewhere herein.

Preferably, the targeted genetic modification is a biallelic modification. Biallelic modifications include events in which the same modification is made to the same locus on corresponding homologous chromosomes (e.g., in a diploid cell), or in which different modifications are made to the same locus on corresponding homologous chromosomes. Homologous chromosomes (i.e., a homologous chromosome pair) include chromosomes that have the same genes at the same loci but possibly different alleles (e.g., chromosomes that are paired during meiosis). The term allele includes any of one or more alternative forms of a genetic sequence. In a diploid cell or organism, the two alleles of a given sequence typically occupy corresponding loci on a pair of homologous chromosomes.

A biallelic modification can result in homozygosity for a targeted genetic modification. Homozygosity includes situations in which both alleles of a target genomic locus (i.e., corresponding alleles on both homologous chromosomes) have the targeted genetic modification. For example, the biallelic modification can comprise, consist essentially of, or consist of homozygous deletion of all or part a gene encoding a self-antigen, or the biallelic modification can comprise, consist essentially of, or consist of homozygous disruption of the start codon of a gene encoding a self-antigen, such that the start codon is no longer functional.

Alternatively, a biallelic modification can result in compound heterozygosity (e.g., hemizygosity) for the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele). For example, in the allele without the targeted modification, a double-strand break created by the Cas protein may have been repaired by non-homologous end joining (NHEJ)-mediated DNA repair, which generates a mutant allele comprising an insertion or a deletion of a nucleic acid sequence and thereby causes disruption of that genomic locus. For example, a biallelic modification can result in compound heterozygosity if the cell has one allele with the targeted modification and another allele that is not capable of being expressed. Compound heterozygosity includes hemizygosity. Hemizygosity includes situations in which only one allele (i.e., an allele on one of two homologous chromosomes) of the target locus is present. For example, a biallelic modification can result in hemizygosity for a targeted modification if the targeted modification occurs in one allele with a corresponding loss or deletion of the other allele.

In a specific example, the biallelic modification can comprise a homozygous deletion between first and second guide RNA recognition sequences or Cas cleavage sites in the pair of first and second homologous chromosomes. Alternatively, the biallelic modification can comprise a biallelic deletion between first and second guide RNA recognition sequences or Cas cleavage sites in the pair of first and second homologous chromosomes (i.e., deletions in both chromosomes, but not necessarily the same deletion in each). The deletions can occur simultaneously, or the deletion can occur initially in the first homologous chromosome, with homozygosity then being achieved by the cell using the first homologous chromosome as a donor sequence to repair one or more double-strand breaks in the second homologous chromosome via homologous recombination, such as by gene conversion.

In another specific example, the biallelic modification can comprise a homozygous disruption of the start codon region of the target gene in the pair of first and second homologous chromosomes. Alternatively, the biallelic disruption of the start codon region of the target gene in the pair of first and second homologous chromosomes (i.e., disruptions in both chromosomes, but not necessarily the same modification in each). The modifications can occur simultaneously, or the modification can occur initially in the first homologous chromosome, with homozygosity then being achieved by the cell using the first homologous chromosome as a donor sequence to repair one or more double-strand breaks in the second homologous chromosome via homologous recombination, such as by gene conversion.

If a donor sequence (e.g., exogenous repair template) is used, the biallelic modification can comprise a deletion between first and second guide RNA recognition sequences or Cas cleavage sites as well as an insertion of the nucleic acid insert between the 5' and 3' target sequences in the pair of first and second homologous chromosomes, thereby resulting in a homozygous modified genome. Alternatively, the biallelic modification can comprise a deletion between the 5' and 3' target sequences as well as an insertion of the nucleic acid insert between the 5' and 3' target sequences in the pair of first and second homologous chromosomes, thereby resulting in a homozygous modified genome. The deletion and insertion can occur simultaneously in both chromosomes, or the deletion and insertion can initially occur in the first homologous chromosome, with homozygosity then being achieved by the cell using the first homologous chromosome as a donor sequence to repair the double-strand break(s) in the second homologous chromosome via homologous recombination, such as by gene conversion. For example, without wishing to be bound by any particular theory, insertion of the nucleic acid insert could occur in the first homologous chromosome (with or without cleavage by the Cas protein), and the second homologous chromosome can then be modified by a gene conversion event that is stimulated by cleavage by the Cas protein on the second homologous chromosome.

Alternatively, if the exogenous repair template comprises 5' and 3' homology arms with no nucleic acid insert, the biallelic modification can comprise a deletion between the 5' and 3' target sequences in the pair of first and second homologous chromosomes, thereby resulting in a homozygous modified genome. The deletion can occur simultaneously in both chromosomes, or the deletion can initially occur in the first homologous chromosome, with homozygosity then being achieved by the cell using the first homologous chromosome as a donor sequence to repair the double-strand break(s) in the second homologous chromosome via homologous recombination, such as by gene conversion. For example, without wishing to be bound by any particular theory, the deletion could occur in the first homologous chromosome (with or without cleavage by the Cas protein), and the second homologous chromosome can then be modified by a gene conversion event that is stimulated by cleavage by the Cas protein on the second homologous chromosome.

The deletion between the first and second guide RNA recognition sequences or the deletion between the 5' and 3' target sequences can be a precise deletion wherein the deleted nucleic acid consists of only the nucleic acid sequence between the first and second nuclease cleavage sites or only the nucleic acid sequence between the 5' and 3' target sequences such that there are no additional deletions or insertions at the modified genomic target locus. The deletion between the first and second guide RNA recognition sequences can also be an imprecise deletion extending beyond the first and second nuclease cleavage sites, consistent with imprecise repair by non-homologous end joining (NHEJ), resulting in additional deletions and/or insertions at the modified genomic locus. For example, the deletion can extend about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more beyond the first and second Cas protein cleavage sites. Likewise, the modified genomic locus can comprise additional insertions consistent with imprecise repair by NHEJ, such as insertions of about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more.

Targeted insertions created through use of exogenous repair template can be of any size. Examples of nucleic acid inserts in exogenous repair templates and examples of sizes of nucleic acid inserts are described elsewhere herein.

Homozygous targeted genetic modifications are advantageous because the process for making genetically modified animals with these modifications (described in more detail below) can be more efficient and less time-consuming. In many situations, such as removing or disrupting a gene to study the effect of its absence, mere heterozygosity for a targeted genetic modification (i.e., modification in one allele and no change to the other allele) is not sufficient. With conventional targeting strategies, F0 generation animals that are heterozygous for a large targeted genomic deletion might be obtainable, but subsequent interbreeding of these heterozygous animals is required to produce F1 generation animals that are homozygous for the deletion. These additional breeding steps are costly and time-consuming. The capability of creating F0 generation genetically modified animals that are homozygous for a targeted genetic modification results in significant efficiency gains and time savings because fewer breeding steps are required.

H. Identifying Cells with Targeted Genetic Modifications

The methods disclosed herein can further comprise identifying a cell having a modified target nucleic acid (e.g., a modified genome). Various methods can be used to identify cells having a targeted genetic modification, such as a deletion or an insertion. Such methods can comprise identifying one cell having the targeted genetic modification at a target genomic locus. Screening can be done to identify such cells with modified genomic loci.

The screening step can comprise a quantitative assay for assessing modification of allele (MOA) (e.g., loss-of-allele (LOA) and/or gain-of-allele (GOA) assays) of a parental chromosome. For example, the quantitative assay can be carried out via a quantitative PCR, such as a real-time PCR (qPCR). The real-time PCR can utilize a first primer set that recognizes the target genomic locus and a second primer set that recognizes a non-targeted reference locus. The primer set can comprise a fluorescent probe that recognizes the amplified sequence.

Figure 4:
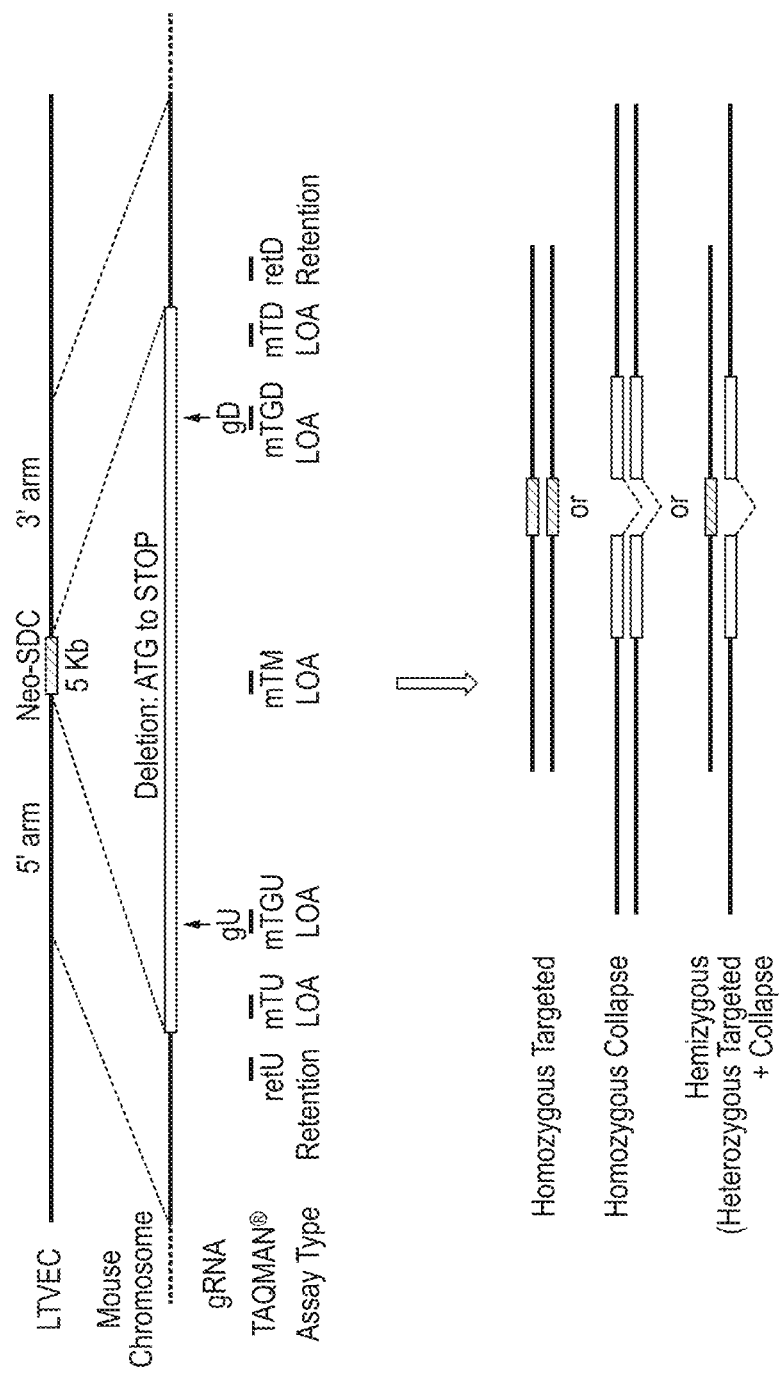
FIG. 4 shows a general schematic for simultaneous deletion of a mouse gene encoding a self-antigen homologous to a foreign target antigen of interest and replacement with a neomycin selection marker using a large targeting vector (LTVEC) and paired upstream and downstream guide RNAs (gU and gD). The positions of the Cas9 cleavage sites guided by the two guide RNAs are indicated by the arrows below the mouse gene sequence. The TAQMAN® assay probes are indicated by the horizontal lines, including retention assay probes and upstream, middle, and downstream loss-of-allele (LOA) assay probes. The bottom portion of the figure indicates the expected targeted allele types.

To identify homozygous collapsed ES cell clones, TAQMAN® probe qPCR strategies can be used with greater efficiency and accuracy compared with traditional methods. Homozygous collapsed alleles can be identified with one qPCR plate due to the inclusion of a "middle" LOA assay (see, e.g., mTM probe in FIG. 4) and the absence of GOA assays. Because every assay used to screen the ES cell clones is an LOA assay, copy numbers can be calculated accurately for every region tested, without using any non-mouse DNA calibrator.

The screening step can also comprise a retention assay, which is an assay used to distinguish between correct targeted insertions of a nucleic acid insert into a target genomic locus from random transgenic insertions of the nucleic acid insert into genomic locations outside of the target genomic locus. Retention assays can also be used to distinguish between correct deletions and deletions that extend beyond the region targeted for deletion. Conventional assays for screening for targeted modifications, such as long-range PCR or Southern blotting, link the inserted targeting vector to the targeted locus. Because of their large homology arm sizes, however, LTVECs do not permit screening by such conventional assays. To screen LTVEC targeting, modification-of-allele (MOA) assays including loss-of-allele (LOA) and gain-of-allele (GOA) assays can be used (see, e.g., US 2014/0178879 and Frendewey et al. (2010)*Methods Enzymol.* 476:295-307, each of which is herein incorporated by reference in its entirety for all purposes). The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells. For a GOA assay, another TAQMAN® probe can be used to determine the Ct of the nucleic acid insert that is replacing the targeted gene(s) or locus(loci) by successful targeting.

Because paired gRNAs can create large Cas-mediated deletions at a target genomic locus, it can be useful augment standard LOA and GOA assays to verify correct targeting by LTVECs (i.e., in cells other than one-cell stage embryos). For example, LOA and GOA assays alone may not distinguish correctly targeted cell clones from clones in which a large Cas-induced deletion of the target genomic locus coincides with random integration of a LTVEC elsewhere in the genome, particularly if the GOA assay employs a probe against a selection cassette within the LTVEC insert. Because the selection pressure in the targeted cell is based on the selection cassette, random transgenic integration of the LTVEC elsewhere in the genome will generally include the selection cassette and adjacent regions of the LTVEC but will exclude more distal regions of the LTVEC. For example, if a portion of an LTVEC is randomly integrated into the genome, and the LTVEC comprises a nucleic acid insert of around 5 kb or more in length with a selection cassette adjacent to the 3' homology arm, generally the 3' homology arm but not the 5' homology arm will be transgenically integrated with the selection cassette. Alternatively, if the selection cassette adjacent to the 5' homology arm, generally the 5' homology arm but not the 3' homology arm will be transgenically integrated with the selection cassette. As an example, if LOA and GOA assays are used to assess targeted integration of the LTVEC, and the GOA assay utilizes probes against the selection cassette, a heterozygous deletion at the target genomic locus combined with a random transgenic integration of the LTVEC will give the same readout as a heterozygous targeted integration of the LTVEC at the target genomic locus. To verify correct targeting by the LTVEC, retention assays can be used, alone or in conjunction with LOA and/or GOA assays.

Retention assays determine copy numbers of a DNA template in the 5' target sequence (corresponding to the 5' homology arm of the LTVEC) and/or the 3' target sequence (corresponding to the 3' homology arm of the LTVEC). In particular, determining the copy number of a DNA template in the target sequence corresponding to the homology arm that is adjacent to the selection cassette is useful. In diploid cells, copy numbers greater than two generally indicate transgenic integration of the LTVEC randomly outside of the target genomic locus rather than at the target genomic locus, which is undesirable. Correctly targeted clones will retain a copy number of two. In addition, copy numbers of less than two in such retention assays generally indicate large Cas-mediated deletions extending beyond the region targeted for deletion, which are also undesirable.

In an exemplary retention assay for identifying a targeted insertion of a nucleic acid insert at a target genomic locus in a diploid cell, DNA is first obtained from a cell having a genome that has been contacted with a large targeting vector (LTVEC) comprising the nucleic acid insert flanked by a first homology arm that hybridizes to a first target sequence and a second homology arm that hybridizes to a second target sequence, wherein the nucleic acid insert comprises a selection cassette adjacent to the first homology arm. Optionally, the selection cassette can comprise a drug resistance gene. The DNA is then exposed a probe that binds within the first target sequence, a probe that binds within the nucleic acid insert, and a probe that binds within a reference gene having a known copy number, wherein each probe generates a detectable signal upon binding. Signals from the binding of each of the probes are then detected. The signal from the reference gene probe is compared to the signal from the first target sequence probe to determine a copy number for the first target sequence, and the signal from the reference gene probe is compared to the signal from the nucleic acid insert probe to determine a copy number for the nucleic acid insert. A nucleic acid insert copy number of one or two and a first target sequence copy number of two generally indicates targeted insertion of the nucleic acid insert at the target genomic locus, and a nucleic acid insert copy number of one or more and a first target sequence copy number of three or more generally indicates a random insertion of the nucleic acid insert at a genomic locus other than the target genomic locus.

The signal from the binding of the first target sequence probe can be used to determine a threshold cycle (Ct) value for the first target sequence, the signal from the binding of the reference gene probe can be used to determine a threshold cycle (Ct) value for the reference gene, and the copy number of the first target sequence can be determined by comparing the first target sequence Ct value and the reference gene Ct value. Likewise, the signal from the binding of the nucleic acid insert probe can be used to determine a threshold cycle (Ct) value for the nucleic acid insert, and the copy number of the nucleic acid insert can be determined by comparing the first target sequence Ct value and the reference gene Ct value.

The nucleic acid insert in the LTVEC can be, for example, at least 5, 10, 20, 30, 40, 50, 60, 70, 80, 90, 100, 150, 200, 250, 300, 350, 400, 450, or 500 kb. The distance between the sequences to which the probes bind in the first target sequence and the selection cassette can be, for example, no more than 100 nucleotides, 200 nucleotides, 300 nucleotides, 400 nucleotides, 500 nucleotides, 600 nucleotides, 700 nucleotides, 800 nucleotides, 900 nucleotides, 1 kb, 1.5 kb, 2 kb, 2.5 kb, 3 kb, 3.5 kb, 4 kb, 4.5 kb, or 5 kb.

Such methods can further comprise additional retention assays to determine the copy number of the second target sequence. For example, such methods can further comprise exposing the DNA of the cell to a probe that binds the second target sequence, detecting the signal from the binding of second target sequence probe, and comparing the signal from the reference gene probe to the signal from the second target sequence probe to determine a copy number for the second target sequence.

Likewise, such methods can further comprise additional GOA assays to determine the copy number of one or more additional sequences within the nucleic acid insert. For example, such methods can further comprise exposing the DNA of the cell to one or more additional probes that bind the nucleic acid insert, detecting the signal from the binding of the one or more additional probes, and comparing the signal from the reference gene probe to the signal from the one or more additional nucleic acid insert probes to determine copy numbers for the one or more additional sequences within the nucleic acid insert.

Likewise, when the LTVEC is designed to delete an endogenous sequence from the target genomic locus or when paired gRNAs are used (e.g., to create paired double-strand breaks at different sites within a single genomic target locus and delete the intervening endogenous sequence), such methods can further comprise a LOA assay to determine the copy number of the endogenous sequences at target genomic locus. For example, such methods can further comprise exposing the DNA of the cell to a probe that binds the endogenous sequence at the target genomic locus, detecting the signal from the binding of the endogenous sequence probe, and comparing the signal from the reference gene probe to the signal from the endogenous sequence probe to determine a copy number for the endogenous sequence.

Retention assays can also be used in experiments in which paired gRNAs are used but an exogenous repair template is not necessarily used. Because paired gRNAs can create large Cas-mediated deletions at a target genomic locus, it can be useful augment standard LOA assays to verify correct targeting deletions by paired gRNAs as opposed to deletions extending beyond the region targeted for deletion due to indels following NHEJ repair.

Retention assays determine copy numbers of a DNA template in a region comprising and/or upstream of the first guide RNA recognition sequence (i.e., the 5' guide RNA recognition sequence) and/or a region comprising and/or downstream of and adjacent to the second guide RNA recognition sequence (i.e., the 3' guide RNA recognition sequence). In diploid cells, copy numbers less than one will indicate large NHEJ-mediated deletions extending beyond the region targeted for deletion, which are undesirable. Correctly targeted clones will retain a copy number of two. The probe to determine copy number can be, for example, within about 100 nucleotides, 200 nucleotides, 300 nucleotides, 400 nucleotides, 500 nucleotides, 600 nucleotides, 700 nucleotides, 800 nucleotides, 900 nucleotides, 1 kb, 1.5 kb, 2 kb, 2.5 kb, 3 kb, 3.5 kb, 4 kb, 4.5 kb, or 5 kb of the guide RNA recognition sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Conventional assays for screening for targeted modifications, such as long-range PCR, Southern blotting, or Sanger sequencing, can also be used. Such assays typically are used to obtain evidence for a linkage between the inserted targeting vector and the targeted genomic locus. For example, for a long-range PCR assay, one primer can recognize a sequence within the inserted DNA while the other recognizes a target genomic locus sequence beyond the ends of the targeting vector's homology arms.

Next generation sequencing (NGS) can also be used for screening, particularly in one-cell stage embryos that have been modified. Next-generation sequencing can also be referred to as "NGS" or "massively parallel sequencing" or "high throughput sequencing." Such NGS can be used as a screening tool in addition to the MOA assays and retention assays to define the exact nature of the targeted genetic modification and to detect mosaicism. Mosaicism refers to the presence of two or more populations of cells with different genotypes in one individual who has developed from a single fertilized egg (i.e., zygote). In the methods disclosed herein, it is not necessary to screen for targeted clones using selection markers. For example, the MOA and NGS assays described herein can be relied on without using selection cassettes.

Targeted cells can also be screened for reduction or elimination of expression of the self-antigen homologous to or sharing an epitope of interest with the foreign antigen of interest. For example, if the self-antigen is a protein, expression can be assessed by any known techniques for assaying protein expression, including, for example, Western blot analysis or protein immunostaining.

III. Methods of Making Genetically Modified Non-Human Animals

Genetically modified non-human animals can be generated employing the various methods disclosed herein. Any convenient method or protocol for producing a genetically modified organism, including the methods described herein, is suitable for producing such a genetically modified non-human animal. Such methods starting with genetically modifying a pluripotent cell such as an embryonic stem (ES) cell generally comprise: (1) modifying the genome of a pluripotent cell that is not a one-cell stage embryo using the methods described herein; (2) identifying or selecting the genetically modified pluripotent cell; (3) introducing the genetically modified pluripotent cell into a host embryo; and (4) implanting and gestating the host embryo comprising the genetically modified pluripotent cell in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein. The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. The pluripotent cell can be, for example, an ES cell (e.g., a rodent ES cell, a mouse ES cell, or a rat ES cell) as discussed elsewhere herein. See, e.g., U.S. Pat. No. 7,294,754, herein incorporated by reference in its entirety for all purposes.

Alternatively, such methods starting with genetically modifying a one-cell stage embryo generally comprise: (1) modifying the genome of a one-cell stage embryo using the methods described herein; (2) identifying or selecting the genetically modified embryo; and (3) implanting and gestating the genetically modified embryo in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of a non-human animal to form an embryo; and (5) allowing the embryo to develop. In such methods, oocytes are generally retrieved from deceased animals, although they may be isolated also from either oviducts and/or ovaries of live animals. Oocytes can be matured in a variety of media known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in medium well known to those of ordinary skill in the art and then transferred to the womb of an animal. See, e.g., US 2008/0092249, WO 1999/005266, US 2004/0177390, WO 2008/

017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal that comprise the targeted genetic modification. It is recognized that depending on the method used to generate the F0 animal, the number of cells within the F0 animal that have the targeted genetic modification will vary. The introduction of the donor ES cells into a pre-morula stage embryo from a corresponding organism (e.g., an 8-cell stage mouse embryo) via, for example, the VELOCIMOUSE® method allows for a greater percentage of the cell population of the F0 animal to comprise cells having the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted genetic modification. In addition, at least one or more of the germ cells of the F0 animal can have the targeted genetic modification.

A. Types of Non-Human Animals and Cells

The methods provided herein employ non-human animals and cells and embryos from non-human animals. Such non-human animals are preferably mammals, such as rodents (e.g., rats, mice, and hamsters). Other non-human mammals include, for example, humans, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). The term "non-human" excludes humans. In some methods provided herein, the non-human animals and cells and embryos from non-human animals are hybrid.

A non-human animal cell employed in the methods provided herein can be, for example, a totipotent cell or a pluripotent cell (e.g., an embryonic stem (ES) cell such as a rodent ES cell, a mouse ES cell, or a rat ES cell)). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The non-human animal cells employed in the methods provided herein can also include one-cell stage embryos (i.e., fertilized oocytes or zygotes). One-cell stage embryos are eukaryotic cells formed by a fertilization event between two gametes. Such one-cell stage embryos can be from any genetic background (e.g., BALB/c, C57BL/6, 129, or a combination thereof), can be fresh or frozen, and can be derived from natural breeding or in vitro fertilization.

Mice and mouse cells employed in the methods provided herein can be, for example, from a 129 strain, a C57BL/6 strain, a BALB/c strain, a Swiss Webster strain, a mix of 129 and C57BL/6, strains, a mix of BALB/c and C57BL/6 strains, a mix of 129 and BALB/c strains, and a mix of BALB/c, C57BL/6, and 129 strains. For example, a mouse or mouse cell employed in the methods provided herein can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mice or mouse cells can have a strain comprising 50% BALB/c, 25% C57BL/6, and 25% 129. Alternatively, the mice or mouse cells can comprise a strain or strain combination that excludes BALB/c. In such mice, the BALB/c background is not required to produce a sufficient repertoire of antigen-binding proteins against a foreign antigen of interest.

Examples of 129 strains include 129P1, 129P2, 129P3, 129X1, 129S1 (e.g., 129S1/SV, 129S1/Sv1m), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10(8):836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/O1a. Mice and mouse cells employed in the methods provided herein can also be from a mix of an aforementioned 129 strain and an aforementioned C57BL/6 strain (e.g., 50% 129 and 50% C57BL/6). Likewise, mice and mouse cells employed in the methods provided herein can be from a mix of aforementioned 129 strains or a mix of aforementioned BL/6 strains (e.g., the 129S6 (129/SvEvTac) strain). A specific example of a mouse ES cell is a VGF1 mouse ES cell. VGF1 mouse ES cells (also known as F1H4) were derived from hybrid embryos produced by crossing a female C57BL/6NTac mouse to a male 12956/SvEvTac mouse. See, e.g., Auerbach et al. (2000) *Biotechniques* 29, 1024-1028, herein incorporated by reference in its entirety for all purposes.

Mice and mouse cells employed in the methods provided herein can also have any combination of MHC haplotypes. The function of MHC molecules is to bind foreign peptide fragments and display them on the cell surface for recognition by the appropriate T cells. For example, the mice and mouse cells can comprise an $MHC^b$ haplotype (e.g., C57BL/6), an $MHC^d$ haplotype (e.g., BALB/c), or can comprise both $MHC^b$ and $MHC^d$ (e.g., a combination of C57BL/6 and BALB/c). Such MHC combinations can result in increased antibody titer.

Rats or rat cells employed in the methods provided herein can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats or rat cells can also be obtained from a strain derived from a mix of two or more strains recited above. For example, the rat or rat cell can be from a DA strain or an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of rat ES cell lines from a DA rat are the DA.2B rat ES cell line and the DA.2C rat ES cell line. In some cases, the rats or rat cells are from an inbred rat strain. See, e.g., US 2014/0235933 A1, herein incorporated by reference in its entirety for all purposes. In other cases, the rats or rat cells are from a hybrid rat strain.

Cells that have been implanted into a host embryo can be referred to as "donor cells." The donor cell can be from the same strain as the host embryo or from a different strain. Likewise, the surrogate mother can be from the same strain as the donor cell and/or the host embryo, or the surrogate mother can be from a different strain as the donor cell and/or the host embryo.

A variety of host embryos can be employed in the methods and compositions disclosed herein. For example, a donor cell (e.g., donor ES cell) can be introduced into a pre-morula stage embryo (e.g., an 8-cell stage embryo) from a corresponding organism. See, e.g., U.S. Pat. Nos. 7,576,259; 7,659,442; 7,294,754; and US 2008/0078000, each of which is herein incorporated by reference in its entirety for all purposes. In other methods, the donor cells may be implanted into a host embryo at the 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo, an uncompacted morula stage embryo, or a compacted morula stage embryo. When employing a mouse embryo, the host embryo stage can be a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York, herein incorporated by reference in its entirety for all purposes. For example, the Theiler Stage can be selected from TS1, TS2, TS3, and TS4. In some methods, the host embryo comprises a zona pellucida, and the donor cell is an ES cell that is introduced into the host embryo through a hole in the zona pellucida. In other methods, the host embryo is a zona-less embryo. In yet other methods, the morula-stage host embryo is aggregated.

B. Non-Human Animals for Generating Antigen-Binding Proteins

The non-human animal used in the methods provided herein can be any non-human animal capable of producing antigen-binding proteins, such as a mammal, a rodent, a rat, or a mouse. For example, a non-human animal (e.g., rodent, such as a rat or mouse) genetically modified to optimize antibody production can be used. Such non-human animals may be non-human animals engineered to facilitate the large scale production of antibodies that could be used as human therapeutics, including non-human animals that comprise a humanized immunoglobulin locus. For example, the non-human animal (e.g., rodent, such as a rat or mouse) can comprise one or more of the following modifications in its germline: the non-human animal (e.g., rodent, such as a rat or mouse) heavy chain variable region locus is replaced, in whole or in part, with a human heavy chain variable gene locus; the non-human animal (e.g., rodent, such as a rat or mouse) kappa light chain variable region locus is replaced, in whole or in part, with a human kappa light chain variable region locus; the non-human animal (e.g., rodent, such as a rat or mouse) lambda light chain variable region locus is replaced, in whole or in part, with a human lambda light chain variable region locus; and the heavy and light chain variable region gene loci are replaced, in whole, with their human homologs or orthologs. The non-human animal (e.g., rodent, such as a rat or mouse) can also comprise one or more of the following modifications in its germline: entirely human heavy and light chain variable region loci operably linked to a non-human animal (e.g., rodent, such as a rat or mouse) constant region nucleic acid sequence such that the non-human animal (e.g., rodent, such as a rat or mouse) produces a B cell or an antibody comprising a human variable domain fused to a non-human animal (e.g., rodent, such as a rat or mouse) constant domain; or a human heavy and/or light chain variable region operably linked to a non-human animal (e.g., rodent, such as a rat or mouse) constant region nucleic acid sequence such that the non-human animal (e.g., rodent, such as a rat or mouse) produces a B cell or an antibody comprising a human variable domain fused to a non-human animal (e.g., rodent, such as a rat or mouse) constant region. As an example, VELOCIMMUNE® mice can be used. See, e.g., U.S. Pat. Nos. 6,596,541, 8,791,323, 8,895,802, 8,895,801, 7,105,348, US 2002/0106629, US 2007/0061900, US 2011/0258710, US 2011/0283376, US 2013/0210137, US 2014/0017781, US 2014/0020124, US 2014/0020125, US 2014/0017782, US 2014/0018522, US 2014/0033337, US 2014/0033336, US 2014/0041068, US 2014/0073010, US 2014/0023637, US 2014/0017238, US 2014/0013457, US 2014/0017229, US 2002/0183275, U.S. Pat. No. 8,502,018, US 2012/0322108, US 2013/0254911, US 2014/0213773, US 2015/0201589, US 2015/0210776, US 2014/0017228, U.S. Pat. Nos. 8,642,835, 8,697,940, and Murphy et al. (2014) Proc. Natl. Acad. Sci. U.S.A. 111(14):5153-5158, each of which is herein incorporated by reference in its entirety for all purposes. VELOCIMMUNE® mice contain a precise, large-scale replacement of germline variable regions that encode mouse immunoglobulin heavy chain (IgH) and immunoglobulin light chain (e.g., κ light chain, Igκ) with corresponding human immunoglobulin variable regions, at the endogenous loci. This precise replacement results in a mouse with hybrid immunoglobulin loci that make heavy and light chains that have human variable regions and a mouse constant region. The precise replacement of mouse $V_H$-$D_H$-$J_H$ and Vκ-Jκ segments leaves flanking mouse sequences intact and functional at the hybrid immunoglobulin loci. The humoral immune system of the mouse functions like that of a wild type mouse. B cell development is unhindered in any significant respect and a rich diversity of human variable regions is generated in the mouse upon antigen challenge.

The non-human animals (e.g., rodents, such as rats or mice) described above (e.g., VELOCIMMUNE® mice) can also comprise in their germline a functional ectopic nucleic acid sequence that encodes a non-human animal (e.g., rodent, such as a rat or mouse) ADAM6 gene or homolog or ortholog or functional fragment thereof. For example, such a non-human animal (e.g., rodent, such as a rat or mouse) can lack a functional endogenous ADAM6 gene and comprise the functional ectopic nucleic acid sequence to complement the loss of non-human animal (e.g., rodent, such as a rat or mouse) ADAM6 function. For example, the functional ectopic sequence can comprise one or more Adam6 genes, such as a mouse Adam6a gene, a mouse Adam6b gene, or both Adam6a and Adam6b genes. The ectopic nucleic acid sequence can be present at the human heavy chain variable region locus or elsewhere. See, e.g., US 2012/0322108; US 2013/0254911; US 2014/0213773; US 2015/0201589; US 2015/0210776; US 2014/0017228; and US 2013/0198879, each of which is herein incorporated by reference in its entirety for all purposes.

Other non-human animals (e.g., rodents, such as rats or mice) that can be used include non-human animals (e.g., rodents, such as rats or mice) genetically modified to express a limited repertoire of human light chain variable domains, or a single human light chain variable domain, from a limited repertoire of human light chain variable region gene segments. Such non-human animals generate "universal light chains" or "common light chains" and can be useful in making bispecific antibodies. See, e.g., US 2011/0195454; US 2012/0021409; US 2012/0192300; US 2015/0059009; US 2013/0045492; US 2013/0198880; US 2013/0185821; US 2013/0302836; US 2013/0247234; US 2014/0329711;

and US 2013/0198879, each of which is herein incorporated by reference in its entirety for all purposes. For example, the non-human animal (e.g., rodent, such as a rat or mouse) can be genetically engineered to include a single unrearranged human light chain variable region gene segment (or two human light chain variable region gene segments) that rearranges to form a rearranged human light chain variable region gene (or two rearranged light chain variable region genes) that express a single light chain (or that express either or both of two light chains). The rearranged human light chain variable domains are capable of pairing with a plurality of affinity-matured human heavy chains selected by the non-human animals (e.g., rodents, such as rats or mice), wherein the heavy chain variable regions specifically bind different epitopes.

To achieve a limited repertoire of light chain options, the non-human animal (e.g., rodent, such as a rat or mouse) can be engineered to render nonfunctional or substantially nonfunctional its ability to make, or rearrange, a native non-human animal (e.g., rodent, such as a rat or mouse) light chain variable domain. This can be achieved, for example, by deleting the non-human animal's (e.g., rodent, such as a rat or mouse) light chain variable region gene segments. The endogenous non-human animal (e.g., rodent, such as a rat or mouse) locus can then be modified by an exogenous suitable human light chain variable region gene segment of choice, operably linked to a non-human animal (e.g., rodent, such as a rat or mouse) light chain constant region, in a manner such that the exogenous human variable region gene segments can rearrange and recombine with the endogenous non-human animal (e.g., rodent, such as a rat or mouse) light chain constant region gene and form a rearranged reverse chimeric light chain gene (human variable, non-human animal (e.g., rodent, such as a rat or mouse) constant).

The non-human animals (e.g., rodents, such as rats or mice) described above (e.g., "universal light chain" or "common light chain") can also comprise in their germline a functional ectopic nucleic acid sequence that encodes a non-human animal (e.g., rodent, such as a rat or mouse) ADAM6 gene or homolog or ortholog or functional fragment thereof. Similarly, any of the other non-human animals (e.g., rodents, such as rats or mice) described herein can also comprise in their germline a functional ectopic nucleic acid sequence that encodes a non-human animal (e.g., rodent, such as a rat or mouse) ADAM6 gene or homolog or ortholog or functional fragment thereof. For example, such a non-human animal (e.g., rodent, such as a rat or mouse) can lack a functional endogenous ADAM6 gene and comprise the functional ectopic nucleic acid sequence to complement the loss of non-human animal (e.g., rodent, such as a rat or mouse) ADAM6 function. The ectopic nucleic acid sequence can be present at the human heavy chain variable region locus or elsewhere. See, e.g., US 2012/0322108; US 2013/0254911; US 2014/0213773; US 2015/0201589; US 2015/0210776; US 2014/0017228; and US 2013/0198879, each of which is herein incorporated by reference in its entirety for all purposes.

Other non-human animals (e.g., rodents, such as rats or mice) that can be used include a non-human animal comprising in its germline an unrearranged light chain V segment and an unrearranged J segment operably linked to a heavy chain constant region nucleic acid sequence. See, e.g., US 2012/0096572, US 2014/0130194, and US 2014/0130193, each of which is herein incorporated by reference in its entirety for all purposes. One example of such a non-human animal is a non-human animal whose germline genome comprises a modified endogenous immunoglobulin heavy chain locus comprising a replacement of all functional endogenous non-human animal immunoglobulin heavy chain variable ($V_H$) gene segments, all functional endogenous non-human animal immunoglobulin heavy chain diversity ($D_H$) gene segments, and all functional endogenous non-human animal immunoglobulin heavy chain joining ($J_H$) gene segments at the endogenous non-human animal immunoglobulin heavy chain locus with a nucleotide sequence that comprises a plurality of unrearranged human immunoglobulin light chain variable (Vκ) gene segments and a plurality of unrearranged human immunoglobulin light chain joining (Jκ) gene segments and is operably linked to an endogenous non-human animal immunoglobulin heavy chain constant ($C_H$) region, wherein the plurality of unrearranged human immunoglobulin light chain V gene segments and the plurality of unrearranged human immunoglobulin light chain J gene segments participate in rearrangement in a B cell during B cell development to form a rearranged human immunoglobulin light chain Vκ/Jκ gene sequence operably linked to the endogenous non-human animal immunoglobulin heavy chain $C_H$ region at the modified endogenous heavy chain locus. Another example of such a non-human animal is a non-human animal comprising in its germline a first unrearranged human kappa light chain variable (Vκ) gene segment and an unrearranged human kappa light chain joining (Jκ) gene segment operably linked to the endogenous non-human animal heavy chain constant region at the endogenous non-human animal heavy chain locus, wherein the first unrearranged human Vκ gene segment and the unrearranged human Jκ gene segment replace all functional endogenous non-human animal heavy chain variable ($V_H$) gene segments, all functional endogenous non-human animal diversity ($D_H$) gene segments and all functional endogenous non-human animal heavy chain joining ($J_H$) gene segments, wherein the first unrearranged human Vκ gene segment and unrearranged human Jκ gene segment participate in rearrangement to form a rearranged Vκ/Jκ sequence operably linked to the endogenous non-human animal heavy chain constant region in the non-human animal, and wherein the non-human animal further comprises in its germline a second human light chain variable ($V_L$) gene segment and a human light chain joining ($J_L$) gene segment operably linked to a non-human animal light chain constant gene. Yet another example of such as non-human animal is a non-human animal whose genome comprises: (a) an endogenous immunoglobulin heavy chain locus modified to comprise a replacement of all functional endogenous non-human animal immunoglobulin heavy chain variable ($V_H$) gene segments, all functional endogenous non-human animal immunoglobulin heavy chain diversity ($D_H$) gene segments, and all functional endogenous non-human animal immunoglobulin heavy chain joining ($J_H$) gene segments at the endogenous non-human animal immunoglobulin heavy chain locus with a first plurality of unrearranged human light chain variable (Vκ) gene segments and a first plurality of unrearranged human light chain joining (Jκ) gene segments, wherein the first pluralities of unrearranged human immunoglobulin light chain Vκ and Jκ gene segments are operably linked to the endogenous heavy chain constant ($C_H$) region nucleic acid sequence at the endogenous immunoglobulin heavy chain locus and participate in rearrangement in a B cell during B cell development to form a first rearranged human light chain Vκ/Jκ gene sequence operably linked to the endogenous non-human animal $C_H$ region nucleic acid sequence; and (b) a modified immunoglobulin light chain locus comprising a second plurality of unrearranged human light chain variable (Vκ)

gene segments and a second plurality of unrearranged human light chain joining (Jκ) gene segments operably linked to an endogenous non-human animal light chain constant (Cκ) region nucleic acid sequence at an endogenous non-human animal light chain locus, wherein the second pluralities of unrearranged human immunoglobulin light chain Vκ and Jκ gene segments replace all functional endogenous non-human animal light chain variable (Vκ) gene segments and all functional endogenous non-human animal light chain joining (Jκ) gene segments at the endogenous chain locus and participate in rearrangement in a B cell during B cell development to form a second rearranged human immunoglobulin light chain Vκ/Jκ region gene sequence operably linked to the endogenous non-human animal Cκ region nucleic acid sequence.

Other non-human animals (e.g., rodents, such as rats or mice) that can be used include a non-human animal comprising in its germline genome an immunoglobulin heavy chain locus that comprises a rearranged human immunoglobulin heavy chain variable region nucleotide sequence operably linked to an endogenous non-human animal immunoglobulin constant region gene sequence. See, e.g., US 2015/0020224, US 2014/0245468, US 2016/0100561, U.S. Pat. No. 9,204,624, and U.S. Ser. No. 14/961,642, each of which is herein incorporated by reference in its entirety for all purposes. One example of such a non-human animal is a non-human animal comprising in its germline genome at an endogenous immunoglobulin heavy chain locus a rearranged human immunoglobulin heavy chain variable region nucleotide sequence operably linked to an endogenous heavy chain constant region gene sequence, wherein the rearranged heavy chain variable region nucleotide sequence encodes the sequence of $V_H3-23/X_1X_2/J_H$, wherein $X_1$ is any amino acid, and $X_2$ is any amino acid. Another example of such a non-human animal is a non-human animal comprising in its germline genome a genetically modified endogenous immunoglobulin heavy chain locus that comprises a rearranged human immunoglobulin heavy chain variable region nucleotide sequence operably linked to an endogenous non-human immunoglobulin constant region gene sequence, wherein the non-human animal exhibits a humoral immune system substantially similar to wild type non-human animals with respect to B cell populations. Yet another example of such a non-human animal is a non-human animal comprising a genetically modified endogenous immunoglobulin heavy chain locus that comprises a rearranged human immunoglobulin heavy chain variable region nucleotide sequence comprising a heavy chain V segment ($V_H$) sequence that is operably linked, via a spacer, to a heavy chain J segment ($J_H$) sequence, wherein the spacer comprises encodes at least two amino acid residues, wherein the rearranged human immunoglobulin heavy chain variable region nucleotide sequence is operably to an endogenous non-human animal immunoglobulin constant region gene sequence. In one example, the $V_H$ segment is $V_H3-23$.

Other non-human animals (e.g., rodents, such as rats or mice) that can be used include a non-human animal whose germline genome comprises: a restricted immunoglobulin heavy chain locus characterized by the presence of a single human unrearranged $V_H$ gene segment, one or more human unrearranged $D_H$ gene segments, and one or more human unrearranged $J_H$ gene segments operably linked to a non-human immunoglobulin heavy chain constant region nucleic acid sequence, wherein the non-human animal further comprises a B cell comprising a rearranged human heavy chain variable region gene sequence derived from the restricted immunoglobulin heavy chain locus. See, e.g., US 2013/0323791 and US 2013/0096287, each of which is herein incorporated by reference in its entirety for all purposes. In some such non-human animals, the single unrearranged human $V_H$ gene segment is $V_H1-69$. In some such non-human animals, the single unrearranged human $V_H$ gene segment is $V_H1-2$. Other non-human animals that can be used include a non-human animal whose endogenous immunoglobulin heavy chain locus is restricted in that it comprises a single human $V_H$ gene segment, one or more human $D_H$ gene segments, and one or more human $J_H$ gene segments and which does not comprise a functional endogenous immunoglobulin heavy chain variable region locus; the non-human animal further comprising one or more human immunoglobulin $V_L$ gene segments operably linked to one or more human $J_L$ gene segments, wherein the single human $V_H$ gene segment, one or more human $D_H$ gene segments, and one or more $J_H$ gene segments are operably linked to a non-human immunoglobulin heavy chain constant region gene, wherein the single human $V_H$ gene segment is $V_H1-69$ or a polymorphic variant thereof.

Other non-human animals (e.g., rodents, such as rats or mice) that can be used include a non-human animal comprising in its germline genome a genetically modified immunoglobulin heavy chain locus comprising an unrearranged human immunoglobulin heavy chain variable region nucleotide sequence, wherein the unrearranged heavy chain variable region nucleotide sequence comprises an addition of at least one histidine codon or a substitution of at least one non-histidine codon with a histidine codon, wherein the histidine codon is not encoded by a corresponding human germline heavy chain variable region gene segment; and wherein the added or substituted histidine codon is present in a complementary determining region 3 (CDR3) encoding sequence. See, e.g., US 2013/0247235, U.S. Pat. No. 9,301,510, and U.S. Ser. No. 14/046,501, each of which is herein incorporated by reference in its entirety for all purposes.

Other non-human animals (e.g., rodents, such as rats or mice) that can be used include a non-human animal comprising a germline genetic modification that comprises a deletion of at least part of a nucleotide sequence encoding a $C_H1$ domain of an endogenous IgG constant region gene; wherein the non-human animal expresses an IgM constant region gene that comprises a functional $C_H1$ domain and the non-human animal expresses in its serum an IgG antibody that lacks a $C_H1$ domain, in whole or in part, and that lacks a cognate light chain. See, e.g., US 2011/0145937, US 2014/0289876, US 2015/0197553, US 2015/0197554, US 2015/0197555, US 2015/0196015, US 2015/0197556, US 2015/0197557, and U.S. Pat. No. 8,754,287, each of which is herein incorporated by reference in its entirety for all purposes. An example of such a non-human animal is a non-human animal comprising a germline modification, which modification comprises: (a) a deletion of a nucleotide sequence encoding a $C_H1$ domain of an endogenous IgG constant region gene; and (b) an inclusion of one or more human heavy chain variable region gene segments, wherein the one or more human heavy chain variable region gene segments is operably linked to the endogenous IgG constant region of (a); wherein the non-human animal comprises an intact IgM constant region gene and the non-human animal expresses an IgG heavy chain antibody comprising a human variable domain, lacking a CH1 domain, in whole or in part, and lacking a cognate light chain and secretes said IgG heavy chain antibody into its serum. See, e.g., US 2011/0145937. Another example of such a non-human animal is a non-human animal comprising a germline modification, which modification comprises: (a) a deletion of a nucleic acid sequence encoding a $C_H1$ domain and a hinge region of an endogenous IgG constant region gene; and (b) an inclusion of one or more human heavy chain variable region gene segments, wherein the one or more human heavy chain variable region gene segments is operably linked to the endogenous IgG constant region of (a); wherein the non-human animal comprises an intact IgM constant region gene. See, e.g., US 2015/0197553. Yet another example of such a non-human animal is a non-human animal comprising a germline modification, which modification comprises: (a) a deletion of a nucleic acid sequence encoding a $C_H1$ domain of an endogenous IgG constant region gene; (b) a deletion of an endogenous IgG2a constant region gene; (c) a deletion of an endogenous IgG2b constant region gene; and (d) an inclusion of one or more human heavy chain variable region gene segments, wherein the one or more human heavy chain variable region gene segments is operably linked to the endogenous IgG constant region of (a); wherein the non-human animal comprises an intact IgM constant region gene. See, e.g., US 2015/0197554. Yet another example of such a non-human animal is a non-human animal comprising a germline modification, which modification comprises: (a) a deletion of a nucleic acid sequence encoding a $C_H1$ domain and a hinge region of an endogenous IgG constant region gene; (b) a deletion of an endogenous IgG2a constant region gene; (c) a deletion of an endogenous IgG2b constant region gene; and (d) an inclusion of one or more human heavy chain variable region gene segments, wherein the one or more human heavy chain variable region gene segments is operably linked to the endogenous IgG constant region of (a); wherein the non-human animal comprises an intact IgM constant region gene. See, e.g., US 2015/0197555. Yet another example of such a non-human animal is a non-human animal comprising a germline modification, which modification comprises: (a) a deletion of a nucleic acid sequence encoding a $C_H1$ domain of an endogenous IgG1 constant region gene; (b) a deletion of an endogenous IgD constant region gene; (c) a deletion of an endogenous IgG3 constant region gene; (d) a deletion of an endogenous IgG2a constant region gene; (e) a deletion of an endogenous IgG2b constant region gene; (f) a deletion of an endogenous IgE constant region gene; (g) a deletion of an endogenous IgA constant region gene; and (h) an inclusion of one or more human heavy chain variable region gene segments, wherein the one or more human heavy chain variable region gene segments is operably linked to the endogenous IgG1 constant region of (a); wherein the non-human animal comprises an intact IgM constant region gene. See, e.g., US 2015/0196015. Yet another example of such a non-human animal is a non-human animal comprising a germline modification, which modification comprises: (a) a deletion of a nucleic acid sequence encoding a $C_H1$ domain of an endogenous IgG1 constant region gene; (b) a deletion of a nucleic acid sequence encoding a $C_H1$ domain of an endogenous IgG2a constant region gene; (c) a deletion of an endogenous IgD constant region gene; (d) a deletion of an endogenous IgG3 constant region gene; (e) a deletion of an endogenous IgG2b constant region gene; (f) a deletion of an endogenous IgE constant region gene; (g) a deletion of an endogenous IgA constant region gene; and (h) an inclusion of one or more human heavy chain variable region gene segments, wherein the one or more human heavy chain variable region gene segments is operably linked to the endogenous IgG1 constant region of (a); wherein the non-human animal comprises an intact IgM constant region gene. See, e.g. US 2015/0197556. Yet another example of such a non-human animal is a non-human animal comprising a germline modification, which modification comprises: (a) a deletion of a nucleic acid sequence encoding a $C_H1$ domain and a hinge region of an endogenous IgG1 constant region gene; (b) a deletion of an endogenous IgD constant region gene; (c) a deletion of an endogenous IgG3 constant region gene; (d) a deletion of an endogenous IgG2a constant region gene; (e) a deletion of an endogenous IgG2b constant region gene; (f) a deletion of an endogenous IgE constant region gene; (g) a deletion of an endogenous IgA constant region gene; and (h) an inclusion of one or more human heavy chain variable region gene segments, wherein the one or more human heavy chain variable region gene segments is operably linked to the endogenous IgG1 constant region of (a); wherein the non-human animal comprises an intact IgM constant region gene. See, e.g., US 2015/0197557.

Other non-human animals (e.g., rodents, such as rats or mice) that can be used include a non-human animal comprising a λ light chain variable region sequence (Vλ) and at least one J sequence (J), contiguous with a non-human animal κ light chain constant region sequence. See, e.g., US 2012/0073004, US 2014/0137275, US 2015/0246976, US 2015/0246977, US 2015/0351371, U.S. Pat. Nos. 9,035,128, 9,066,502, 9,163,092, and 9,150,662, each of which is herein incorporated by reference in its entirety for all purposes. One example of such a non-human animal is a non-human animal comprising: (a) at least 12 to at least 40 unrearranged human λ light chain variable region gene segments and at least one human Jλ, gene segment at an endogenous non-human animal light chain locus; (b) a human Vκ-Jκ intergenic sequence located between the at least 12 to at least 40 human light chain variable region gene segments and the at least one human Jλ sequence; wherein the non-human animal expresses an antibody that comprises a light chain comprising a human Vλ domain and a non-human animal Cκ domain. Yet another example of such a non-human animal is a non-human animal comprising at an endogenous κ light chain locus in its germline: (a) an unrearranged light chain variable region comprising a plurality of contiguous unrearranged functional human λ light chain V (hVλ) gene segments and a plurality of contiguous unrearranged functional human λ light chain J (hJλ) gene segments, wherein the plurality of hVλ gene segments and the plurality of hJλ gene segments are the only functional variable region gene segments in the unrearranged light chain variable region; and (b) a non-human animal κ light chain constant region gene, wherein the plurality of contiguous unrearranged human λ light chain V (hVλ) gene segments and the plurality of contiguous unrearranged human λ light chain J (hJλ) gene segments are operably linked to the non-human animal κ light chain constant region gene such that the unrearranged light chain variable region is capable of rearranging to form a rearranged human λ light chain variable region and the non-human animal expresses antibodies comprising a light chain comprising a variable region encoded by the rearranged human λ light chain variable region and a constant region encoded by the non-human animal κ light chain constant region gene. Yet another example of such a non-human animal is a non-human animal comprising at an endogenous κ light chain locus in its germline: (a) an unrearranged light chain variable region comprising: (i) at least 12 contiguous unrearranged functional human λ light chain variable region (hVλ) gene segments and a plurality of contiguous unrearranged functional human λ light chain J (hJλ) gene segments, wherein the at least 12 functional hVλ gene segments and the plurality of functional hJλ gene segments are the only functional variable region gene segments in the unrearranged light chain variable region; and (ii) a human Vκ-Jκ intergenic sequence located between the contiguous hVλ gene segments and the plurality of contiguous hJλ gene segments; and (b) a non-human animal κ light chain constant region gene; wherein the at least 12 contiguous unrearranged functional human λ light chain V (hVλ) gene segments and the plurality of contiguous unrearranged functional human λ light chain J (hJλ) gene segments are operably linked to the non-human animal κ light chain constant region gene such that the unrearranged light chain variable region is capable of rearranging to form a rearranged human λ light chain variable region and the non-human animal expresses antibodies comprising a light chain comprising a variable region encoded by the rearranged human λ light chain variable region and a constant region encoded by the non-human animal κ light chain constant region gene. Yet another example of such a non-human animal is a non-human animal comprising in its germline: (a) an unrearranged light chain variable region comprising a plurality of contiguous unrearranged functional human λ light chain V (hVλ) gene segments and a plurality of contiguous unrearranged functional human λ light chain J (hJλ) gene segments, wherein the plurality of hVλ gene segments and the plurality of hJλ gene segments are the only functional variable region gene segments in the unrearranged light chain variable region; and (b) a non-human animal κ light chain constant region gene, wherein the plurality of contiguous unrearranged functional hVλ gene segments and the plurality of contiguous unrearranged functional hJλ gene segments are operably linked to the non-human animal κ light chain constant region gene such that the unrearranged light chain variable region is capable of rearranging to form a rearranged human λ light chain variable region and the non-human animal expresses antibodies comprising a light chain comprising a variable domain encoded by the rearranged human λ light chain variable region and a constant domain encoded by the non-human animal κ light chain constant region gene. Yet another example of such a non-human animal is a non-human animal comprising in its germline: (a) an unrearranged light chain variable region comprising: (i) at least 12 contiguous unrearranged functional human λ light chain V (hVλ) gene segments and a plurality of contiguous unrearranged functional human λ light chain J (hJλ) gene segments, wherein the at least 12 functional hVλ gene segments and the plurality of functional hJλ gene segments are the only functional variable region gene segments in the unrearranged light chain variable region; and (ii) a human Vκ-Jκ intergenic sequence located between the contiguous hVλ gene segments and the plurality of contiguous hJλ gene segments; and (b) a non-human animal κ light chain constant region gene; wherein the at least 12 contiguous unrearranged functional hVλ gene segments and the plurality of contiguous unrearranged functional hJλ gene segments are operably linked to the non-human animal κ light chain constant region gene such that the unrearranged light chain variable region is capable of rearranging to form a rearranged human λ light chain variable region and the non-human animal expresses antibodies comprising a light chain comprising a variable domain encoded by the rearranged human λ light chain variable region and a constant domain encoded by the non-human animal κ light chain constant region gene. Yet another example of such a non-human animal is a non-human animal whose genome comprises an immunoglobulin locus comprising human Vλ and Jλ gene segments operably linked to a non-human animal Cκ gene such that the non-human animal expresses an immunoglobulin light chain that comprises a human λ variable domain sequence fused with a non-human animal κ constant domain. See, e.g., U.S. Pat. No. 9,226,484.

Other non-human animals (e.g., rodents, such as rats or mice) that can be used include a non-human animal comprising in its germline, at an endogenous non-human animal light chain locus, a human λ light chain variable region sequence, wherein the human lambda variable region sequence is expressed in a light chain that comprises a non-human animal immunoglobulin constant region gene sequence. See, e.g., US 2013/0323790, US 2013/0326647, US 2015/0089680, US 2015/0173331, US 2015/0176002, US 2015/0173332, US 2012/0070861, US 2015/0320023, US 2016/0060359, US 2016/0057979, U.S. Pat. Nos. 9,029,628, 9,006,511, 9,012,717, 9,206,261, 9,206,262, 9,206,263, and 9,226,484, each of which is herein incorporated by reference in its entirety for all purposes. An example of such a non-human animal is a non-human animal that expresses an immunoglobulin light chain that comprises a human lambda variable sequence fused with a non-human animal constant region, wherein the non-human animal exhibits a κ usage to λ usage ratio of about 1:1. See, e.g., U.S. Pat. No. 9,029,628. Yet another example of such a non-human animal is a non-human animal whose genome comprises an endogenous unrearranged κ light chain immunoglobulin locus comprising a replacement of endogenous Vκ and Jλ gene segments with human Vλ and Jλ gene segments, and wherein the human Vλ and Jλ gene segments are operably linked to a non-human animal Cκ gene such that the non-human animal expresses an immunoglobulin light chain that comprises a human λ variable sequence fused with a non-human animal κ constant region. See, e.g., U.S. Pat. No. 9,006,511. Yet another example of such a non-human animal is a non-human animal whose genome comprises an endogenous λ light chain immunoglobulin locus comprising: (i) a deletion of a first endogenous Vλ-Jλ-Cλ gene cluster; and (ii) a replacement a fragment of endogenous Vλ and Jλ gene segments in a second endogenous Vλ-Jλ-Cλ gene cluster with human Vλ and Jλ gene segments, wherein the human Vλ and Jλ gene segments comprise at least one human Vλ gene segment and at least one human Jλ gene segment, and wherein the human Vλ and Jλ gene segments are operably linked to a non-human animal Cλ gene. See, e.g., U.S. Pat. No. 9,012,717.

Other non-human animals (e.g., rodents, such as rats or mice) that can be used include a non-human animal having a genome comprising a modification of an immunoglobulin heavy chain locus, wherein the modification reduces or eliminates endogenous ADAM6 function, and the non-human animal further comprises a nucleic acid sequence encoding a non-human animal ADAM6 protein or an ortholog or homolog thereof or a functional fragment of the corresponding ADAM6 protein. See, e.g., US 2012/0322108, US 2013/0254911, US 2014/0213773, US 2015/0201589, US 2015/0210776, US 2014/0017228, U.S. Pat. Nos. 8,642,835, and 8,697,940, each of which is herein incorporated by reference in its entirety for all purposes. An example of such a non-human animal is a non-human animal whose genome comprises: (a) ectopic placement of an ADAM6 gene; and (b) a human immunoglobulin heavy chain variable region locus comprising an insertion of one or more human $V_H$ gene segments, one or more human $D_H$ gene segments, and one or more human $J_H$ gene segments into the endogenous non-human animal heavy chain locus, wherein the human $V_H$, $D_H$ and $J_H$ gene segments are operably linked to a heavy chain constant region gene; so that the non-human animal is characterized in that: (i) it is fertile; and (ii) when it is immunized with an antigen, it generates antibodies comprising heavy chain variable domains encoded by the one or more human $V_H$, one or more human $D_H$, and one or more human $J_H$ gene segments, operably linked to heavy chain constant domains encoded by the heavy chain constant region gene, wherein the antibodies show specific binding to the antigen. See, e.g., U.S. Pat. No. 8,642,835.

Other non-human animals (e.g., rodents, such as rats or mice) that can be used include a non-human animal comprising: (a) an insertion of one or more human Vλ and Jλ gene segments upstream of an non-human immunoglobulin light chain constant region, (b) an insertion of one or more human $V_H$, one or more human $D_H$ and one or more human $J_H$ gene segments upstream of an non-human immunoglobulin heavy chain constant region, and (c) a nucleotide sequence that encodes an ADAM6 protein or a functional fragment thereof, wherein the ADAM6 protein is expressed from an ectopic ADAM6 nucleic acid sequence. See, e.g., US 2013/0160153 and US 2014/0017228, each of which is herein incorporated by reference in its entirety for all purposes. An example of such a non-human animal is a non-human animal whose genome comprises: (a) an insertion of one or more human Vλ, gene segments and one or more human Jλ gene segments upstream of a non-human animal immunoglobulin light chain constant region gene, (b) an insertion of one or more human $V_H$ gene segments, one or more human $D_H$ gene segments, and one or more human $J_H$ gene segments upstream of a non-human animal immunoglobulin heavy chain constant region gene, and (c) a an ectopic nucleotide sequence that encodes a non-human animal ADAM6 protein, wherein the non-human animal ADAM6 protein is expressed from an the ectopic nucleotide sequence. See, e.g., US 2013/0160153.

Other non-human animals (e.g., rodents, such as rats or mice) that can be used include a non-human animal comprising in its germline an immunoglobulin locus that comprises an unrearranged immunoglobulin variable gene sequence comprising in a CDR3 encoding sequence a substitution of at least one non-histidine codon with a histidine codon or an insertion of at least one histidine codon, wherein the non-human animal further comprises in vivo a diverse repertoire of antibodies, each of which is specific for an antigen of interest and comprises in a CDR3 of a variable domain at least one histidine amino acid encoded by the at least one histidine codon substitution or insertion in the unrearranged immunoglobulin variable gene sequence. See, e.g., US 2013/0247236 and US 2014/0082760, each of which is herein incorporated by reference in its entirety for all purposes. In one example, the first immunoglobulin variable region gene locus comprises a functional portion of an unrearranged immunoglobulin heavy chain variable region sequence that comprises unrearranged $V_H$, $D_H$, and $J_H$ gene segments, and wherein one or more of the unrearranged $V_H$, $D_H$, and $J_H$ gene segments comprises the inserted or substituted histidine codon that is not encoded by a corresponding wild type germline gene segment. In another example, the unrearranged $V_H$, $D_H$, and $J_H$ gene segments are unrearranged human $V_H$, unrearranged human $D_H$, and unrearranged human $J_H$ gene segments. In another embodiment, comprise in its germline a second immunoglobulin variable region gene locus comprising an immunoglobulin light chain variable region sequence comprising an insertion of at least one histidine codon or a substitution of at least one non histidine codon with a histidine codon, wherein the inserted or substituted histidine codon is not encoded by a corresponding wild type germline immunoglobulin variable region sequence, wherein the non-human animal expresses an immunoglobulin light chain variable domain that comprises a histidine derived from a histidine substitution or insertion in the germline of the non-human animal. See, e.g., US 2013/0247236.

Other non-human animals (e.g., rodents, such as rats or mice) that can be used include a non-human animal comprising: (a) an insertion of one or more human $V_L$ and one or more human $J_L$ gene segments upstream of an non-human immunoglobulin light chain constant region; (b) an insertion of one or more human $V_L$ and one or more human $J_L$ gene segments upstream of an non-human immunoglobulin heavy chain constant region; and (c) a nucleotide sequence that encodes an ADAM6 protein or a functional fragment thereof, wherein the ADAM6 protein is expressed from an ectopic ADAM6 nucleic acid sequence. See, e.g., US 2013/0212719, herein incorporated by reference in its entirety for all purposes. An example of such a non-human animal is a non-human animal whose genome comprises: (a) an insertion of one or more human $V_L$ gene segments and one or more human $J_L$ gene segments upstream of a non-human immunoglobulin light chain constant region gene, wherein the one or more human $V_L$ gene segments and one or more human $J_L$ gene segments are operably linked to the non-human immunoglobulin light chain constant region gene; (b) an insertion of one or more human $V_L$ gene segments and one or more human $J_L$ gene segments upstream of a non-human immunoglobulin heavy chain constant region gene, wherein the one or more human $V_L$ gene segments and one or more human $J_L$ gene segments are operably linked to the non-human immunoglobulin heavy chain constant region gene; and (c) an inserted nucleic acid sequence that encodes a non-human animal (e.g., rodent, such as a rat or mouse) ADAM6 protein, wherein the non-human animal (e.g., rodent, such as a rat or mouse) ADAM6 protein is expressed from the inserted nucleic acid sequence, so that B cells of the non-human animal express antibodies that each include two immunoglobulin light chains paired with two immunoglobulin heavy chains, wherein each light chain comprises a human light chain variable domain and a non-human light chain constant domain and each heavy chain comprises a human light chain variable domain and a non-human heavy chain constant domain. See, e.g., US 2013/0212719.

Other non-human animals (e.g., rodents, such as rats or mice) that can be used include a non-human animal having in its germline: (a) a human genomic sequence comprising a single human $V_H$ gene segment, one or more $D_H$ gene segments, and one or more $J_H$ gene segments; and (b) a sequence that encodes an ADAM6 protein that is functional in a male non-human animal, wherein the sequence that encodes the ADAM6 is located at a position different than an ADAM6 locus of a wild type non-human animal. See, e.g., US 2013/0333057, herein incorporated by reference in its entirety for all purposes. An example of such a non-human animal is a non-human animal having in its germline: (a) an unrearranged human genomic sequence comprising a single human $V_H$ gene segment, one or more human $D_H$ gene segments, and one or more human $J_H$ gene segments, wherein the single human $V_H$ gene segment is $V_H$1-2, $V_H$1-69, $V_H$2-26, $V_H$2-70, or a polymorphic variant thereof; and (b) a sequence that encodes an ADAM6 protein that is functional in a male non-human animal, wherein the sequence that encodes the ADAM6 protein is located at a position different than an ADAM6 locus of a wild type non-human animal. See, e.g., US 2013/0333057.

Other non-human animals (e.g., rodents, such as rats or mice) that can be used include a non-human animal comprising: (a) a single rearranged human immunoglobulin light chain variable region ($V_L/J_L$) that encodes a human $V_L$ domain of an immunoglobulin light chain, wherein the single rearranged human $V_L/J_L$ region is selected from a human Vκ1-39/J gene segment or a human Vκ3-20/J gene segment (e.g., a Vκ1-39/Jκ5 gene segment or a human Vκ3-20/Jκ1 gene segment); and (b) a replacement of endogenous heavy chain variable ($V_H$) gene segments with one or more human $V_H$ gene segments, wherein the human $V_H$ gene segments are operably linked to an endogenous heavy chain constant ($C_H$) region gene, and the human $V_H$ gene segments are capable of rearranging and forming a human/non-human animal chimeric heavy chain gene. Such non-human animals can be referred to as "Universal Light Chain" (ULC) or "Common Light Chain" non-human animals. See, e.g., US 2011/0195454, US 2012/0021409, US 2012/0192300, US 2015/0059009, US 2013/0045492, US 2013/0198880, US 2013/0185821, US 2013/0302836, US 2015/0313193, and U.S. Ser. No. 15/056,713, each of which is herein incorporated by reference in its entirety for all purposes. Likewise, another non-human animal (e.g., rodent, such as a rat or mouse) that can be used includes a non-human animal that expresses a population of antibodies, wherein the non-human animal's germline includes only a single immunoglobulin kappa light chain variable region gene, which is a rearranged human germline kappa light chain variable region gene, which non-human animal is either heterozygous for the single immunoglobulin kappa light chain variable region gene in that it contains only one copy, or is homozygous for the single immunoglobulin kappa light chain variable region gene in that it contains two copies; the non-human animal being characterized by active affinity maturation so that: (i) each immunoglobulin kappa light chain of the population comprises a light chain variable domain that is encoded by the rearranged human germline kappa light chain variable region gene, or by a somatically mutated variant thereof; (ii) the population includes antibodies comprising the immunoglobulin kappa light chains whose light chain variable domain is encoded by the rearranged human germline kappa light chain variable region gene and antibodies comprising the immunoglobulin kappa light chains whose light chain variable domain is encoded by the somatically mutated variants thereof; and (iii) the non-human animal generates a diverse collection of somatically mutated high affinity heavy chains that successfully pair with the immunoglobulin kappa light chains to form the antibodies of the population. An example of such a non-human animal is a non-human animal that is heterozygous or homozygous in its germline for: (a) an insertion at an endogenous non-human animal κ immunoglobulin light chain variable region locus of a rearranged Vκ/Jκ sequence comprising: a single human germline Vκ sequence, which single human germline Vκ sequence is present in SEQ ID NO: 148 or SEQ ID NO: 149; and a single human germline Jκ sequence, wherein the rearranged Vκ/Jκ sequence is operably linked to the endogenous non-human animal κ constant region; and (b) an insertion at an endogenous non-human animal immunoglobulin heavy chain variable region locus of a plurality of human immunoglobulin heavy chain variable region gene segments, wherein the human immunoglobulin heavy chain variable region gene segments are operably linked to an endogenous non-human animal immunoglobulin heavy chain constant region, and the human immunoglobulin heavy chain variable region gene segments are capable of rearranging and forming a rearranged human/non-human animal chimeric immunoglobulin heavy chain gene. SEQ ID NO: 148 is the sequence of an engineered human Vκ1-39Jκ5 locus, and SEQ ID NO: 149 is the sequence of an engineered human Vκ3-20Jκ1 locus. See, e.g., US 2011/0195454, herein incorporated by reference in its entirety for all purposes.

Other non-human animals (e.g., rodents, such as rats or mice) that can be used include a non-human animal useful for generating a human $V_L/C_H \times ULC$ domain comprising in its germline genome: (i) a hybrid immunoglobulin locus that encodes an immunoglobulin hybrid chain, wherein the hybrid immunoglobulin locus comprises unrearranged human immunoglobulin light chain variable region gene segments ($V_L$ and $J_L$) operably linked to an immunoglobulin heavy chain constant region nucleic acid sequence comprising one or more heavy chain constant region genes, each of which encodes at least a functional $C_H1$ domain, wherein the $V_L$ and $J_L$ gene segments are capable of rearranging to form a hybrid sequence comprising a rearranged human $V_L/J_L$ gene sequence operably linked to the immunoglobulin heavy chain constant region nucleic acid sequence; (ii) a light chain locus that encodes a human universal light chain and comprises a human universal rearranged light chain variable region nucleotide sequence operably linked to an immunoglobulin light chain constant region nucleic acid sequence; wherein the non-human animal is capable of producing an antigen-binding protein that comprises a human immunoglobulin hybrid chain derived from the hybrid locus and a cognate human universal light chain derived from the light chain locus, wherein the human immunoglobulin hybrid chain comprises a human immunoglobulin light chain variable ($hV_L/C_H \times ULC$) domain fused to a heavy chain constant IgD, IgG, IgE or IgA region comprising a functional $C_H1$ domain, and wherein the human universal light chain comprises a human immunoglobulin light chain fused to a light chain constant domain. See, e.g., PCT/US2016/023289, herein incorporated by reference in its entirety for all purposes. An example of such a non-human animal is non-human animal useful for generating a human $V_L/C_H \times ULC$ domain comprising in its germline genome: (i) a modified endogenous immunoglobulin heavy chain locus comprising a replacement of all functional endogenous non-human animal immunoglobulin heavy chain variable $V_H$ gene segments, all functional endogenous non-human animal immunoglobulin heavy chain diversity $D_H$ gene segments and all functional endogenous non-human animal immunoglobulin heavy chain joining $J_H$ gene segments with a plurality of unrearranged human immunoglobulin light chain variable Vκ gene segments and a plurality of unrearranged human immunoglobulin light chain joining Jκ gene segments operably linked to an endogenous non-human animal immunoglobulin heavy chain constant region nucleic acid comprising one or more heavy chain constant region genes, each of which encodes at least a functional $C_H1$ domain, wherein the plurality of unrearranged human immunoglobulin light chain Vκ gene segments and the plurality of unrearranged human immunoglobulin light chain Jκ gene segments participate in rearrangement in a B cell during B cell development to form a first rearranged human immunoglobulin light chain variable region Vκ/Jκ nucleotide sequence operably linked to the endogenous non-human animal immunoglobulin heavy chain constant region nucleic acid sequence at the endogenous non-human animal immunoglobulin heavy chain locus; and (ii) a modified endogenous light chain locus comprising a single rearranged human immunoglobulin light chain variable region gene sequence derived from a rearranged Vκ1-39/Jκ5 or Vκ3-20/Jκ1 gene sequence, wherein the single rearranged human immunoglobulin light chain variable region gene sequence is operably inked to an endogenous non-human animal immunoglobulin light chain constant region k gene sequence; wherein the non-human animal is capable of producing an antigen-binding protein that comprises a human immunoglobulin hybrid chain derived from the modified endogenous immunoglobulin heavy chain locus and a cognate human universal light chain derived from the modified endogenous light chain locus, wherein the human immunoglobulin hybrid chain comprises a human immunoglobulin light chain variable (hV$_L$/C$_H$× ULC) domain fused to a heavy chain constant IgD, IgG, IgE or IgA region comprising a functional C$_H$1 domain, and wherein the human universal light chain comprises a human immunoglobulin light chain fused to a light chain constant domain.

Other non-human animals (e.g., rodents, such as rats or mice) that can be used include a non-human animal comprising in its germline genome a light chain immunoglobulin locus, e.g., at an endogenous non-human light chain locus, comprising a rearranged human immunoglobulin light chain variable region nucleotide sequence operably linked to an immunoglobulin light chain constant region nucleic acid sequence, wherein the rearranged human immunoglobulin light chain variable region nucleotide sequence operably linked to an immunoglobulin light chain constant region nucleic acid sequence encodes a universal light chain, and wherein the non-human animal is capable of producing or does produce a cell, e.g., a lymphocyte, e.g., a B cell, that expresses an antigen-binding protein comprising the immunoglobulin hybrid chain and the universal light chain. See, e.g., US 2013/0247234, US 2014/0329711, US 2014/0013456, US 2015/0119556, US 2015/0250151, U.S. Pat. Nos. 9,334,334, and 9,332,742, each of which is herein incorporated by reference in its entirety for all purposes. Some such non-human animals are homozygous for the rearranged human immunoglobulin light chain variable region nucleotide sequence. Some such non-human animals are heterozygous for the rearranged human immunoglobulin light chain variable region nucleotide sequence. In some such non-human animals, the light chain constant region nucleic acid sequence is a kappa sequence. In some such non-human animals, the light chain constant region nucleic acid sequence is a lambda sequence. In some such non-human animals, the second immunoglobulin locus is a light chain kappa locus. In some embodiments, the second immunoglobulin locus is a light chain lambda locus. An example of such a non-human animal is a non-human animal comprising in its germline an immunoglobulin light chain locus that comprises a single rearranged human immunoglobulin light chain variable region gene sequence comprising human Vκ and Jκ segment sequences, wherein the Vκ segment sequence is derived from a human Vκ1-39 or Vκ3-20 gene segment, and wherein the single rearranged human immunoglobulin light chain variable region gene sequence comprises a substitution of at least one non-histidine codon of the Vκ segment sequence with a histidine codon that is expressed at a position selected from the group consisting of 105, 106, 107, 108, 109, 111 and a combination thereof (according to IMGT numbering).

Other non-human animals (e.g., rodents, such as rats or mice) that can be used include a non-human animal whose genome comprises: (a) a humanized immunoglobulin heavy chain variable locus comprising at least one unrearranged human V$_H$, at least one unrearranged human D$_H$, and at least one unrearranged human J$_H$ segment operably linked to a heavy chain constant region gene; (b) a humanized immunoglobulin light chain variable locus comprising no more than one, or no more than two, rearranged human light chain V/J sequences operably linked to a light chain constant region gene; and (c) an ectopic nucleic acid sequence that expresses a functional non-human animal ADAM6 protein or functional ortholog or functional homolog or functional fragment thereof. See, e.g., US 2013/0198879, herein incorporated by reference in its entirety for all purposes. An example of such a non-human animal is a non-human animal comprising in its germline: (a) a humanized immunoglobulin heavy chain variable locus comprising at least one unrearranged human V$_H$ gene segment, at least one unrearranged human D$_H$ gene segment, and at least one unrearranged human J$_H$ gene segment, wherein the humanized immunoglobulin heavy chain variable locus is operably linked to an immunoglobulin heavy chain constant region gene; (b) a humanized immunoglobulin light chain variable locus comprising (i) a single rearranged human light chain V/J sequence, wherein the single rearranged human light chain V/J sequence is a rearranged human Vκ1-39/Jκ sequence or a rearranged human Vκ3-20/Jκ sequence, or (ii) no more than one human light chain V gene segment and no more than one human light chain J gene segment, wherein the no more than one human light chain V gene segment is Vκ1-39 or Vκ3-20, wherein the humanized immunoglobulin light chain variable locus is operably linked to an immunoglobulin light chain constant region gene; and (c) an ectopic nucleic acid sequence that expresses a non-human animal ADAM6 protein or ortholog or homolog or functional fragment thereof, which is functional in a male non-human animal.

Other non-human animals (e.g., rodents, such as rats or mice) that can be used include a non-human animal comprising in its germline: (a) a deletion or inactivating mutation in a nucleotide sequence encoding a C$_H$1 domain of at least one endogenous immunoglobulin heavy chain constant region gene at an endogenous immunoglobulin heavy chain locus, wherein the at least one endogenous immunoglobulin heavy chain constant region gene is IgG, IgA, IgE, IgD, or a combination thereof; and (b) either or both (i) a nucleic acid sequence comprising at least one unrearranged immunoglobulin light chain variable region (V$_L$) gene segment and at least one unrearranged immunoglobulin light chain joining (J$_L$) gene segment, wherein the unrearranged V$_L$ and J$_L$ gene segments are capable of recombining to form a rearranged immunoglobulin light chain variable region (V$_L$/J$_L$) nucleotide sequence operably linked to the immunoglobulin heavy chain constant region gene comprising the deletion or inactivating mutation in the nucleotide sequence encoding the C$_H$1 domain; and/or (ii) an immunoglobulin light chain locus that comprises a single rearranged immunoglobulin light chain variable region V$_L$/J$_L$ gene sequence comprising V$_L$ and J$_L$ gene segment sequences, wherein the single rearranged immunoglobulin light chain variable region gene sequence is operably linked to an immunoglobulin light chain constant region gene sequence. See, e.g., US 2015/0289489, herein incorporated by reference in its entirety for all purposes. An example of such a non-human animal is a non-human animal comprising: (a) a replacement at a non-human animal heavy chain locus of all or substantially all endogenous immunoglobulin heavy chain V, D, and J gene segments with either (i) one or more unrearranged human immunoglobulin heavy chain V$_H$ gene segments, one or more unrearranged human immunoglobulin heavy chain D$_H$ gene segments, and one or more unrearranged human immunoglobulin heavy chain J$_H$ gene segments, wherein the one or more human unrearranged immunoglobulin heavy chain $V_H$, $D_H$, and $J_H$ gene segments are operably linked to a non-human animal heavy chain constant region gene sequence; or (ii) one or more unrearranged human light chain $V_L$ gene segments and one or more human unrearranged light chain $J_L$ gene segments, wherein the one or more unrearranged human light chain $V_L$, and $J_L$ gene segments are operably linked to non-human animal heavy chain constant region gene sequence, wherein the non-human animal heavy chain constant region gene sequence comprises a full-length IgM gene and a deletion or an inactivating mutation in a nucleotide sequence encoding a $C_H1$ domain in an IgG gene selected from the group consisting of an IgG1, IgG2a, IgG2b, IgG2c, IgG3, and a combination thereof; and (b) a replacement of all or substantially all endogenous immunoglobulin light chain V and J gene segments with a single rearranged human variable Wax gene sequence, and wherein the non-human animal expresses a B cell receptor that comprises an IgM heavy chain associated with a cognate light chain.

Other non-human animals (e.g., rodents, such as rats or mice) that can be used include a non-human animal comprising in its germline an immunoglobulin light chain locus comprising no more than two human $V_L$ gene segments and one or more human $J_L$ gene segments operably linked to an immunoglobulin light chain constant region sequence, wherein each of the no more than two human $V_L$ gene segments comprises at least one histidine codon that is not encoded by the corresponding human germline $V_L$ gene segment, and wherein the human $V_L$ gene segments and $J_L$ gene segments are capable of rearranging and encoding a human light chain variable domain of an antibody. See, e.g., US 2014/0013456, US 2015/0119556, US 2015/0250151, US 2013/0247234, and U.S. Pat. No. 9,332,742, each of which is herein incorporated by reference in its entirety for all purposes. An example of such a non-human animal is a non-human animal that comprises no more than two human $V_L$ gene segments, each of which is capable of rearranging with a human $J_L$ gene segment (selected from one or a plurality of $J_L$ segments) and encoding a human variable domain of an immunoglobulin light chain, wherein each of the no more than two $V_L$ gene segments and/or the $J_L$ gene segment comprise a substitution of at least one non-histidine residue with a histidine residue. See, e.g., US 2014/0013456. Yet another example of such a non-human animal is a non-human animal comprising in its germline an immunoglobulin light chain locus comprising two unrearranged human Vκ gene segments and one or more unrearranged human Jκ gene segment(s) operably linked to an immunoglobulin light chain constant region sequence, wherein the two unrearranged human Vκ gene segments are human Vκ1-39 and Vκ3-20 gene segments each comprising one or more substitutions of a non-histidine codon with a histidine codon, and wherein the human Vκ and Jκ gene segments are capable of rearranging and the human Vκ and Jκ gene segments encode a human light chain variable domain comprising one or more histidines at a position selected from the group consisting of 105, 106, 107, 108, 109, 111 (according to IMGT numbering), and a combination thereof, wherein the one or more histidines are derived from the one or more substitutions. See, e.g., US 2015/0250151.

IV. Methods of Generating Antigen-Binding Proteins

The genetically modified F0 generation non-human animals generated by the methods disclosed herein can be used to make an antigen-binding protein against a foreign target antigen of interest. Several techniques for the producing antigen-binding proteins (e.g., antibodies) have been described. Antigen-binding proteins can be isolated directly from B cells of an immunized mouse (see, e.g., US 2007/0280945, herein incorporated by reference in its entirety for all purposes) and/or the B cells of the immunized mouse can be used to make hybridomas (see, e.g., Kohler and Milstein (1975) *Nature* 256:495-497, herein incorporated by reference in its entirety for all purposes). DNA encoding the antigen-binding proteins (heavy and/or light chains) from non-human animals as described herein can be readily isolated and sequenced using conventional techniques. Hybridomas and/or B cells derived from non-human animals as described herein serve as a preferred source of such DNA. Once isolated, the DNA may be placed into expression vectors, which are then transfected into host cells that do not otherwise produce immunoglobulin protein, to obtain the synthesis of monoclonal antibodies in the recombinant host cells.

For example, the genetically modified F0 generation non-human animals generated by the methods disclosed herein can be exposed to the target antigen and maintained under conditions sufficient to initiate an immune response to a foreign target antigen of interest. A first nucleic acid sequence encoding a human immunoglobulin heavy chain variable domain and/or a second nucleic acid sequence encoding a human immunoglobulin light chain variable domain can then be obtained from the genetically modified F0 generation non-human animal. Alternatively, an antigen-binding protein can then be isolated from the genetically modified F0 generation non-human animal. As an example, a clonally selected lymphocyte can be identified that expresses an antibody that specifically binds the foreign antigen of interest.

In one example, antigen-binding proteins can be generated by immunizing the genetically modified F0 generation non-human animal with the foreign target antigen of interest, allowing the non-human animal to mount an immune response, harvesting a lymphocyte (e.g., a B cell) from the immunized animal, fusing the lymphocyte with a myeloma cell to form a hybridoma cell, obtaining from the hybridoma cell a nucleic acid sequence that encodes a $V_H$ domain that specifically binds the target antigen and/or a nucleic acid sequence that encodes a $V_L$ domain that specifically binds the target antigen, cloning the nucleic acid sequence in frame (i.e., in operable linkage) with a nucleic acid sequence encoding an immunoglobulin constant region or functional fragment thereof sequence to create an immunoglobulin heavy chain and/or an immunoglobulin light chain, and expressing the heavy and light chains in a cell (e.g., CHO cell) capable of expressing antigen-binding protein.

In another example, antigen-binding proteins can be generated by immunizing the genetically modified F0 generation non-human animal with the foreign target antigen of interest, allowing the non-human animal to mount an immune response, harvesting a lymphocyte (e.g., a B cell) from the immunized animal, obtaining from the lymphocyte a nucleic acid sequence that encodes a $V_H$ domain that specifically binds the target antigen and/or a nucleic acid sequence that encodes a $V_L$ domain that specifically binds the target antigen, cloning the nucleic acid sequence in frame (i.e., in operable linkage) with a nucleic acid sequence encoding an immunoglobulin constant region or functional fragment thereof sequence to create an immunoglobulin heavy chain and/or an immunoglobulin light chain, and expressing the heavy and light chains in a cell (e.g., CHO cell) capable of expressing the antigen-binding protein.

The immunization with the foreign antigen of interest can be carried out with protein, DNA, a combination of DNA and protein, or cells expressing the foreign antigen of interest. The lymphocytes that are obtained can be from any source, including, for example, the spleen, a lymph node, or bone marrow from the immunized animal.

In some such methods, the $V_H$ domain and/or the $V_L$ domain are human (e.g., when the genetically modified F0 generation non-human animal is homozygous humanized at both IgH and Igκ), the $V_H$ domain and/or the $V_L$ domain is cloned in frame with a nucleic acid sequence encoding a human constant region, and the antigen-binding proteins that are produced are fully human antibodies.

Production of antigen-binding proteins against the foreign antigen of interest produced in the genetically modified F0 generation non-human animals described herein (i.e., genetically modified at the first target genomic locus) is typically increased when compared with control non-human animals (i.e., that are wild type at the first target genomic locus. That is, antigen-binding proteins against the foreign antigen of interest produced in the genetically modified F0 generation non-human animals described herein (i.e., genetically modified at the first target genomic locus) typically have a higher titer than antigen-binding proteins obtained following immunization of a control non-human animal that is wild type at the first target genomic locus. For example, the titer can be at least 1.5-fold, 2-fold, 3-fold, 4-fold, 5-fold, 6-fold, 7-fold, 8-fold, 9-fold, or 10-fold higher. The term antibody titer includes a measurement of a concentration of a specific antibody present in the serum. For example, an antibody titer can be a measurement of how much antibody an organism has produced that recognizes a particular epitope, expressed as the inverse of the greatest dilution that still gives a positive result. Likewise, a more diverse repertoire of antigen-binding proteins against the foreign antigen of interest is typically obtained following immunization of the genetically modified F0 generation non-human animals with the foreign antigen of interest compared with antigen-binding proteins obtained following immunization of a control non-human animal that is wild type at the first target genomic locus. A control non-human animal refers to a non-human animal that is wild type at the first target genomic locus. Preferably, the only substantial difference between the genetically modified F0 generation non-human animal and the control animal is the status of the first target genomic locus. For example, preferably the control animal has no other substantial genetic modifications and is the same species of non-human animal, is the same strain of non-human animal, has the same genetic background (other than the first target genomic locus), and is the same age as the genetically modified F0 generation non-human animal.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 1

Description of Sequences.

| SEQ ID NO | Type | Description |
|---|---|---|
| 1 | DNA | Guide RNA Recognition Sequence v.1 |
| 2 | DNA | Guide RNA Recognition Sequence v.2 |
| 3 | DNA | Guide RNA Recognition Sequence v.3 |
| 4 | DNA | C5 (Hc) gRNA A DNA-targeting segment (100 bp from target locus endpoint) |
| 5 | DNA | C5 (Hc) gRNA B DNA-targeting segment (500 bp from target locus endpoint) |
| 6 | DNA | C5 (Hc) gRNA C DNA-targeting segment (38200 and 37500 bp from target locus endpoints) |
| 7 | DNA | C5 (Hc) gRNA D DNA-targeting segment (43500 and 32200 bp from target locus endpoints) |
| 8 | DNA | C5 (Hc) gRNA E DNA-targeting segment (500 bp from target locus endpoint) |
| 9 | DNA | C5 (Hc) gRNA E2 DNA-targeting segment (100 bp from target locus endpoint) |
| 10 | DNA | Lrp5 gRNA A DNA-targeting segment (50 bp from target locus end point) |
| 11 | DNA | Lrp5 gRNA B DNA-targeting segment (500 bp from target locus end point) |
| 12 | DNA | Lrp5 gRNA B2 DNA-targeting segment (1000 bp from target locus end point) |
| 13 | DNA | Lrp5 gRNA C DNA-targeting segment (29900 and 38430 bp from target locus end points) |
| 14 | DNA | Lrp5 gRNA D DNA-targeting segment (29950 and 38380 bp from target locus end points) |
| 15 | DNA | Lrp5 gRNA E2 DNA-targeting segment (1000 bp from target locus end point) |
| 16 | DNA | Lrp5 gRNA E DNA-targeting segment (500 bp from target locus end point) |
| 17 | DNA | Lrp5 gRNA F DNA-targeting segment (50 bp from target locus end point) |
| 18 | DNA | Ror1 gRNA A DNA-targeting segment (200 bp from target locus end point) |

TABLE 1-continued

Description of Sequences.

Figure 6:
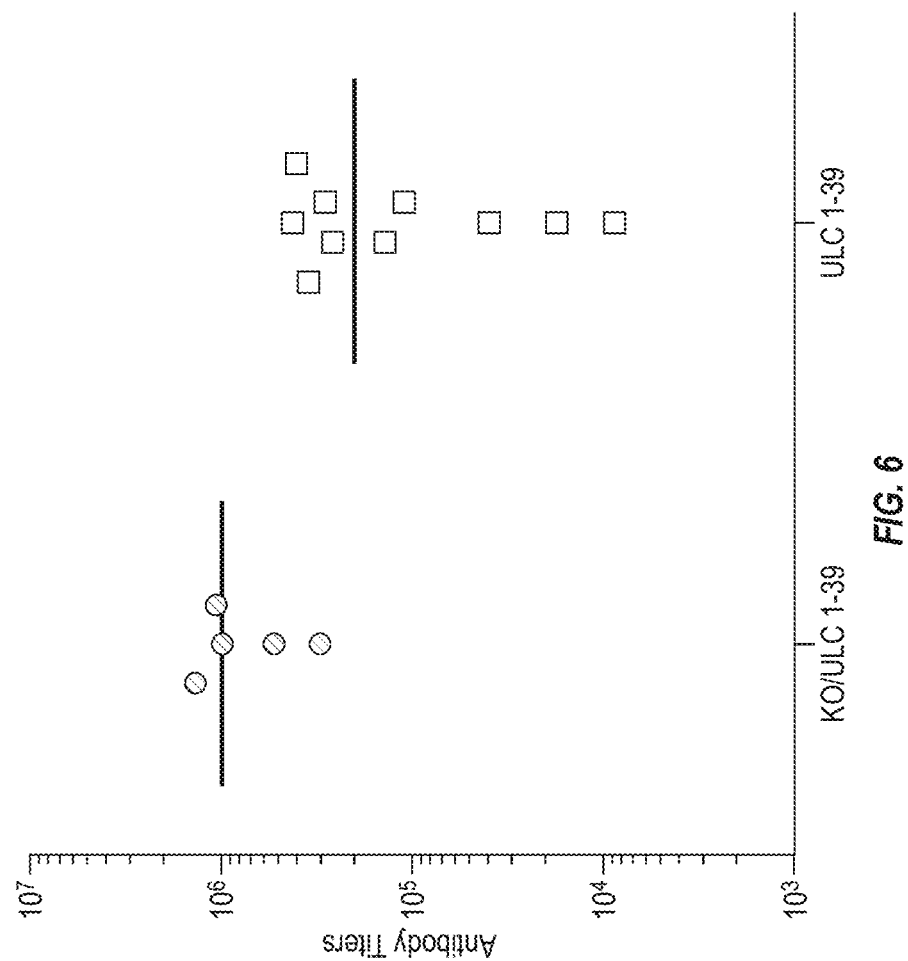
FIG. 6 shows antibody titer data for a human target antigen (Target 8) in wild type Universal Light Chain (ULC 1-39) mice and in ULC 1-39 mice, which are homozygous null for an endogenous gene encoding a self-antigen orthologous to Target 8 (Self-Antigen 8).

| SEQ ID NO | Type | Description |
|---|---|---|
| 19 | DNA | Ror1 gRNA B DNA-targeting segment (1000 bp from target locus end point) |
| 20 | DNA | Ror1 gRNA D DNA-targeting segment (54300 and 55500 bp from target locus end points) |
| 21 | DNA | Ror1 gRNA C DNA-targeting segment (54500 and 55300 bp from target locus end points) |
| 22 | DNA | Ror1 gRNA E DNA-targeting segment (1000 bp from target locus end point) |
| 23 | DNA | Ror1 gRNA F DNA-targeting segment (200 bp from target locus end point) |
| 24 | DNA | Trpa1 gRNA A DNA-targeting segment (100 bp from target locus end point) |
| 25 | DNA | Trpa1 gRNA A2 DNA-targeting segment (500 bp from target locus end point) |
| 26 | DNA | Trpa1 gRNA B DNA-targeting segment (1000 bp from target locus end point) |
| 27 | DNA | Trpa1 gRNA C DNA-targeting segment (25600 and 19740 bp from target locus end points) |
| 28 | DNA | Trpa1 gRNA D DNA-targeting segment (26970 and 18370 bp from target locus end points) |
| 29 | DNA | Trpa1 gRNA E2 DNA-targeting segment (1000 bp from target locus end point) |
| 30 | DNA | Trpa1 gRNA E DNA-targeting segment (500 bp from target locus end point) |
| 31 | DNA | Trpa1 gRNA F DNA-targeting segment (100 bp from target locus end point) |
| 32 | DNA | 190045 forward primer |
| 33 | DNA | 190061 forward primer |
| 34 | DNA | 190068 forward primer |
| 35 | DNA | 190030 forward primer |
| 36 | DNA | 190033 forward primer (same as forward primer for SV 48.3 in FIG. 6) |
| 37 | DNA | 190013 forward primer |
| 38 | DNA | 190045 reverse primer |
| 39 | DNA | 190061 reverse primer |
| 40 | DNA | 190068 reverse primer |
| 41 | DNA | 190030 reverse primer |
| 42 | DNA | 190033 reverse primer (same as reverse primer for SV 48.3 in FIG. 6) |
| 43 | DNA | 190013 reverse primer |
| 44 | DNA | C2 probe (B6)-SNV 0.32 in FIG. 6 |
| 45 | DNA | T3 probe (B6)-SNV 1.2 in FIG. 6 |
| 46 | DNA | T6 probe (B6)-SNV 11.1 in FIG. 6 |
| 47 | DNA | T7 probe (B6)-SNV 13.2 in FIG. 6 |
| 48 | DNA | T8 probe (B6)-SNV 17.5 in FIG. 6 |
| 49 | DNA | T9 probe (B6)-SNV 25.8 in FIG. 6 |
| 50 | DNA | T10 probe (B6)-SNV 33.0 in FIG. 6 |
| 51 | DNA | T11 probe (B6)-SNV 38.3 in FIG. 6 |
| 52 | DNA | T13 probe (B6)-SNV 49.6 in FIG. 6 |
| 53 | DNA | T14 probe (B6)-SNV 57.2 in FIG. 6 |
| 54 | DNA | C2 probe (129) - SNV 0.32 in FIG. 6 |
| 55 | DNA | T3 probe (129) - SNV 1.2 in FIG. 6 |
| 56 | DNA | T6 probe (129) - SNV 11.1 in FIG. 6 |
| 57 | DNA | T7 probe (129) - SNV 13.2 in FIG. 6 |
| 58 | DNA | T8 probe (129) - SNV 17.5 in FIG. 6 |
| 59 | DNA | T9 probe (129) - SNV 25.8 in FIG. 6 |
| 60 | DNA | T10 probe (129) - SNV 33.0 in FIG. 6 |
| 61 | DNA | T11 probe (129) - SNV 38.3 in FIG. 6 |
| 62 | DNA | T13 probe (129) - SNV 49.6 in FIG. 6 |
| 63 | DNA | T14 probe (129) - SNV 57.2 in FIG. 6 |
| 64 | DNA | C2 forward primer - SNV 0.32 in FIG. 6 |
| 65 | DNA | T3 forward primer - SNV 1.2 in FIG. 6 |
| 66 | DNA | T6 forward primer - SNV 11.1 in FIG. 6 |
| 67 | DNA | T7 forward primer - SNV 13.2 in FIG. 6 |
| 68 | DNA | T8 forward primer - SNV 17.5 in FIG. 6 |
| 69 | DNA | T9 forward primer - SNV 25.8 in FIG. 6 |
| 70 | DNA | T10 forward primer - SNV 33.0 in FIG. 6 |
| 71 | DNA | T11 forward primer - SNV 38.3 in FIG. 6 |
| 72 | DNA | T13 forward primer - SNV 49.6 in FIG. 6 |
| 73 | DNA | T14 forward primer - SNV 57.2 in FIG. 6 |
| 74 | DNA | C2 reverse primer - SNV 0.32 in FIG. 6 |
| 75 | DNA | T3 reverse primer - SNV 1.2 in FIG. 6 |
| 76 | DNA | T6 reverse primer - SNV 11.1 in FIG. 6 |
| 77 | DNA | T7 reverse primer - SNV 13.2 in FIG. 6 |
| 78 | DNA | T8 reverse primer - SNV 17.5 in FIG. 6 |
| 79 | DNA | T9 reverse primer - SNV 25.8 in FIG. 6 |
| 80 | DNA | T10 reverse primer - SNV 33.0 in FIG. 6 |
| 81 | DNA | T11 reverse primer - SNV 38.3 in FIG. 6 |
| 82 | DNA | T13 reverse primer - SNV 49.6 in FIG. 6 |
| 83 | DNA | T14 reverse primer - SNV 57.2 in FIG. 6 |
| 84 | DNA | Forward primer for SV 13.7 in FIG. 6 |
| 85 | DNA | Reverse primer for SV 13.7 in FIG. 6 |
| 86 | DNA | Forward primer for SV 20.0 in FIG. 6 |
| 87 | DNA | Reverse primer for SV 20.0 in FIG. 6 |
| 88 | DNA | Forward primer for SV 36.9 in FIG. 6 |
| 89 | DNA | Reverse primer for SV 36.9 in FIG. 6 |
| 90 | DNA | Forward primer for SV 56.7 in FIG. 6 |
| 91 | DNA | Reverse primer for SV 56.7 in FIG. 6 |
| 92 | DNA | m-lr-f primer for Lrp5 locus |
| 93 | DNA | m-5'-f primer for Lrp5 locus |

TABLE 1-continued

Description of Sequences.

Figure 8:
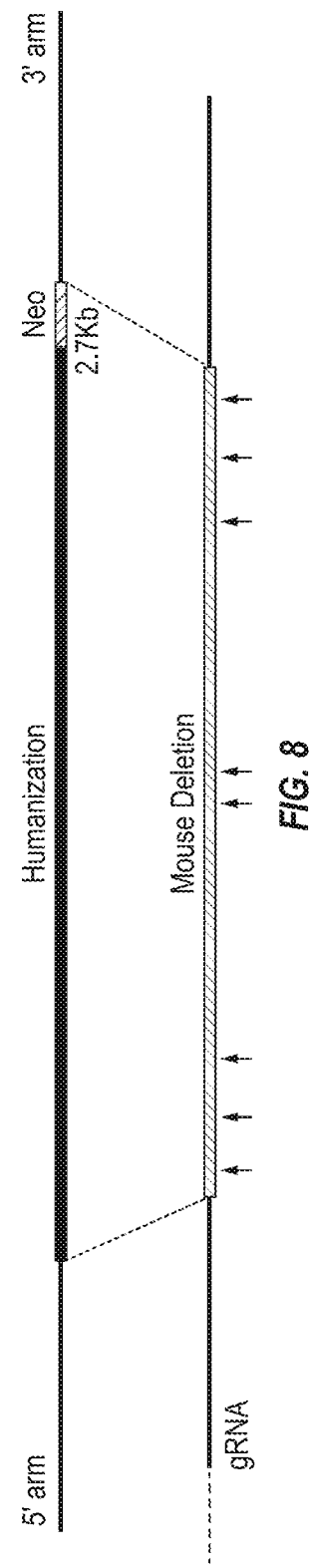
FIG. 8 shows a schematic for simultaneous deletion of a mouse gene or portion of a mouse gene and replacement with a corresponding human version using an LTVEC and either one or two 5' region, middle region, and 3' region gRNAs. The LTVEC is shown in the top portion of the figure, and the mouse gene locus is shown in the bottom portion of the figure. The positions of the Cas9 cleavage sites guided by the eight guide RNAs are indicated by the vertical arrows below the mouse gene sequence.

| SEQ ID NO | Type | Description |
|---|---|---|
| 94 | DNA | m-A primer for Lrp5 locus |
| 95 | DNA | h-lr-r primer for Lrp5 locus |
| 96 | DNA | m-5'-r primer for Lrp5 locus |
| 97 | DNA | h-5'-r primer for Lrp5 locus |
| 98 | DNA | m-F primer for Lrp5 locus |
| 99 | DNA | m-E2 primer for Lrp5 locus |
| 100 | DNA | 7064retU forward primer |
| 101 | DNA | 7064retU reverse primer |
| 102 | DNA | 7064retU TAQMAN ® probe |
| 103 | DNA | 7064retD forward primer |
| 104 | DNA | 7064retD reverse primer |
| 105 | DNA | 7064retD TAQMAN ® probe |
| 106 | DNA | 7140retU forward primer |
| 107 | DNA | 7140retU reverse primer |
| 108 | DNA | 7140retU TAQMAN ® probe |
| 109 | DNA | 7140retD forward primer |
| 110 | DNA | 7140retD reverse primer |
| 111 | DNA | 7140retD TAQMAN ® probe |
| 112 | DNA | Folh1 gRNA A DNA-targeting segment |
| 113 | DNA | Folh1 gRNA A2 DNA-targeting segment |
| 114 | DNA | Folh1 gRNA B DNA-targeting segment |
| 115 | DNA | Folh1 gRNA C DNA-targeting segment |
| 116 | DNA | Folh1 gRNA D DNA-targeting segment |
| 117 | DNA | Folh1 gRNA E DNA-targeting segment |
| 118 | DNA | Folh1 gRNA E2 DNA-targeting segment |
| 119 | DNA | Folh1 gRNA F DNA-targeting segment |
| 120 | DNA | Adamts5 gRNA A DNA-targeting segment |
| 121 | DNA | Adamts5 gRNA A2 DNA-targeting segment |
| 122 | DNA | Adamts5 gRNA B DNA-targeting segment |
| 123 | DNA | Adamts5 gRNA C DNA-targeting segment |
| 124 | DNA | Adamts5 gRNA D DNA-targeting segment |
| 125 | DNA | Adamts5 gRNA E2 DNA-targeting segment |
| 126 | DNA | Adamts5 gRNA E DNA-targeting segment |
| 127 | DNA | Adamts5 gRNA F DNA-targeting segment |
| 128 | DNA | Dpp4 gRNA A DNA-targeting segment |
| 129 | DNA | Dpp4 gRNA B DNA-targeting segment |
| 130 | DNA | Dpp4 gRNA B2 DNA-targeting segment |
| 131 | DNA | Dpp4 gRNA C DNA-targeting segment |
| 132 | DNA | Dpp4 gRNA D DNA-targeting segment |
| 133 | DNA | Dpp4 gRNA E2 DNA-targeting segment |
| 134 | DNA | Dpp4 gRNA E DNA-targeting segment |
| 135 | DNA | Dpp4 gRNA F DNA-targeting segment |
| 136 | DNA | Forward primer for SV 6.1 in FIG. 8 |
| 137 | DNA | Reverse primer for SV 6.1 in FIG. 8 |
| 138 | DNA | Forward primer for SV 6.3 in FIG. 8 |
| 139 | DNA | Reverse primer for SV 6.3 in FIG. 8 |
| 140 | DNA | Forward primer for SV 7.8 in FIG. 8 |
| 141 | DNA | Reverse primer for SV 7.8 in FIG. 8 |
| 142 | DNA | Forward primer for SV 16 in FIG. 8 |
| 143 | DNA | Reverse primer for SV 16 in FIG. 8 |
| 144 | DNA | Forward primer for SV 25.5 in FIG. 8 |
| 145 | DNA | Reverse primer for SV 25.5 in FIG. 8 |
| 146 | DNA | *S. aureus* Cas9 PAM sequence |
| 147 | DNA | *S. aureus* Cas9 PAM sequence |
| 148 | DNA | Engineered Human Vκ1-39Jκ5 Locus |
| 149 | DNA | Engineered Human Vκ3-20Jκ1 Locus |
| 150 | DNA | Guide RNA scaffold v1 |
| 151 | DNA | Guide RNA scaffold v2 |
| 152 | DNA | Guide RNA scaffold v3 |

EXAMPLES

Example 1. Generating KO Embryonic Stem (ES) Cells, One-Cell Stage Embryos, and Mice for Antibody Production Using Paired Guide RNAs Targeting Start and Stop Codons The VELOCIGENE® and VELOCIMOUSE® technologies have allowed the generation of the VELOCIMMUNE® mouse, which enables production of fully human antibodies. VELOCIMMUNE® mice express immunoglobulin kappa (Igκ) and heavy (IgH) chains in which a fully humanized variable region is joined to the mouse constant region. Because functionally important regions of proteins tend to be conserved across species, immunological tolerance to self-antigens often poses a challenge to the generation of antibodies to these key epitopes. Traditionally, VELOCIMMUNE® mice were bred to F0 mice carrying a heterozygous knockout mutation at a self-antigen target of interest to overcome immunological tolerance. In order to generate triple homozygous mice (homozygous null for the target of interest and homozygous humanized at both IgH and Igκ) suitable for immunization, two more generations of breeding, and 15 to 16 months of total time, were required. To accelerate this process, VELOCIMMUNE® embryonic stem (ES) cells were derived, which can be targeted to create null alleles at the target of interest. Unfortunately, however, sequential targeting steps are required to obtain homozygous null VELOCIMMUNE® ES cell clones, which is time-consuming. More importantly, not only do VELOCIMMUNE® ES cell clones traditionally exhibit a low capacity to produce fully ES-cell-derived F0 VELOCIMICE® (i.e., fully ES-cell-derived F0 generation mice obtained from the injection of ES cells into 8-cell-stage embryos) in KO for immunization projects (see, e.g., Table 2), but also sequentially targeted VELOCIMMUNE® ES cell clones exhibit an even further reduced capacity to produce fully ES-cell-derived F0 VELOCIMICE® (i.e., fully ES-cell-derived F0 generation mice obtained from the injection of ES cells into 8-cell-stage embryos). See, e.g., Table 3 (comparing VELOCIMOUSE® production efficiency using a typical ES cell line used for generating targeted genetic modifications and VELOCIMICE® (F1H4 ES cell line) and two Universal Light Chain (ULC) ES cell lines and a VELOCIMMUNE® ES cell line (VI-3Adam6)).

TABLE 2

VELOCIMOUSE ® Production Efficiency of ES Cell Lines in KO for Immunization Projects.

| ESC Line | Total Genotyped VELOCIMICE ® | Total Injected Embryos | VELOCIMOUSE ® Production Yield |
|---|---|---|---|
| ULC1-39 F2 | 36 | 6788 | 0.50% |
| ULC1-39 A4 | 2 | 150 | 1.30% |
| VI3Adam-B3 | 163 | 2112 | 7.72% |

TABLE 3

Overall VELOCIMOUSE ® Production Efficiency of ES Cell Lines.

| | % VELOCIMICE ® per Embryo Microinjected | |
|---|---|---|
| ESC Line | First Electroporation | Sequential Electroporation |
| F1H4 | 18.5% | 16.6% |
| ULC1-39 A4 | 2.0% | 2.6% |
| ULC 1-39F2 | 2.1% | 0.9% |
| VI-3Adam6 B3 | 11.1% | 5.2% |

In order to generate mice with reduced tolerance to foreign human target antigens of interest, we have developed a method to rapidly generate VELOCIMMUNE® ES cells comprising a functional ectopic mouse Adam6 gene, which are homozygous for null alleles at a target of interest in a single modification step. We have optimized a procedure for using a pair of guide RNAs to efficiently create large deletions on both alleles of a target of interest in VELOCIMMUNE® ES cells comprising a functional ectopic mouse Adam6 gene, thereby obviating the need to design and produce large targeting vectors (LTVECs). Using this approach, F0 VELOCIMICE® homozygous for a null allele at the target of interest and ready for immunization can be delivered in 4 to 5 months instead of 15 to 16 months (mouse pups homozygous for a null allele at the target of interest can be delivered in ~3 months but are then aged for 4-5 weeks for immunization). In this experiment, paired guide RNAs were designed and cloned to target self-antigens orthologous to those foreign target antigens of interest for homozygous deletion. The guide RNAs were designed to target the start and stop codon regions of the endogenous genes encoding the self-antigens. For some targets, two pairs of gRNAs were designed (v1 and v2). The guide RNA design process is described in the Materials and Methods below. The guide RNAs were electroporated or nucleofected together with Cas9 into ES cells derived from VELOCIMMUNE® mice comprising a functional ectopic mouse Adam6 gene (VI-3 Adam6) mice (replaced endogenous mouse immunoglobulin heavy and light chain variable region with the corresponding human DNA along with a reinserted mouse Adam6 gene) or Universal Light Chain (ULC 1-39) mice (mice with a single rearranged human immunoglobulin light chain variable region that is the human Vκ1-39/J gene segment). See FIG. 32. The protocols for electroporation and nucleofection are described in the Materials and Methods below. In some experiments, the Cas9 and paired guide RNAs were electroporated together with a large targeting vector (LTVEC) targeting the endogenous gene encoding the self-antigen for deletion (see, e.g., FIG. 4). Comparable deletion efficiencies were observed using CRISPR/Cas9 (CC9) with or without LTVECs (see Table 4).

TABLE 4

Biallelic Deletion Efficiencies.

| Self-Antigen | Parental ESC | EP Type | Clones Screened | Clones with Biallelic Deletions | Efficiency (%) |
|---|---|---|---|---|---|
| Self-Antigen 1 (Cytoplasmic) | ULC1-39 F2 | LTVEC + CC9v1 | 384 | 19 | 4.9 |
| | | CC9v1 | 384 | 20 | 5.2 |
| | | CC9v2 | 176 | 14 | 7.9 |
| | VI-3Adam6 B3 | LTVEC + CC9v1 | 384 | 9 | 2.3 |
| | | CC9v1 | 384 | 15 | 3.9 |
| | | CC9v2 | 352 | 19 | 5.4 |
| Self-Antigen 2 (Transmembrane) | ULC1-39 F2 | LTVEC + CC9v1 | 384 | 14 | 3.6 |
| | | CC9v1 | 384 | 21 | 5.5 |
| | | CC9v2 | 352 | 42 | 11.9 |
| | VI-3Adam6 B3 | LTVEC + CC9v2 | 384 | 11 | 2.9 |
| | | CC9v2 | 384 | 11 | 2.9 |
| | | CC9v2 | 176 | 20 | 11.3 |
| Self-Antigen 3 (Transmembrane) | ULC1-39 F2 | LTVEC + CC9 | 384 | 12 | 3.1 |
| | | CC9 | 384 | 11 | 2.9 |
| | VI-3Adam6 B3 | LTVEC + CC9 | 384 | 11 | 2.9 |

TABLE 4-continued

Biallelic Deletion Efficiencies.

| Self-Antigen | Parental ESC | EP Type | Clones Screened | Clones with Biallelic Deletions | Efficiency (%) |
|---|---|---|---|---|---|
| Self-Antigen 4 (Transmembrane) | ULC1-39 F2 | LTVEC + CC9 | 176 | 11 | 6.3 |
|  |  | CC9 | 176 | 3 | 1.7 |
|  | VI-3Adam6 B3 | CC9 | 352 | 76 | 21.6 |
| Self-Antigen 5 (Transmembrane) | ULC1-39 F2 | LTVEC + CC9 | 192 | 8 | 4.2 |
|  |  | CC9 | 384 | 8 | 2.1 |
|  | VI-3Adam6 B3 | CC9 | 352 | 15 | 4.3 |
| Self-Antigen 6 (Transmembrane) | ULC1-39 F2 | CC9 | 176 | 10 | 5.6 |
| Self-Antigen 7 (Transmembrane) | ULC1-39 F2 | LTVEC + CC9 | 352 | 10 | 2.8 |
|  |  | CC9 | 352 | 5 | 1.4 |
|  | VI-3Adam6 B3 | CC9 | 352 | 7 | 2 |

The timeline from the beginning of the experiment (gRNA design) to the end (genotyped F0 mouse with a homozygous null allele for the endogenous gene encoding the self-antigen) was approximately 3 months. As an example, the timeline for producing F0 mice homozygous null for the self-antigen corresponding to Target 1 (Self-Antigen 1) is shown in Table 5.

TABLE 5

Timeline to Deliver Homozygous Null Allele for Self-Antigen 1 in VI-3 Adam6 Mice.

| Process | Date |
|---|---|
| gRNA and TAQMAN ® Design | Sep. 21, 2015 |
| gRNA Preparation | Oct. 6, 2015 |
| Electroporation | Oct. 16, 2015 |
| Primary ES Cell Screening | Nov. 2, 2015 |
| Reconfirmation Screening | Nov. 18, 2015 |
| ES Cell Clones Microinjected | Nov. 23, 2015 |
| F0 Mouse Date of Birth | Dec. 11, 2015 |
| F0 Mouse Genotyped | Dec. 21, 2015 |

Several experiments were performed to target various self-antigens for deletion in embryonic stem (ES) cells from VI-3-Adam6 and ULC 1-39 mice, using paired guide RNAs targeting the start and stop codon regions of each self-antigen, alone or together with a large targeting vector (LTVEC) targeting the self-antigen for deletion. The Cas9 and guide RNAs were introduced into the ES cells in the form of DNA. As shown in Table 6 and FIG. 28, deletion (i.e., collapse) was achieved for all self-antigens tested, with deletion sizes ranging between 0.1 kb and 165 kb, and there was a negative correlation between the size of the deletion (i.e., collapse) and the efficiency of producing the deletion (i.e., collapse). Biallelic collapse can also be achieved for much larger sizes. For example, we have achieved a biallelic collapse for a deletion size of ~400 kb. Likewise, a ~900 kb-1 Mb biallelic collapse at the mouse IgH locus was achieved through use of two 5' gRNAs and two 3' gRNAs and a repair vector with an efficiency of ~1.2% (data not shown).

TABLE 6

Effect of Deletion (Collapse) Size on Deletion (Collapse) Efficiency.

| Mouse Target | Collapse Size (kb) | Clones Screened | NHEJ Biallelic InDel Collapse | NHEJ Biallelic InDel Collapse Efficiency (%) |
|---|---|---|---|---|
| Self-Antigen 4 | 0.1 | 528 | 76 | 14.3 |
| Self-Antigen 10 | 0.1 | 352 | 48 | 13.6 |
| Self-Antigen 11 | 1.3 | 352 | 4 | 1.1 |
| Self-Antigen 12 | 1.6 | 176 | 29 | 16.5 |
| Self-Antigen 5 | 2.2 | 736 | 7 | 0.9 |
| Self-Antigen 13 | 2.6 | 352 | 52 | 14.8 |
| Self-Antigen 14 | 2.8 | 352 | 18 | 5.1 |
| Self-Antigen 15 | 4.3 | 352 | 39 | 11.1 |
| Self-Antigen 16 | 4.5 | 352 | 30 | 8.5 |
| Self-Antigen 17 | 4.6 | 352 | 36 | 10.2 |
| Self-Antigen 18 | 6 | 176 | 24 | 13.6 |
| Self-Antigen 2 | 15.1 | 528 | 62 | 11.7 |
| Self-Antigen 9 | 18.4 | 440 | 119 | 27 |
| Self-Antigen 19 | 24.5 | 176 | 25 | 14.2 |
| Self-Antigen 7 | 25.3 | 704 | 12 | 1.7 |
| Self-Antigen 20 | 25.7 | 352 | 45 | 12.8 |
| Self-Antigen 21 | 26.2 | 352 | 30 | 8.5 |
| Self-Antigen 6 | 28.9 | 176 | 10 | 5.7 |
| Self-Antigen 3 | 39 | 280 | 11 | 3.9 |
| Self-Antigen 1 | 45.7 | 528 | 33 | 6.3 |
| Self-Antigen 22 | 58 | 176 | 2 | 1.1 |
| Self-Antigen 23 | 84.4 | 352 | 9 | 2.6 |
| Self-Antigen 24 | 95.4 | 792 | 8 | 1 |
| Self-Antigen 25 | 165 | 704 | 13 | 2.4 |

Similar to the procedure using ES cells, in order to generate mice with reduced tolerance to foreign human target antigens of interest, we have also developed a method to rapidly generate one-cell stage embryos that are homozygous for null alleles at a target of interest in a single modification step. We have optimized a procedure for using a pair of guide RNAs to efficiently create large deletions on both alleles of a target of interest in one-cell stage embryos, thereby obviating the need to design and produce large targeting vectors (LTVECs). In addition, use of one-cell stage embryos can improve production efficiency of targeted mice compared to using ES cell lines (e.g., ULC 1-39 ES cell lines). Using this approach, F0 mice homozygous for a null allele at the target of interest that are ready for immunization can be delivered in 4 to 5 months (F0 mouse pups homozygous for a null allele at the target of interest can be delivered in ~3 months) instead of 15 to 16 months. In this experiment, paired guide RNAs were designed and cloned to target self-antigens orthologous to those foreign target antigens of interest for homozygous deletion. The guide RNAs were designed to target the start and stop codon regions of the endogenous genes encoding the self-antigens. The guide RNA design process is described in the Materials and Methods below. Briefly, super-ovulated females were mated with stud males to generate embryos. If only a few males were available, in vitro fertilization was used. The female age range was 3-16 weeks, the oocytes per donor ranged from 15-46 (median=32 oocytes), and the zygotes per donor ranged from 5-32 (median=15 zygotes). The guide RNAs were microinjected (cytoplasmic injection) together with Cas9 mRNAs into one-cell stage embryos from VELOCIMMUNE® mice comprising a functional ectopic mouse Adam6 gene (VI-3 Adam6) mice (replaced endogenous mouse immunoglobulin heavy and light chain variable region with the corresponding human DNA along with a reinserted mouse Adam6 gene) or Universal Light Chain (ULC 1-39) mice (mice with a single rearranged human immunoglobulin light chain variable region that is the human Vκ1-39/Jκ5 gene segment). The number of embryos injected ranged from 99-784 (median=334), the percentage of embryos that survived ranged from 56%-73% (median=63%), the number of embryos transferred ranged from 59-442 (median=226), the number of pups for each project ranged from 10-46 (median=32), and the birth rate ranged from 2%-59% (median=13%). As shown in Table 7 and FIG. 29, live pups bearing the targeted deletion (i.e., collapse) were produced for all self-antigens tested, with deletion sizes ranging between 0.1 kb and 94 kb, and there was a negative correlation between the size of the deletion (i.e., collapse) and the efficiency of producing mouse pups bearing the deletion (i.e., collapse).

Materials and Methods

Guide RNA and TAQMAN® Assay Design: Guide RNAs (gRNA) with a length of 23 base pairs were designed based on the Consensus Coding Sequence (CCDS) for each locus in the format 5' NNNNNNNNNNNNNNNNNnnNNNGG 3' (SEQ ID NO: 2), where N is any nucleotide. The last three nucleotides (NGG) are the protospacer adjacent motif (PAM), and double-stranded blunt-end DNA cleavage by the Cas9 enzyme occurs 3 nucleotides 5' to the NGG (between the lowercase residues above). The gRNAs were chosen based on scores obtained from various gRNA search engines, including crispr.mit.edu, crispr.med.harvard.edu/sgRNAScorer/, and broadinstitute.org/rnai/public/analysis-tools/sgrna-design. Briefly, 100-150 bp of sequence directly 5' and 3' of the start ATG and 100-150 bp directly 5' and 3' of the stop codon, respectively, were assayed for gRNAs on both DNA strands. Two gRNAs (overlapping each other by no more than 25%) near the ATG and two gRNAs near the stop codon with high scores from all search engines used were further interrogated for uniqueness in the mouse genome and no single nucleotide variations (SNV) in the Universal Light Chain (ULC, or Common Light Chain), VELOCIMMUNE® mice comprising a functional ectopic mouse Adam6 gene (VI-3-Adam6), and VGB6 VELOCIGENE® mouse embryonic stem cell (ESC) lines. If no high scoring guides were found using the search specifications above, additional sequence around the ATG and stop codons was searched until two high quality guides were found.

TAQMAN® assays were designed using PRIMER EXPRESS® with the APPLIED BIOSYSTEMS® Custom TAQMAN® MGB Probes so that probe sequences always overlapped the cas9 cut sites for each guide. Some

TABLE 7

Knockout via Cas9 Injection in Embryos.

| Self-Antigen # | Size (kb) | Age (weeks) | Egg Donors | Egg/Donor | Zygote/Donor | # of injected | # of ET | # of Pups | Birth % | Exon 1 NHEJ Efficiency | Collapse Efficiency of Live Pups (# Null Pups) |
|---|---|---|---|---|---|---|---|---|---|---|---|
| 3 | 39 | 7 | 5 | 33 | 20 | 99 | 59 | 35 | 59% | 66% | 27% (10 pups) |
| 4 | 0.1 | 3~7 | 30 | 25 | 9* | 275 | 169 | 28 | 17% | 96% | 25% (7 pups) |
| 26 | 15 | 6~7 | 20 | 16 | 9* | 267 | 189 | 19 | 10% | 100% | 58% (11 pups) |
| 14 | 2.7 | 7~10 | 21 | 35 | 16 | 334 | 226 | 43 | 19% | 98% | 85% (36 pups) |
| 10 | 3.9 | 7~15 | 49 | 30 | 13 | 784 | 442 | 10 | 2% | N/A | 66% (6 pups) |
| 17 | 4.5 | 10 | 6 | 38 | 16 | 290 | 212 | 39 | 18% | 99% | 57% (22 pups) |
| 6 | 29 | 10~11 | 21 | 39 | 20 | 556 | 366 | 46 | 13% | 91% | 31% (14 pups) |
| 1 | 46 | 10~16 | 25 | 32 | 19 | 470 | 275 | 32 | 12% | 84% | 22% (7 pups) |
| 27 | 19.8 | 11~16 | 24 | 32 | 20 | 491 | 307 | 24 | 8% | 80% | 45% (10 pups) |
| 13 | 2.6 | 14~15 | 17 | 31 | 19 | 326 | 223 | 47 | 21% | 100% | 86% (40 pups) |
| 16 | 4.5 | 14~15 | 17 | 34 | 17 | 286 | 173 | 43 | 25% | 97% | 83% (34 pups) |
| 23 | 84 | 11~13 | 20 | 34 | 19 | 253 | 130 | 11 | 8% | 76% | 7% (3 pups) |
| 24 | 94 | 12~15 | 36 | 25 | 13 | 463 | 317 | 56 | 18% | 83% | 13% (1 pup) |
| 15 | 4.2 | 12~15 | 23 | 24 | 12 | 286 | 174 | 44 | 25% | 88% | 50% (10 pups) |

*IVF or Triad (instead of paired natural mating

TAQMAN® assays were also obtained using Biosearch Technologies Dual Labeled BHQ® Probes (biosearchtech.com/ProbeITy/design/inputsequences.aspx). These assays serve as loss-of-allele assays if Cas9 cuts the sequence bound by the guide. All assays were screened for SNVs. Guides were named as follows: mGU and mGU2 (for mouse genomic upstream); and mGD and mGD2 (for mouse genomic downstream). TAQMAN® assays were named as follows: mTGU and mTGU2 (for TAQMAN® assays encompassing mGU and mGU2, respectively), and mTGD and mTGD2 (for TAQMAN® assays encompassing mGD and mGD2, respectively). An additional TAQMAN® assay was designed roughly equidistant from guides mGU/mGU2 and mGD/mGD2 in the middle of the locus to be collapsed, termed mTM (for mouse TAQMAN® Middle). This loss-of-allele assay determines whether deletion of the region flanked by the guide (collapse) occurs.

Further TAQMAN® assays were designed 200-800 bp upstream of mGU/mGU2 (whichever was most 5') and downstream of mGD/mGD2 (whichever was most 3'). These assays were called retU (for retention upstream) and retD (for retention downstream), respectively. These assays delineate the largest acceptable deletion size and were screened for SNVs as above.

Guide RNA Cloning: Guide RNA duplexes were designed and synthesized. Because the U6 promoter prefers to start with a guanine, a guanine was added to the 5' if the sequence did not already start with a guanine. Lyophilized gRNA duplexes were resuspended to 100 µM with sterile water, and the following ligation reaction was set up in a 0.5 mL microcentrifuge tube: 14.5 µL PCR certified water; 2 µL 10×T4 DNA Ligase Buffer (NEB), 1 µL pMB_sgRNA_B-smBI Vector (~60 ng), 1 µL gRNA duplex (100 µM), and 1.5 µL T4 DNA ligase (40 U/µL; NEB). The ligation reaction was then incubated for 1 hour at room temperature and was subsequently used in a transformation reaction in TOP10 cells. Colonies were then picked and checked via PCR and sequencing.

BTX® Electroporation Protocol: The guide mixture was prepared as follows: 10 of each sgRNA plasmid, and 5 µg of Cas9 wild type plasmid. On the electroporation day, the cells were fed with ES medium half an hour to an hour before the electroporation process. The cells were then washed twice with PBS, and 0.25% Trypsin-EDTA was added and the cells were incubated at 37° C. for 15 minutes. The plate(s) were tapped following incubation, ES medium was added to neutralize the trypsin, the cells were gently pipetted 4 times to break the cell clumps and transfer to gelatinized plate(s), and the cells were incubated for 20 minutes at 37° C. The plate(s) were shook and gently washed once with medium, and all of the cells were then transferred to 15-mL tubes, which were then spun for 5 minutes at 1200 rpm. All of the pellets were combined in 10 mL of PBS, and the cells were counted and diluted if necessary. A volume of 20 µl of the cell suspension was added to a CELLOMETER® slide and counted using the Nexcelom CELLOMETER AUTO T4™ Cell Viability Counter. The tubes were then centrifuged for 5 minutes at 1200 rpm. The pellet was re-suspended in electroporation buffer, using $7.5 \times 10^6$ cells for each electroporation. The cells were added to the guide mixture in micro centrifuge tubes, with a volume in each tube of 120 µl. The tubes were mixed 2-3 times and transferred to a 96-well electroporation cuvette (2 mm gap) using wide orifice tips, and the cuvette was sealed. An electric pulse was delivered at 700V, 400 Ω, 25 uF using a BTX® ECM® 630 Electroporator. The cuvette was then incubated on ice for 10 minutes. The electroporated cells were then transferred to a deep well plate (adding 0.8 mL/well while the cuvette is on ice). The cells were plated onto 2×15 cm gelatinized plates/project with 25 mL medium in each plate. Transient selection was started with 1 µg/mL puromycin for 3 days, and the medium was changed to a non-selection medium until 10 days post-electroporation, at which point colonies were picked.

NUCLEOFECTOR® Electroporation Protocol: On the electroporation day, the cells were fed with ES medium half an hour to an hour before the electroporation process. The cells were then washed twice with 10 mL PBS, and 2 mL of 0.25% Trypsin-EDTA was added and the cells were incubated at 37° C. for 15 minutes. The plate(s) were tapped following incubation, 8 mL of ES medium was added to neutralize the trypsin, the cells were gently pipetted 4 times to break the cell clumps and transfer to gelatinized plate(s), and the cells were incubated for 20 minutes at 37° C. The plate(s) were shook and gently washed once with medium, and all of the cells were then transferred to 15-mL tubes, which were then spun for 3 minutes at 90×g. The pellets were re-suspended in 10 mL of PBS, and the cells were counted and diluted if necessary. A volume of 20 µl of the cell suspension was added to a CELLOMETER® slide and counted using the Nexcelom Vision CBA System. A total of $2 \times 10^6$ cells were aliquoted and centrifuged in EPPENDORF® tubes for 3 minutes at 90×g. The pellet was then re-suspended in LONZA® P4 Buffer mixed with 5 µg Cas9 wild type plasmid and 2.5 µg of each sgRNA plasmid in a total volume of 100 µL. The cells were then transferred to a large LONZA® cuvette. An electrical pulse was delivered using the LONZA® 4D-NUCLEOFECTOR™ and program CP-105. A volume of 400 µL of fresh ES medium was added, and the cells were transferred to a new EPPENDORF® tube to mix. The cells were then plated onto 2×10 cm gelatinized plates with 10 mL of ES medium. Transient selection was started 2 days post-EP with puromycin (1.5 µg/mL) for 2 days. After selection, non-selection medium was used until 10 days post-electroporation, at which point colonies were picked.

Screening: Cutting by Cas9 with guides mGU, mGU2, mGD, and mGD2 was assessed using TAQMAN® assays mTGU, mTGU2, mTGD, and mTGD2. Cutting at one allele but not the other was determined when copy numbers decreased from two (parental, unmodified control DNA) to one. Homozygous cleavage by Cas9 was determined when assays yielded a copy number of zero. As Cas9 cutting near the ATG and stop codon does not guarantee removal of intervening sequence, heterozygous and homozygous collapse was assessed when mTM assay numbers went from two (parental) to one or zero, respectively. Finally, an outer limit in deletion size was set using retU and retD assays. The retention assays were to remain intact (retained) with copy number two, like the parental.

ESC clones obtained after electroporation with mGU, mGU2, mGD, and mGD2, or some combination thereof, were first screened for Cas9 cleavage and/or collapse using assays mTGU, mTGU2, mTM, mTGD, and mTGD2, or some combination thereof. Colonies with zero copy numbers for all assays were then further screened using retU and retD, and only colonies with retU and retD copy number of two were passed for further analysis.

Primary and Reconfirmation Screening of Mouse Embryonic Stem Cells: Modified mESC colonies were screened for homozygous deletion of a target locus via TAQMAN® LOA (Loss-Of-Allele) multiplex (4-plex) qPCR. For the first pass of screening (primary), the DNA of 176 unique clones was isolated in columns 1-11 of two 96-well plates. Column 12 was filled with wild type ES cell DNA that was previously isolated from the same mESC parental strain and was used as a calibrator for copy number; so that each DNA plate to be screened contains 88 modified clones and 8 calibrator clones. The DNA of each clone was dispensed in quadruplicate to a 384-well plate and assayed for homozygous LOA across three regions of the target locus in a single reaction mix, with TAQMAN® probes in FAM, VIC, ABY and Quasar used to simultaneously determine copy number in the relative Upstream, Middle, and Downstream regions of the target gene, with Quasar amplifying Wnt-2b to calibrate for DNA concentration. After copy numbers were determined, up to eight of the "best" quality clones with zero copies of all three assays spanning the target locus were selected for a subsequent growth expansion, re-plating, and subjected to an expanded repertoire of copy number assays (reconfirmation). Each expanded clone was plated and DNA isolated in replicates of six, occupying the first six columns of one row (A-H) of a 96-well plate, thereby providing additional genetic material and data replicates for the additional assays used. The assays used in primary screening were repeated to confirm the primary genotype, and retention assays were used to determine the extent of the deletion. Retention assays were positioned just upstream and downstream of the region targeted for deletion, and typically equal two copies. Additional assays were used to confirm the parental ESC genotype at the mouse Immunoglobulin Heavy (IgH) and Kappa (Igκ) loci (LOA for IgH and Igκ mouse, and GOA for humanization).

Next Generation Sequencing (NGS) to Identify Cas9-Mediated Alleles: A small tail biopsy from Cas9-modified F0 mice was extracted for genomic DNA using standard salt precipitation methods. For each target locus, PCR primers were designed with the following considerations: (1) the amplicon size is between 280-380 bp in length; (2) the gRNA cleavage sites are centered within the PCR product with the primers at least 35 bp away to accommodate larger insertions/deletions (indels), (3) the length of the primer is 22-25 bp with a melting temperature (Tm) of between 62-65° C., with a 2 bp CG clamp on the 3' end; and (4) the primers are checked against the genomic sequences for BALB/c, C57BL/6, or 129 strain single-nucleotide variations. Specific universal adaptor sequences provided by ILLUMINA® were then added to the locus-specific sequences. The resulting amplicons were visualized on agarose gels and purified/normalized using the THERMO FISHER SCIENTIFIC® SEQUALPREP™ Normalization Plate Kit. Products were quantified via QUBIT® and 1 ng of each product was used as template for barcoding via additional PCR with NEXTERA® primers and NEXTERA® PCR master mix. PCR was conducted in a thermocycler at 72° C. for 3 minutes, 95° C. for 30 seconds, 12 cycles of {95° C. for 10 seconds, 55° C. for 30 seconds, 72° C. for 30 seconds}, 72° C. for 5 minutes, and 10° C. hold. The resulting barcoded PCR products were purified via AMPURE® XP Beads, normalized using ILLUMINA® normalization beads in the NEXTERA® XT kit, pooled, and loaded into the MISEQ™ for sequencing and raw data collection.

Microinjection of 8-Cell Stage Mouse Embryos: Approximately 2 mL of standard ES Cell media (−LIF) was added to a sterile 35 mm culture dish lid and covered with filtered mineral oil. ES cells were plated onto the lower half of the dish using a mouth pipette. Cryopreserved 8-cell stage SW host embryos were deposited towards the top of the dish. In order to help minimize embryo damage during injection, the tip of a new injection pipette was dulled by gently striking against a holding pipette. ES cells were chosen based on morphology and brightness and gathered into an injection pipette. The embryo was positioned on the holding pipette such that a space between blastomeres is present at the 3 o'clock position. ES cells were introduced into the perivitelline space of the embryo by carefully puncturing through the zona at the 3 o'clock position and depositing the cells at that spot. A total of 7-9 ES cells were introduced per embryo. Injected embryos were placed into a 35 mm dish containing a drop of KSOM embryo culture medium covered with filtered mineral oil, and the embryos were cultured overnight at 37.0° C. with 7.5% CO2. Embryos were surgically transferred into pseudopregnant females the following morning.

Figure 5:
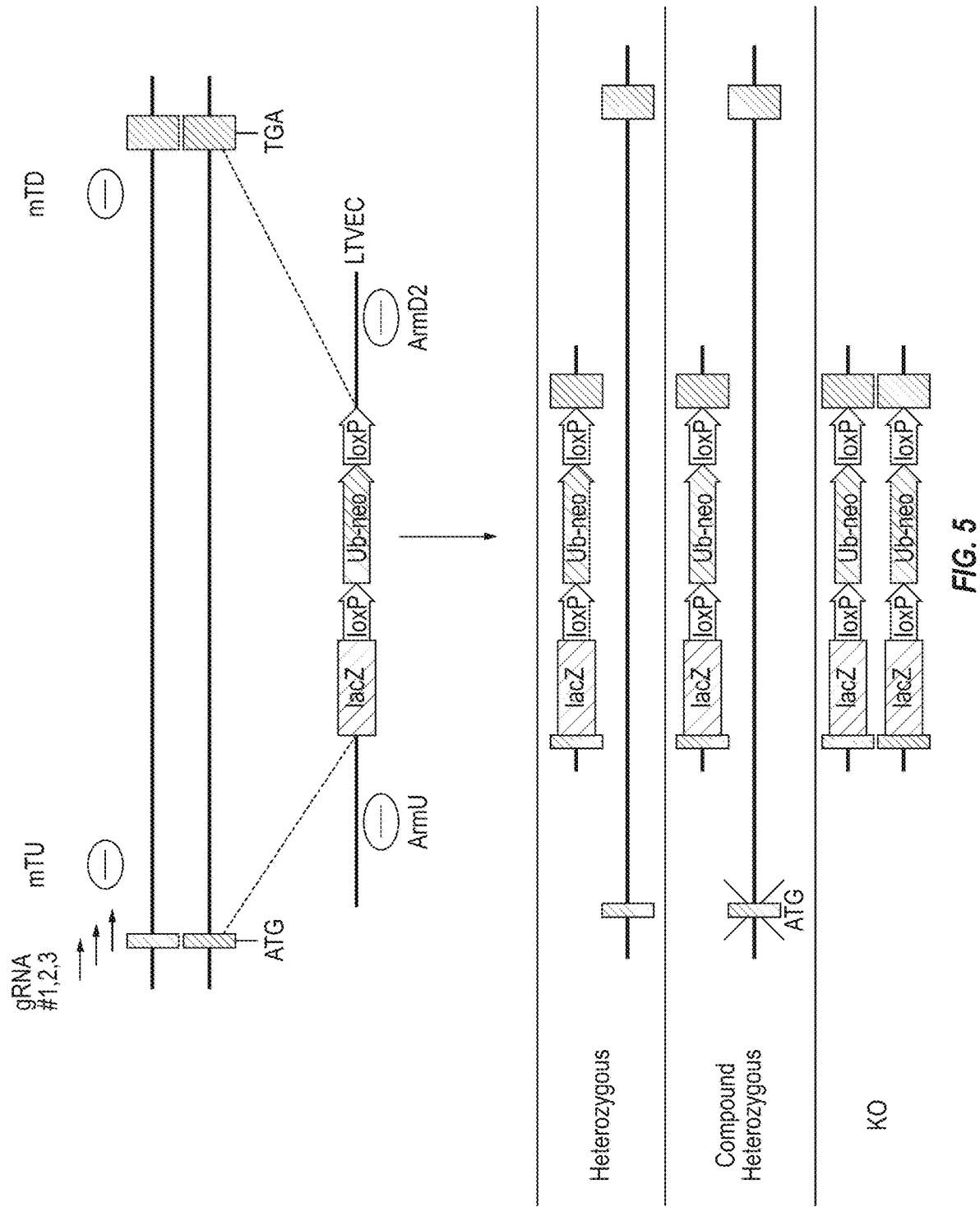
FIG. 5 shows a general schematic for simultaneous deletion of a mouse gene encoding a self-antigen homologous to a foreign target antigen of interest and replacement with a foxed neomycin selection marker and lacZ using a large targeting vector (LTVEC) and three overlapping guide RNAs each targeting the mouse ATG start codon. The guide RNAs are indicated by the horizontal arrows, and the TAQMAN® assay probes are indicated by the encircled horizontal lines. The bottom portion of the figure indicates the expected targeted allele types.

Example 2. Generating KO ES Cells and Mice for Antibody Production Using Multiple Guide RNAs Targeting Region of Start Codon In another experiment to generate mice with reduced tolerance to foreign target antigens of interest, three guide RNAs were designed and cloned to target self-antigens orthologous to those foreign target antigens for homozygous deletion. The three overlapping guide RNAs were designed to target overlapping regions encompassing the start codon of the endogenous gene encoding the self-antigen (see FIG. 5). The guide RNAs were electroporated or nucleofected together with Cas9 into ES cells derived from Universal Light Chain (ULC 1-39) mice (mice comprising in their germline: (i) an insertion at an endogenous mouse κ immunoglobulin light chain variable region locus of a rearranged Vκ/Jκ sequence comprising: a single human germline Vκ sequence; and a single human germline Jκ sequence, wherein the rearranged Vκ/Jκ sequence is operably linked to the endogenous mouse κ constant region; and (ii) an insertion at an endogenous mouse immunoglobulin heavy chain variable region locus of a plurality of human immunoglobulin heavy chain variable region gene segments operably linked to an endogenous mouse immunoglobulin heavy chain constant region). In some experiments, the Cas9 and the three guide RNAs were electroporated together with a large targeting vector (LTVEC) targeting the endogenous gene encoding the self-antigen for deletion (see, e.g., FIG. 5). Use of an LTVEC in combination with CRISPR/Cas9 (CC9) significantly increased the chances of getting a biallelic mutation at the target locus (see Table 8), but targeting with an LTVEC and CRISPR/Cas9 requires much more screening in order to rule out false positives.

TABLE 8

Biallelic Deletion Efficiencies.

| Self-Antigen | Parental ESC | EP Type | Colonies Screened | Clones with Biallelic Modifications | Efficiency (%) |
|---|---|---|---|---|---|
| Self-Antigen 8 (Transmembrane) | ULC1-39 F2 | LTVEC + CC9 | 384 | 111 | 28.9 |
| | | CC9 | 192 | 28 | 14.6 |

Example 3. Immunization of Mice and Analysis of Serum Antibody Responses to Immunogens Immunization VELOCIMMUNE® mice comprising a functional ectopic mouse Adam6 gene (VI-3), Universal Light Chain (ULC 1-39) mice (mice comprising in their germline: (i) an insertion at an endogenous mouse κ immunoglobulin light chain variable region locus of a rearranged Vκ/Jκ sequence comprising: a single human germline Vκ sequence; and a single human germline Jκ sequence, wherein the rearranged Vκ/Jκ sequence is operably linked to the endogenous mouse κ constant region; and (ii) an insertion at an endogenous mouse immunoglobulin heavy chain variable region locus of a plurality of human immunoglobulin heavy chain variable region gene segments operably linked to an endogenous mouse immunoglobulin heavy chain constant region), KO (knockout)/VI-3 mice (VI-3 mice in which self-antigens orthologous to foreign target antigens are knocked out), and KO/ULC 1-39 mice (ULC 1-39 mice in which self-antigens orthologous to foreign target antigens are knocked out) were immunized with numerous trans-membrane targets using a variety of immunogens such as proteins. Pre-immune serum was collected from the mice prior to the initiation of immunization. The mice were boosted via different routes at varying time intervals for a total of 3-6 boosts using standard adjuvants. The mice were bled periodically and anti-serum titers were assayed on respective antigens. In the example of Target 8, the mice were immunized with a recombinant extracellular domain of Target 8 with a mouse Fc tag via the footpad route. Titers were from the $2^{nd}$ bleed (following prime+6 boosts for ULC 1-39) or $3^{rd}$ bleed (following prime+3 boosts for Self-Antigen-8-KO/ULC 1-39).

Anti-Serum Titer Determination

Antibody titers in serum against respective immunogens were determined using ELISA. Ninety-six-well microtiter plates (THERMO SCIENTIFIC®) were coated with respective target antigens in phosphate-buffered saline (PBS, IRVINE SCIENTIFIC®) overnight at 2 μg/mL. Plates were washed with phosphate-buffered saline containing 0.05% Tween 20 (PBS-T, SIGMA-ALDRICH®) and blocked with 250 μl of 0.5% bovine serum albumin (BSA, SIGMA-ALDRICH®) in PBS for 1 hour at room temperature. The plates were washed with PBS-T. Pre-immune and immune anti-sera were serially diluted three-fold in 0.5% BSA-PBS and added to the plates for 1 hour at room temperature. The plates were washed and goat anti-mouse IgG-Fc-Horse Radish Peroxidase (HRP) conjugated secondary antibody (Jackson ImmunoResearch) was added to the plates and incubated for 1 hour at room temperature. Plates were washed and developed using TMB/$H_2O_2$ as substrate by incubating for 20 minutes. The reaction was stopped with acid and plates read on a spectrophotometer (VICTOR®, PERKINELMER) at 450 nm. Antibody titers were computed using GRAPHPAD PRISM® software. In the example of Target 8, the titer antigen used was a recombinant extracellular domain of human Target 8 with Myc-Myc-His tags.

Results

The humoral immune responses in VI-3, ULC1-39, KO/VI-3 and KO/ULC 1-39 mice were investigated by immunizing with different trans-membrane targets. High antibody titers were elicited in KO/VI-3 and KO/ULC 1-39 strains for all targets immunized. Titers were also high in VI-3 and ULC 1-39 strains of mice. In general, however, the KO strains appeared to have a greater titer response. The immune response elicited is represented in Table 9 as antibody titers, defined as the reciprocal of the highest serum dilution at which antigen binding absorbance is two-fold higher over background. Therefore, the higher the number, the greater is the humoral immune response to the immunogen. In total, over 16 targets have been successfully immunized in KO strains. Monoclonal antibodies have been isolated by BST and hybridoma platforms to Targets 1 and 9 and by BST to Targets 4 and 5, and further characterization of these antibodies is ongoing. Data for antibody production against one human target antigen of interest (Target 8; orthologous to mouse Self-Antigen 8, above) in ULC 1-39 and Self-Antigen-8-KO/ULC 1-39 mice are provided in Table 9 and in FIG. 6. F0 KO mice elicited an approximately 5-fold higher response to protein challenge than wild type ULC 1-39 mice, as indicated by the median antibody titer to target. Also provided in Table 9 are the number of antibodies that bind to the antigen specifically (at absorbance twice over the background absorbance). Similar results are shown in Self-Antigen-9-KO/VI-3 mice compared to VI-3 mice. See FIGS. 30A and 30B. In this experiment, wild type VI-3-Adam6 mice and Self-Antigen-9-KO/VI-3-Adam6 mice were immunized with either DNA encoding wild-type Target 9 by intradermal route. Titers were determined using cells engineered to express Target 9 or parental VI-3T3 cells. Whereas antibody titers from VI-3-Adam6 mice were no better than control, antibody titers were greatly increased in the Self-Antigen-9-KO/VI-3-Adam6 mice. This shows that both KO/VI-3 and KO/ULC strains elicit robust immune responses.

TABLE 9

Comparing Immune Responses in ULC 1-39 and KO/ULC 1-39 Strains.

| Target | Median Antibody Titer to Target | | Antigen Positive Monoclonal Antibodies | |
|---|---|---|---|---|
| | KO/ULC 1-39 (n = 5) | ULC 1-39 (n = 10) | KO/ULC 1-39 (n = 2) | ULC 1-39 (n = 2) |
| Target 8 | 986,890 | 200,387 | 76 | 61 |

Example 4. Immunization of Mice and Analysis of Antibody Diversity and Usage of V Gene Segments VELOCIMMUNE® mice comprising a functional ectopic mouse Adam6 gene (VI-3) and Self-Antigen-3-KO (knockout)/VI-3 mice were immunized with Target 3. Pre-immune serum was collected from the mice prior to the initiation of immunization. The mice were boosted via different routes at varying time intervals for a total of 3-6 boosts using standard adjuvants. The mice were bled periodically and anti-serum titers were assayed on respective antigens.

B cells were isolated from the spleens of the wild type VI-3 and Self-Antigen-3-KO VI-3 mice, and antibodies were sequenced to determine V gene usage. DNA encoding $V_H$ and $V_L$ domains was isolated directly from single antigen-positive B cells and sequenced. See, e.g., U.S. Pat. No. 7,582,298, herein incorporated by reference in its entirety for all purposes. The V gene usage data for the wild type VI-3 mice is presented in Table 10, and the V gene usage data for the Self-Antigen-3-KO VI-3 mice is presented in Table 11. As shown in Tables 10 and 11, a greater diversity in usage of both heavy chain V gene segments and light chain V gene segments was observed in the Self-Antigen-3-KO VI-3 mice compared to the wild type VI-3 mice. For example, only 4 heavy chain V gene segments and 6 light chain V gene segments were used for antibodies in the wild type VI-3 mice, and 79% of the antibodies used the IgH V4-59 and Igκ V1-12 V gene segments. In contrast, 6 heavy chain V gene segments and 10 light chain V gene segments were used for antibodies in the Self-Antigen-3-KO VI-3 mice, with the most prevalent usage combination (IgH V3-23 and Igκ V4-1) accounting for only 42% of the antibodies.

shared between mouse Self-Antigen 4 and human Target 4) is advantageous because it expands the pool of antibodies: no antibodies with cross-reactivity to mouse Self-Antigen 3 were generated in the wild type VI-3 mice. In addition, the

TABLE 10

V Gene Usage for Antibodies Against Target 3 in Wild Type VI-3 mice.

| WT VI3 Mice | Igκ V1-5 | Igκ V1-9 | Igκ V1-12 | Igκ V1-16 | Igκ V1-17 | Igκ V1-33 | Igκ V1-39 | Igκ V3-11 | Igκ V3-15 | Igκ V3-20 | Igκ V4-1 | No Vκ Seq | Total |
|---|---|---|---|---|---|---|---|---|---|---|---|---|---|
| IgH V1-18 | | | | | | | | | | | | | 0 |
| IgH V3-11 | | | | | | 1 | | | | | | 2 | 3 |
| IgH V3-23 | | | 29 | | | | | | | | | | 29 |
| IgH V3-33 | | | | | | | | | | | | | 0 |
| IgH V3-7 | | | | | | | | | | | | | 0 |
| IgH V3-9 | | | | | | | | | | 1 | | | 1 |
| IgH V4-59 | 3 | 1 | 150 | | | 2 | | | | | | | 156 |
| No VH Seq | | 1 | | | | | | | | | | | 1 |
| Total | 3 | 1 | 180 | 0 | 0 | 2 | 0 | 1 | 0 | 1 | 0 | 2 | 190 |

TABLE 11

V Gene Usage for Antibodies Against Target 3 in Self-Antigen-3-KO VI-3 mice.

| KO VI3 Mice | Igκ V1-5 | Igκ V1-9 | Igκ V1-12 | Igκ V1-16 | Igκ V1-17 | Igκ V1-33 | Igκ V1-39 | Igκ V3-11 | Igκ V3-15 | Igκ V3-20 | Igκ V4-1 | No Vκ Seq | Total |
|---|---|---|---|---|---|---|---|---|---|---|---|---|---|
| IgH V1-18 | | | | | 2 | | | | | | | | 2 |
| IgH V3-11 | 1 | | 1 | | | | | | | | | | 2 |
| IgH V3-23 | | 33 | | 2 | 1 | | | | | | 56 | | 92 |
| IgH V3-33 | | 1 | | | | 2 | | | | | | | 3 |
| IgH V3-7 | | | | | | | | | | | 1 | | 1 |
| IgH V3-9 | | | | | | | | | | | | | 0 |
| IgH V4-59 | 4 | 1 | 3 | 3 | 1 | 8 | 6 | | 1 | 4 | | | 31 |
| No VH Seq | | 1 | | | | | | | | | | | 1 |
| Total | 5 | 34 | 6 | 3 | 3 | 11 | 8 | 0 | 1 | 4 | 57 | 0 | 132 |

In addition, antibodies with cross-reactivity to mouse Self-Antigen 3 (i.e., antibodies that bind both human Target 3 and mouse Self-Antigen 3) were produced in the Self-Antigen-3-KO VI-3 mice (see, e.g., Table 12). Similar results were seen with Self-Antigen 4 and human Target 4 in both VI-3 and ULC 1-39 mice. See FIGS. 31A and 31B. In this experiment, Self-Antigen-4-KO/VI-3-Adam6 and Self-Antigen-4-KO/ULC 1-39 mice were immunized with His-tagged human Target 4 protein and/or His-tagged mouse Self-Antigen 4 protein (His-tagged) using the footpad route. Titers were determined using His-tagged human Target 4, His-tagged mouse Self-Antigen 4, or His-tagged Fel d 1 (control) as the coating antigen.

The ability to generate antibodies against epitopes that are shared between mouse Self-Antigen 3 and Target 3 (or pharmacokinetic properties of cross-reacting antibodies can be tested more easily in vivo because of their cross-reactivity with endogenous self-antigens in wild type mice. Consequently, mice genetically engineered to express the target antigens (e.g., the human target antigens) of such cross-reacting antibodies may not need to be generated.

TABLE 12

Antibodies with Cross-Reactivity to Self-Antigen 3 Produced in Self-Antigen-3-KO VI-3 Mice.

| VH | Vκ | Number of Antibodies |
|---|---|---|
| IgH V3-23 | Igκ V1-17 | 2 |
| IgH V3-23 | Igκ V1-9 | 1 |

TABLE 12-continued

Antibodies with Cross-Reactivity to Self-Antigen 3 Produced in Self-Antigen-3-KO VI-3 Mice.

| VH | Vκ | Number of Antibodies |
|---|---|---|
| IgH V3-23 | Igκ V4-1 | 55 |
| IgH V4-59 | Igκ V3-20 | 1 |

Example 5. CRISPR/Cas9-Mediated Targeting Using One Guide RNA or Two Guide RNAs

Materials and Methods

ES Cell Culture, Screening, and Electroporation

Figure 7:
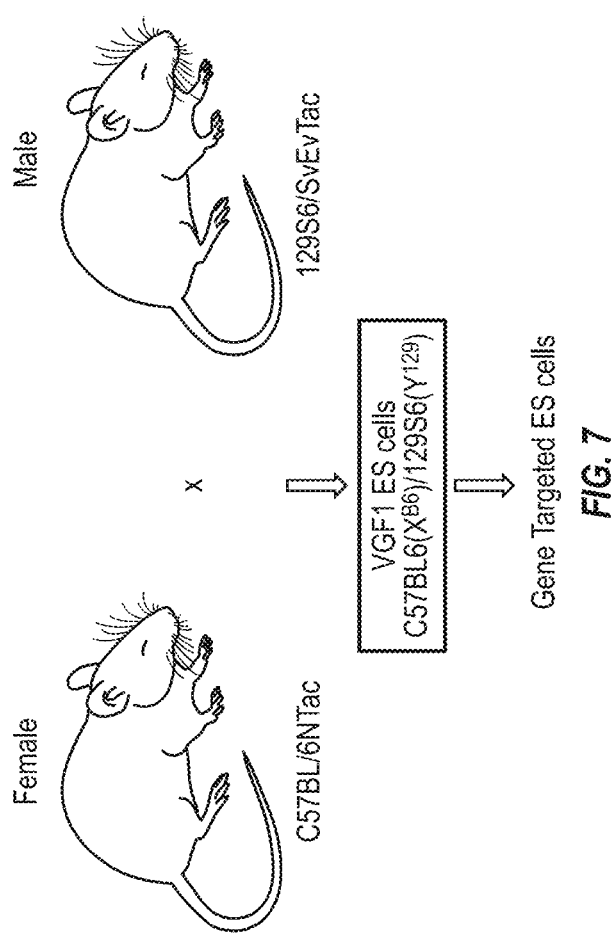
FIG. 7 shows the breeding undertaken to produce hybrid VGF1 (F1H4) ES cells (C57BL6($X^{B6}$)/12956($Y^{129}$)).

The experiments described herein were performed with VGF1, our C57BL6NTac/129S6SvEvF1 hybrid XY ES cell line (Poueymirou et al. (2007) Nat. Biotechnol. 25:91-99; Valenzuela et al. (2003) Nat. Biotechnol. 21:652-659). ES cells were cultured as previously described (Matise et al. (2000) in Joyner, A. L. ed. Gene Targeting: a practical approach, pp. 100-132, Oxford University Press, New York). The VGF1 cells were created by crossing a female C57BL/6NTac mouser with a Male 129S6/SvEvTac mouse to produce C57BL6($X^{B6}$)/129S6($Y^{129}$) mice. See FIG. 7.

Electroporations (EPs) were performed with 7.5 million cells in a 2 mm gap cuvette in a final volume of 0.12 ml. Electrical conditions for EP were 700V, 400 ohms resistance, and 25 microF capacitance using a BTX ECM 630 electroporation system (Harvard Apparatus, Holliston, MA). The amount of LTVEC per EP was 0.0015 mg, Cas9 expressing plasmid was 0.005 mg and sgRNA expressing plasmid was 0.010 mg. Some EPs were performed with the addition of 100 ng of a plasmid conferring puromycin resistance to allow for the selection of clones without selecting for neomycin resistance expressed by the LTVECs. Following EP, cells were plated onto two 15 cm gelatinized dishes and media was changed daily. Selection media containing either 100 ug/ml G-418 sulfate or 0.0015 mg/ml puromycin began 48 hours after EP and continued until 10 days post-EP. Colonies were picked in PBS and added to a 96-well dish containing 0.05% trypsin and allowed to dissociate for 15 minutes, neutralized with media and used for the isolation of DNA for screening.

The modification-of-allele method (Frendewey et al. (2010)*Methods Enzymol.* 476:295-307) was used to identify correctly targeted ES cell clones and to determine mouse allele genotypes.

Design of Guide Sequences

Approximately 200 bp of DNA surrounding the 50 bp, 100 bp, 500 bp, or 1 kb position inside the deleted portion of Lrp5 or other targeted genes, both upstream and downstream, was entered into the CRISPR design tool (crispr.mit.edu) to retrieve possible gRNA sequences. Potential gRNA sequences were then filtered to ensure that they would only allow for cutting of the endogenous DNA and not the humanization insert in the LTVEC.

Single Guide RNA Cloning sgRNAs were either cloned as duplex oligos (IDT) into pMB_sgRNA (U6 promoter) at BsmbI sites fused to the 77 bp scaffold for seamless RNA expression, or purchased as validated expression plasmids from GeneCopoeia (LRP5 guides A, B, B2, E2, E, and F). In-house-produced plasmids were confirmed by PCR and Sanger sequencing.

DNA Template for Genotype Confirmation

DNA was purified from ES cell, clones derived from ES cells that had been electroporated with a targeting vector and a plasmid expressing Cas9 and a plasmid expressing one of several guide RNAs (gRNAs) or two plasmids expressing different gRNA combinations. Clones identified by modification-of-allele (i.e., loss-of-allele or gain-of-allele) quantitative PCR assays as having a targeted deletion of the mouse target locus and insertion of the targeting vector or having Cas9/gRNA-induced deletions were selected for follow-up conventional PCR assays.

Oligonucleotide Design

Two PCR assays were designed for each combination of gRNAs. The first PCR was a deletion assay to detect collapse between the guide RNA recognition sequences of different gRNA combinations. The second PCR assay, which is a 5' assay, included two PCR assays. The first was a 5' human assay for humanized alleles and was designed across the mouse-human junction. The second was a 5' mouse assay for endogenous mouse alleles and was designed across the 5' targeted deletion junction.

PCR Reaction and TOPO Cloning

TaKaRa LA Taq DNA Polymerase (Cat. #RR002M) was used to amplify the ES cell DNA template. Each PCR assay reaction mix was run with a water negative control. Assay mixtures contained the following: 0.005 mL ES cell DNA Template; 1×LA PCR Buffer II ($Mg^{2+}$plus); 0.01 mM dNTP mixture; 0.0075 mM Forward Oligo (each); 0.0075 mM Reverse Oligo (each); 5000 units/mL LA Taq Polymerase; and ddH$_2$O to 0.025 mL.

The PCR Thermocycle program consisted of 94° C. for one minute; followed by 35 cycles of 94° C. for 30 seconds, 60° C. annealing gradient for 30 seconds, and 68° C. for one minute per kb amplified; followed by polymerization at 72° C. for 10 minutes.

PCR products were fractionated by electrophoresis on a 2% agarose gel with an Invitrogen 1 kb plus DNA ladder (Cat. #10787-018) and/or Invitrogen 50 bp DNA Ladder (Cat. #10416-014). Remaining PCR products were cloned into pCR4-TOPO Vector following instructions from Invitrogen's TOPO TA cloning kit (Cat. #K4575-02) for sequencing. Cloning reactions were chemically transformed into One Shot Top10 cells and plated on 0.06 mg/mL X-gal and 0.025 mg/mL kanamycin agar plates.

Sequencing

White colonies were inoculated into LB containing 0.025 mg/mL kanamycin and incubated overnight with shaking at 37° C. Each colony represented one amplicon from a population of assayed products. DNA was extracted from each bacterial culture using the QIAGEN plasmid miniprep kit (Cat. #12123). The DNA sequence of the inserts was determined in a sequencing reaction mix that included 0.002 mL TOPO cloned PCR, 1×PCRx Enhancer Solution (10× stock) (Cat. X11495-017), 0.0075 mM oligo (M13F or M13R), and ddH$_2$O to 0.015 mL.

Sequencing Analysis

Sequencing results were trimmed of indeterminate sequence and pCR4-TOPO Vector sequence, isolating the PCR insert sequence. Sequenced fragments were then aligned to a reference and variations were analyzed.

Sequencing Collapsed Clones

PCR products from the collapsed positive clones were cloned into the pCR4-TOPO Vector following the manufacturer's instructions (Invitrogen cat. #K4575-02), then chemically transformed into One Shot Top10 cells and plated on 0.060 mg/mL X-gal and 0.025 mg/mL Kanamycin agar plates. DNA was extracted from bacterial cultures using QIAGEN plasmid miniprep kit (Cat. #12123). Insert sequencing results were then aligned to a predicted collapse reference and indel variations were analyzed. Cas9 was predicted to cleave 3 base pairs from the PAM into the sequence recognized by the gRNA. The sequence within the predicted cleavage was deleted from the reference and the remaining was used to align to the results.

TAQMAN® Allelic Discrimination Assays for Single Nucleotide Variants (SNVs)

The TAQMAN® Allelic Discrimination reaction was 0.008 ml containing genomic DNA, specific probes/primers for each polymorphism, and TAQMAN® Gene Expression PCR Master mix. The probes were ordered from Life Technologies (Thermo) and the primers from IDT. The probe for allele 129 was labeled with VIC dye; the probe for allele B6 was labeled with FAM dye. Each TAQMAN® allelic assay was performed in quadruplicate on a 384-well plate and run on Applied BioSystems ViiA 7 platform. The SNV PCR cycling program was as follows: 95° C. for 10 minutes follow by 40 cycles of the following: 95° C. for 15 seconds, 60° C. for 60 seconds, and 60° C. for 30 seconds. The analysis of the run and evaluation of the results was done using ViiA 7 Software v1.1.

FISH Analysis

Selected ES cell clones were analyzed by either Cell Line Genetics (Madison, Wisconsin) or the Van Andel Institute (Grand Rapids, Michigan) using fluorescence in situ hybridization (FISH) by their standard procedures. We provided mouse and human BACs as probes for 2-color analysis.

Enhanced Genome Collapsing and/or Humanization of Target Loci

To effect a precise, single-step deletion of all or part of a rodent gene and optionally simultaneous replacement with all or part of its human homolog, we introduced by electroporation into rodent ES cells the following nucleic acid molecules: (1) an LTVEC; (2) a plasmid or mRNA encoding a Cas9 endonuclease; and (3) one or more plasmids encoding one or more CRISPR single guide RNAs (gRNAs) or the gRNAs themselves. In each experiment, the LTVEC was linearized. In some experiments, the LTVEC comprised all or part of a human gene that encodes the gene product (protein or RNA) flanked by homology arms of rodent DNA designed to direct a homologous recombination event that deletes the rodent gene and inserts the human gene. In other experiments, the LTVEC was designed to target a separate locus such as the Ch25h locus. In either case, the LTVEC also carried a drug selection cassette that directs the expression of an enzyme (e.g., neomycin phosphotransferase) that imparts resistance to an antibiotic drug (for example, G418).

ES cells that took up the LTVEC and incorporated it into their genomes were able to grow and form colonies on a tissue culture dish in a growth medium containing the antibiotic drug. Because we introduced 500 to 1,000 times more CRISPR/Cas9-encoding and gRNA-encoding nucleic molecules than LTVEC molecules, most of the LTVEC-containing drug resistant colonies also contained, at least transiently, the CRISPR/Cas9 components. We picked drug resistant colonies and screened them by the modification-of-allele method (Valenzuela et al. (2003) Nat. Biotech. 21:652-660; Frendewey et al. (2010) Methods Enzymol. 476:295-307; incorporated herein by reference in their entireties) to identify clones that had the correctly targeted humanized allele. In addition, real-time PCR assays recognizing sequences in the homology arms of the LTVEC, referred to as retention assays, were used to verify correct targeting of the LTVEC into the mouse genome. Determining the copy number of these retention assays provided further clarification to help distinguish correctly targeted ES clones, which retained a copy number of two, from clones in which a large Cas9-induced deletion of the target mouse locus coincides with random integration of the LTVEC elsewhere in the genome, in which case retention assays had a copy number of three (or more). The ability of paired gRNAs to create large Cas9-mediated deletions at the target mouse locus meant that standard LOA and GOA assays as previously described could be augmented by retention assays to provide further clarification and to verify correct targeting. Therefore, retention assays were designed and used in conjunction with LOA and GOA assays.

In each experiment, either one or two gRNAs were used. The gRNAs used singly directed Cas9 cleavage near the 5' end of the target locus (i.e., the targeted mouse gene deletion), the middle of the target locus, or the 3' end of the target locus. When two gRNAs were used, one gRNA directed Cas9 cleavage near the 5' end of the target locus and the other gRNA directed Cas9 cleavage in the middle of the target locus or near the 3' end of the target locus.

Lrp5 Locus

In one set of experiments, the LTVEC was designed to create a 68 kb deletion of the portion of the mouse Lrp5 (low-density lipoprotein receptor-related protein 5) gene encoding the ectodomain and a simultaneous replacement with a 91 kb fragment of the homologous sequence from the human LRP5 gene (see FIG. 8). The LTVEC comprised the 91 kb fragment of the human LRP5 gene flanked by homology arms containing 7 kb and 33 kb of genomic DNA derived from parts of the mouse Lrp5 locus that flank the 68 kb sequence of the mouse Lrp5 gene intended for deletion. In separate experiments, the Lrp5 humanizing LTVEC was combined with a plasmid encoding Cas9 and a second plasmid encoding one of eight gRNAs (A, B, B2, C, D, E2, E, F) designed to create double-strand breaks within the region of the mouse Lrp5 gene that was targeted for deletion. The gRNAs were designed to avoid recognition of any sequence in the inserted portion of the human LRP5 gene. In other experiments, we combined the LTVEC and the Cas9-encoding plasmid with plasmids encoding two different gRNAs that target different sites within the region of the mouse Lrp5 gene that was targeted for deletion.

Drug-resistant ES cell clones were screened for targeted humanizations by modification-of-allele assays (Valenzuela et al. (2003) Nat. Biotechnol. 21:652-659; Frendewey et al. (2010)Methods Enzymol. 476:295-307) for sequences within the deletion and for sequences within the drug selection cassette and the human gene insert. Clones were scored as correctly targeted if they had lost one of the two endogenous mouse gene sequences and gained one copy of the human insert, and also retained two copies of retention sequences (located in the homology arm of the LTVEC). The two retention assays for this screening were TAQMAN® assays using the following primers and probes: 7064retU forward primer CCTCCTGAGCTTTCCTTTGCAG (SEQ ID NO: 100); 7064retU reverse primer CCTAGACAACACAGACACTGTATCA (SEQ ID NO: 101); 7064retU TAQMAN® probe TTCTGCCCTTGAAAAGGAGAGGC (SEQ ID NO: 102); 7064retD forward primer CCTCTGAGGCCACCTGAA (SEQ ID NO: 103); 7064retD reverse primer CCCTGACAAGTTCTGCCTTCTAC (SEQ ID NO: 104); 7064retD TAQMAN® probe TGCCCAAGCCTCTGCAGCTTT (SEQ ID NO: 105).

The results of the CRISPR/Cas9-assisted humanization of the Lrp5 gene are summarized in Table 13. When the LTVEC alone was introduced into ES cells, 1.9% of the screened drug resistant clones carried a correctly targeted heterozygous humanized allele (see Het. Targ. column in Table 13, which includes clones in which the non-targeted allele was not mutated at all or had a small CRISPR-induced mutation such as a small deletion caused by NHEJ). In contrast, combining the LTVEC with Cas9 endonucleases guided by seven of the eight tested gRNAs (A, B, B2, C, D, E2, E and F; see Table 1) produced correctly targeted monoallelic heterozygous mutations at efficiencies that ranged from 2.1 to 7.8%. For Cas9-guided cleavage by B2 and D, in addition to monoallelic targeting, biallelic homozygous humanization was detected at a frequency of 1.0-2.1%. We have never observed biallelic targeting with an LTVEC on its own, even for small, simple deletion alleles. The homozygous Lrp5 humanized ES cells can be converted by the VELOCIMOUSE® method (Poueymirou et al. (2007) Nat. Biotech. 25:91-99, incorporated herein by reference in its entirety) directly into completely ES cell-derived mice ready for phenotypic and drug efficacy studies.

MOA assays devised to detect gRNA/Cas9-induced NHEJ mutations at or near the predicted cleavage sites demonstrated mutation activity for all the gRNAs tested (data not shown). The proportion of either monoallelic or biallelic gRNA-induced mutations detected among all clones assayed varied by locus and position. There was not a strong correlation between gRNA mutation activity and LTVEC targeting, but the lowest targeting efficiencies were often associated with gRNAs that had the lowest mutation frequencies.

Combining two gRNAs that recognize different ends of the region of the Lrp5 gene that was targeted for deletion increased the total humanization targeting efficiency, predominantly by increasing the frequency of homozygous targeting events for three of the five combinations tested (Table 13). Because the combination of gRNAs has the potential to create large deletions between the Cas9 cleavage sites programmed by the gRNAs, we also observed hemizygous ES cell clones that carried a targeted humanization on one Lrp5 allele and a large CRISPR-induced deletion on the other allele (gRNA combination A+F, Table 13). In addition, for two of the gRNA combinations (A+F and A+E2), we identified ES cell clones with a unique genotype: large CRISPR-mediated deletions on both Lrp5 alleles.

TABLE 13

Screening Results for CRISPR/Cas9-Assisted Humanization of the Lrp5 Ectodomain Using Individual gRNAs and Combined gRNAs.

| gRNA | Distance of gRNA Site from 5'/3' Ends of Targeted Deletion (bp) | Targeting Efficiency by Allele Type | | | | |
|---|---|---|---|---|---|---|
| | | Het. Targ. (% Eff.) | Hemi. Targ. (% Eff.) | Homo. Targ. (% Eff.) | Total Targ. (% Eff.) | Homo. Del. (% Eff.) |
| A | 50 (5') | 7.8 | | | 7.8 | |
| B | 500 (5') | 4.2 | | | 4.2 | |
| B2 | 1000 (5') | 6.2 | | 1.0 | 7.2 | |
| C | 29900 (5')/ 38430 (3') | 4.1 | | | 4.1 | |
| D | 29950 (5')/ 38380 (3') | 5.2 | | 2.1 | 7.3 | |
| E2 | 1000 (3') | 2.1 | | | 2.1 | |
| E | 500 (3') | 0.0 | | | 0.0 | |
| F | 50 (3') | 4.2 | | | 4.2 | |
| A + F | A: 50 (5') F: 50 (3') | 6.6 | 2.9 | 2.2 | 11.7 | 2.9 |
| B + E | B: 500 (5') E: 500 (3') | 2.5 | | | 2.5 | |
| B2 + E2 | B2: 1000 (5') E2: 1000 (3') | 4.2 | | 2.1 | 6.3 | |
| A + E | A: 50 (5') E: 500 (3') | 4.6 | | 6.2 | 10.8 | |
| A + E2 | A: 50 (5') E2: 1000 (3') | 2.0 | | 4.0 | 6.0 | 4.0 |
| None | N/A | 1.9 | | | 1.9 | |

As demonstrated in Table 13, a significant increase in the percentage of clones that had biallelic targeting was observed when using two gRNAs that target a single locus rather than one gRNA (see FIG. 9A), indicating that use of gRNA combinations promotes biallelic modifications. FIG. 9A shows a general schematic for simultaneous deletion of a mouse gene and replacement with a corresponding human version using an LTVEC and two guide RNAs (A and B). Unique mutant allele types that are observed at a much higher frequency when using two gRNAs include homozygously collapsed alleles (FIG. 9B; Δ/Δ), homozygously targeted alleles (FIG. 9C; Hum/Hum), hemizygously targeted alleles (FIG. 9D; (Hum/Δ)), and other compound heterozygously targeted alleles (e.g., one allele has an LTVEC-targeted humanization and the other allele has a CRISPR-induced mutation such as a small deletion) (FIG. 9E).

Figure 10B:
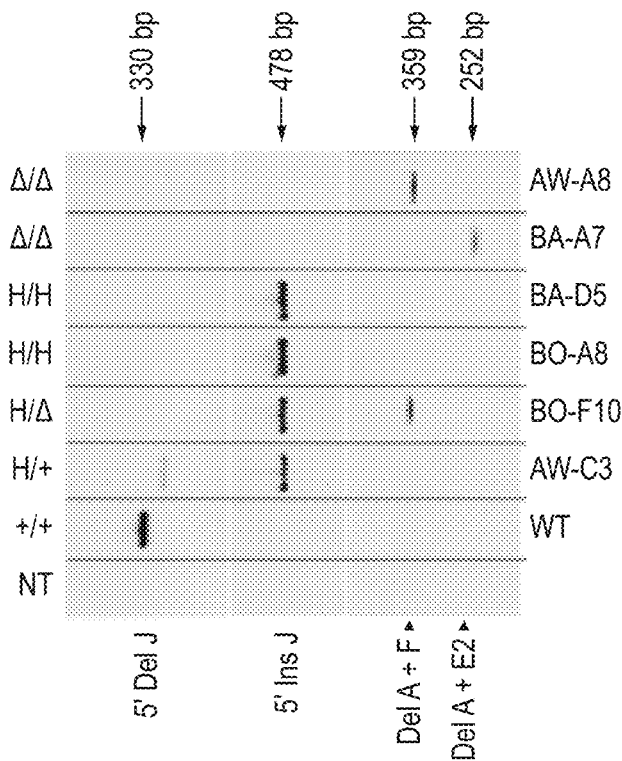
FIGS. 10A and 10B show PCR assays confirming genotypes of selected clones.
Figure 10A:
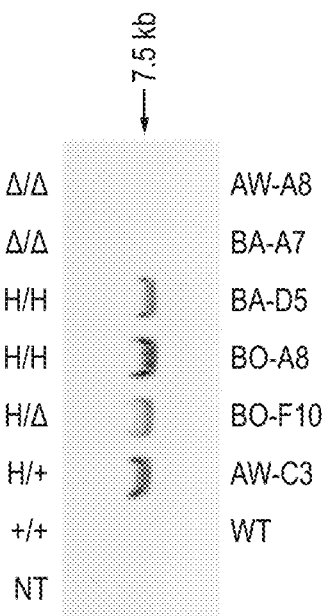

Several PCR assays were performed to support and confirm the genotypes based on MOA assays. The primers can be found in Table 1. The Lrp5 LTVEC had a 5' homology arm that was short enough (6.9 kb) to prove targeting by a PCR that assayed for a physical connection between the human insert and the adjacent mouse genomic sequence. We observed the expected 7.5 kb PCR product with DNA from clones scored as heterozygous, hemizygous, or homozygous but not with DNA from the parental ES cell line or from clones scored as having biallelic large deletions (FIG. 10A), thus confirming the targeting calls made by MOA (i.e., LOA and GOA) screening and supporting the inferred biallelic large deletions. The 5'-Del-J PCR assay, which examined sequences at the deletion and insertion junctions (FIG. 10B), produced a 330 bp product with DNA from the parental ES cell line and from most heterozygous humanized clones (data not shown). For heterozygous clone AW-C3, the 5'-Del-J assay produced a smaller than expected product (FIG. 10B), suggesting that gRNA A/Cas9 cleavage induced a small deletion mutation on the non-targeted allele, which was also detected by a MOA assay for gRNA A cleavage (data not shown). As expected, the 5'-Del-J assay was negative for clones with hemizygous, homozygous, and biallelic deletion alleles. The 5'-Ins-J PCR (FIG. 10B), which examined sequences at the junction between the 5' end of the human DNA insert and the adjacent mouse flanking sequence, produced a 478 bp product in heterozygous, hemizygous, and homozygous clones, as these have at least one targeted humanized allele. The 5'-Ins-J PCR assay produced no product for clones with biallelic large deletions (FIG. 10B). To confirm the large deletions in hemizygous and biallelic deletion clones, we performed PCRs with primers that recognized sequences outside of the dual gRNA target sites. The Del(A+F) PCR, which assayed for a deletion between the A and F gRNA sites, produced a single product of approximately 360 bp with DNA from clones AW-A8 and BO-F10 (FIG. 10B), confirming that at least one of the Lrp5 alleles had a large deletion. Likewise, the Del(A+E2) PCR, which assayed for a large deletion between the A and E2 gRNA sites, produced a single product of approximately 250 bp with DNA from clone BA-A7. The deletion PCRs, together with the junction, LOA, and GOA assays, support a biallelic large deletion genotype. The assay results shown in FIGS. 10A and 10B are representative examples of similar assays that we performed in addition to fluorescent in situ hybridization (FISH; FIG. 11A-C) to confirm the biallelic genotypes summarized in Table 13.

Fluorescence in situ hybridization (FISH) was used to confirm homozygous targeted humanization of the Lrp5 gene. ES cell clones scored by quantitative and conventional PCR assays as homozygous targeted from targeting experiments in which the Lrp5 humanization LTVEC was combined with Cas9 and two gRNAs (A plus F or A plus E2) were sent to a commercial cytology service for FISH and karyotype analysis. A bacterial artificial chromosome (BAC) carrying the mouse Lrp5 gene was labeled with a red fluorescent marker and used as a probe to identify endogenous Lrp5 loci, and a BAC carrying the human LRP5 gene was labeled with a green fluorescent marker and used as a probe to identify the chromatids targeted with the human insert. The labeled BAC probes were hybridized to metaphase spreads from the targeted clones and visualized by fluorescence microscopy. Chromosomes on the spreads were visualized by staining with DAPI (4',6-diamidino-2-phenylindole), and separate karyotypes for each clone were determined by Giemsa staining. A typical result is shown in FIG. 11A for clone AW-D9, which was found to have a normal 40XY karyotype (not shown). The composite photograph in FIG. 11A shows that both the red mouse BAC probe signal and the green human BAC probe signal co-localized to cytological band B on both copies of mouse chromosome 19, the known location of the Lrp5 gene. The composite photograph in FIG. 11C shows the same homozygous targeting for another clone (BA-D5). These results confirm that the 91 kb fragment of the human LRP5 gene in the humanization LTVEC was correctly inserted at the intended mouse Lrp5 locus on both chromosome 19 homologs in clones AW-D9 and BA-D5. In contrast, the composite photograph in FIG. 11B shows that both the red mouse BAC probe signal and the green human BAC probe signal co-localized to cytological band B on a single copy of mouse chromosome 19 (solid arrow), whereas only the red mouse BAC probe signal localizes to cytological band B on the other copy of mouse chromosome 19. These results confirm that the 91 kb fragment of the human LRP5 gene in the humanization LTVEC was correctly inserted at the intended mouse Lrp5 locus on only one copy of chromosome 19 (heterozygous targeting). They also indicate (along with other controls not shown) that the human BAC probe does not cross-hybridize to the mouse Lrp5 locus but only recognizes the human LRP5 insert.

The presence in certain clones of identical CRISPR-induced indel mutations formed at both alleles by apparent non-homologous end-joining repair suggested the occurrence of gene conversion events in F1H4 hybrid cells (which are comprised of 50% 129SvS6 strain and 50% C57BL/6N strain). To gain insight into the mechanism underlying the enhanced biallelic targeting when two gRNAs are used, seven clones were screened that had either targeted homozygous humanizations or homozygous CRISPR-induced large deletions following targeting with the LTVEC and either the A plus F or the A plus E2 gRNA combinations.

Figure 12:
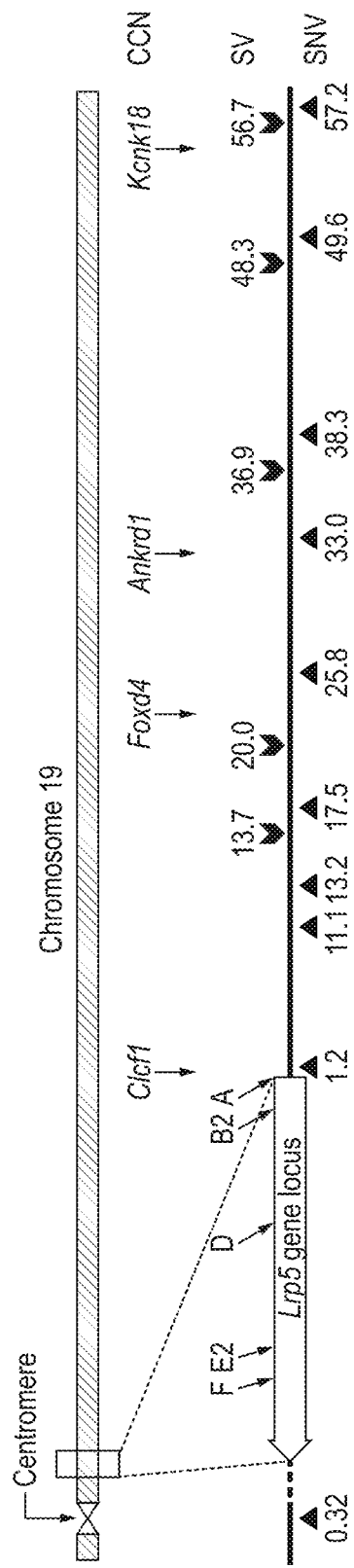
FIG. 12 shows a schematic of chromosome 19 with assays designed to examine gene conversion or mitotic recombination events mediated by two guide RNAs by analyzing loss of heterozygosity (LOH) in VGF1 hybrid ES cells. The approximate positions of TAQMAN® qPCR chromosomal copy number (CCN) probes are shown by arrows. The approximate positions of the structural variant (SV) polymorphism PCR probes are shown by chevrons with their distances (in Mb) from the Lrp5 locus given above. The approximate positions of the single nucleotide variant (SNV) TAQMAN® allelic discrimination probes are shown by arrowheads with their distances (in Mb) from the Lrp5 locus given below. The positions of the gRNA recognition sequences for F, E2, D, B2, and A are shown by diagonal arrows above the representation of the Lrp5 gene.

FIG. 12 shows examples of assays designed to examine gene conversion events mediated by two guide RNAs. Specifically, the possibility of gene conversion was examined by analyzing loss of heterozygosity (LOH) in F1H4 hybrid ES cells (which are comprised of 50% 129 SvS6 strain and 50% C57BL/6N strain). Gene conversion can be demonstrated by loss of heterozygosity in known polymorphisms between 129SvS6 (129) and C57BL/6N (B6), and thus PCR assays were designed to differentiate between these two allele types. Structural variants (SV) polymorphisms were assayed by conventional PCRs designed to detect the differences between the 129 and B6 alleles. Although only one of the SV assays used below is shown in FIG. 12, the concept is the same for each. Primers were designed based on structural variations (SVs) between B6 and 129 mouse strains and are shown in Table 1. The primer design conditions were constrained to identify ~25 bp SVs and produce ~300 bp PCR products; these conditions were selected such that any changes would be visible by gel electrophoresis.

Prior to running PCRs on the clones, the assays were validated and optimized against wild-type ES-cell DNA from the B6, 129 strains and from the F1H4 ES cell line. Primer sets that produced distinguishable PCR bands specific to either B6 or 129 alleles and were consistent in producing these same two distinguishable bands using F1H4 DNA were selected for testing on clones. For chromosome 19 (the location of the Lrp5 gene), six primer sets—IDs 190045, 190061, 190068, 190030, 190033, 190013—were selected for use on Lrp5 humanized clones genotyped as either "homozygous targeted" or "homozygous collapsed" by modification-of-allele (MOA) assays and conventional PCR. The SV PCR assays were spaced out along chromosome 19 from the Lrp5 locus to the telomeric end of the chromosome, ranging from ~13.7 to ~56.2 Mb from the Lrp5 locus. The approximate distances (in Mb) of the SV assays on chromosome 19 from the Lrp5 locus are as follows: 13.7 for assay 190045, 19.0 for assay 190061, 35.0 for assay 190068, 37.4 for assay 190030, 48.3 for assay 190033, and 56.2 for assay 190013. Only assay 190033 is shown in FIG. 12 (shown as SV 48.3), but the primers for assays 190045, 190061, 190068, 190030, 190033, and 190013 are shown in Table 1.

PCRs were run on DNA from these clones as well as on F1H4 control DNA, 129 control DNA, and B6 control DNA. PCR products were fractionated by electrophoresis on 6% polyacrylamide gels, which were subsequently stained with GelRed. Clones producing two bands matched up to the F1H4 control, which from the previous optimization showed that the top band was specific to the 129 allele and the bottom band was specific to the B6 allele. Clones that produced only one band displayed either just the B6 or just the 129 band. Clones AW-A7, AW-F10, BA-D5, BA-F2, BC-H9, and BR-B4 showed only the B6 band for all six assays, whereas clone BO-A8 showed only the 129 band for all six assays. As previously mentioned, these clones were genotyped as either homozygous targeted or homozygous collapsed by MOA and/or PCR, and involved various gRNA combinations (A plus F, A plus E2, B2, and D). The presence of just a single allelic band suggested that a gene conversion event is taking place—if there were no conversion, both bands would still be present as in the F1H4 control.

In addition, single nucleotide variants (SNVs) between the 129 and B6 alleles were assayed by TAQMAN® allelic discrimination assays. The approximate positions of the SNV assays on the chromosome 19 map in FIG. 12 are shown by arrowheads with their distances (in Mb) from the Lrp5 locus given below. The distances (in Mb) from the Lrp5 locus are as follows: 0.32 centromeric of Lrp5 (C2), 1.2 telomeric of Lrp5 (T3), 11.1 telomeric of Lrp5 (T6), 13.2 telomeric of Lrp5 (T7), 17.5 telomeric of Lrp5 (T8), 25.8 telomeric of Lrp5 (T9), 33.0 telomeric of Lrp5 (T10), 38.3 telomeric of Lrp5 (T11), 49.6 telomeric of Lrp5 (T13), and 57.2 telomeric of Lrp5 (T14). The 129-specific and B6-specific probes and the primer pairs are shown in Table 1.

Table 14 shows seven examples of ES cell clones that exhibited apparent gene conversion events over the long arm of chromosome 19 in a direction telomeric from the Lrp5 target locus by LOH for both SV and SNV alleles. The ES cell clones were derived from independent targeting experiments that combined the Lrp5 humanization LTVEC with one or two gRNAs, as indicated. The positions of the gRNA recognition sequences are shown above the representation of the Lrp5 gene in FIG. 12 (thick leftward pointing arrow). Genotyping assays indicated that six of the seven clones had homozygously targeted humanizations of the Lrp5 gene, while the one had a homozygous collapse (large deletion between the gRNA sites). In six of the seven clones, the 129 alleles were lost, leaving only the B6 alleles. In the other clone, the B6 alleles were lost, leaving only the 129 alleles. All clones remained heterozygous for alleles assayed on the centromeric side of the Lrp5 locus (i.e., all clones were heterozygous B6/129 with the C2 SNV assay). The LOH observed in the seven clones indicates that one mechanism by which homozygous genetically modified alleles are obtained when an LTVEC is combined with one, or more frequently, two gRNAs is a first targeted genetic modification on one allele followed by a homology directed recombination gene conversion event that copies the targeted genetic modification from one chromosome to its homolog.

TABLE 14

Loss of Heterozygosity Assay Results.

| Clone | gRNAs | Lrp5 Allele Type | Loss of Heterozygosity Assays (SV and SNV) |
|---|---|---|---|
| AW-A7 | A + F | Homozygous Targeted | Only B6 alleles detected |
| AW-F10 | A + F | Homozygous Collapse | Only B6 alleles detected |
| BO-A8 | A + F | Homozygous Targeted | Only 129 alleles detected |

TABLE 14-continued

Loss of Heterozygosity Assay Results.

| Clone | gRNAs | Lrp5 Allele Type | Loss of Heterozygosity Assays (SV and SNV) |
|---|---|---|---|
| BA-D5 | A + E2 | Homozygous Targeted | Only B6 alleles detected |
| BA-F2 | A + E2 | Homozygous Targeted | Only B6 alleles detected |
| BC-H9 | B2 | Homozygous Targeted | Only B6 alleles detected |
| BR-B4 | D | Homozygous Targeted | Only B6 alleles detected |

C5 (Hc) Locus

In another set of experiments, the LTVEC was designed to create a 76 kb deletion of the mouse gene for complement component 5 (C5 or Hc (hemolytic complement)) and a simultaneous replacement with a 97 kb fragment of the homologous human C5 gene. The target locus comprised exon 2 to the stop codon of the C5 (Hc) gene. The LTVEC comprised the 97 kb fragment of the human C5 gene flanked by homology arms containing 35 kb and 31 kb of genomic DNA derived from parts of the mouse C5 (Hc) locus that flank the 76 kb sequence of the mouse C5 (Hc) gene intended for deletion. In separate experiments, the C5 (Hc) humanizing LTVEC was combined with a plasmid encoding Cas9 and a second plasmid encoding one of six gRNAs (A, B, C, D, E, and E2; see Table 1) designed to create double-strand breaks within the region of the mouse C5 (Hc) gene that was targeted for deletion. The gRNAs were designed to avoid recognition of any sequence in the inserted portion of the human C5 gene. In other experiments, we combined the LTVEC and the Cas9-encoding plasmid with plasmids encoding two different gRNAs that target different sites within the region of the mouse C5 (Hc) gene that was targeted for deletion. In some experiments, a control LTVEC that targets the Ch25h locus was used instead of the C5 (Hc) humanizing LTVEC. The control LTVEC, which is designed to delete the entire coding sequence of Ch25h (~1 kb) and insert puromycin and neomycin selection cassettes into the Ch25h locus, was used as a means to select drug-resistant clones that were not targeted for homologous recombination at the C5 (Hc) locus.

The results of the CRISPR/Cas9-assisted humanization of the C5 (Hc) gene are shown in Table 15 and are similar to the results obtained for CRISPR/Cas9-assisted humanization of the Lrp5 gene. The targeting efficiency with the LTVEC alone was higher (6.1%) for the C5 (Hc) humanization than for Lrp5, but addition of Cas9 and gRNAs enhanced the targeting efficiency for four of the six gRNAs tested. As with Lrp5, combining gRNAs (i.e., use of two gRNAs) for the C5 (Hc) humanization further increased total targeting efficiency, predominantly by increasing the frequency of hemizygous and homozygous targeting events. We also found ES cell clones with large CRISPR-induced deletions on both alleles (observed at frequencies of 1.8% to 3.6%). In addition, when the LTVEC targeting the Ch25h locus was used in combination with two C5 (Hc) gRNAs, clones with homozygous alleles that were collapsed between the two guide RNA recognition sequences were observed at frequencies of 1.2% to 6%, indicating that the collapse events occur independently of homologous recombination events at the target locus. As with Lrp5, retention assays were used to confirm correctly targeted clones. The two retention assays for this screening were TAQMAN® assays using the following primers and probes: 7140retU forward primer CCCAGCATCTGACGACACC (SEQ ID NO: 106); 7140retU reverse primer GACCACTGTGGG-CATCTGTAG (SEQ ID NO: 107); 7140retU TAQMAN® probe CCGAGTCTGCTGTTACTGTTAGCATCA (SEQ ID NO: 108); 7140retD forward primer CCCGACACCTTCT-GAGCATG (SEQ ID NO: 109); 7140retD reverse primer TGCAGGCTGAGTCAGGATTTG (SEQ ID NO: 110); 7140retD TAQMAN® probe TAGT-CACGTTTTGTGACACCCAGA (SEQ ID NO: 111).

signal localizes to the C5 (Hc) locus on the other copy of mouse chromosome 2. These results confirm that the 97 kb fragment of the human C5 gene in the humanization LTVEC was correctly inserted at the intended mouse C5 (Hc) locus on only one copy of chromosome 2 (heterozygous targeting) in clone Q-E9.

Clones were then assayed to examine gene conversion events mediated by the two guide RNAs. Specifically, the possibility of gene conversion was examined by analyzing

TABLE 15

Screening Results for CRISPR/Cas9-Assisted Humanization of the C5 (Hc) Gene Using Individual gRNAs and Combined gRNAs.

| gRNA | Distance of gRNA Site from 5'/3' Ends of Targeted Deletion (bp) | LTVEC | Het. Targ. (% Eff.) | Hemi. Targ. (% Eff.) | Homo. Targ. (% Eff.) | Total Targ. (% Eff.) | Homo. Del. (% Eff.) |
|---|---|---|---|---|---|---|---|
| A | 100 (5') | C5 | 16.6 | | | 16.6 | |
| B | 500 (5') | C5 | 14.5 | | | 14.5 | |
| C | 38200 (5')/ 37500 (3') | C5 | 11.4 | | | 11.4 | |
| D | 43500 (5')/ 32200 (3') | C5 | 7.3 | | | 7.3 | |
| E | 500 (3') | C5 | 4.2 | | | 4.2 | |
| E2 | 100 (3') | C5 | 6.2 | | | 6.2 | |
| A + C | A: 100 (5') C: 3.7500 (3') | C5 | 19.6 | 7.1 | 0.6 | 27.3 | 0.6 |
| A + C | A: 100 (5') C: 3.7500 (3') | Ch25h | N/A | N/A | N/A | N/A | 6.0 |
| A + E2 | A: 100 (5') E2: 100 (3') | C5 | 19.0 | 3.6 | 1.2 | 23.8 | 3.0 |
| A + E2 | A: 100 (5') E2: 100 (3') | Ch25h | N/A | N/A | N/A | N/A | 1.2 |
| None | N/A | C5 | 6.1 | | | 6.1 | |

Fluorescence in situ hybridization (FISH) was used to confirm homozygous targeted humanization of the C5 (Hc) gene. ES cell clones scored by quantitative and conventional PCR assays as homozygous targeted from targeting experiments in which the C5 (Hc) humanization LTVEC was combined with Cas9 and two gRNAs were sent to a commercial cytology service for FISH and karyotype analysis. A bacterial artificial chromosome (BAC) carrying the mouse C5 (Hc) gene was labeled with a red fluorescent marker and used as a probe to identify endogenous loci, and a BAC carrying the human C5 gene was labeled with a green fluorescent marker and used as a probe to identify chromatids targeted with the human insert. The labeled BAC probes were hybridized to metaphase spreads from the targeted clones and visualized by fluorescence microscopy. Chromosomes on the spreads were visualized by staining with DAPI (4',6-diamidino-2-phenylindole), and separate karyotypes for each clone were determined by Giemsa staining. A typical result is shown in FIG. 13B for clone O-E. The composite photograph in FIG. 13B shows that both the red mouse BAC probe signal and the green human BAC probe signal co-localized to the C5 (Hc) locus on both copies of mouse chromosome 2, the known location of the C5 (Hc) gene. These results confirm that the 97 kb fragment of the human C5 gene in the humanization LTVEC was correctly inserted at the intended mouse C5 (Hc) locus on both chromosome 2 homologs in clone O-E3. In contrast, the composite photograph in FIG. 13A shows that both the red mouse BAC probe signal and the green human BAC probe signal co-localized on a single copy of mouse chromosome 2 (solid arrow), whereas only the red mouse BAC probe loss of heterozygosity (LOH) in F1H4 hybrid ES cells (which are comprised of 50% 129 SvS6 strain and 50% C57BL/6N strain). Gene conversion can be demonstrated by loss of heterozygosity in known polymorphisms between 129SvS6 (129) and C57BL/6N (B6), and thus PCR assays were designed to differentiate between these two allele types. Structural variants (SV) polymorphisms were assayed by conventional PCRs designed to detect the differences between the 129 and B6 alleles. Primers were designed based on structural variations (SVs) between B6 and 129 mouse strains and are shown in Table 1. The primer design conditions were constrained to identify ~25 bp SVs and produce ~300 bp PCR products; these conditions were selected such that any changes would be visible by gel electrophoresis.

Prior to running PCRs on the clones, the assays were validated and optimized against wild-type ES-cell DNA from the B6, 129 strains and from the F1H4 ES cell line. Primer sets that produced distinguishable PCR bands specific to either B6 or 129 alleles and were consistent in producing these same two distinguishable bands using F1H4 DNA were selected for testing on clones. Five primer sets—IDs SV 6.1, SV 6.3, SV 7.8, SV 16, and SV 25.5—were selected for use on clones from the targeting experiment. Four of the SV PCR assays were spaced out along the chromosome from the C5 locus to the telomeric end of the chromosome, ranging from ~6.3 to ~25.5 Mb from the C5 locus. The final SV PCR assay was ~6.1 Mb centromeric to the C5 locus. The approximate distances (in Mb) of the SV assays from the C5 locus are as follows: 6.1 (centromeric) for assay SV 6.1, 6.3 (telomeric) for assay SV 6.3, 7.8

(telomeric) for assay SV 7.8, 16.0 for assay SV 16.0, and 25.5 for assay SV25.5 (see FIG. 14).

All 21 clones remained heterozygous for alleles assayed on the centromeric side of the C4 locus (i.e., all clones were heterozygous B6/129). Two out of the 21 clones tested exhibited apparent gene conversion events in a direction telomeric from the C5 target locus by LOH (see Table 16). Genotyping assays indicated that one of the clones had homozygously targeted humanization of the C5 gene, and the other clone had a homozygous collapse. The LOH observed in the two clones indicates that one mechanism by which homozygous genetically modified alleles are obtained when an LTVEC is combined with one, or more frequently, two gRNAs is a first targeted genetic modification on one allele followed by a homology directed recombination gene conversion event that copies the targeted genetic modification from one chromosome to its homolog.

TABLE 16

Loss of Heterozygosity Assay Results.

| Clone | gRNAs | C5 Allele Type | Gene Conversion Assay |
|---|---|---|---|
| R-E2 | A + E2 | Homozygous Targeted | Only 129 alleles detected |
| R-E8 | A + E2 | Homozygous Collapse | Only 129 alleles detected | second plasmid encoding one of six gRNAs (A, B, C, D, E, and F; see Table 1) designed to create double-strand breaks within the region of the mouse Ror1 gene that was targeted for deletion. The gRNAs were designed to avoid recognition of any sequence in the inserted portion of the human ROR1 gene. In other experiments, we combined the LTVEC and the Cas9-encoding plasmid with plasmids encoding two different gRNAs that target different sites within the Ror1 gene that was targeted for deletion.

The results of the CRISPR/Cas9-assisted humanization of the Ror1 gene are shown in Table 17 and are similar to the results obtained for CRISPR/Cas9-assisted humanization of the Lrp5 and C5 (Hc) genes. The targeting efficiency with LTVEC alone was 0.3%, and addition of Cas9 and gRNAs slightly increased the targeting efficiency for two of the six gRNAs tested. Combining the A and F gRNAs increased the total Ron 1 targeting efficiency to 6.3% by increasing the frequency of both the heterozygous and hemizygous targeting events. We also found ES cell clones with large CRISPR-induced deletions on both alleles (observed at a frequency of 1.6%). No homozygous targeted clones were observed. In additional experiments, gRNAs A and D were also combined, but still no homozygous targeting was observed.

TABLE 17

Screening Results for CRISPR/Cas9-Assisted Humanization of the Ror1 Gene Using Individual gRNAs and Combined gRNAs.

| gRNA | Distance of gRNA Site from 5'/3' Ends of Targeted Deletion (bp) | Targeting Efficiency by Allele Type | | | | |
|---|---|---|---|---|---|---|
| | | Het. Targ. (% Eff.) | Hemi. Targ. (% Eff.) | Homo. Targ. (% Eff.) | Total Targ. (% Eff.) | Homo. Del. (% Eff.) |
| A | 200 (5') | 0.7 | | | 0.7 | |
| B | 1000 (5') | 0.0 | | | 0.0 | |
| D | 54300 (5')/ 55500 (3') | 0.7 | | | 0.7 | |
| C | 54500 (5')/ 55300 (3') | 0.0 | | | 0.0 | |
| E | 1000 (3') | 0.0 | | | 0.0 | |
| F | 200 (3') | 0.3 | | | 0.3 | |
| A + F | A: 200 (5') F: 200 (3') | 4.2 | 2.1 | | 6.3 | 1.6 |
| A + D | A: 200 (5') D: 55500 (3') | 1.0 | | | 1.0 | |
| None | N/A | 0.3 | | | 0.3 | |

Ror 1 Locus

In another set of experiments, the LTVEC was designed to create a 110 kb deletion of the mouse Ror1 (tyrosine-protein kinase transmembrane receptor ROR1) gene and a simultaneous replacement with a 134 kb fragment of the homologous human ROR1 gene. The LTVEC comprised the 134 kb fragment of the human ROR1 gene flanked by homology arms containing 41.8 kb and 96.4 kb of genomic DNA derived from parts of the mouse Ror1 locus that flank the 110 kb sequence of the mouse Ron 1 gene intended for deletion. In separate experiments, the Ron 1 humanizing LTVEC was combined with a plasmid encoding Cas9 and a Trpa1 Locus In another set of experiments, the LTVEC was designed to create a 45.3 kb deletion of the mouse Trpa1 (transient receptor potential cation channel, subfamily A, member 1) gene and a simultaneous replacement with a 54.5 kb fragment of the homologous human TRPA1 gene. The LTVEC comprised the 54.5 kb fragment of the human TRPA1 gene flanked by homology arms containing 41.0 kb and 58.0 kb of genomic DNA derived from parts of the mouse Trpa1 locus that flank the 45.3 kb sequence of the mouse Trpa1 gene intended for deletion. In separate experiments, the Trpa1 humanizing LTVEC was combined with a plasmid encoding Cas9 and a second plasmid encoding one of eight gRNAs (A, A2, B, C, D, E2, E, and F; see Table 1) designed to create double-strand breaks within the region of the mouse Trpa1 gene that was targeted for deletion. The gRNAs were designed to avoid recognition of any sequence in the inserted portion of the human TRPA1 gene. In other experiments, we combined the LTVEC and the Cas9-encoding plasmid with plasmids encoding two different gRNAs that target different sites within the Trpa1 gene that was targeted for deletion.

The results of the CRISPR/Cas9-assisted humanization of the Trpa1 gene are shown in Table 18 and are similar to the results obtained for CRISPR/Cas9-assisted humanization of the Lrp5 and C5 (Hc) genes. The targeting efficiency with LTVEC alone was 0.3%, and addition of Cas9 and gRNAs increased the targeting efficiency for six of the eight gRNAs tested. Combining the B and F gRNAs increased the total Trpa1 targeting efficiency to 3.4% by increasing the frequency of the heterozygous, hemizygous, and homozygous targeting events. We also found ES cell clones with large CRISPR-induced deletions on both alleles (observed at a frequency of 0.3%).

gous targeting when using two gRNAs with the targeting vector (see Tables 15 and 18). Similarly, we found correctly targeted clones that were hemizygous for the gene modification (i.e., they had a precisely targeted humanization on one allele and a very large, sometimes gene ablating, deletion on the other allele) for Lrp5 targeting, C5 (Hc) targeting, Ror1 targeting, and Trpa1 targeting. Such modifications did not occur at all when using one gRNA to achieve Lrp5, C5 (Hc), Ror1, or Trpa1 humanization (see Tables 13, 15, 17, and 18, respectively).

Second, we found clones that had identical very large deletions (>45 kb) induced by Cas9 cleavage events guided by both gRNAs on both targeted alleles (i.e., the cells were homozygous for a large, sometimes gene-ablating, deletion at the target locus). These types of mutations do not require the targeting vector directed against the same gene. For example, as shown in Table 15, we have obtained ES cells with homozygous CRISPR-induced deletions by combining Cas9 and two gRNAs with a targeting vector directed against a different gene unrelated to the one targeted by the gRNAs. Thus, a Cas9 nuclease guided by two gRNAs can

TABLE 18

Screening Results for CRISPR/Cas9-Assisted Humanization of the Trpa1 Gene Using Individual gRNAs and Combined gRNAs.

| gRNA | Distance of gRNA Site from 5'/3' Ends of Targeted Deletion (bp) | Targeting Efficiency by Allele Type | | | | |
|---|---|---|---|---|---|---|
| | | Het. Targ. (% Eff.) | Hemi. Targ. (% Eff.) | Homo. Targ. (% Eff.) | Total Targ. (% Eff.) | Homo. Del. (% Eff.) |
| A | 100 (5') | 1.0 | | | 1.0 | |
| A2 | 500 (5') | 2.1 | | | 2.1 | |
| B | 1000 (5') | 1.4 | | | 1.4 | |
| C | 25600 (5')/ 19740 (3') | 1.0 | | | 1.0 | |
| D | 26970 (5')/ 18370 (3') | 2.1 | | | 2.1 | |
| E2 | 1000 (3') | 0.0 | | | 0.0 | |
| E | 500 (3') | 0.0 | | | 0.0 | |
| F | 100 (3') | 0.7 | | | 0.7 | |
| B + F | B: 1000 (5') F: 100 (3') | 2.8 | 0.3 | 0.3 | 3.4 | 0.3 |
| None | N/A | 0.3 | | | 0.3 | |

As these examples illustrate, use of dual guide RNAs at widely separated sites improved the enhancement of heterozygous humanization compared with single gRNAs. In addition, use of dual guide RNAs promoted biallelic events compared to single gRNAs. In contrast to targeting with one gRNA, targeting with two gRNAs results in the creation of homozygously targeted cells (Hum/Hum) in which both alleles had a targeted humanization, homozygously deleted cells (Δ/Δ) in which neither allele was targeted with the humanizing LTVEC but both had large deletions, and hemizygously targeted cells (Hum/Δ) in which one allele had a targeted humanization and the other had a large dual gRNA/Cas9-induced deletion. First, we found correctly targeted clones that had precise and identical very large humanizations at both target alleles (e.g., cells that were homozygous for the targeted gene modification). Although homozygously targeted clones were also observed when we used one gRNA to achieve Lrp5 humanization, they occurred at a much lower frequency than when we employed two gRNAs (see Table 13). Likewise, we did not observe homozygous targeting when using one gRNA to achieve C5 (Hc) humanization or Trpa1 humanization, but we did observe homozyinduce a large deletion in cells without addition of a targeting vector. In such cases, transient or stable drug selection provided by a vector that expresses a drug resistance gene can facilitate the isolation of rare homozygous deletion clones by enrichment for ES cells that have taken up DNA.

Example 6. Analysis of Large Deletions Induced by Combined gRNAs

Allele Structures for Large Deletions Induced by Combined gRNAs

Additional sequence analysis was performed on clones comprising large deletions induced by Cas9 cleavage events guided by two gRNAs (see Table 19). These large deletions appeared to be independent of the LTVEC-directed homologous recombination events at the same locus in that we obtained large deletions at the Lrp5 locus at approximately the same frequency when we combined the gRNAs with either an Lrp5 LTVEC or one targeting the Ch25h gene nearly 30 Mb away (data not shown). To characterize the large deletions, we performed deletion-spanning PCRs on 40 clones, 15 hemizygous and 25 with biallelic large deletions, from six humanizations, and sequenced individual clones of the PCR products. The sequences confirmed the large deletions, which ranged from 38 kb to 109 kb. Three of the ES cell clones (Lrp5 clones AW-A8 and BP-D3 and Adamts5 clone X-B11) had perfectly repaired precise deletions (68.2 kb) between the predicted Cas9 cleavage sites, while one clone (Hc clone P-B12) had a single base pair insertion in addition to the 38.1 kb deletion. Twenty-seven of the ES cell clones had deletions that extended beyond the Cas9 cleavage sites, consistent with imprecise repair by non-homologous end joining (NHEJ). The remaining nine ES cell clones had mutations that combined apparent NHEJ-induced deletions and insertions (e.g., Lrp5 clone BP-F6 and Hc clone O-E4), five of which had insertions of greater than 200 bp that we could map to their source genomic loci (data not shown). The 210 bp insertion in Lrp5 clone BO-E9 was in an inverted orientation with respect to an identical sequence lying approximately 2,600 bp outside of the gRNA F target site in the centromeric direction (chromosome 19+, 3589138-3589347). This sequence was present in the long 3' homology arm of the Lrp5 LTVEC. Lrp5 clones BP-F6 and BP-G7 were derived from an experiment in which we combined Lrp5 gRNAs A and F with Cas9 and an LTVEC that targeted the Ch25h gene 30 Mb away from Lrp5 in the telomeric direction. Clone BP-F6 had a 266 bp insertion that appeared to be derived from one end of the Ch25h LTVEC in that it was composed of a 103 bp fragment identical to part of the vector backbone linked to a 163 bp fragment that was identical to a sequence near Ch25h and also present in the long arm of the LTVEC (chromosome 19+, 34478136-34478298); this fragment was inserted at the deletion in an inverted orientation with respect to the endogenous chromosomal sequence. Hc clone O-E4 had a 254 bp insertion that was inverted with respect to an identical sequence found within the deleted sequence approximately 3.1 kb away from the gRNA A recognition sequence. The 1,304 bp insertion in Hc clone S-D5 was composed of two fragments: a 1,238 bp piece that was in the same orientation as an identical sequence found within the deleted sequence approximately 1.4 kb away from the predicted gRNA E2-directed Cas9 cleavage site and a second 66 bp piece that was a duplication in an inverted orientation of an identical sequence 25 bp outside of the gRNA E2 cut site.

TABLE 19

Allele Structures for Large Deletions Induced by Combined gRNAs.

| Gene | ES Cell Clone | Genotype[1] | gRNAs | Positions Within Targeted Deletion (bp) | Size of Deletion (kb) | Additional Sequence Deleted (bp) | Insertion (bp) | PCR Clones |
|---|---|---|---|---|---|---|---|---|
| Lrp5 | AW-A8 | Δ/Δ | A + F | 5'-50/50-3' | 68.2 | — | — | 40 |
|  | BO-E9 | Δ/Δ |  |  |  | 12 | 210 | 17 |
|  | BP-D3 | Δ/Δ |  |  |  | — | — | 11 |
|  | BP-F6 | Δ/Δ |  |  |  | 30 | 266 | 6 |
|  | BP-G7 | Δ/Δ |  |  |  | 77 |  | 9 |
|  | BA-A7 | Δ/Δ | A + E2 | 5'-50/1,000-3' | 67.3 | 7 |  | 19 |
|  | BA-C7 | Δ/Δ |  |  |  | 84 |  | 32 |
| Hc | N-A11 | Δ/Δ | A + C | 5'-100/38,200-3' | 38.1 | 14 |  | 12 |
|  | N-D4 | Δ/Δ |  |  |  | 10 |  | 15 |
|  | N-D11 | Hum/Δ |  |  |  | 20 |  | 10 |
|  |  |  |  |  |  | 10 |  | 1 |
|  | N-E1 | Hum/Δ |  |  |  | 10 |  | 13 |
|  | N-E9 | Hum/Δ |  |  |  | 20 |  | 16 |
|  | O-C5 | Hum/Δ |  |  |  | 31 |  | 21 |
|  | O-D2 | Hum/Δ |  |  |  | 5 |  | 12 |
|  | O-E4 | Hum/Δ |  |  |  | 19 | 254 | 18 |
|  | O-E5 | Hum/Δ |  |  |  | 35 | 2 | 16 |
|  | O-E6 | Hum/Δ |  |  |  | 6 |  | 17 |
|  | O-F11 | Hum/Δ |  |  |  | 12 | 7 | 18 |
|  | O-F12 | Hum/Δ |  |  |  | 41 |  | 6 |
|  |  |  |  |  |  | 35 |  | 1 |
|  | P-B12 | Δ/Δ |  |  |  |  | 1 | 7 |
|  | P-C12 | Δ/Δ |  |  |  | 20 |  | 15 |
|  | P-D1 | Δ/Δ |  |  |  | 33 |  | 10 |
|  | P-G8 | Δ/Δ |  |  |  | 5 |  | 2 |
|  | Q-F5 | Hum/Δ | A + E2 | 5'-100/100-3' | 75.6 | 3 | 3 | 15 |
|  | Q-F10 | Δ/Δ |  |  |  | 46 |  | 13 |
|  | R-A5 | Δ/Δ |  |  |  | 18 |  | 14 |
|  | R-A7 | Δ/Δ |  |  |  | 37 |  | 15 |
|  | R-A9 | Hum/Δ |  |  |  | 261 |  | 8 |
|  | R-C8 | Hum/Δ |  |  |  | 180 |  | 11 |
|  | R-D12 | Hum/Δ |  |  |  | 182 |  | 10 |
|  | R-F11 | Hum/Δ |  |  |  | 19 |  | 11 |
|  | S-A11 | Δ/Δ |  |  |  | 122 |  | 11 |
|  |  |  |  |  |  | 46 |  | 1 |
|  | S-D5 | Δ/Δ |  |  |  | 216 | 1304 | 8 |
| Ror1 | Y-B5 | Δ/Δ | A + F | 5'-200/200-3' | 109 | 18 |  | 6 |
|  | Y-C7 | Δ/Δ |  |  |  | 23 |  | 7 |
|  | Y-E1 | Δ/Δ |  |  |  | 12 |  | 3 |

TABLE 19-continued

Allele Structures for Large Deletions Induced by Combined gRNAs.

| Gene | ES Cell Clone | Genotype[1] | gRNAs | Positions Within Targeted Deletion (bp) | Size of Deletion (kb) | Additional Sequence Deleted (bp) | Insertion (bp) | PCR Clones |
|---|---|---|---|---|---|---|---|---|
| Trpa1 | AD-C7 | Δ/Δ | B + F | 5'-1,000/100-3' | 44.6 | 30 | | 8 |
| Dpp4 | S-F1 | Δ/Δ | | 5'-50/38,100-3' | 40.7 | 18 | 877 | 20 |
| | S-G6 | Δ/Δ | | | | 35 | 3 | 17 |
| Adamts5 | X-B11 | Δ/Δ | | 5'-1000/100-3' | 37.4 | | | 11 |

[1]Hum/+, targeted humanization of one of the two native alleles resulting in a heterozygous genotype; Hum/Δ, a biallelic modification in which one allele has a targeted humanization and the other has a large Cas9-gRNA-induced deletion resulting in a hemizygous genotype; Hum/Hum, a biallelic modification in which both alleles have a targeted humanization resulting in a homozygous genotype; Δ/Δ a biallelic modification in which both alleles have a large Cas9-gRNA-induced deletion.

Evidence for Gene Conversion at Homozygous Alleles

Twenty-four of the twenty-five ES cell clones with biallelic large deletions had only a single, unique sequence (Table 19), indicating that they were homozygous alleles. For Hc clone S-All, we found the same sequence in 11 of 12 PCR clones. The single clone with a different sequence might suggest two different deletion alleles, but we also found the same result for two of the Hc hemizygous clones, N-D11 and O-F12. The distinct homozygous deletion alleles in multiple clones suggested they might have arisen by a gene conversion mechanism in which a deletion on one chromosome served as a template for homologous recombination repair of Cas9 cleavages on the homologous chromosome. We took advantage of the 129S6SvEvTac (129) and C57BL/6NTac (B6) F1 hybrid composition of the VGF1 ES cell line (Poueymirou et al. (2007) Nat. Biotechnol. 25:91-99; Valenzuela et al. (2003) Nat. Biotechnol. 21:652-659) to assay for gene conversion as loss of heterozygosity (Lefebvre et al. (2001) Nat. Genet. 27:257-258) for structural (SV) and single nucleotide (SNV) variants between the strains around the Lrp5 locus on chromosome 19 (see FIG. 12 for the five SV assays and ten SNV assays used below) and the Hc locus on chromosome 2 (not shown). To confirm that any loss of heterozygosity was not the result of whole chromosome loss, we performed chromosome copy number (CCN) assays at sites that were identical between the 129 and B6 strains. For Lrp5 humanized or deleted alleles we assayed multiple SVs and SNVs positioned from 1.2 Mb away from Lrp5 in the telomeric direction to the end of the long arm of chromosome 19 (FIG. 12). Because of Lrp5's location close to the centromere, we found no SVs and only one SNV on the centromeric side of the gene. For Hc, we were able to assay for multiple SVs and SNVs on either side of the gene on chromosome 2 (not shown). The results for six of the Lrp5 clones are shown in FIGS. 15A-E and 16A-C.

FIG. 15A-E shows results for five SV assays, whose positions ranged from 13.7 Mb away from Lrp5 to 56.7 Mb away near the telomeric end of the long arm. The five SV assays produced two different sized products for the 129 (larger) and B6 (smaller) alleles in the 129, B6, and VGF1 controls. The approximate positions of the SV assays on the chromosome 19 map are shown in FIG. 12 (see assay SV 13.7, assay SV 20.0, assay SV 36.9, assay SV 48.3, and assay SV 56.7). The assay number represents the number of Mb telomeric to Lrp5. Primers for these assays are shown in Table 1, and the results are shown in FIG. 15A-E. Two of the clones, BC-H9 (Lrp5$^{Hum/Hum}$, gRNA B2) and BR-B4 (Lrp5$^{Hum/Hum}$, gRNA D), displayed a loss of heterozygosity that retained all of the B6 SV alleles, while a third clone, BO-A8 (Lrp5$^{Hum/Hum}$, gRNAs A+F), retained all of the 129 alleles. The other three clones, BO-F10 (Lrp5$^{Hum/Hum}$, gRNAs A+F), BO-G11 (Lrp5$^{Hum/Hum}$, gRNAs A+F), and BP-G7 (Lrp5$^{Δ/Δ}$, gRNAs A+F), remained heterozygous.

Figure 16A:
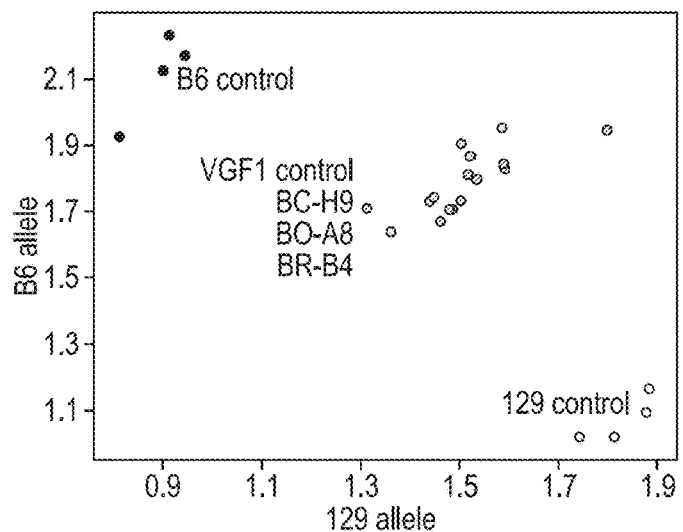
FIGS. 16A-16C show allelic discrimination plots for the 0.32 Mb centromeric of Lrp5 (FIG. 16A), 1.2 Mb telomeric of Lrp5 (FIG. 16B), and 57.2 Mb telomeric of Lrp5 (FIG. 16C). The values on each axis represent relative fluorescence intensity. The plots depict four replicates for each sample, which are shown as solid dots (B6 allele), open dots (129 allele), and dots with diagonal lines (both B6/129 alleles).
Figure 16B:
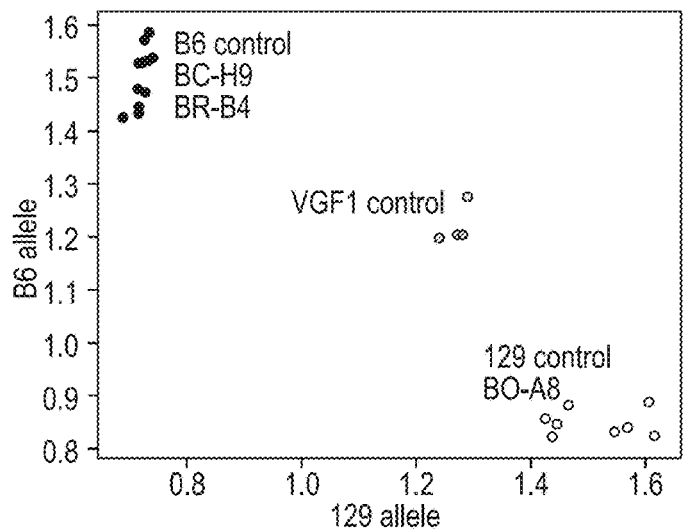
Figure 16C:
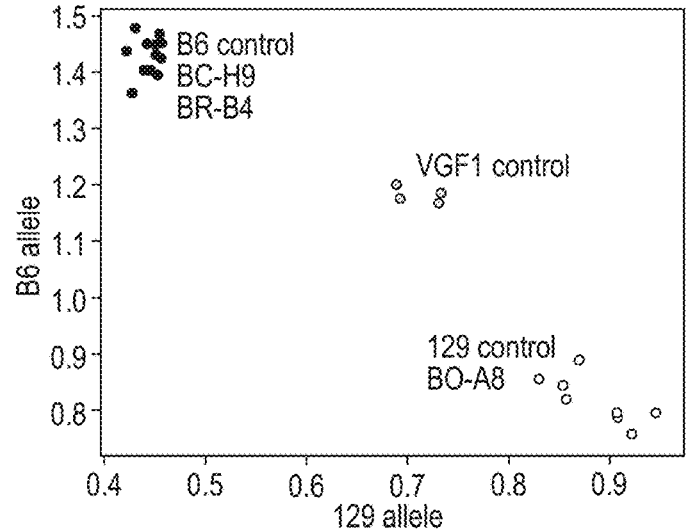
Figure 18A:
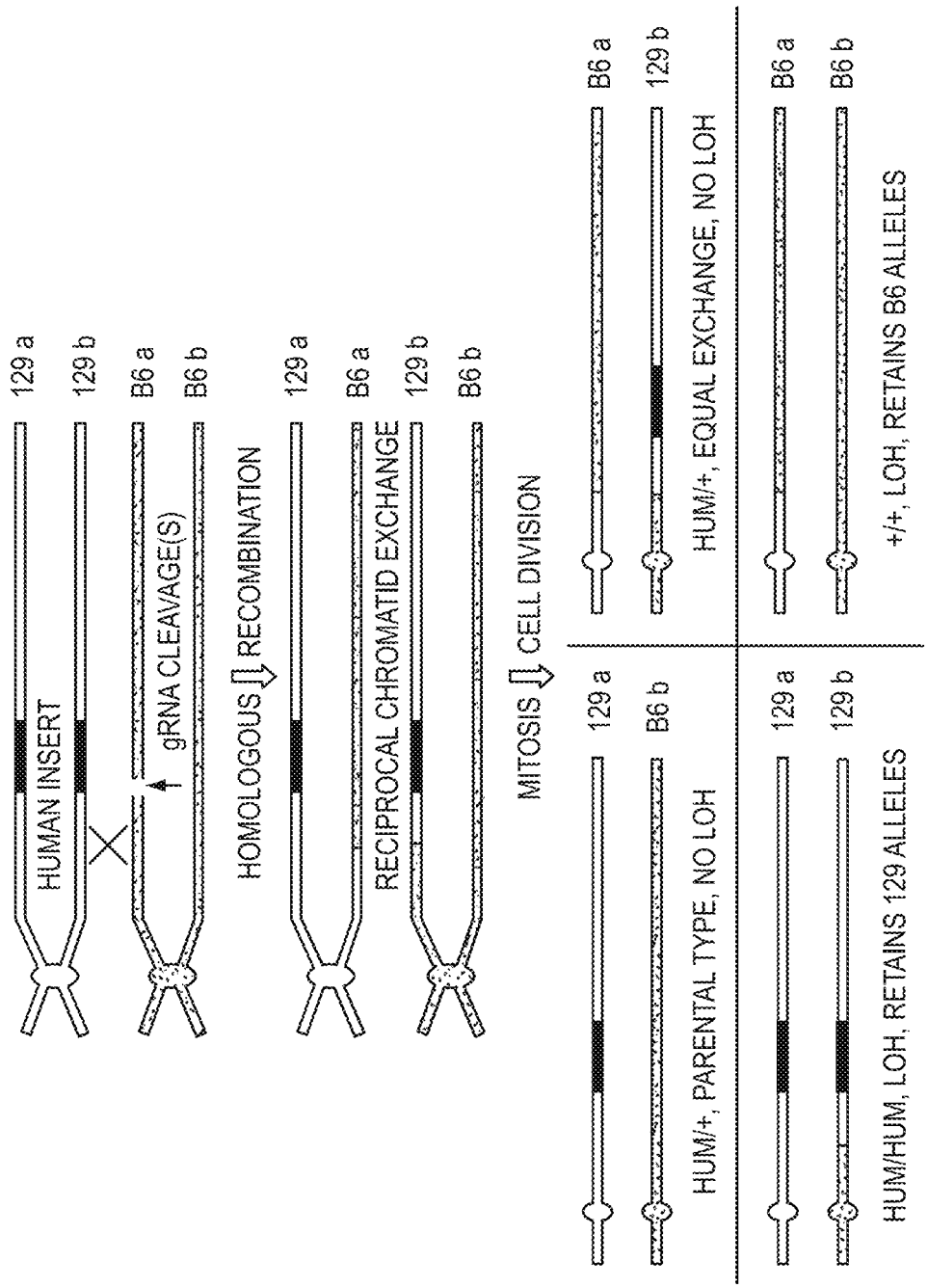
FIGS. 18A-18F show possible mechanisms explaining the results observed, including loss of heterozygosity (LOH), in CRISPR/Cas9-assisted humanization experiments in F1 hybrid mouse ES cells having one haploid chromosome complement derived from the 12956/SvEvTac mouse strain and one haploid chromosome complement derived from the C57BL/6NTac (B6) mouse strain.
Figure 18B:
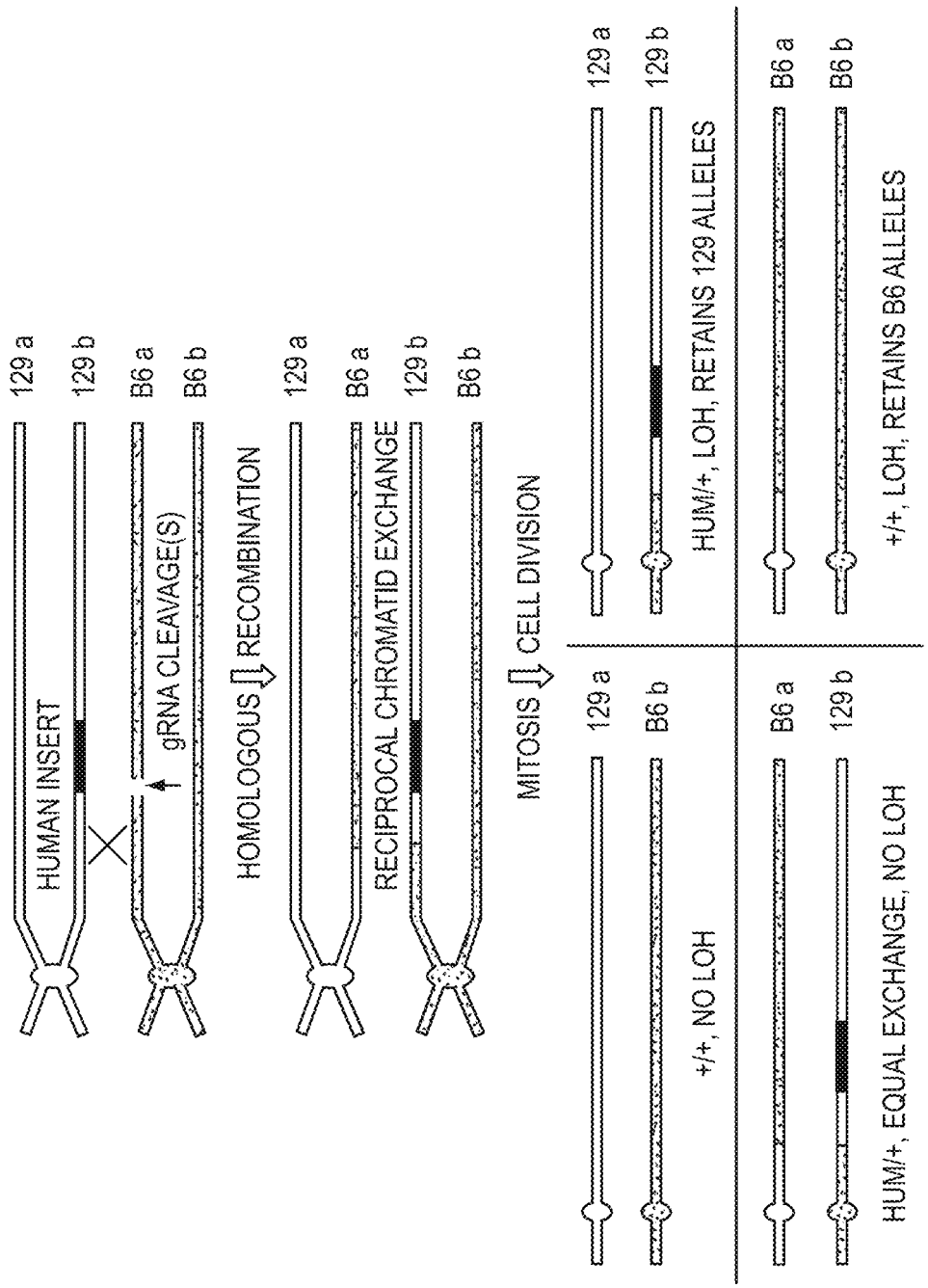
Figure 18C:
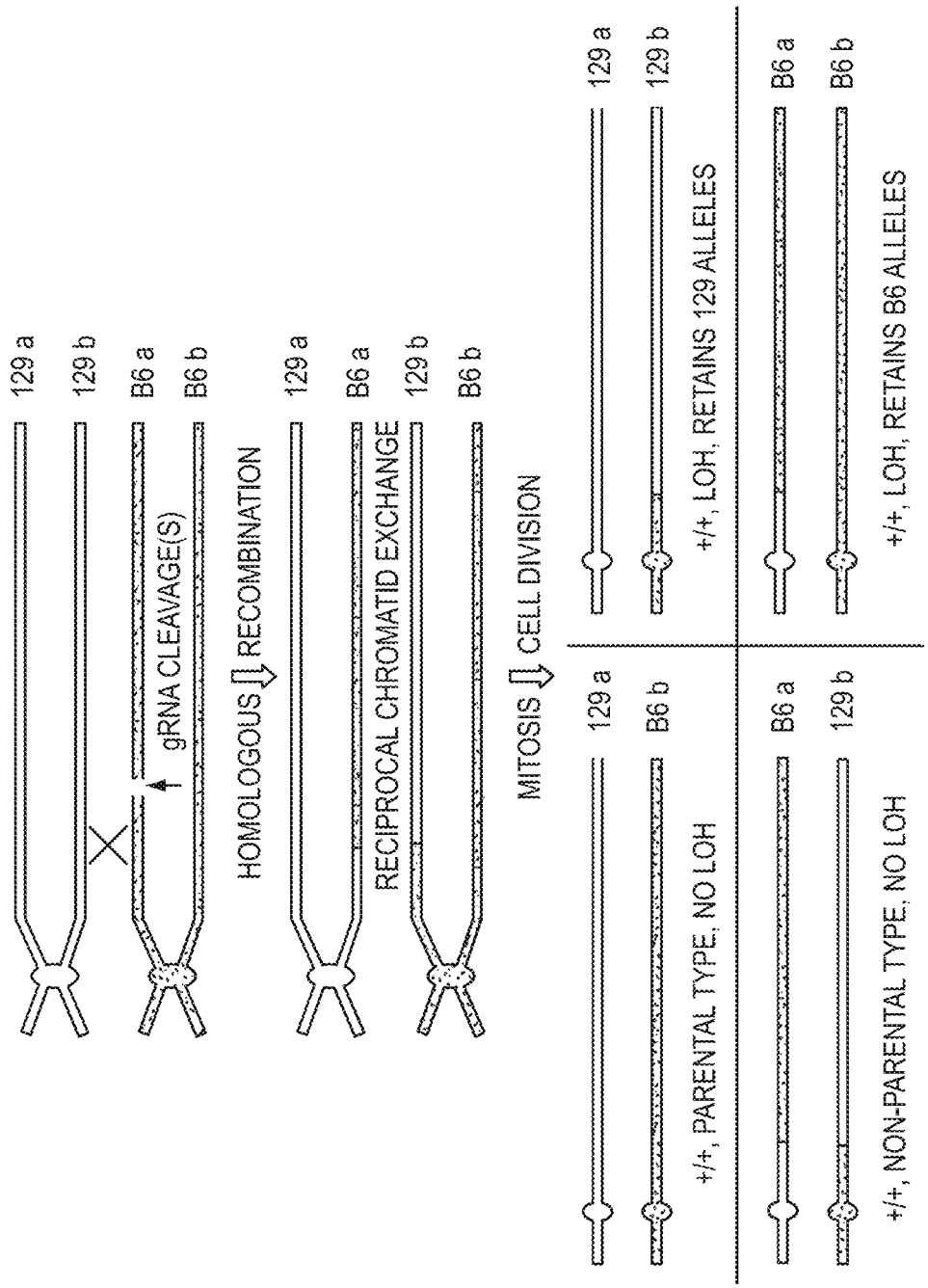
Figure 18D:
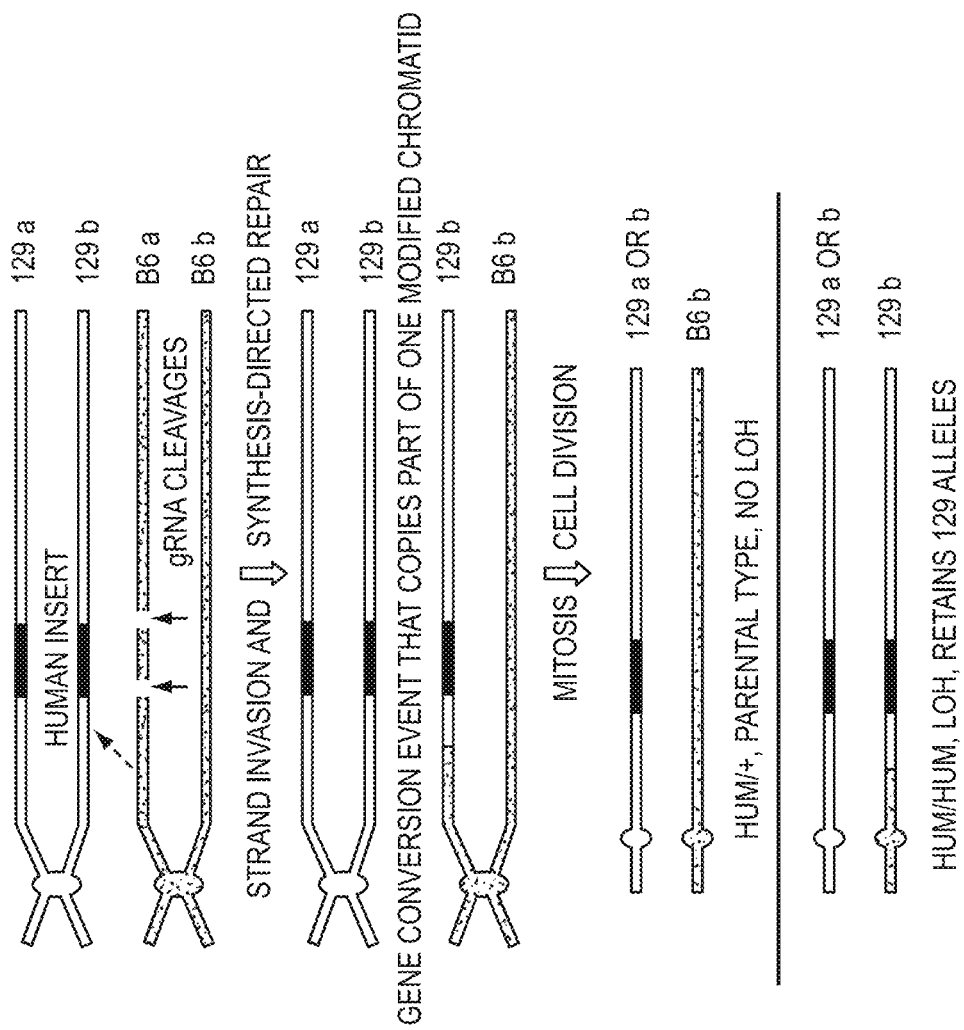
Figure 18E:
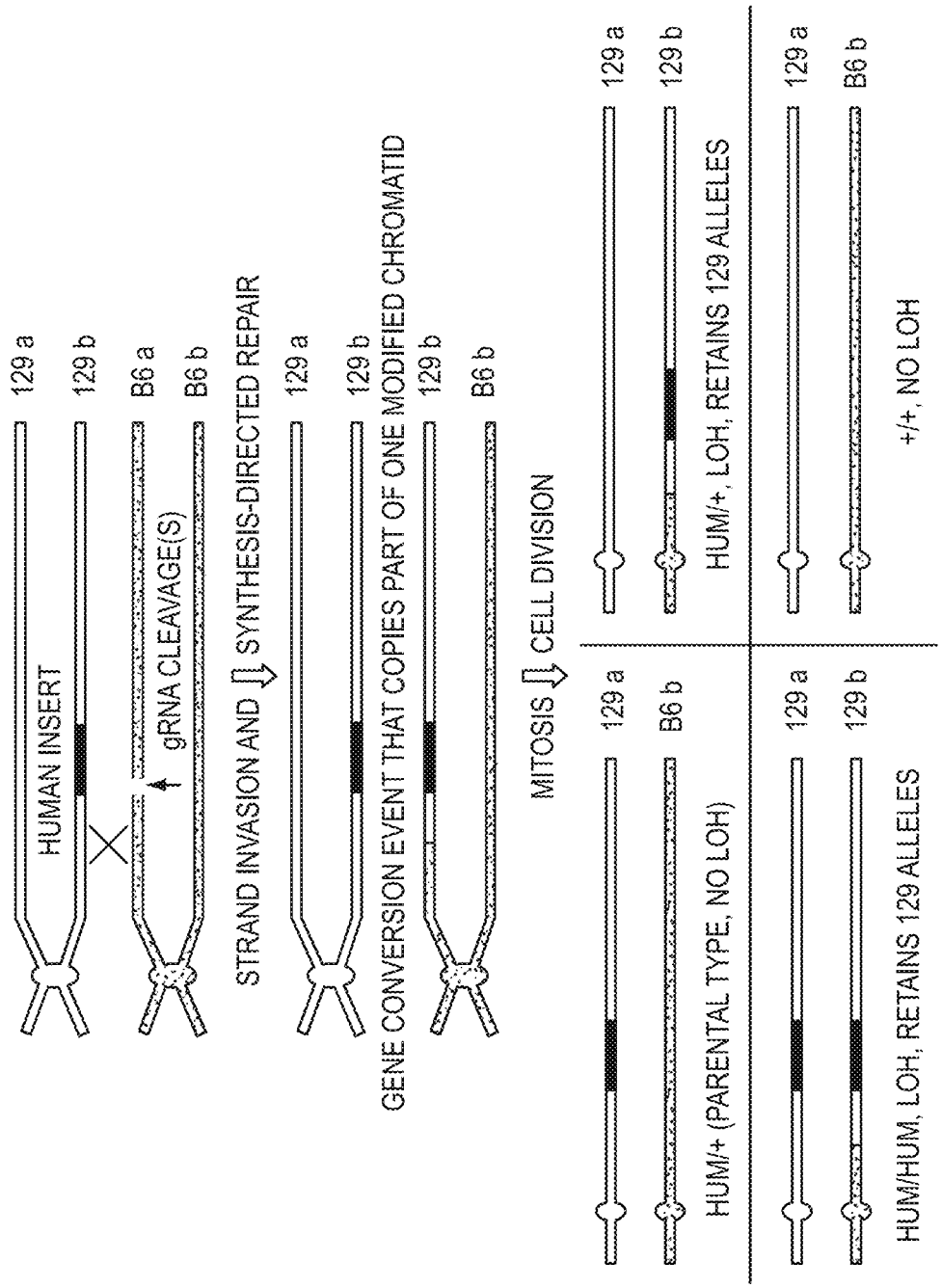
Figure 18F:
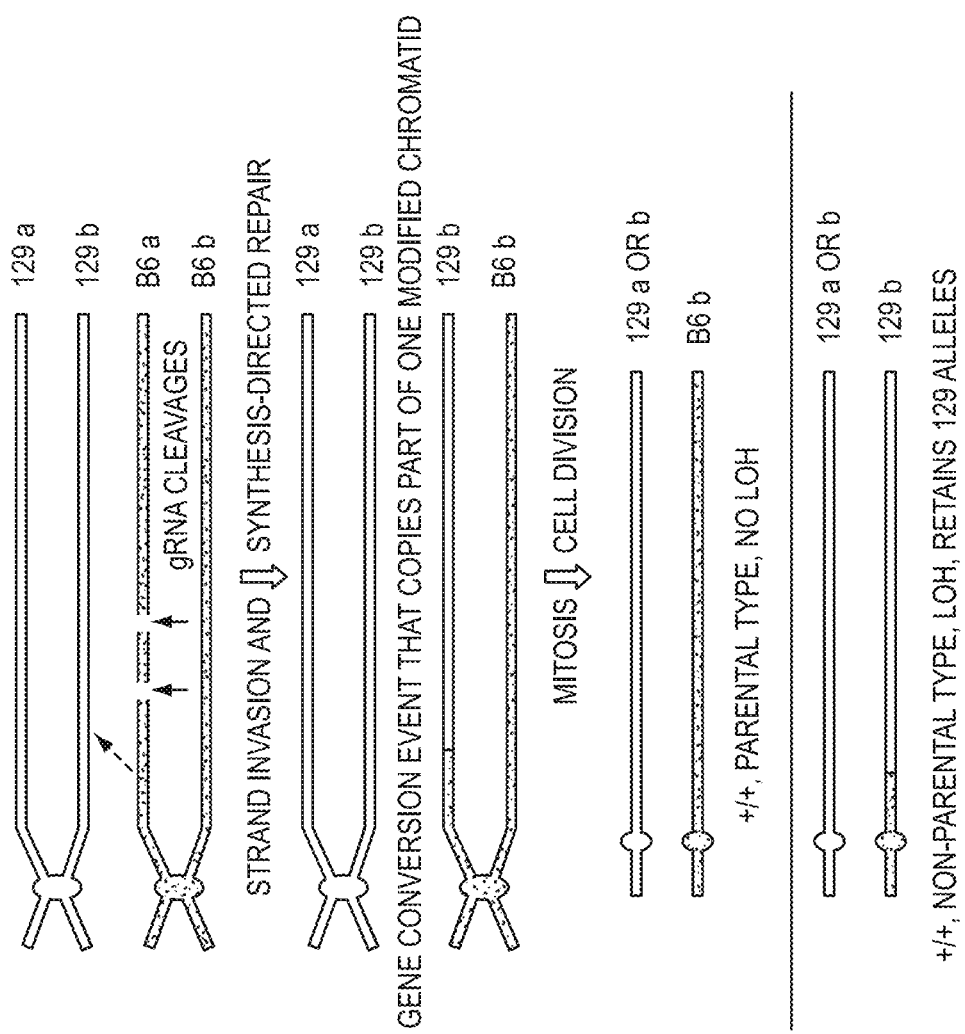

In addition, single nucleotide variants (SNVs) between the 129 and B6 alleles were assayed by TAQMAN® allelic discrimination assays. The approximate positions of the SNV assays on the chromosome 19 map in FIG. 12 are shown by arrowheads with assay numbers underneath, and their distances (in Mb) from the Lrp5 locus are given below. The distances (in Mb) from the Lrp5 locus are as follows: 0.32 centromeric of Lrp5 (C2), 1.2 telomeric of Lrp5 (T3), 11.1 telomeric of Lrp5 (T6), 13.2 telomeric of Lrp5 (T7), 17.5 telomeric of Lrp5 (T8), 25.8 telomeric of Lrp5 (T9), 33.0 telomeric of Lrp5 (T10), 38.3 telomeric of Lrp5 (T11), 49.6 telomeric of Lrp5 (T13), and 57.2 telomeric of Lrp5 (T14). The 129-specific and B6-specific probes and the primer pairs are shown in Table 1. The results for three clones (BC-H9, BO-A8, and BR-B4) that showed telomeric loss-of-heterozygosity (LOH) by SV assays are shown in FIG. 16A-C. The SNV assays (FIG. 16A-C and data not shown) confirmed the gene conversion events over the long arm of chromosome 19 on the telomeric side of Lrp5 (SNV 1.2 and SNV 57.2; see FIG. 16B and FIG. 16C, respectively), but the SNV 0.32 assay (see FIG. 16A) showed that all clones remained heterozygous for an allele 320 kb away from Lrp5 on the centromeric side. Of the 24 Lrp5$^{Hum/Hum}$ or Lrp5$^{Δ/Δ}$ clones assayed, we found six that had evidence of loss of heterozygosity over the entire long arm of chromosome 19 on the telomeric side of Lrp5. Five of the clones (four Lrp5$^{Hum/Hum}$ and one Lrp5$^{Δ/Δ}$) converted from heterozygous to homozygous B6, while a sixth clone (Lrp5$^{Hum/Hum}$) converted to homozygous 129. CCN assays demonstrated retention of two copies of chromosome 19. Similar loss of heterozygosity assays for 21 Hc homozygous clones revealed that two, R-E2 (Hc$^{Hum/Hum}$, gRNAs A+F) and R-E8 (Hc$^{Δ/Δ}$, gRNAs A+F), showed loss of heterozygosity to homozygous 129 for all SVs and SNVs on the telomeric side of the Hc gene while retaining heterozygosity for all alleles on the centromeric side. CCN assays indicated no loss of chromosome 2.

Our results demonstrate for the first time that CRISPR/Cas9 can enhance homology-directed repair for large single-step humanizations of over 100 kb, which expands the possibilities for large-scale genome engineering. The most remarkable and unexpected benefit of combining LTVECs and gRNA/Cas9 was their ability to promote homozygous targeted humanizations. Although biallelic mutations and homozygous targeting events have been reported in other CRISPR/Cas9 experiments, most of these gene modifications and insertions have been orders of magnitude smaller than our humanized alleles. Prior to the use of CRISPR/

Cas9, we had never found homozygous targeting by an LTVEC, nor had we seen simultaneous targeting of more than one gene when we combined multiple LTVECs targeting separate genes. Given this experience, the gRNA/Cas9-induced homozygous targeting suggested that rather than two LTVECs separately targeting both alleles, an initial targeting event on one allele might serve as a template for the homologous conversion of the other allele promoted by one or more Cas9 cuts. The revelation that the dual gRNA/Cas9-induced large biallelic deletions were also homozygous (Table 19) provided further support for a gene conversion mechanism.

Loss of heterozygosity assays (FIG. 12) demonstrated that large-scale gene conversion of multiple alleles covering a large fragment of the chromosome on the telomeric side of the target gene was responsible for some of the homozygous humanizations and large deletions. This type of long-range directional gene conversion is consistent with mitotic recombination between the replicated chromatids of homologous chromosomes in the G2 phase of the cell cycle (Lefebvre et al. (2001) Nat. Genet. 27:257-258) (FIG. 17A-C). Although it explained only a minority of the homozygous events, this mechanism could provide a means by which gRNA/Cas9 cleavage can be used to promote large-scale conversion from heterozygous to homozygous for multiple alleles over a large portion of a chromosome. Most of the homozygous events, however, appear to have been the result of local gene conversion whose mechanism deserves further investigation.

Further evidence for long-range directional gene conversion was provided by analysis of three clones obtained after electroporating F1H4 hybrid ES cells (which are comprised of 50% 129SvS6 strain and 50% C57BL/6N strain) with plasmids encoding Lrp5 gRNAs A and F, a plasmid encoding Cas9, and an LTVEC that targeted the Ch25h gene 30 Mb away from Lrp5 in the telomeric direction. Three clones initially scored as wild type following primary screening using TAQMAN® assays inside the predicted deletion between the 2 gRNAs (500 bp away at the 5' end and 2 kb at the 3' end), but subsequent TAQMAN® allelic discrimination assays assaying single nucleotide variants (SNVs) between the 129 and B6 alleles surprisingly revealed loss of heterozygosity. The SNV assays used were one centromeric assay (SNV 0.32) and two telomeric assays (SNV 1.2 and SNV 57.2) (see FIG. 12). As shown in Table 20, the centromeric SNV assay (0.32 Mb) confirmed retention of heterozygosity in all three clones. However, both telomeric SNV assays showed that BP-E7 and BP-H4 were homozygous for the 129 allele, and both telomeric SNV assays showed that BP-E6 was homozygous for the B6 allele. All three clones showed retention of two copies of chromosome 19, and all three clones were transgenic for LTVEC targeting (i.e., the Ch25h locus was targeted). These results open the possibility to forced homozygosity using targeted CRISPR/Cas9 cleavage.

TABLE 20

Screening Results for SNV Allelic Discrimination Assays.

| Clone | SNV 0.32 | SNV 1.2 | SNV 57.2 |
|---|---|---|---|
| BP-E7 | 129/B6 | 129/129 | 129/129 |
| BP-H4 | 129/B6 | 129/129 | 129/129 |
| BP-E6 | 129/B6 | B6/B6 | B6/B6 |

Several possible mechanisms can explain the results observed in the CRISPR/Cas9-assisted LTVEC humanization experiments in mouse F1H4 hybrid ES cells (which are comprised of 50% 129SvS6 strain and 50% C57BL/6N strain) (see FIG. 18A-F). Such mechanisms could occur through reciprocal chromatid exchange by mitotic cross over (see FIG. 18A-C), or by chromatid copying by break-induced replication (see FIG. 18D-E). In either case, a heterozygous modification could occur in which either the 129 chromosome or the B6 chromosome is targeted by the LTVEC before genome replication (see FIGS. 18A and 18D). Alternatively, a single 129 chromatid or a single B6 chromatid could be targeted by the LTVEC after genome replication, followed by inter-chromatid gene conversion (see FIGS. 18B and 18E). Alternatively, there can be a lack of LTVEC targeting at the target genomic locus, but Cas9 cleavage can occur on either the 129 or B6 chromosome (see FIGS. 18C and 18F). This latter possibility can explain the results seen with the BP-E7, BP-H4, and BP-E6 clones. The potential outcomes are shown in FIG. 18A-F. For FIG. 18F, it is also possible to observe loss of heterozygosity (LOH) retaining the B6 alleles if the Cas9 cleaves a 129 chromatid. In the experiments described above, loss of heterozygosity events have been observed resulting in both alleles being targeted (Hum/Hum) or both alleles being wild type alleles (+/+).

Example 7. Homozygous Targeting for Genes with Least Variation Between B6 and 129 Alleles Several other loci were also tested for homozygous targeting. In another experiment, the LTVEC was designed to create a 38 kb deletion of the mouse Adamts5 (a disintegrin and metalloproteinase with thrombospondin motifs 5) gene and a simultaneous replacement with a 43 kb fragment of the human ADAMTS5 gene. The LTVEC comprised the 43 kb fragment of the human ADAMTS5 gene flanked by homology arms containing 22 kb and 46 kb of genomic DNA derived from parts of the mouse Adamts5 locus that flank the 38 kb sequence of the mouse Adamts5 gene intended for deletion. In separate experiments, we combined the Adamts5 humanizing LTVEC with a plasmid encoding Cas9 and a second plasmid or plasmids encoding one or two of eight sgRNAs (gA, gA2, gB, gC, gD, gE, gE2, and gF) designed to create double strand breaks within the region of the mouse Adamts5 gene that was targeted for deletion. The sgRNAs were designed to avoid recognition of any sequence in the inserted portion of the human ADAMTS5.

The results of the CRISPR/Cas9-assisted humanization of the Adamts5 gene are shown in Table 21. When the LTVEC alone was introduced into ES cells, we found that none of the 96 screened drug resistant clones carried a correctly targeted monoallelic heterozygous humanized allele. In contrast, combining the LTVEC with Cas9 endonuclease guided by two of eight tested sgRNAs (B and F; see Table 1) produced correctly targeted monoallelic heterozygous mutations or biallelic compound heterozygous mutations at an efficiency of 1.0%. No homozygous targeted modifications were observed. In additional experiments, gRNAs A2 and E2 were also combined, but still no homozygous targeting was observed.

TABLE 21

Screening Results for CRISPR/Cas9-Assisted Humanization of the Adamts5 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 85.7 | 96 | 0 | 0 | 0 |
| 5' | 500 | gRNA A2 | 54.8 | 96 | 0 | 0 | 0 |
| 5' | 1000 | gRNA B | 66.7 | 96 | 1 | 0 | 0 |
| middle | 18700/18950 | gRNA C | 9.5 | 96 | 0 | 0 | 0 |
| middle | 18800/18850 | gRNA D | 4.8 | 96 | 0 | 0 | 0 |
| 3' | 1000 | gRNA F | 36.9 | 96 | 0 | 1 | 0 |
| 3' | 500 | gRNA E | 54.8 | 96 | 0 | 0 | 0 |
| 3' | 100 | gRNA E2 | 54.8 | 96 | 0 | 0 | 0 |
| 5' and 3' | 500/100 | A2 + E2 | no assay | 96 | 0 | 0 | 0 |
| N/A | N/A | none | N/A | 96 | 0 | 0 | 0 |

In another experiment, the LTVEC was designed to create a 79 kb deletion of the mouse Dpp4 (dipeptidyl peptidase 4) gene and a simultaneous replacement with an 82 kb fragment of the homologous human DPP4 gene. The LTVEC comprised the 82 kb fragment of the human DPP4 gene flanked by 5' and 3' homology arms, each containing 46 kb of genomic DNA derived from parts of the mouse Dpp4 locus that flank the 79 kb sequence of the mouse Dpp4 gene intended for deletion. In separate experiments, we combined the Dpp4 humanizing LTVEC with a plasmid encoding Cas9 and a second plasmid or plasmids encoding one or two of eight sgRNAs (gA, gB, gB2, gC, gD, gE, gE2, and gF) designed to create double strand breaks within the region of the mouse Dpp4 gene that was targeted for deletion. The sgRNAs were designed to avoid recognition of any sequence in the inserted portion of the human DPP4 gene.

The results of the CRISPR/Cas9-assisted humanization of the Dpp4 gene are shown in Table 22. When the LTVEC alone was introduced into ES cells, we found that 2.1% of the screened drug resistant clones carried a correctly targeted monoallelic heterozygous humanized allele. In contrast, combining the LTVEC with Cas9 endonuclease guided by any one of eight tested sgRNAs (A, B, B2, C, D, E, E2, and F; see Table 1) produced correctly targeted monoallelic heterozygous mutations at efficiencies that ranged from 2.1 to 7.3%. No homozygous targeted modifications were observed. In additional experiments, gRNAs A and F or gRNAs A and D were combined, but still no homozygous targeting was observed.

In another experiment, the LTVEC was designed to create a 55 kb deletion of the mouse Folh1 (glutamate carboxypeptidase 2) gene and a simultaneous replacement with a 61 kb fragment of the homologous human FOLH1 gene. The LTVEC comprised the 61 kb fragment of the human FOLH1 gene flanked by homology arms containing 22 kb and 46 kb of genomic DNA derived from parts of the mouse Folh1 locus that flank the 55 kb sequence of the mouse Folh1 gene intended for deletion. In separate experiments, we combined the Folh1 humanizing LTVEC with a plasmid encoding Cas9 and a second plasmid or plasmids encoding one or two of eight sgRNAs (gA, gA2, gB, gC, gD, gF, gE, and gE2) designed to create double strand breaks within the region of the mouse Folh1 gene that was targeted for deletion. The sgRNAs were designed to avoid recognition of any sequence in the inserted portion of the human FOLH1 gene.

The results of the CRISPR/Cas9-assisted humanization of the Folh1 gene are shown in Table 23. When the LTVEC alone was introduced into ES cells, we found that none of the 96 screened drug resistant clones carried a correctly targeted monoallelic heterozygous humanized allele. In contrast, combining the LTVEC with Cas9 endonuclease guided by three of six tested sgRNAs (A, D, and E2; see Table 1) produced correctly targeted monoallelic heterozygous mutations at efficiencies that ranged from 1.0 to 3.1%. No homozygous targeted modifications were observed. In additional experiments, gRNAs A and E2 or gRNAs A and D were combined, but still no homozygous targeting was observed.

TABLE 22

Screening Results for CRISPR/Cas9-Assisted Humanization of the Dpp4 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 50 | gRNA A | no assay | 96 | 7 | 0 | 0 |
| 5' | 400 | gRNA B | no assay | 96 | 2 | 0 | 0 |
| 5' | 900 | gRNA B2 | no assay | 96 | 5 | 0 | 0 |
| middle | 38800/40200 | gRNA C | no assay | 96 | 3 | 0 | 0 |
| middle | 40800/38100 | gRNA D | no assay | 96 | 3 | 0 | 0 |
| 3' | 900 | gRNA E2 | no assay | 96 | 2 | 0 | 0 |
| 3' | 500 | gRNA E | no assay | 96 | 6 | 0 | 0 |
| 3' | 200 | gRNA F | no assay | 96 | 5 | 0 | 0 |
| 5' and 3' | 50/38100 | A + D | no assay | 384 | 4 | 0 | 0 |
| 5' and 3' | 50/200 | A + F | no assay | 384 | 9 | 0 | 0 |
| N/A | N/A | none | N/A | 96 | 2 | 0 | 0 |

TABLE 23

Screening Results for CRISPR/Cas9-Assisted Humanization of the Folh1 Gene.

| sgRNA Position | Approximate Distance from Deletion Endpoint (bp) | gRNA | CRISPR Activity (%) | Clones Screened | Heterozygous Targeted | Compound Heterozygous | Homozygous Targeted |
|---|---|---|---|---|---|---|---|
| 5' | 100 | gRNA A | 45.2 | 96 | 2 | 0 | 0 |
| 5' | 500 | gRNA A2 | 61.9 | 96 | 0 | 0 | 0 |
| 5' | 1000 | gRNA B | N/A | N/A | N/A | N/A | N/A |
| middle | 30300/24800 | gRNA C | 7.1 | 96 | 0 | 0 | 0 |
| middle | 31290/23810 | gRNA D | 39.2 | 96 | 1 | 0 | 0 |
| 3' | 1000 | gRNA F | N/A | N/A | N/A | N/A | N/A |
| 3' | 500 | gRNA E2 | no assay | 96 | 1 | 0 | 0 |
| 3' | 100 | gRNA E | 1.2 | 96 | 0 | 0 | 0 |
| 5' and 3' | 100/23810 | A + D | no assay | 96 | 3 | 0 | 0 |
| 5' and 3' | 100/500 | A + E2 | no assay | 96 | 0 | 0 | 0 |
| N/A | N/A | none | N/A | 96 | 0 | 0 | 0 |

A summary of the homozygous targeted clones observed when targeting different loci is provided in Table 24.

TABLE 24

Number of Homozygous Targeted Clones at Different Loci.

| Gene | Adamts5 | Trpa1 | Folh1 | Lrp5 | C5 | Dpp4 | Ror1 |
|---|---|---|---|---|---|---|---|
| MAID # | 7028 | 7002 | 7044 | 7064 | 7140 | 7326 | 7292 |
| Del/Ins (kb) | 38/43 | 45/55 | 55/61 | 68/91 | 76/97 | 79/82 | 110/134 |
| gRNA Combinations | A2 + E2 | B + F | A + D, A + E2 | A + F, B + E, B2 + E2, A + E, A + E2 | A + C, A + E2 | A + F, A + D | A + D, A + F |
| Homozygous Targeted Clones | 0 | 1 | 0 | 12 | 4 | 0 | 0 |
| Genome for Designing Homology Arms | 129 Bac | 129 Bac | B6 Bac | 129 Bac | 129 Bac | B6 Bac | B6 Bac |

Figure 19:
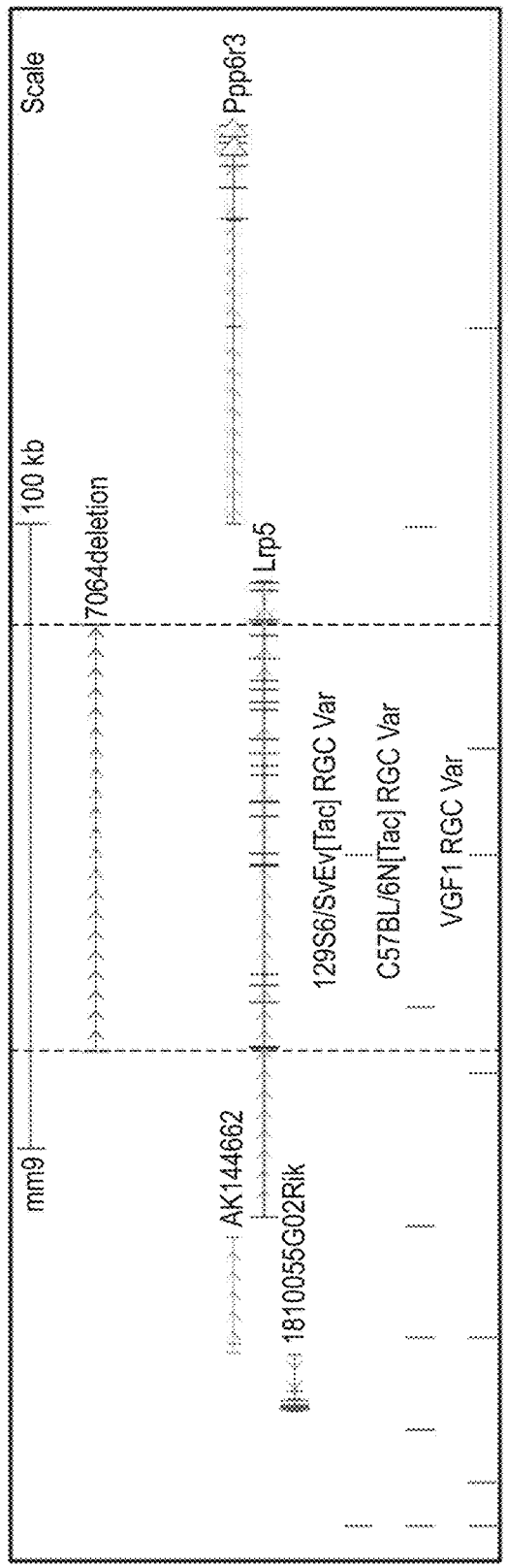
FIG. 19 shows a schematic of the mouse Lrp5 locus being targeted for deletion and replacement with a corresponding human LRP5 locus using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.
Figure 20:
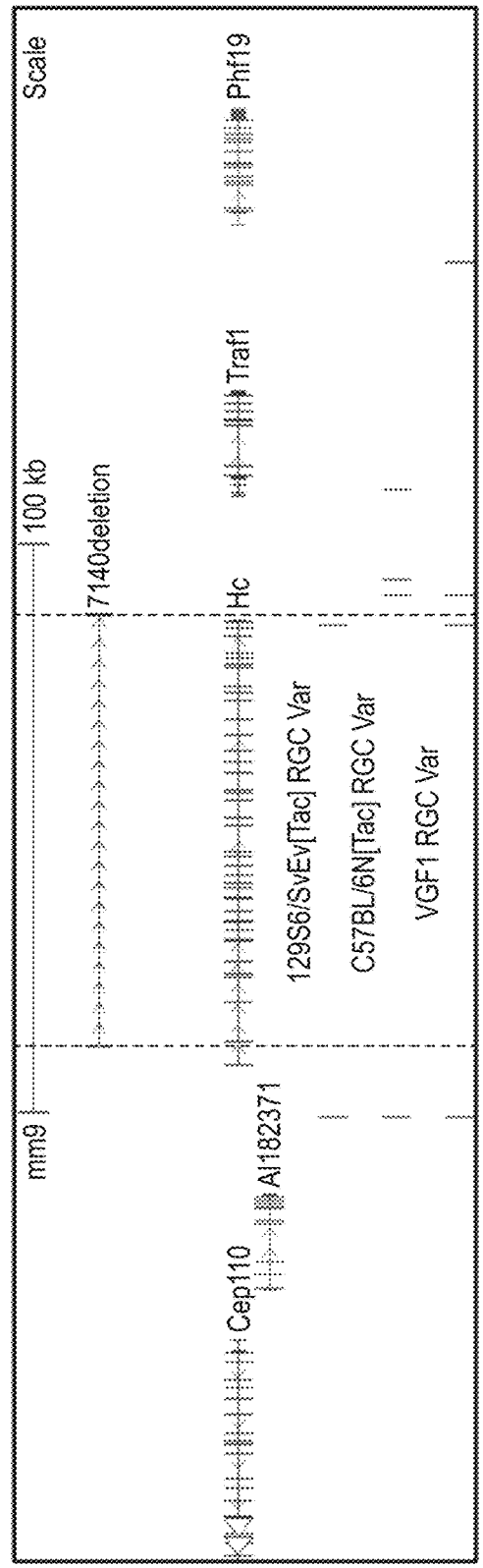
FIG. 20 shows a schematic of the mouse Hc locus being targeted for deletion and replacement with a corresponding human version using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.

In these experiments, homozygous targeting was highest for genes with the least sequence variation between the B6 and the 129 alleles. This is demonstrated in FIGS. 19-25. The region inside the dotted vertical lines is in each figure indicates the targeted region (the region inside the 5' and 3' target sequences of the LTVEC). For example, for Lrp5 (see FIG. 19), the homology arms of the LTVEC were designed based on the 129 genome. The reference sequence for determining single nucleotide variations was the genomic sequence of the C57BL/6J mouse strain from Jackson Laboratory. This reference sequence was compared to the 129S6/SvEv strain from Taconic Biosciences, the C57BL/6N strain from Taconic Biosciences, and the VGF1 hybrid cell line produced from the 129S6/SvEv strain and the C57BL/6N strain. The vertical lines represent the single nucleotide variations compared to the reference sequence. FIGS. 20-25 provide similar analysis for Hc, Trpa1, Adamts5, Folh1, Dpp4, Ror1, and CD3, respectively.

As shown in Table 24 and in FIGS. 19-25, the highest number of homozygous targeted clones were produced at the Lrp5 locus (12 homozygous clones) and the Hc/C5 locus (4 homozygous clones). Each of these target genomic loci had very few single nucleotide variations, particularly at or near the gRNA recognition sequences or flanking the region intended for deletion and replacement (see FIGS. 19 (Lrp5) and 20 (C5)).

Figure 21:
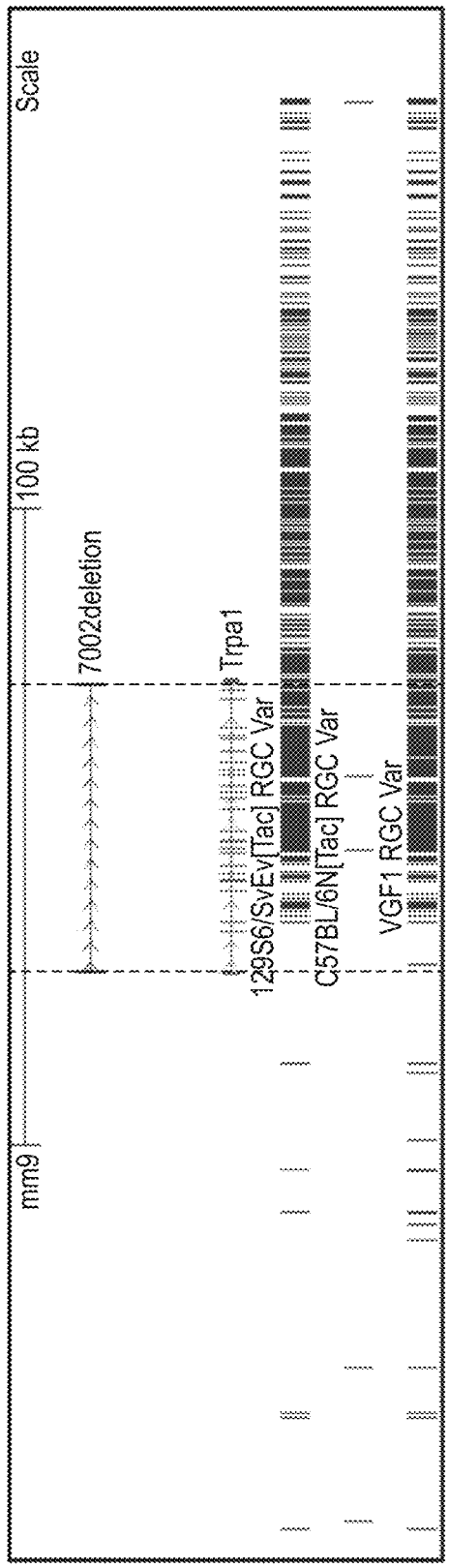
FIG. 21 shows a schematic of the mouse Trpa1 locus being targeted for deletion and replacement with a corresponding human version using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.
Figure 22:
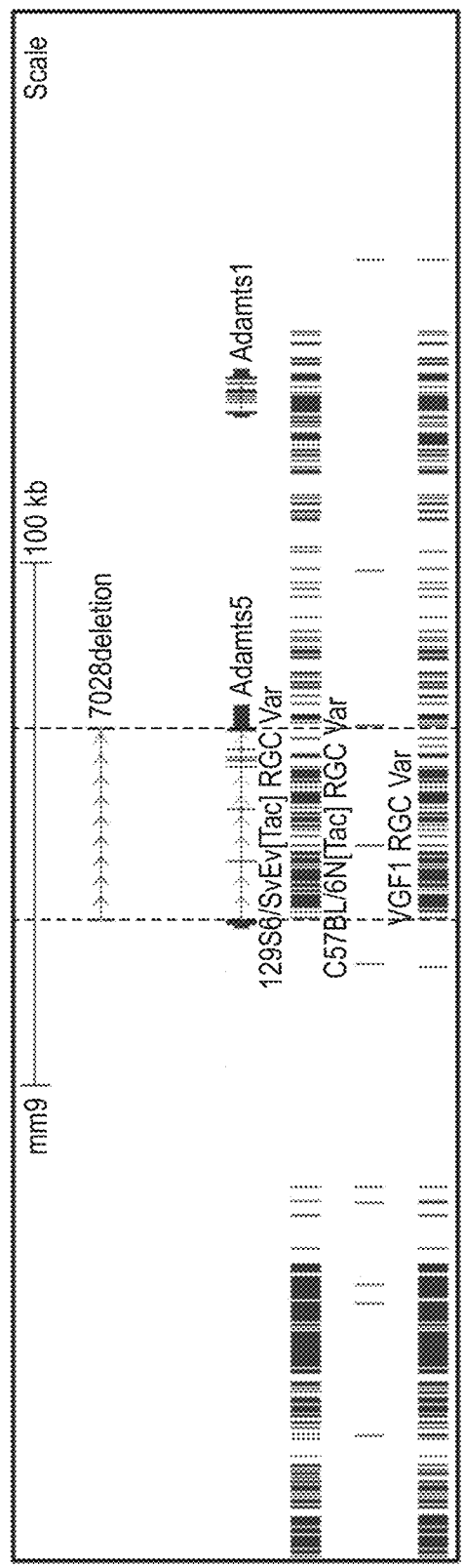
FIG. 22 shows a schematic of the mouse Adamts5 locus being targeted for deletion and replacement with a corresponding human version using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.
Figure 23:
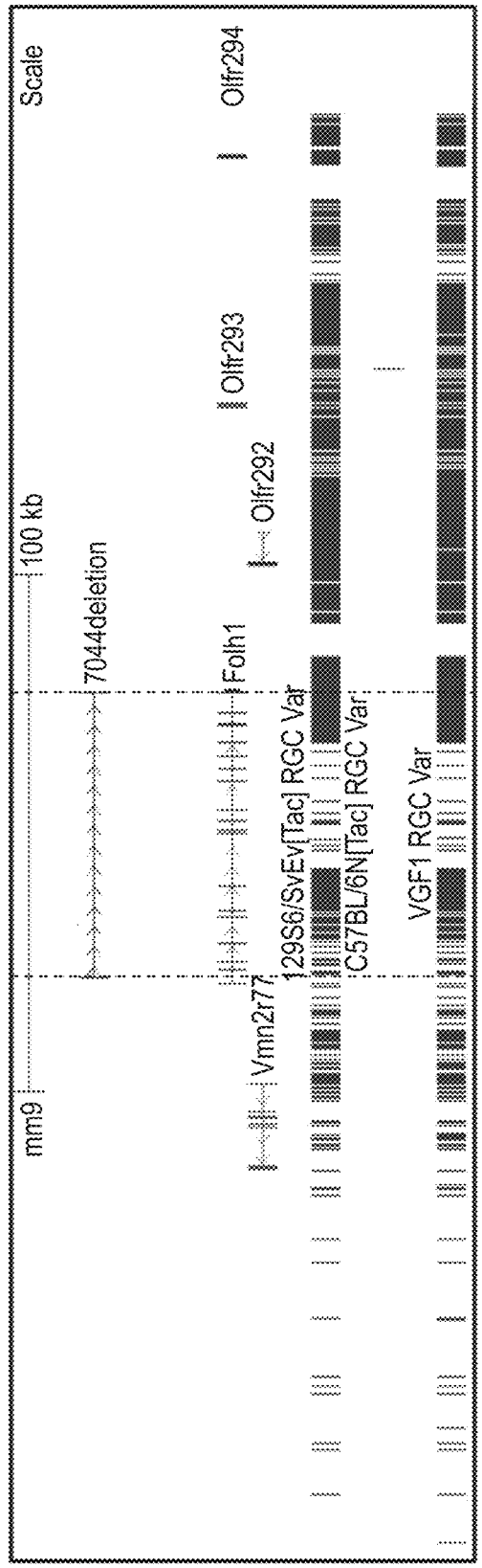
FIG. 23 shows a schematic of the mouse Folh1 locus being targeted for deletion and replacement with a corresponding human version using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.
Figure 24:
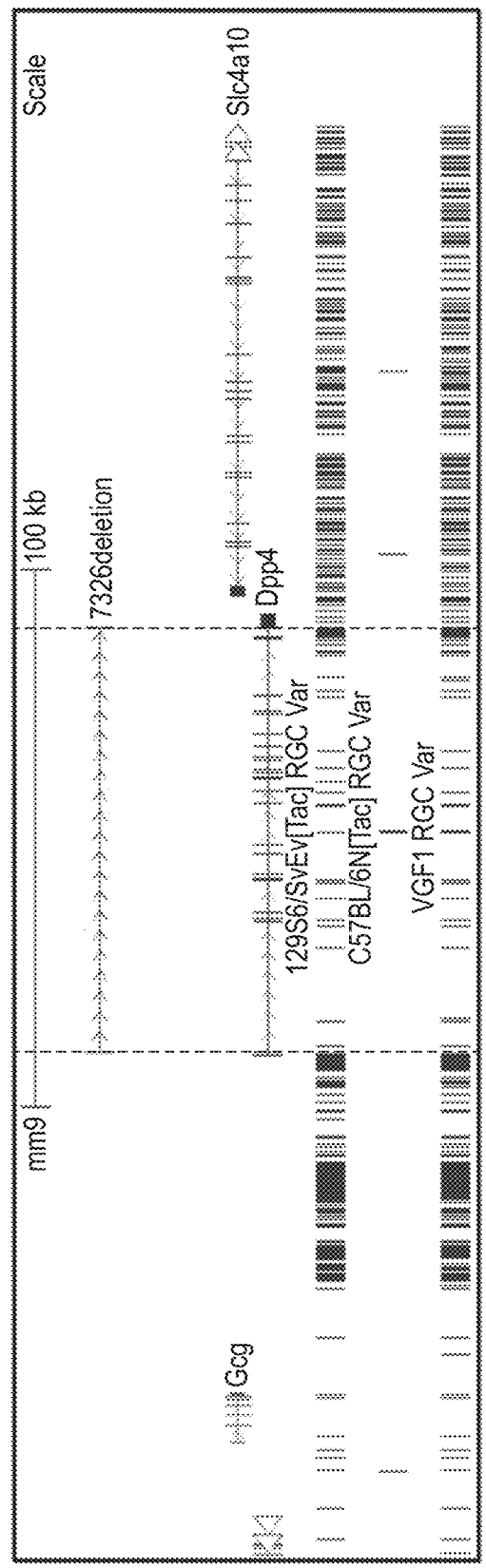
FIG. 24 shows a schematic of the mouse Dpp4 locus being targeted for deletion and replacement with a corresponding human version using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.
Figure 25:
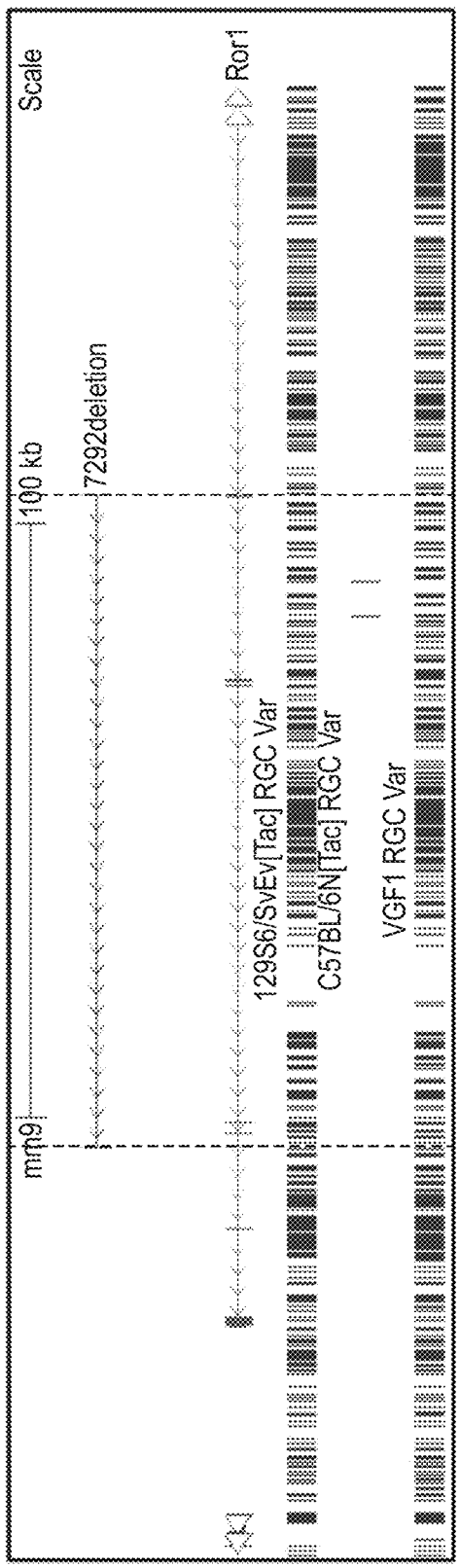
FIG. 25 shows a schematic of the mouse Ron 1 locus being targeted for deletion and replacement with a corresponding human version using an LTVEC and one or more gRNAs in VGF1 hybrid ES cells. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain from Taconic Biosciences, the C57BL/6N strain from Taconic Biosciences, and the VGF1 hybrid cell line produced from the 12956/SvEv strain and the C57BL/6N strain (represented in the three rows in the bottom portion of the figure). The vertical lines in each of the three rows represent the single nucleotide variations compared to the reference sequence.

In contrast, homozygous targeting was low or absent for genes with a high density of allelic sequence variation between the B6 and 129 alleles, particularly at or near the gRNA recognition sequences or flanking the region intended for deletion and replacement. For example, no homozygous clones were produced when targeting the Adamts5, Folh1, Dpp4, or Ron 1 loci (FIGS. 22-25, respectively). However, a homozygous clone was produced when targeting the Trpa1 locus, which has a high density of allelic sequence variation 3' of the region intended for deletion and replacement but a low density of allelic sequence variation 5' of the region intended for deletion and replacement (i.e., at or near the 5' gRNA recognition sequence) (FIG. 21).

Figure 26:
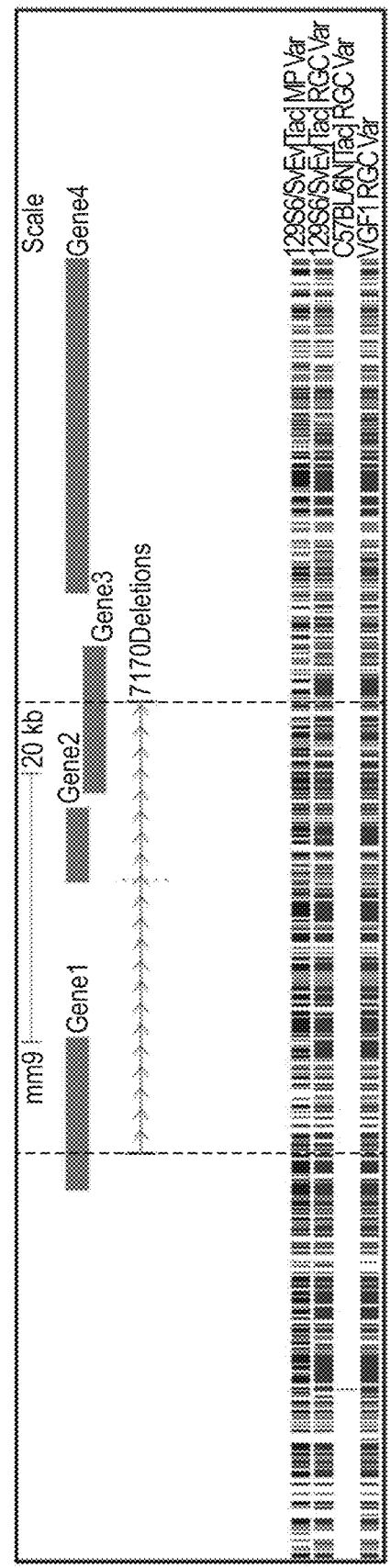
FIG. 26 shows a schematic of a mouse locus including a gene encoding a transmembrane protein; the mouse locus is being targeted for deletion and replacement with a corresponding human version using an LTVEC and one or more gRNAs in VGF1 hybrid ES cells. The rectangles represent different genes within the target genomic region. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 12956/SvEv strain MP variant from Taconic Biosciences, the C57BL/6N strain RGC variant from Taconic Biosciences, and the VGF1 hybrid cell line produced from the 12956/SvEv strain and the C57BL/

Example 8. Use of Targeting Vectors Designed Against Each Chromosome in a Homologous Chromosome Pair does not Increase Homozygous Targeting To further test whether homozygous targeted modifications were being generated through independent targeting events on each chromosome in a homologous chromosome pair or through a targeting event on one chromosome in a homologous chromosome pair and then a gene conversion or loss of heterozygosity even between the homologous chromosome pair, another genomic locus was targeted that has a large amount of allelic sequence variation between the homologous chromosome pair at or near the gRNA recognition sequence or flanking the region intended for deletion and replacement. See, e.g., FIG. 26. This allowed us to examine the effect of allelic variation on homozygous collapse or homozygous targeting. The region inside the dotted vertical lines is the targeted region (the region inside the 5' and 3' target sequences of the LTVEC). The reference sequence for determining single nucleotide variations was the genomic sequence of the C57BL/6J mouse strain from Jackson Laboratory. This reference sequence was compared to the 129S6/SvEv strain MP variant from Taconic Biosciences, the C57BL/6N strain RGC variant from Taconic Biosciences, and the VGF1 hybrid cell line produced from the 129S6/SvEv strain and the C57BL/6N strain (represented in the three rows in the bottom portion of the figure). The vertical lines in each of the three rows represent the single nucleotide variations compared to the reference sequence.

In this experiment, two LTVECs were designed to create a 33 kb deletion of the mouse locus and a simultaneous replacement with a 34.5 kb fragment including a three segments (6.8 kb, 0.1 kb, and 1.7 kb) of the orthologous human gene with intervening segments of the mouse locus between the human segments. The experiments were performed with VGF1 (F1H4), our C57BL6NTac/129S6SvEvF1 hybrid XY ES cell line (Poueymirou et al. (2007) *Nat. Biotechnol.* 25:91-99; Valenzuela et al. (2003) *Nat. Biotechnol.* 21:652-659). ES cells were cultured as previously described (Matise et al. (2000) in Joyner, A. L. ed. *Gene Targeting: a practical approach*, pp. 100-132, Oxford University Press, New York). The VGF1 cells were created by crossing a female C57BL/6NTac mouser with a Male 129S6/SvEvTac mouse to produce C57BL6($X^{B6}$)/129S6($Y^{129}$) mice. See FIG. 7.

One LTVEC had homology arms designed against the 129 chromosome in the VGF1 cells and included a Neo selection cassette (MAID #7170), and the other LTVEC had homology arms designed against the C57BL6 chromosome and included a Hyg selection cassette (MAID #7314). The two LTVECs were otherwise the same.

In separate experiments, we combined the two humanizing LTVECs with a plasmid encoding Cas9 and a second plasmid or plasmids encoding four sgRNAs (mGU, mGU2, mGD, mGD2) designed to create double strand breaks within the region of the mouse gene that was targeted for deletion. The sgRNAs were designed to avoid recognition of any sequence in the inserted portion of the human gene.

A total of 192 Neo+ clones, 128 Hyg+ clones, and 16 Neo+/Hyg+ clones were screened. Combining the LTVEC with Cas9 endonuclease guided by the four sgRNAs produced some heterozygous targeted clones, hemizygous targeted clones, biallelic collapsed clones, heterozygous targeted clones with NHEJ deletions, clones with biallelic NHEJ deletions, and heterozygous collapsed clones with NHEJ deletions. However, no homozygous targeted clones were observed. This suggests that local gene conversion events are responsible for the homozygous targeted clones observed in other experiments rather than separate targeting events on each chromosome within a homologous chromosome pair. If independent targeting events on each chromosome within the homologous chromosome pair were responsible for the homozygous targeted clones observed in the other experiments, use of two targeting vectors specifically tailored for each of the two chromosomes within the homologous chromosome pair would be expected to produce homozygous targeted clones notwithstanding the high percentage of allelic sequence variation within the 5' and 3' target sequences for the 5' and 3' homology arms, because the targeting vectors tailored for each chromosome address that allelic sequence variation within the 5' and 3' target sequences. However, use of the two LTVECs did not produce any homozygous targeted clones. This further supports the idea that the homozygous targeted modifications or produced through local gene conversion events as depicted in FIG. 27. We have observed local loss of heterozygosity on both sides of targeted deletions and insertions at a higher rate than polar gene conversion.

We claim:

1. A method of generating antigen-binding proteins against a human foreign antigen of interest, comprising:
   (a) making a transgenic mouse with reduced tolerance to the human foreign antigen of interest, comprising:
      (i) introducing into a population of mouse one-cell stage embryos or a population of mouse embryonic stem (ES) cells:
         (I) a Cas9 protein or a nucleic acid encoding a Cas9 protein;
         (II) a first guide RNA or a DNA encoding the first guide RNA, wherein the first guide RNA hybridizes to a first guide RNA recognition sequence within a target genomic locus, wherein the target genomic locus comprises all or part of a gene encoding a self-antigen orthologous to the human foreign antigen of interest;
         (III) a second guide RNA or a DNA encoding the second guide RNA, wherein the second guide RNA hybridizes to a second guide RNA recognition sequence within the target genomic locus;
      (ii) screening the population of mouse one-cell stage embryos or the population of mouse ES cells for a modified mouse one-cell stage embryo or a modified mouse ES cell, wherein the target genomic locus is modified in a pair of corresponding first and second chromosomes to produce the modified mouse one-cell stage embryo or the modified mouse ES cell with a biallelic modification, wherein the biallelic modification comprises a biallelic deletion of all or part of the gene encoding the self-antigen, wherein expression of the self-antigen is eliminated;
      (iii) producing a transgenic F0 generation mouse from the modified mouse one-cell stage embryo or the modified mouse ES cell, wherein the target genomic locus is modified in the pair of corresponding first and second chromosomes in the transgenic F0 generation mouse such that expression of the self-antigen is eliminated;
   (b) immunizing the transgenic F0 generation mouse produced in step (a) with the human foreign antigen of interest,
   wherein the transgenic F0 generation mouse comprises in its germline:
      (i) an ectopic nucleic acid sequence encoding a mouse ADAM6 protein, wherein the mouse ADAM6 protein is functional in a male mouse;
      (ii) a heavy chain locus comprising human immunoglobulin heavy chain V, D, and J gene segments, wherein the human immunoglobulin heavy chain V, D, and J gene segments are operably linked to a mouse immunoglobulin heavy chain constant region gene, wherein the mouse immunoglobulin heavy chain constant region gene is at an endogenous mouse immunoglobulin locus; and
      (iii) a light chain locus comprising human immunoglobulin light chain V and J gene segments, wherein the human immunoglobulin light chain V and J gene segments are operably linked to a mouse immunoglobulin light chain constant region gene sequence,
   wherein (ii) rearranges to form a heavy chain sequence comprising a human heavy chain variable region operably linked to a mouse heavy chain constant region, and (iii) rearranges to form a light chain sequence comprising a human light chain variable region operably linked to a mouse light chain constant region, and
   wherein the mouse is incapable of forming an antibody that comprises a human variable region and a human constant region; and
   (c) maintaining the transgenic F0 generation mouse under conditions sufficient to initiate an immune response to the human foreign antigen of interest, wherein the transgenic F0 generation mouse produces antigen-binding proteins against the human foreign antigen of interest.

2. The method of claim 1, wherein producing the transgenic F0 generation mouse in step (a)(iii) comprises introducing the modified mouse ES cell into a host embryo and implanting the host embryo into a surrogate mother to produce the transgenic F0 generation mouse, or
   wherein producing the transgenic F0 generation mouse in step (a)(iii) comprises implanting the modified mouse one-cell stage embryo into a surrogate mother to produce the transgenic F0 generation mouse.

3. The method of claim 1, further comprising making a hybridoma from B cells isolated from the immunized transgenic F0 generation mouse.

4. The method of claim 1, further comprising obtaining from the immunized transgenic F0 generation mouse at least one of a first nucleic acid sequence encoding an immunoglobulin heavy chain variable domain of one of the antigen-binding proteins against the human foreign antigen of interest and a second nucleic acid sequence encoding an immunoglobulin light chain variable domain of one of the antigen-binding proteins against the human foreign antigen of interest, wherein at least one of the first nucleic acid sequence and the second nucleic acid sequence are obtained from a lymphocyte of the transgenic F0 generation mouse or from a hybridoma produced from the lymphocyte.

5. The method of claim 1, wherein the first guide RNA recognition sequence is 5' of the second guide RNA recognition sequence in the target genomic locus, and
   wherein step (a)(ii) comprises performing a retention assay to determine the copy number for at least one of a region 5' and within about 1 kb of the first guide RNA recognition sequence and a region 3' and within about 1 kb of the second guide RNA recognition sequence.

6. The method of claim 1, wherein the biallelic deletion is a precise deletion without random insertions and deletions.

7. The method of claim 1, wherein the first guide RNA recognition sequence comprises the start codon for the gene encoding the self-antigen or is within about 1,000 nucleotides of the start codon, and the second guide RNA recognition sequence comprises the stop codon for the gene encoding the self-antigen or is within about 1,000 nucleotides of the stop codon.

8. The method of claim 1, wherein the first and second guide RNA recognition sequences are different, and each of the first and second guide RNA recognition sequences comprises the start codon for the gene encoding the self-antigen or is within about 1,000 nucleotides of the start codon.

9. The method of claim 1, wherein the biallelic deletion is between about 0.1 kb to about 200 kb.

10. The method of claim 1, wherein the biallelic modification comprises a biallelic disruption of the start codon of the gene encoding the self-antigen.

11. The method of claim 1, wherein the introducing step (a)(i) further comprises introducing into the population of mouse one-cell stage embryos or the population of mouse ES cells at least one of:
(iv) a third guide RNA or a DNA encoding the third guide RNA, wherein the third guide RNA hybridizes to a third guide RNA recognition sequence within the target genomic locus; and
(v) a fourth guide RNA or a DNA encoding the fourth guide RNA, wherein the fourth guide RNA hybridizes to a fourth guide RNA recognition sequence within the target genomic locus.

12. The method of claim 1, wherein step (a)(i) comprises introducing the nucleic acid encoding the Cas9 protein, the DNA encoding the first guide RNA, and the DNA encoding the second guide RNA into the population of mouse ES cells, wherein the nucleic acid encoding the Cas9 protein is DNA, or
wherein the Cas9 protein or the nucleic acid encoding the Cas9 protein, the first guide RNA or the DNA encoding the first guide RNA, and the second guide RNA or the DNA encoding the second guide RNA are each introduced into the population of mouse ES cells by electroporation or nucleofection.

13. The method of claim 1, wherein step (a)(i) comprises introducing the nucleic acid encoding the Cas9 protein, the first guide RNA, and the second guide RNA into the population of mouse one-cell stage embryos, wherein the nucleic acid encoding the Cas9 protein is RNA, or
wherein the Cas9 protein or the nucleic acid encoding the Cas9 protein, the first guide RNA or the DNA encoding the first guide RNA, and the second guide RNA or the DNA encoding the second guide RNA are introduced into the population of mouse one-cell stage embryos by pronuclear injection or cytoplasmic injection.

14. The method of claim 1, wherein the method does not comprise introducing an exogenous repair template into the population of mouse one-cell stage embryos or the population of mouse ES cells.

15. The method of claim 1, wherein:
(I) the introducing step (a)(i) further comprises introducing into the population of mouse one-cell stage embryos an exogenous repair template comprising a 5' homology arm that hybridizes to a 5' target sequence at the target genomic locus and a 3' homology arm that hybridizes to a 3' target sequence at the target genomic locus, wherein the exogenous repair template is no more than about 5 kb in length; or
(II) the introducing step (a)(i) further comprises introducing into the population of mouse ES cells an exogenous repair template comprising a 5' homology arm that hybridizes to a 5' target sequence at the target genomic locus and a 3' homology arm that hybridizes to a 3' target sequence at the target genomic locus.

16. The method of claim 15, wherein the exogenous repair template further comprises a nucleic acid insert flanked by the 5' homology arm and the 3' homology arm.

17. The method of claim 1, wherein the mouse strain is a mix of BALB/c, C57BL/6, and 129 strains.

18. The method of claim 17, wherein the mouse strain is 50% BALB/c, 25% C57BL/6, and 25% 129.

19. The method of claim 1, wherein the MHC haplotype of the mouse is $MHC^{b/d}$.

20. The method of claim 1, wherein the Cas9 protein has double-strand-break-inducing activity, and wherein paired double-strand breaks are created at different sites within the target genomic locus.

* * * * *